US006841147B2

(12) United States Patent
Zsebo et al.

(10) Patent No.: US 6,841,147 B2
(45) Date of Patent: Jan. 11, 2005

(54) STEM CELL FACTOR COMPOSITIONS

(75) Inventors: Krisztina M. Zsebo, Thousand Oaks, CA (US); Robert A. Bosselman, Thousand Oaks, CA (US); Sidney V. Suggs, Newbury Park, CA (US); Francis H. Martin, Thousand Oaks, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 09/224,683

(22) Filed: Dec. 31, 1998

(65) Prior Publication Data

US 2002/0031491 A1 Mar. 14, 2002

Related U.S. Application Data

(60) Division of application No. 09/005,893, filed on Jan. 12, 1998, which is a division of application No. 08/449,653, filed on May 24, 1995, now Pat. No. 6,248,319, which is a division of application No. 08/172,329, filed on Dec. 21, 1993, now Pat. No. 6,218,148, which is a continuation of application No. 07/982,255, filed on Nov. 25, 1992, now Pat. No. 6,204,363, which is a continuation of application No. 07/684,535, filed on Apr. 10, 1991, now abandoned, which is a continuation-in-part of application No. 07/589,701, filed on Oct. 1, 1990, now abandoned, which is a continuation-in-part of application No. 07/573,616, filed on Aug. 24, 1990, now abandoned, which is a continuation-in-part of application No. 07/537,198, filed on Jun. 11, 1990, now abandoned, which is a continuation-in-part of application No. 07/422,383, filed on Oct. 16, 1989, now abandoned.

(51) Int. Cl.$^7$ .......................... A61K 38/19; C07K 14/52

(52) U.S. Cl. ...................... 424/85.1; 424/198.1; 514/2; 514/12; 530/300; 530/350; 530/351; 530/399

(58) Field of Search ............................... 424/85.1, 85.2, 424/85.3, 185.1, 198.1; 514/2, 12; 530/300, 350, 351, 399

(56) References Cited

U.S. PATENT DOCUMENTS

| | | | |
|---|---|---|---|
| 4,847,325 A | 7/1989 | Shadle et al. | ............... 525/54.1 |
| 4,959,455 A | 9/1990 | Clark et al. | ................. 530/351 |
| 5,767,074 A | 6/1998 | Besmer et al. | ................ 514/12 |
| 5,772,992 A | 6/1998 | Bauer et al. | ............... 424/85.2 |
| 5,786,323 A | 7/1998 | Nakahata | ........................ 514/2 |
| 6,204,363 B1 * | 3/2001 | Zsebo et al. | ................. 530/351 |

FOREIGN PATENT DOCUMENTS

| | | |
|---|---|---|
| EP | 0 845 268 A2 | 6/1998 |
| JP | 62-223126 | 10/1987 |
| WO | WO 95/06112 | 3/1995 |
| WO | WO 98/18924 | 5/1998 |
| WO | WO 98/23773 | 6/1998 |

OTHER PUBLICATIONS

Groopman et al. Hematopoietic growth factors. N Engl J Medicine 321(21): 1449–1459, 1989.*
Brenner, S.E. Errors in genome function. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*
Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Corti et al., *Exp. Neurol.*, 177: 443–452 (2002).
Costa et al., *J. Exp. Med.*, 183: 2681–2686 (1996).
Kawakami et al., *J. Invest. Dermatol.*, 118: 471–478 (2002).
Bodine et al., "Combination of Interleukin 3 and 6 Preserves Stem Cell Function in Culture and Enhances Retrovirus––Mediated Gene Transfer Into Hematopoietic Stem Cells," *Proc. Nat'l Acad. Sci., USA*, 6:8897–8901 (1989).
Broxmeyer et al., "Cell–Free Granulocyte Colony Inhibiting Activity Derived from Human Polymorphonuclear Neutrophils," *Exp. Hemat.*, 5:87–102 (1977).
Dexter, T.M., "Haemopoietic Growth Factors," *British Medical Bulletin*, 45(2):337–349 (1989).
Dick et al., "Introduction of New Genes into Hematopoietic Stem Cells," *J. Cell. Biol., Supplement 11A*, p. 187 (1987) (Abstract D 026).
Dick et al., "Introduction of Selectable Gene into Primitive Stem Cells Capable of Long–Term Reconstitution of the Hemopoietic System of W/W$^v$ Mice," *Cell*, 42:71–79 (1985).
Hiraoka et al., "Further Characterization of the Biological Properties of Human Hematopoietic Survival and Growth Factor," *Expl. Cell. Biol.*, 57:27–34 (1989).
Hiraoka et al., "Human Hematopoietic Survival and Growth Factor," *Cell Biology International Reports*, 10(5):347–355 (1986).

(List continued on next page.)

*Primary Examiner*—Elizabeth Kemmerer
*Assistant Examiner*—Bridget E. Bunner
(74) *Attorney, Agent, or Firm*—Marshall, Gerstein & Borun LLP

(57) ABSTRACT

Novel stem cell factors, oligonucleotides encoding the same, and methods of production, are disclosed. Pharmaceutical compositions and methods of treating disorders involving blood cells are also disclosed.

24 Claims, 119 Drawing Sheets

OTHER PUBLICATIONS

Hiraoka et al., "Monoclonal Antibodies Against Human Hematopoietic Survival and Growth Factor," *Biomed. Biochim. Acta*, 46(5):419–427 (1987).

Hiraoka et al., "Production of Human Hematopoietic Survival and Growth Factor by a Myeloid Leukemia Cell Line (KPB–M15) and Placenta as Detected by a Monoclonal Antibody," *Cancer Research*, 47:5025–5030 (1987).

Hollands, "Differentiation of Embryonic Haemopoietic Stem Cells from Mouse Blastocysts Growth in Vitro," *Development*, 102:135–141 (1988).

Humphries et al., "Aplastic Anemia and Stem Cell Biology," *Aplastic Anemia: Stem Cell Biology and Advances in Treatment*, Alan R. Liss, Inc., New York, New York, pp. 3–12 (1984).

Jones et al., "Cyclic Hematopoiesis: Animal Models," *Exp. Hematol.*, 11(7):571–580 (1983).

Kamamoto et al., "Establishment of Two Ph$^1$ Chromosome–Positive Cell Lines, KPB–M8 and KPB–M15," *Jpn. J. Clin. Oncol.*, 16(2):107–115 (1986).

Kriegler et al., "Partial Purification and Characterization of a Growth Factor for Macrophage Progenitor Cells with High Proliferative Potential in Mouse Bone Marrow," *Blood*, 60(2):503–508 (1982).

Langley et al., "Soluble Stem Cell Factor in Human Serum," *Blood*, 81(3):656–660 (1993).

Lyman et al., "Molecular Cloning of a Ligand for the flt3/flk–2 Tyrosine Kinase Receptor: A Proliferative Factor for Primitive Hematopoietic Cells," *Cell*, 75:1157–1167 (1993).

March et al., "Cloning, Sequence and Expression of Two Distinct Human Interleukin–1 Complementary DNAs," *Nature*, 315:641–647 (1985).

Martin et al., "Primary Structure and Functional Expression of Rat and Human Stem Cell Factor DNAs," *Cell*, 63:203–211 (1990).

Martin, P., "HEL Cells: A New Human Erythroleukemia Cell Line with Spontaneous and Induced Globin Expression," *Science*, 216:1233–1235 (1982).

McDermott et al., "Inhibition of Cell Proliferation in Renal Failure and Its Significance to the Uraemic Syndrome: A Review," *Scot. Med. J.*, 20:317–327 (1975).

McNiece et al., "Studies on the Myeloid Synergistic Factor From 5637: Comparison with Interleukin –1 Alpha," *Blood* 73(4):919–923 (1989).

Moore, M.A.S., "Clinical Implications of Positive and Negative Hematopoietic Stem Cell Regulators," *Blood*, 78(1):1–19 (1991).

Mori et al., "Myeloproliferative Sarcoma Virus Stimulates Pluripotent Hematopoietic Stem Cells and Provokes Tumoral Transformation of the Hematopoietic Microenvironment in Vitro," *Leukemia Research*, 7(1):77–86 (1983).

Nabel et al., "Inducer T Lymphocytes Synthesize a Factor That Stimulates Proliferation of Cloned Mast Cells," *Nature*, 291:332–334 (1981).

Qui et al., "Primary Structure of c–kit: Relationship with the CSF–1/PDGF Receptor Kinase Family–Oncogenic Activation of v–kit Involves Deletion of Extracellular Domain and C Terminus," *EMBO J.*, 7(4):1003–1011 (1988).

Schrader, "Role of a Single Haemopoietic Growth Factor in Multiple Proliferative Disorders of Haemopoietic and Related Cells," *Lancet*, 2:133–137 (1984).

Spangrude et al., "Purification and Characterization of Mouse Hematopoietic Stem Cells," *Science*, 214:58–62 (1988).

Watson et al., "Molecular Cloning of the Polypeptide Factors That Stimulate Growth, Maturation, and Function of Blood Cells$^{60-66}$," *Molecular Biology of the Gene*, Fourth Edition, pp. 983–992 (1987).

Welte et al., "Recombinant Human Granulocyte Colony––Stimulating Factor," *J. Exp. Med.*, 165:941–948 (1987).

Yarden et al., "Human Proto–Oncogene c–kit: a New Cell Surface Receptor Tyrosine Kinase for an Unidentified Ligand," *EMBO J.*, 6(11):3341–3351 (1987).

Zajicek, "Inflammation Initiates Cancer by Depleting Stem Cells," *Medical Hypotheses*, 18:207–219 (1985).

Zsebo et al. "Effects of Hematopoietin–1 and Interleukin 1 Activities on Early Hematopoietic Cells of the Bone Marrow," *Blood*, 71(4):962–968 (1988).

Zsebo et al., "Stem Cell Factor Is Encoded at the SI Locus of the Mouse and Is the Ligand for the c–kit Tyrosine Kinase Receptor," *Cell*, 63:213–224 (1990).

\* cited by examiner

HPP-CFC (Colony #)

FIG. 11

```
1                         10                        20
pE E I C R N P V T D N V K D I T K L V A N L P N D
  |--------------------------------------------- Sequencing after
                                         |-------- T-5a --------|
              30                        40                      50
Y M I T L N Y V A G M D V L P S H C W L R D M V T
<Glu Aminopeptidase Treatment --------------->
                                            |--------------------
------------------------------------- T-5a ----------------|
      |---------- CB-6a ----------|-------- CB-8; CB-10 ----------|
                      60                        70
H L S V S L T T L L D K F S N I S E G L S N Y S I
------ Sequencing after Trp Cleavage ----------------
              80                        90                      100
I D K L G K I V D D L V A C M E E N A P K N V K E
 --------------------------->
              --------------------- T-3 ---------------------|
                                                                --
                                                                --
                                          |-CB-14;CB-15;CB-16 -
                                          |-------- S-1----------|
                      110                       120
S L K K P E T R N F T P E E F F S I F N R S I D A
--- T-1 --------------- ---- T-4(N109 nonglyco) -----|----------
----- T-7(N120 glyco);T-8(N109 nonglyco)-----
---------------------------- CB-14; CB-15; CB-16 --------------------
---------------- S-5 or S-6 (N109 nonglyco)------------------
              130                       140                     150
F K D F M V A S D T S D C V L S S T L G P E K D S
---------------------------- T-5b -----------------------------
--------------------------------------- CB-6B -------------------------
------- S-5 or S-6-----------
                      160
R V S V T K P F M L P P V A(A)
--|------ T-2 ---|              <-- <-- (Carboxypeptidase)
|------ CB-6B ----------|
|----------------- S-2 -----------------|
```

FIG.12A

| OLIGO | SEQUENCE | LOCATION |
|---|---|---|
| 219-21 | ACATTCTTTGGTGCATTCTCCTCCAT<br>      G T        G T  T | 393-368 |
| 219-22 | AAAAACTCCCTCTGGTGTAAAATT<br>      G T T        G G | 447-425 |
| 219-25 | GTTTCNGGTTTTT<br>    C  C C | 420-407 |
| 219-26 | ATGGAAGAAAACGCCCCCAAAAACGT<br>           G      T      G T | 368-393 |
| 222-11 | CCNAATGATTATATGATAAC<br>  C    C    C      C<br>                T | 167-186 |
| 222-12 | GGNGGNAACATAAANGGCTT<br>      G   G        T | 566-585 |
| 223-6 | ACCATAAAATCTTTAAATCGATC<br>          G   G C G      G | 492-470 |
| 224-24 | GTATTTCAATAGATCCATTGA | 450-471 |
| 224-25 | CCAACTATGTCGCC | 190-202 |
| 224-27 | GTAGTCAAGCTGACTGATAAG | 273-253 |

FIG. I2A CONT.

| | | |
|---|---|---|
| 224-28 | TAACCAACAATGACTAGGCAA | 235-215 |
| 225-31 | TTCCAGAGTCAGTGTC | 547-562 |
| 227-29 | GCGAAGCTTGCCTTTCCTTATGAAGAAGA | 16-35 * |
| 227-30 | GCGCCGCGGTTACGGTAACATGAAGGGCTTTGTGA | 586-561 * |
| 228-30 | GATAAATGCAAGTGATAATCC | 45-65 |
| 230-25 | GCGGTCGACCCGGGAACTTTAAGTCCATGCAACAC | 705-685 * |
| 237-19 | CACCCGCGGTTATGCAACAGGGGGTAACATAAATGG | 569-592 * |
| 237-20 | CACCCGCGGTTAGGCTGCAACAGGGGGTAACATAAA | 572-595 * |

FIG.12B

| OLIGO | SEQUENCE | LOCATION |
|---|---|---|
| 231-27 | CTTAATGTTGAAGAAACC | 703-686 |
| 233-13 | GATGGTAGTACAATTGTCAGAC | 410-431 |
| 233-14 | GTCTGACAATTGTACTACCATC | 431-410 |
| 235-29 | CAATTTAGTGACGTCTTTTACA | 302-323 |
| 235-30 | TTAGATGAGTTTTCTTTCACGCAC | 556-533 |
| 235-31 | AAATCATTCAAGAGCCCAGAACCC | 566-589 |
| 236-31 | AACATCCATCCCGGGGAC | 366-383 |
| 238-31 | CTGGCAATATTTTAAGTCTCAAGAAGACC | |
| 241-6 | GCGCCGCGGCTCCTATAGGTGCTAATTGG | |
| 254-9 | CCTCACCACTGTTTGTGCTGGATCGCA | 153-179 |
| 262-13 | GGTGTCTAGACTTGTGTCTTCTTCATAAGGA | 209-190 * |

FIG.12C

| OLIGO | SEQUENCE |
|---|---|
| 201-7 | CCCCCCCGG<br>        T<br>        A |
| 220-3 | TTTTTTTTTTTTTTTTGG |
| 220-7 | TTTTTTTTTTTTTTTTAG |
| 220-11 | TTTTTTTTTTTTTTTTCG |
| 221-11 | TTCGGCGATCAGGCCCCCCCC |
| 221-12 | TTCGGCGGATAGGCCTTTTTTTTTTTT |
| 228-28 | GGCCGGATAGGCCTCACNNNNNNT |
| 228-29 | GGCCGGATAGGCCTCAC |

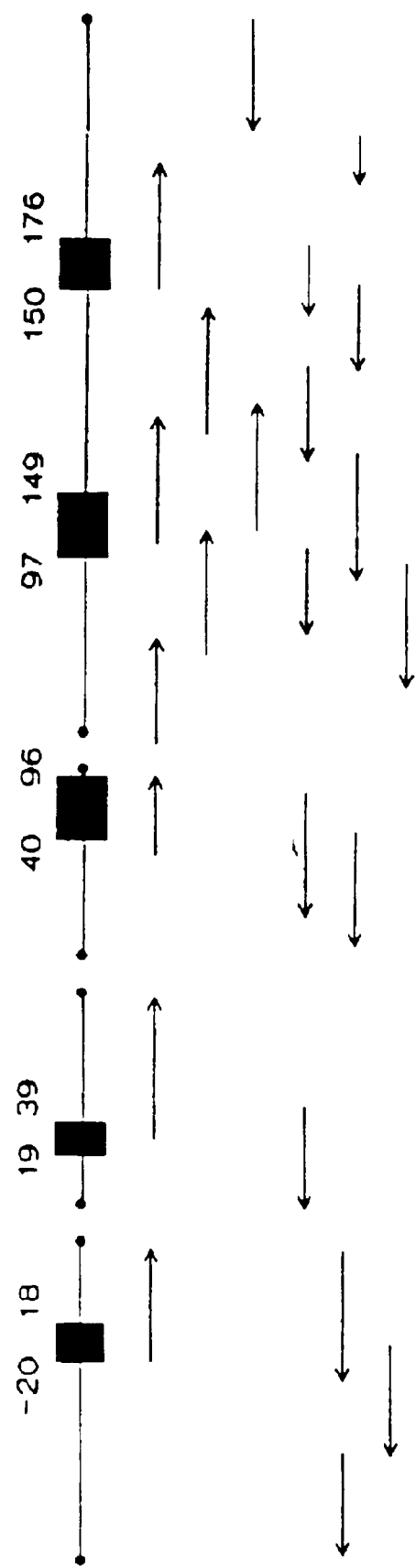

FIG. 14B

```
AAAGTATCTTTCTATTGGCGAAGGACATGTTTTCCcATAAGTGGT      45

AAACAnACTGTCTGCACATAATAATTATCTTGCTGCCGTAAAGAT      90

TAGGTTAAATTCTGcCTTCGATCTAAAAACACACCCTTCTGTCAA     135

TCCGAGGAGCAGTGTGCTAGTCTAGAGGTCTAAATGAAGGCTCCT     180

TTCACGGTTGTATTTCTGCTCCCAAATTGTCCACATTTAAAAGG      225

AGAGTGCTTCTTTTCAGCCTTAGGCTCTGAATTTCATGCATTCCT     270

CCATTTTCCGAGGTCCCccCcAAGTGATAATTCTGTTACACGTTG     315

CTACAAGTTCATCCCTAATTGCCGTCAAGAAACTGACTGTAGAAG     360

GCTTACCACAGACGTTGTAACCGACAGTAAAGCCATTGAAAGAGT     405

AATTCAAACAGGATGGAAGCCAGGAGTATTTTGTGGCTGTTGCTC     450

TTTTTCTTTTCAGTTTGGTGAGAGCAGCTTGAATGCTTAACATTT     495

AAGCCATCAGCTTAAAACAAAACAAAACAAAACAAAAAAAACCC     540

CGCTCTGGCATATTTGCACTTAACACATACGGTATAAGGTGTTAC     585

TGGTTTGCATAGTTCTGGATTTTTTTTTTTAAAAACTGATGGAC     630
```

```
                                   -20
                        ThrTrpIleIleThrC
ACCAAGAAATGTTTCTGTTCTTTGTTAGACTTGGATTATCACTT     675
```

```
         -10
ysIleTyrLeuGlnLeuLeuLeuPheAsnProLeuValLysThrG
GCATTTATCTTCAACTGCTCCTATTAATCCTCTCGTCAAACTC      720
```

```
  1                  10
lnGluIleCysArgAsnProValThrAspAsnValLysAspIleT
AGGAGATCTGCAGGAATCCTGTGACTGATAATGTAAAGACATTA     765

18
hrLysLeu
```

FIG.14B CONT.'

```
CAAAACTGGTAAGTAAAGAATGATTTTGGCATCTATAAGTCTTCC      810

CTGTGCTTGCTGACCACATAGGTTCAGGGCACTCCCGACAGGAGT      855

TCCCAGCTTTCTAAGATAAGGAATCACTGTACGAGTCTGAAGTGC      900

TTCTTCTGGGCAAATGGGAGATGCTTAGGTCATGGAGGGTTTATC      945

TGTATAACTGGCCCTTTGCACACCAACAAAGTGACTGACTGGCTT      990

TTGCCTGTTACCTACTG                                 1007
```

Intervening sequence of unknown length

```
TCTCCAGTCCTGGGCATGGTATATACTTAGGCACCCAAGATTGGA       45

TTTACAACTCAAGCATTATATATTGGACAACnACGGGGTATGAGA       90

TATTAATGATATGTCAGGTTGGATGGATGAGTTTTCTCAAGAAAT      135

19
                                         Val
TCTCTTGTATTTACTCACGTTTTCATTTCTTGGTCTCTGTAGGTG      180

30
AlaAsnLeuProAsnAspTyrMetIleThrLeuAsnTyrValAla
GCGAATCTTCCAAATGACTATATGATAACCCTCAACTATGTCGCC      225

39
GlyMetAspValLeu
GGGATGGATGTTTTGGTATGTAGTCCACACACTTCTGAGTTGCCT      270

TTTAGTAGCTAATGGGTGACCTGTGCTTATTCACATTGAAGACAT      315

TATTTGCTCTTTGTCGTTTTAGATGTTGACCTATAATTTTTCCT      360

TCAAGCTGCTGCTAAGATTATCAGTGAGCATTTCAGTATGTGTTT      405

TAAGCCTACTCATTAAAAGGAAATGGCTCATCTTAGACGTAGCAA      450
```

FIG. 14B CONT.'

```
CCGATGTTAATTTTTCCCCAGGCATCTCTCAGAGGGACTTGAATG    495

TTAAAATCATGTTAAATTTCCTCCTTGGCTATGTTATTTCTCATG    540

GCTATGTTATTCCTATTCGTATTTCATTTAAAGGGACGGAATATT    585

TATTGTATTTCTGAACTTTTTCAGGCATGCATCCGGGTCTTTGAA    630

TAAAA                                            635
```

Intervening sequence of unknown length

```
CACTAAGACTCCTTCTAGTAATGTTTGTAATCCTGTCTGTATCGA    45

ATGTCTTTGAAAACGCAGTGACTAAGCCATAAATAATCTTCCACA    90

GAACGTCCAGTGGTTCATGAACTTTGTATGTGGGGGTGGGGCAAG    135

AATTGTCTCACTATTGGTCAAGGAAGAGAAGGTAAGGTATGCAAG    180

GGTGGTTTAATCTTCTTCCGTGGAAGGACAAAATCATCTATCATT    225

TCCTCTGATCTCTATGCATTTGTTTGTTTTGAACTGAATCTGACT    270

TGAGCAAGAGTTGGCGTCCTGTGTTCTGAGGAAACTCTTTGTCCT    315

GCAGTCAGTGACTAAAAGTGCTGAGAGATCTGAAGAGCACTCTGA    360

ATCTGCCATATTTTAATAGATGCTTTGTCTTCTCTTTGAATTTC    405
```

```
                     40                        50
         ProSerHisCysTrpLeuArgAspMetValThrHisLeu
TTCCAGCCTAGTCATTGTTGGTTACGAGATATGGTAACACACTTA    450

60
         SerValSerLeuThrThrLeuLeuAspLysPheSerAsnIleSer
TCAGTCAGCTTGACTACTCTTCTGGACAAGTTTTCAAATATTTCT    495

70                        80
         GluGlyLeuSerAsnTyrSerIleIleAspLysLeuGlyLysIle
```

FIG.14B CONT.'

```
                                                      540
GAAGGCTTGAGTAATTATTCCATCATAGACAAACTTGGGAAAATA 90                     96
        ValAspAspLeuValAlaCysMetGluGluAsnAlaProLys
GTGGATGACCTCGTGGCATGTATGGAAGAAAATGCACCTAAGGTA         585

ACTTGGTATTCATCAGAATTATTTTTCTTATACT                    619
```

Intervening sequence of unknown length

```
GAGCTCATGATGAGCAATTCACAACCACTTGTAATTCCAGCTCCA         45

GAGGACATTATCCCCTCTTTGGATGCCATAGGAATCTGCTCTCAA         90

ATATGTAGATACCACCTCTGCCACCTCAGCACATACATACACATA         135

ATTAAAAAATAGAAACATTAAAGGAGTTCCAATCAATCCTTATTC         180

TTTTCTGTATTCAGTATGCCCAGATGTAAATTCTAGGAATATGTT         225

TTAAAGGCTAATTCTTATTTGTAATAAGCAGCTTTAAAATTCTT          270

AATTGTTTTTTCGGGTCACTTTATTGTCCTATTGCCACGACATTG         315

TCCTGTCCCATTGTCTGTTATTCCTTCTGTTTTGTTTATTGTTCC         360

CTAGTTACTTTGATCATGAGATTGACCTGTTACCCGTTGTTATTC         405

TCTGTAGCCATTTTGAGTTGTGTCTATTAGAACAGCTGTTAAATT         450

ACTTGAATCATTGAGGACATAGTCAATAATCTATTATGCTGATCC         495

AGTCAAGTCTATGAGTTATTTGAAAACTAGAATCTTTGTTAATTA         540

97
                                    AsnValLys
TTTGTTTGCTTGTTTGTTTGTTTATTATTTGTCTAGAATGTAAAA         585

100                     110
GluSerLeuLysLysProGluThrArgAsnPheThrProGluGlu
```

FIG.14B CONT.'

```
                                                        630
GAATCACTGAAGAAGCCAGAAACTAGAAACTTTACTCCTGAAGAA

120
PhePheSerIlePheAsnArgSerIleAspAlaPheLysAspPhe
TTCTTTAGTATTTTCAATAGATCCATTGATGCCTTCAAGGACTTC         675

130                          140
MetValAlaSerAspThrSerAspCysValLeuSerSerThrLeu
ATGGTGGCATCTGACACTAGTGATTGTGCTCTCTTCAACATTA           720

148
GlyProGluLysA
GGTCCTGAGAAAGGTAAGGCTTTTAAGCATTTCTTGTTTAAATGT         765

ACATAGAAAGCCTGAACTTCTGTAAGCCTCTACTGCTGAATCAAC         810

TAAATGTGTTGCTGTAGAAAGAACGTGTGGGTTTTTCTGATAAAA         855

ACAAAAAGCAAATATCAATGACTACCAATGATTATTATCTAGCTT         900

GAGAGATATGCCCTAAGACAGCGATTCTCGATATTTCTAAATTAA         945

AGAATTGTGTGATGGTGGCTCACATATTTCTAACTGTGATATTT          990

GCCAGGAGAGTAGAATAATGTTATTCTTCATCCCCAGAATTCCTA        1035

AGATTTCACGTCTCATGTCTTTTCCATAAGGTTCAAACTCTGAGA        1080

CTTGAGTTCTGAGCCTCAGCAGGTCATTCTGAATCCCCACTCTCC        1125

CCGAGCTGGGTCCCTATGGGGGAACTAACTTCATTGCTTTCTTTT        1170

AAAACATGACGAGTTACCAACAGCTCCTCGCTATTATAAACATGT        1215

TCCTAAGCATGTCTGTCATGCaATAAGCCTTCACTCTACAAGAC         1260

AGTTATGGTGTATCGCTTGACAAACTGAGCAGCCAAGCTGAGTA         1305

TGAAATAATAATCTAGACTTGGGAGGCAGACCCAGCACCTACTGT        1350

GATATTGCACTTCGCCTTTGGGGGACTCTATGATTCAAAAGTTCA        1395
```

FIG.14B CONT.'

```
                            150
                     spSerArgV
CCATGTAACACTGACACATTATTGCTTTCTATTTAGATTCCAGAG    1440

160
alSerValThrLysProPheMetLeuProProValAlaAlaSerS
TCAGTGTCACAAAACCATTTATGTTACCCCTGTtGCAGCCAGTT    1485

170              176
erLeuArgAsnAspSerSerSerSerAsn_
CCCTTAGGAATGACAGCAGTAGCAGTAATAGTAAGTACACATATC   1530

TGATTTACTGCATGCATGGCTCCAAGTATCCTCTATAGGAGTGTT   1575

GCATGGACTTAAAGTTTATAAATCACTACTAATAATGCTGTTCTG   1620

TCACTGTTATTCCTTGTATGGGCTTCCTGACAATTAAATATCTGG   1665

TTTGTAGAATCGGATCTCCTTAGAGGTTAAGATGACCATGACAAA   1710

ATTAGGCCAATCAACTTTCTGCGAAGGTTATTTTAAATAAGGCAC   1755

GAAATTAATTGAAGGAAAAAAAATACAAGCAAGGCCTTATTTTG    1800

AATCATGGTAGGCTTAAAATAGACTTTGTGGAGAATGTCCCTGAT   1845

CAAAGTGGAGTTTTCAGATTTCAAGTGCATGTGCTAACTCTCCAC   1890

AATGTCAAGGCTATTTTCAGTTTTGTGTCTCCATATTTACTACTG   1935

CATGTTTGGAAATTTGCTGATGCTGTTAGATTACCTAAGAATGTA   1980

TGTTGAAGAAGAATGGACTTCTTTCCCTAAAATTTCTGTCCTCTT   2025

TGcCCAAGAACCCAcGTTCCTGGAAGACTATCTTATTTTCATGTC   2070

TGTGCAATGATCATTATAAAGATTATTGAATATACTGGGAATACT   2115

CTGGTTTCTGTTTTTACAGATTCATAATAGCTTATTCAGTCTTTA   2160

AAGAAAGTTCTCTGAAGTCCATGCTTTAGAATGTTTCTCTATCAA   2205
```

FIG.14B CONT.'

| Sequence | Position |
|---|---|
| AACTTGACCTGGACCTTAAATAAAGCTATATTTAGTCTTTTTATC | 2250 |
| CCTGAAAAATATATTTCACAGTGTAGACATTTGATATACATCTAA | 2295 |
| GGGAAGGATGCTGCCAGAATGCTCGGCTGGCAGTCTACAAAGTC | 2340 |
| CACTGCTCTCAGGATGGACTTCTGAAAGCGGAAATTGTGAACTGC | 2385 |
| ATGCATATAACATATCAGATCCTCGAGC | 2413 |

FIG.14C

```
                                                                                              60
CTGGATCGCAGGCGCTGCCTTCCTTATGAAGAAGACACAAACTTGGATTATCACTTGCAT
                    M  K  K  T  Q  T  W  I  I  T  C  I
                   -25                -20

120
TTATCTTCAACTGCTCCTATTTAATCCTCTGTCAAAACTCAGGAGATCTGCAGGAATCC
 Y  L  Q  L  L  F  N  P  L  V  K  T  Q  E  I  C  R  N  P
        -10                              1

180
TGTGACTGATAATGTAAAAGACATTACAAAACTGGTGGCGAATCTTCCAAATGACTATAT
 V  T  D  N  V  K  D  I  T  K  L  V  A  N  L  P  N  D  Y  M
            10                       20

240
GATAACCCTCAACTATGTCGCCGGGATGATGTTTTGCCTAGTCATTGTTGGTTACGAGA
 I  T  L  N  Y  V  A  G  M  D  V  L  P  S  H  C  W  L  R  D
            30                       40

300
TATGGTAACACACTTATCAGTCAGTCTTGACTACTCTTCTGACAAGTTTTCAAATATTTC
 M  V  T  H  L  S  V  S  L  T  T  L  L  D  K  F  S  N  I  S
            50                       60

360
TGAAGGCTTGAGTAATTATTCCATCATAGACAAACTTGGGAAAATAGTGGATGACCTCGT
 E  G  L  S  N  Y  S  I  I  D  K  L  G  K  I  V  D  D  L  V
            70                       80

420
GGCATGTATGGAAGAAAATGCACCTAAGAATGTAAAAGAATCACTGAAGAAGCCAGAAAC
 A  C  M  E  E  N  A  P  K  N  V  K  E  S  L  K  K  P  E  T
            90                      100

480
TAGAAACTTTACTCCTGAAGAATTCTTTAGTATTTTCAATAGATCCATTGATGCCTTCAA
 R  N  F  T  P  E  E  F  F  S  I  F  N  R  S  I  D  A  F  K
           110                      120
```

FIG.14C CONT.'

```
        130             140
    D   F   M   V   A   S   D   T   S   D   C   V   L   S   S   T   L   G   P   E
GGACTTCATGGTGGCATCTGACACTAGTGATTGTGTGCTCTCTTCAACATTAGGTCCTGA                        540

150             160
    K   D   S   R   V   S   V   T   K   P   F   M   L   P   P   V   A   A   S   S
GAAAGATTCCAGAGTCAGTGTCACAAAACCATTTATGTTACCCCCTGTGTTGCAGCCAGTTC                       600

170             180
    L   R   N   D   S   S   S   N   R   K   A   A   K   S   P   E   D   P   G
CCTTAGGAATGACAGCAGTAGCAGTAATAGGAAAGCCGCAAAGTCCCCTGAAGACCCAGG                         660

190             200
    L   Q   W   T   A   M   A   L   P   A   L   I   S   L   V   I   G   F   A   F
CCTACAATGGACAGCAATGGCCACTGCCGGCTCTCATTTCGCTTGTAATTGGCTTTGCTTT                        720

210             220
    G   A   L   Y   W   K   K   Q   S   S   L   T   R   A   V   E   N   I   Q
TGGAGCCTTATACTGGAAGAAGAAACAGTCAAGTCTTACAAGGCAGTTGAAAATATACA                          780

230             240
    I   N   E   E   D   N   E   I   S   M   L   Q   Q   K   E   R   E   F   Q   E
GATTAATGAAGAGGATAATGAGATAAGTATGTTGCAACAGAAAGAGAGAGTTTCAAGA                           840

248
    V
GGTGTAATT                                                                            849
```

FIG.15B

-21
hrGln

| | |
|---|---|
| CACAAGTGAGTAGGGCGCGCCCGGGAGCTCCCAGGCTCTCCAGGA | 45 |
| AAAATCGCCCCGGTGCCCCGGGGaAGCCGGCGCTCCCTGGGACT | 90 |
| TGCAGCTGGGGCGTGCAGGGCTGTGCCTGCCGGGTG | 126 |

Intervening sequence of unknown length

| | |
|---|---|
| AGATACTACAAAGATAAATCAGTTGCACAAGTTCTTGAAACTCTA | 45 |
| CAGTGTAATAAGGAAAAATAAGTCATGCATAAAAGCAACTATAAT | 90 |
| ACATAATAGAAATGTTATTTTCAAGCCGATGTGTAGGTTATGTG | 135 |
| TGTTCGAGAGAGAGAGAGAAGACAGATTACTTTCTGCTAGGGT | 180 |
| TCAAGAATGCCTTCCTGTTGGCTAAGGAAATATTTTCCTTAAGTG | 225 |
| GCTAAAAGCTGTGTTTCAAAATATTCTTTTGATGTCTCACAAAT | 270 |
| TCAGTGGAATTCTCTTAGGTCTAAAAATATACATCTCTCACTT | 315 |
| TAACTTGGTGTGCTATTGTAGATTATTGGATTAAAGCACTGCTCA | 360 |
| GGGATTATGCTGCTTCTTGCCAAGCAGTCTACATTTAAAGTAGAA | 405 |
| ATAAGATGTTTCTTTTGGTGCCATAAGGTATACATTTTATGCATT | 450 |
| CTCTAGTTTTTAGAAGATACCCTAAGGGCTAAGTCTTTAACATGC | 495 |
| TGCTACAAGTTTATTCCTAATTGCCATTGGGAAATTGGCTGAAGA | 540 |
| AAGTTTTTAACAAAAGTTAACAATATTGTCATTGAGAGAATAATT | 585 |
| CAAAATGGATTTTAACTAAAAGCTTTTAAAAACTTTGGTGAGCAT | 630 |
| AGCTTGAATGCGTAATATTTAATTGCATTTAAGCCAATAACATAT | 675 |

FIG.15B CONT.'

```
ATTAGACTGGTCTTTTTGTGCATCAAGGCATTAGATGTTAAAAGT    720

TTGAATGATTACAGATCTTAACTGATGATCACCAAGCAATTTTC     765

-20                          -10
           ThrTrpIleLeuThrCysIleTyrLeuGlnLe
TGTTTTCATTTAGACTTGGATTCTCACTTGCATTTATCTTCAGCT    810

1
uLeuLeuPheAsnProLeuValLysThrGluGlyIleCysArgAs
GCTCCTATTTAATCCTCTCGTCAAAACTGAAGGGATCTGCAGGAA    855

10                       18
nArgValThrAsnAsnValLysAspValThrLysLeu
TCGTGTGACTAATAATGTAAAAGACGTCACTAAATTGGTAAGTAA    900

GGAATGCTTTACCGTGCTGTGTAAAAAGAGCTGTGGCTCTTTTT    945

CCTGTGCTTGTTGATAAAGATTTAGATTTTTCTTGCCCCAAAGT    990

AATGTTTTCCTAAAGTGGGGAAAGTAATCACTGGGTTACAATAAA   1035

GGGTTTATAGAAAGCAGGTAGTGAGATATTTAGGGTCATGGATAA   1080

TTTGTTGGTAAAACTGGCTAGTTGCACACCACTGCTGTGACTGCT   1125

TCTTTGCTGGTCTTCTCCCCATCCTTCATAGGCAGTGAAGGACCT   1170

TGGAGAGTTCGCTGTGTGCTGATGGGCTTGCCCCAGCTTGTTCCC   1215

CATAATCTCTCCAGTGGGTTTCCCAGCATGTTCTATTCCCCTTCA   1260

CATGTCTTCCTACTCTTCTTTAAAAAGCCTAACGAAAGGAAATCT   1305

GAAATGGCTATTCTCCCAATTCAATCAGCAGGAAGACCCTGTCAC   1350

ATGTCAGTGGGTGTTTGCTCCTTCAGGGAACATAGAGAGGTGATT   1395

CATTGCCCACATGTTGAAGGGACTCATCTCCCTGGTTTGTCACAT   1440

TGAACTCTTCCCTCAGCGAAAGCATTTGCATTGCTTCCC         1479
```

FIG. 15B CONT.'

Intervening sequence of unknown length

| | |
|---|---|
| GAATTCCAAGATCACAGGTGGAAGCTGAAATTCAGATCATGTTTC | 45 |
| CAAAACTCAGTAGGTTATACCTAGCCAGGCATAACTGAATTTGGA | 90 |
| GTCTAAAGATCTGTATTATCACTTTTTTATTTTGAAGGATGCCT | 135 |
| TTTGATTACAGAGGGAAATCAAGGATTAAAAATCAATATACATGT | 180 |
| AAATATTGAAATTCATTGGTAACTTTAAAAAGCACAACAGTTTTG | 225 |
| TGTGCTTTTCTCCAAAGCACTACAAATATGATTAATTGATGTATA | 270 |

```
                                    19
                                    ValAlaA
AGAATTTTCTTATGGAATTTTTTTTTTGTCTCTGTAGGTGGCAA    315
                  30
snLeuProLysAspTyrMetIleThrLeuLysTyrValProGlyM
ATCTTCCAAAAGACTACATGATAACCCTCAAATATGTCCCCGGGA    360
         39
etAspValLeu
TGGATGTTTTGGTATGTAAACTACATTCTGAGTTTCATTTTAGT    405
```

| | |
|---|---|
| AGCTCATAGAAGAAATGGGATCATTCATATTGAGATAGTACACTA | 450 |
| GCTGCTATTTAGGAGCTTGCTTATTGTCAGGATTTGAAGAATTTA | 495 |
| TCTTTGGAATTTGACTTGCAGGCTTTTTTTCCCCCTCTT  535 | |

Intervening sequence of unknown length

| | |
|---|---|
| CCTGTTACAAGAGTCCCTCCTCCTATTACAATAGTCCCTCCTCCT | 45 |
| CCTGTCACACTAGTCCCTTCTCTTCCTGTTACAATAACCCCTGTC | 90 |

FIG.15B CONT.'

```
CTCCTATTACAACATTTTAAGTAATGTAATATTAATTTTAAAAAT       135

CTGGCCAGGCACGGTGGTTCATGCTTGTAATCCCAGCACATTGGG       180

AAGCTGAGACGGGTGGATCATTTGAGGTCAGGAAGTTTGAGACAG       225

CCTGGCCAACATGGTGAAACTTCCTCTCTACTAAAAATAAAAAAG       270

TAGCCAGGCATGGTGGCAGGCACTTGTAATCTGAGCTACTCGAGA       315

GGCTGAGGCAGGAGAATCACTTGAGTAACTAAAACGATAGCTTTG       360

AAGAGTACTCCGAGTTTTATGGCACTTACTTATTAAAATAGCTGT       405

40
                         ProSerHisCysTrpIleS
TTTGTCTCTTTTTTCATATCTTGCAGCCAAGTCATTGTTGGATAA       450

50                                60
erGluMetValValGlnLeuSerAspSerLeuThrAspLeuLeuA
GCGAGATGGTAGTACAATTGTCAGACAGCTTGACTGATCTTCTGG       495

70
spLysPheSerAsnIleSerGluGlyLeuSerAsnTyrSerIleI
ACAAGTTTTCAAATATTTCTGAAGGCTTGAGTAATTATTCCATCA       540

80                          90
leAspLysLeuValAsnIleValAspAspLeuValGluCysValL
TAGACAAACTTGTAATATAGTGGATGACCTTGTGGAGTGCGTGA       585

96
ysGluAsnSerSerLys
AAGAAAACTCATCTAAGGTAACTTTGTGTTCATTGGGATTATTTT       630

TCATTACGCTTCTCTAAAAACCCATGCTTCTTGGTGCTGTTGGGG       675

AAAATGAGGCACCTTTATTTATGATATTTGATTGTATAAACTTC       720

AAATTTAAAAATCTTGTTCAGATGAGCAAAGAAACAAGTATTTG       765

CAGTTATACTGCAATACTGAAGTGCACATTC       796
```

FIG.15B CONT.'

Intervening sequence of unknown length

```
TTGTGTTCACTGCCCCAGATTCAACTTGTGATCCCACTGGGATCA      45

CTACCCTGCATTACCAATCTGAATTACATACGTTAAAACAGCCAT      90

CTAAAAGTGCTAGTTGTAAGAGTCTAAATACTTGAATCTTTGAGA     135

GACATATTTATAGTCCATTATCTTCACCTCAGTTAAGTCTAAGA      180
```

97
                       AspLeuLysL
```
CTATTTGAAAAATGTAATCCTATTTTTTCTTCTAGGATCTAAAAA     225
```

110
ysSerPheLysSerProGluProArgLeuPheThrProGluGluP
```
AATCATTCAAGAGCCCAGAACCCAGGCTCTTTACTCCTGAAGAAT     270
```

120                             130
hePheArgIlePheAsnArgSerIleAspAlaPheLysAspPheV
```
TCTTTAGAATTTTTAATAGATCCATTGATGCCTTCAAGGACTTTG     315
```

140
alValAlaSerGluThrSerAspCysValValSerSerThrLeuS
```
TAGTGGCATCTGAAACTAGTGATTGTGGTTTCTTCAACATTAA       360
```

148
erProGluLysA
```
GTCCTGAGAAAGGTAAGACATGTAAGCATTCCAGTTCAAATGTA      405

AACAACAAACTTAAATCTTCCCTATGTAGTAAGAATCTACCTCTG     450

TGTTAAGCTGTAGCAAGATACATGCATGTACGTCTAATAAAAAG      495

CAGATATCAATAGCACAGAAGAAA                          519
```

Intervening sequence of unknown length

FIG.15B CONT.'

```
                                                       45
CTCTATAACTCATACAAATCACCATATAACACTGACACATTATTG 150                              160
      spSerArgValSerValThrLysProPheMetL
CTTTCTATTTAGATTCCAGAGTCAGTGTCACAAAACCATTTATGT          90

170
euProProValAlaAlaSerSerLeuArgAsnAspSerSerSerS
TACCCCCTGTTGCAGCCAGCTCCCTTAGGAATGACAGCAGTAGCA          135

176
erAsnA
GTAATAGTAAGTACATATATCTGATTTAATGCATGCATGGCTCCA          180

ATTAGCACCTATAGGAGTATTGCATGGGCTTTCAAGGAAACTTCT          225

ACATTTATTATTATTGATACTGTTCTGTTACTGTTATTCCTTTTA          270

TGGTCTTCTTGAGACTTAAGTTTGTAGAATTAAATTTCCCTAGAG          315

CTGGAGATAATGTTTAGAGAATTAGGCCAATAAATTT                  352
```

FIG.15C

```
                -25                    -20                                          -15
              M   K   K   T   Q   T   W   I   L   T   C   I   Y   L   Q
AAGCTTGCCTTTCCTTATGAAGAAGACACAAACTGGATTCTCACTTGCATTTATCTTCAG                          61

-10                                     1                                            10
  L   L   F   N   P   L   V   K   T   E   G   I   C   R   N   R   V   T   N
CTGCTCCTATTTAATCCTCTCGTCAAAACTGAAGGGATCTGCAGGAATCGTGTGACTAAT                         121

20                                      30
  N   V   K   D   V   T   K   L   V   A   N   L   P   K   D   Y   M   I   T   L
AATGTAAAAGACGTCACTAAATTGGTGGCAAATCTTCCAAAAGACTACATGATAACCCTC                         181

40                                      50
  K   Y   V   P   G   M   D   V   L   P   S   H   C   W   I   S   E   M   V   V
AAATATGTCCCCGGGATGGATGTTTTGCCAAGTCATTGTTGGATAAGCGAGATGGTAGTA                         241

60                                      70
  Q   L   S   D   S   L   T   D   L   L   D   K   F   S   N   I   S   E   G   L
CAATTGTCAGACAGCTTGACTGATCTTCTGGACAAGTTTTCAAATATTTCTGAAGGCTTG                         301

80                                      90
  S   N   Y   S   I   I   D   K   L   V   N   I   V   D   D   L   V   E   C   V
AGTAATTATTCCATCATAGACAAACTTGTGAATATAGTGGATGACCTTGTGGAGTGCGTG                         361

100                                     110
  K   E   N   S   S   K   D   L   K   K   S   F   K   S   P   E   P   R   L   F
AAAGAAAACTCATCTAAGGATCTAAAAAAATCATTCAAGAGCCCAGAACCCAGGCTCTTT                         421
```

FIG. 15C CONT.

```
      120                        130
T  P  E  E  F  F  R  I  E  F  N  R  S  I  D  A  F  K  D  F  V
ACTCCTGAAGAATTCTTTAGAATTTTAATAGATCCATTGATGCCTTCAAGGACTTTGTA    481

140                        150
V  A  S  E  T  S  D  C  V  V  S  S  T  L  S  P  E  K  D  S
GTGGCATCTGAAACTAGTGATTGTGTGGTTTCTTCAACATTAAGTCCTGAGAAAGATTCC   541

160                        170
R  V  S  V  T  K  P  F  M  L  P  P  V  A  A  S  S  L  R  N
AGAGTCAGTGTCACAAAACCATTTATGTTACCCCCTGTTGCAGCCAGCTCCCTTAGGAAT   601

180       183
D  S  S  S  N  S  K  Y  I  Y  L  I
GACAGCAGTAGCAGTAATAGTAAGTACATATATCTGATTTAATGCATGGCTCCAAT       661

TAGCACCTATAGGAGTATTGCATGGGCTTTCAAGGAAACTTCTACATTTATTATTATTGA   721

TACTGTTCTGTTACTGTTATTCCTTTTATGGTCTCTTCTTGAGACTTAAGTTTGTAGAATTA 781

AATTCCCTAGAGCTGGAGATAATGTTTAGAGAATTAGG                         820
```

FIG. 15D

```
GAGCTCCGAGCcCTCtCTGGCGCgCgAGGTATTTCGTCTGTnCCCGGGGTGCCAGGTGA          60
GCCCAGCGGATCCGGGAGGGTAAGCTGGGACTCCTCGCGAGCAGTAGCTGCAGGGTACC         120
AAGCTTCGCCCTCTGCGTCCCCGCGCTTCGCGGTCTCCCGCCAGTGCAGGTCGGGGGCC         180
CCCAGGCGAGCGGGACAAGGTTGGCCTAATCTGCCAAACTTCTGGGGCATTTACCGTGCTC       240
TGGCCGCCCCTCCCGATTCTTCCCTCCGCGCCCCTTGCCTGCTTCTCGCTACCCCGGGCTC       300
CGGAAGGGAAGGAGGCGTGTCCGGAGCAGGCGGGGAACTGTATAAAAGCGCGGGG             360
CTCAGCAGCCGGCTTCGCTCGCGCCTCGGCTGCGCTACCCAATGCGTGGACTATCTGCCCGCTGT   420
GACnGTGGAGnAGGCGCTGCGCTACCCAATGCGTGGACTATCTGCCCGCTGT                480
TCGnTCnAACnnnTGGAGCTCCAGAACAGCTAAACGGAGTCGCCACACCACTGTTTGTGC        540
                                    -25      -21
                                    MetLysLysThrGln
TnGATnGnnnnnTGCCTTTCCTTATGAAGAAGACACAAGTGAGTAGGCGCGCCCGGGA          600
GCTCCCAGGCTnTCCAGGAAAAATCGCGCCCGGTGCCCCGGGAAGCCGGCGCTCCCCTGG        660
GACTTGCAGCTGGGCGTGCAGGGCTGTGCCTGCCGGGTGAGACAAGAGGATGCGGGGGA         720
GGCCGGGCTGGTGTGTGATCCGAGCCGAGCGGnnTGAGCCAGGGAGAAAAGGAGTGGGA         780
GTnCTGAGAGGGAGCCAGTGTCAAGTTTGGAGCCTCAGCAGTTAAGTTTTGAGCTGTCAG        840
TCGGAAACCGTAATTCCCGTCTGGTGAAAGATTGGCTTTTnGnCCACGGAATGTAAGTT         900

ATCAC                                                                905
```

FIG. 15D CONT.

```
Intervening sequence of unknown length

AGATACTACAAAGATAAATCAGTTGCACAAGTTCTTGAAACTCTACAGTGTAATAAGGAA      60
AAATAAGTCATGCATAAAAGCAACTATAATACATAATAGAAAATGTTATTTTCAAGCCGA     120
TGTGTAGGTTATGTGTTCGAGAGAGAGAGAGAGACAGATTACTTTCTGCTAGGGT          180
TCAAGAATGCCTTCCTGTTGGCTAAGGAAATATTTCCTTAAGTGGCTAAAAAGCTGTGT      240
TTCAAAATATTCTTTGATGTCTCACAAATTCAGTGGAATTCTCTTAGGTCTAAAAATAT     300
ACATCTCTCACTTAACTTGGTGTGCTATTGTAGATTATTGGATTAAAGCACTGCTCA       360
GGGATTATGCTGCTTCTTGCCAAGCAGTCTACATTTAAAGTAGAAATAAGATGTTTCTTT    420
TGGTGCCATAAGTTATACATTTATGCATTCTCTAGTTTTTAGAAGATACCCTAAGGGCT    480
AAGTCTTTAACAGCTGCTACAAGTTAACATATGTCATTGAGAGAATAATTCAAAATGGATTTAA  540
AAGTTTTTAAAAAGTTAACAAATTTGGTGAGCATAGCTTGAATGCGTAATATTTAATTGCATTT  600
CTAAAAGCTTTTAAAAACTTGGTGAGCATAGCTTGAATGCGTAATATTTAATTGCATTT      660
AAGCCAATAACATATATTAGACTGGTCTTTTTGTGCATCAAGGCATTAGATGTTAAAAGT    720
                                                              -20
                                                               Th
TTGAATGATTACAGATCTTAACTGATGATCACCAAGCAATTTTCTGTTTCATTAGAC       780
                         -10
rTrpIleLeuThrCysIleTyrLeuGlnLeuLeuLeuPheAsnProLeuValLysThrGl
TTGGATTCTCACTTGCATTTATCTTCAGCTGCTCCTATTTAATCCTCTCGTCAAAACTGA   840
```

FIG. 15D CONT.

```
            1                                       10                                       18
          uGlyIleCysArgAsnArgValThrAsnAsnValLysAspValThrLysLeu
          AGGGATCTGCAGGAATCGTGTGACTAATAATGTAAAAGACGTCACTAAATTGGTAAGTAA       900
          GGAATGCTTTACCGTGTCGTGTGCTGTGTAAAAAAGAGCTGTGGCTCTCTTTTCCTGTGCTTGTGAT  960
          AAAAGATTTAGATTTTTCTTGCCCCAAAGTAATGTTTCCTAAAGTGGGGAAAGTAATCA      1020
          CTGGGTTACAATAAGGGTTTATAGAAAGCAGTAGTGAGATATTTAGGGTCATGGATAA      1080
          TTTGTTGGTAAAACTGGCTAGTTGCACACCACTGCTGTGACTGCTTCTTTGCTGGTCTTC    1140
          TCCCCATCCTTCATAGGCAGTGAAGGACCCTTGGAGAGTTCGCTGTGTGCTGATGGGCTTG   1200
          CCCCAGCTTGTTCCCCATAATCTCTCCAGTGGGTTTCCCAGCATGTTCTATTCCCCTTCA    1260
          CATGTCTCTCCTACTCTCTTCTTTAAAAAGCCTAACGAAAGGAAATCTGAAATGGCTATTCTC   1320
          CCAATTCAATAGCAGGAAGACCCTGTCACATGTCAGTGGGTGTTGCTCCTCCTTCAGGGAA   1380
          CATAGAGAGTGATTCATTGCCCACATGTTGAAGGGACTCATCTCCCTGGTTTGTCACAT     1440
          TGAACTCTTCCCTCAGCGAAAGCATTGCATTGCTTCCC                          1479

Intervening sequence of unknown length

GAATTCCAAGATCACAGGTGGAAGGTGAAATTCAGATCATGTTCCAAAACTCAGTAGGT      60
          TATACCTAGCCAGGCATAACTGAATTTGGAGTCTAAAAGATCTGTATTATCACTTTTTA     120
          TTTTGAAGGATGCCTTTTGATTACAGAGGGAAATCAAGGATTAAAAATCAATATACATGT    180
```

FIG. 15D CONT.

```
AAATATTGAAATTCATTGGTAACTTTAAAAGCACAACAGTTTGTGTGCTTTTCTCCAA         240
AGCACTACAAATATGATTAATGTGTATAAGAATTTTCTTATGGAATTTTTTTTGT            300
              19                          30
         ValAlaAsnLeuProLysAspTyrMetIleThrLeuLysTyrValProGlyM
CTCTGTAGGTGGCAAATCTTCCAAAGACTACAATGATAACCCTCAAATATGTCCCGGGA        360
              39
etAspValLeu
TGGATGTTTTGGTATGTAAACTACATTTCTGAGTTTCATTTTAGTAGCTCATAGAAGAAA       420
TGGGATCATTCATATTGAGATAGTGCTATTTAGGAGCTGCTTATTGTCAG                 480
GATTTGAAGAATTTATCTTTGAATTTGACTTGCAGGCTTTTTTTTCCCCTCTT              535
                    Intervening sequence of unknown length CCTGTTACAAGA  TCCCTCCTCCTCCTATTACAATAGTCCCTCCTCCTGTCACACTAGTC       60
CC TCT T   TT  TTACAATAACCCCTGTCCTCCTATTACAACATTTTAAGTAATGTAAT     120
ATTAATTTTAAAAATCTGGCCAGGCACGGTGGTTCATGCTGTAATCCCAGCACATTGGG        180
AAGCTGAGACGGGTGGATCATTTGAGGTCAGGAAGTTTGAGACAGCCTGGCCAACATGGT       240
GAAACTTCCTCTCTACTAAAAATAAAAAGTAGCCAGGCATGGTGGCAGGCACTTGTAAT        300
CTGAGCTACTCGAGAGGCTGAGGCAGGAGAATCACTTGAGTAACTAAAACGATAGCTTTG       360
AAGAGTACTCCGAGTTTATGCCACTTACTACTTATTAAAATAGCTGTTTGTCTCTTTTTC       420
```

FIG. 15D CONT.

```
            40                         50
         ProSerHisCysTrpIleSerGluMetValValGlnLeuSerAspSerL
ATATCTTGCAGCCAAGTCATTGTTGGATAAGCGAGAGTGGTAGTACAATTGTCAGACAGCT    480

60                         70
euThrAspLeuLeuAspLysPheSerAsnIleSerGluGlyLeuSerAsnTyrSerIleI
TGACTGATCTTCTGGACAAGTTTTCAAATATTTCTGAAGGCTTGAGTAATTATTCCATCA    540

80                         90
leAspLysLeuValAsnIleValAlaAspAspLeuValValGluCysValLysGluAsnSerL
TAGACAAACTTGTGAATATAGTGGATGACCTTGTGGAGTGCGTGAAAGAAAACTCATCTA    600
96
ys
AGGTAACTTTGTGTTCATTGGGATTATTTTCATTACGCTTCTCTAAAAACCATGCTTC      660

TTGGTGCTGTTGGGGAAATGAGGCACCTTTATTTATGATATTTGATTGTATAAACTTC      720

AAATTTAAAAATGTTGTTCAGATGAGCAAAGAAAACAAGTATTTGCAGTTATACTGCAAT    780

ACTGAAGTG...ATTC                                                  796

Intervening sequence of unknown length

TTGTGTTCACTGCCCCAGATTCAACTTGTGATCCCACTGGGATCACTACCCTGCATTACC    60

AATCTGAATTACATACGTTAAAACAGCCATCTAAAAGTGCTAGTGTAAGAGTCTAAATA    120

CTTGAATCTTTGAGAGACATATTTATAGTCCATTATCTTCACCTCAGTTAAGTCTGAAGA    180

97
                    AspLeuLysLysSerPheLysSerP
CTATTTGAAAAATGTAATCCTATTTTTTCTTCTAGGATCTAAAAAAATCATTCAAGAGCC    240
```

FIG. 15D CONT.

```
                    110                                    120
roGluProArgLeuPheThrProGluGluPhePheArgIlePheAsnArgSerIleAspA
CAGAACCCAGGCTCTTTACTCCTGAAGAATTCTTTAGAATTTTAATAGATCCATTGATG    300

130                                    140
laPheLysAspPheValValAlaSerGluThrSerAspCysValValSerThrLeuS
CCTTCAAGGACTTTGTAGTGGCATCTGAAACTAGTGATTGTGTGTTCTTCAACATTAA    360

148
erProGluLysA
GTCCTGAGAAAGGTAAGACATGTAAGCATTTCCAGTTCAAATGTAAACAACAAACTAAA    420

TCTTCCCTATGTAGTAAGAATCTACCTCTGTGTTAAGCTGTAGCAAGATACATGCATGTA    480

CGTCTAATAAAAAAGCAGATATCAATAGCACAGAAGAAACTAATGATTGTAGATTTGTGGG    541

Intervening sequence of unknown length spS
CTCTATAAC....ACAAATCACCATATAACACTGACACATTATTGCTTTCTATTTAGATT     60

150                              160
erArgValSerValThrLysProPheMetLeuProProValAlaAlaSerLeuArgA
CCAGAGTCAGTGTCACAAAACCATTTATGTTACCCCGTGTTGCAGCCAGTCCCCTTAGGA    120

170            176
snAspSerSerSerAsnA
ATGACAGCAGTAGCAGTAATAGTACAGTACATATATCTGATTTAATGCATGCATGGCTCCA    180

ATTAGCACCTATAGGAGTATTGCATGGGCTTTCAAGGAAACTTCTACATTTATTATTATT    240

GATACTGTTCTGTACTGTTATTCCTTTATGGTCTTCTTGAGACTTAAGTTTGTAGAAT    300
```

FIG. 15D CONT.

```
TAAATTTCCCTAGAGCTGGAGATAATGTTTAGAGAATTAGGCCAATAAATTTTCTGCTGA      360
GGTTATTTAAATAAGACATAAAATTAATTTTAGAAATATGATTTATGCCTTTTGTTGAA      420
TCATTAACATATAT                                                    434

Intervening sequence of unknown length

60
ACAGAAACAGTTAAACAACCACCAGCATAAGAGnAAAACTTCTAGAATGGATATGCTGTA
                                  178
                                     rgLysAlaLysAsnProProGlyAspSerSerL
TTCATCAGTGTGTTCTTTAAATTATAGGGAAGGCCAAAAATCCCCCTGGAGACTCCAGCC      120
                             200
euHisTrpAlaAlaMetAlaLeuProAlaLeuPheSerLeuIleIleGlyPheAlaPheG
TACACTGnGGnAGnGCATGGCATTGCCAGCATTGTTTTCTCTTATAATTGGCTTTGCTTTTG    180
    190
lyAlaLeuTyrCysTrpLys
                 213
GAGCCTTATACTGGAAGGTAAGTGGTACCATTCCTTTCTTTTAAAAATATGCTATGTTTAC    240
ATAAATTATCATCTTTTTTTCCTCAAGAAATGATCCTtAAGAAAACAGTGAATCTACCT     300
TAGCTTATACTAAACAAAATTTAAATTTTATAAAGTTTCCTGTTTCTCATTATGTCTGGA    360
GACAATCCCCTCTAGCTGATAATTCACGCTTAAGAATTAGGAACT                    404

Intervening sequence of unknown length
```

FIG. 15D CONT.

```
AAAACTGTTATTGGAGTTATTGCCATAAAGATAAAGTGGAGTCCACTTACCTCTTAAA         60
                                                    214
                                                    LysArgG
TATTAGACCATTCATTGATTATTTTACAGTATATGTCTTTCTTCTTTTCCAGAAGAGAC        120
       220                          230          235
lnProSerLeuThrArgAlaValGluAsnIleGlnIleAsnGluGluAspAsnGluIleS
AGCCAAGTCTTACAAGGGCAGTTGAAATATACAAATTAATGAAGAGGATAATGAGATAA        180
e
GGTATTTTGTTTGCTAAATGTGTGCCCAATCAAGCATGACATTGCCATTTCACACACTG        240
TGTACCTGCCCATAATGTCTTTAAGAAGTCCTTCACTCATGACAGTAGCTCCTAACCAGT      300
GAGTCCCAACTCTATCCATGTTTCTGATGTCTCACTCTCTCTTC                       344

Intervening sequence of unknown length

GTATGTGTATA GCATATACAGAGAAAGAAATGTTTAACTACTTGGAAAGACTACCTTA         60
AGACAAATGAA TCTTCCCTCTCCCTATAGTAATAAGAAGGTAGGCTCCCCATTCAAT          120
TTTGCAATCTTCTGCTACTATATTTACAGAAAAAGCTGCCTTTTACAATGCCGAGATCATG      180
                                                           rM
GTGTACCTCAGAATCTCTGACCAAGAGAGCAAATAAGCATTTtTTCTTATTGTTTTTCAGTA     240
                                                   248
237                                               etLeuGlnGluVal
etLeuGlnGluLysGluArgGluPheGlnGluVal
TGTTGCAAGAGAAAGAGAGAGAGTTTCAAGAAGTGTAATTGGGCTTGTATCAACACTGT       300
TACTTTCGTACATTGGTAAGTTTTTTTCTTCTTTCCTTTTTCTTTTTTTATTATA            360
```

FIG. 15D CONT.

CTTTAAGTTCTAGGGTACATGTGCACAATGTGTGCAGGTTTGTTACGTATGTTTACATGTGC 420

CATGTT 426

FIG.16A

```
            -25                                                          25
Human    MKKTQTWILT CIYLQLLLFN PLVKTEGICR NRVTNNVKDV TKLVANLPKD
Monkey   MKKTQTWILT CIYLQLLLFN PLVKTEGICR NRVTNNVKDV TKLVANLPKD
Dog      MKKTQTWIIT CIYLQLLLFN PLVKTKGICG KRVTDDVKDV TKLVANLPKD
Cat      MKKTQTWIVT CIYLQXLLFN PLVKTKGLCR NRVTDDVKDV TKLVANLPKD
Cow      MKKTQTWIIT CIYLQLLLFN PLVHTQGICS NRVTDDVKDV TKLVANLPKD
Rat      MKKTQTWIIT CIYLQLLLFN PLVKTQEICR NRVTDNVKDI TKLVANLPND
Mouse    MKKTQTWIIT CIYLQLLLFN PLVKTKEICG NPVTDNVKDI TKLVANLPND
Chicken     TWIIT CFCLQLLLLN PLVKAQSCG NPVTDDVNDI ARLVGNLPND
Scfpep   MkKTQTWIiT CiyLQlLlFN PLvKt.giCr nrVTd.VkDv tKlVaNLPkD 26                                                          72
Human    YMITLKYVPG MDVLPSHCWI SEMVVQLSDS LTDLLDKFSN ISEG...LSN
Monkey   YMITLKYVPG MDVLPSHCWI SEMVVQLSDS LTDLLDKFSN ISEG...LSN
Dog      YKIALKYVPG MDVLPSHCWI SVMVEQLSVS LTDLLDKFSN ISEG...LSN
Cat      YKIALKYVPG MDVLPSHCWI SVMVEQLSVS LTDLLDKFSN ISEG...LSN
Cow      YMITLKYVPG MDVLPSHCWI SEMVEQLSVS LTDLLDKFSN ISEG...LSN
Rat      YMITLNYVAG MDVLPSHCWL RDMVTHLSVS LTTLLDKFSN ISEG...LSN
Mouse    YMITLNYVAG MDVLPSHCWL RDMVIQLSLS LTTLLDKFSN ISEG...LSN
Chicken  YLITLKYVPK MDSLPNHCWL HLMVPEFSRS LHNLLQKFSD ISDMSDVLSN
Scfpep   YmItLkYVpg MDvLPsHCWi seMVeqlSvS LtdLLdKFSn ISeg...LSN 73                                                         121
Human    YSIIDKLVNI VDDLVECVKE NSSKD.LKKS FKSPEPRLFT PEEFFRIFNR
Monkey   YSIIDKLVNI VDDLVECVKE NSSKD.LKKS FKSPEPRLFT PEEFFRIFNR
Dog      YSIIDKLVKI VDDLVECTEG YSFEN.VKKA PKSPELRLFT PEEFFRIFNR
Cat      YSIIDKLVKI VDDLVECVEG HSSEN.VKKS SKSPEPRLFT PEEFFRIFNR
Cow      YCIIDKLVKI VDDLVECMEX HSSEN.VKKS SKSPEPRQFT PEKFFGIFNK
Rat      YSIIDKLGKI VDDLVACMEE NAPKN.VKES LKKPETRNFT PEEFFSIFNR
Mouse    YSIIDKLGKI VDDLVLCMEE NAPKN.IKES PKRPETRSFT PEEFFSIFNR
Chicken  YSIINNLTRI INDLMACLAF DKNKDFIKEN GHLYEEDRFI PENEFRLFNS
Scfpep   YsIIdkLvkI vdDLveC.ee nsskn.vKks .kspEprlFt PEeFFriFNr
```

FIG.16B

```
        122
Human   SIDAFKDF.V  VASETSDCVV  SSTL.SPEKD  SRVSVTKPFM  LPPVAASSLR   169
Monkey  SIDAFKDF.A  VASETSDCVV  SSTL.SPEKD  SRVSVTKPFM  LPPVAASSLR
Dog     SIDAFKDLET  VASKSSECVV  SSTL.SPDKD  SRVSVTKPFM  LPPVAASSLR
Cat     SIDAFKDLEM  VASKTSECVV  SSTL.SPEKD  SRVSVTKPFM  LPPVAASSLR
Cow     SIDAFKDLEI  VASKMSECVI  SSTS.SPEKD  SRVSVTKPFM  LPPVAASSLR
Rat     SIDAFKDE.M  VASDTSDCVL  SSTL.GPEKD  SRVSVTKPFM  LPPVAASSLR
Mouse   SIDAFKDF.M  VASDTSDCVL  SSTL.GPEKD  SRVSVTKPFM  LPPVAASSLR
Chicken TIEVYKEFAD  SLDK.NDCIM  PSTVETPEND  SRVAVTKTIS  FPPVAASSLR
Scfpep  sidafKdf.m  vasktsdCvv  sSTl.sPekD  SRVsVTkpfm  lPPVAASSLR 170
Human   NDSSSSSNRKA  KNFPGD....  ..SSLHWAAM  ALPALFSLII  GFAFGALYWK  213
Monkey  NDSSSSSNRKA  KNPTGD....  ..SSLHWAAM  ALPAFFSLII  GFAFGALYWK
Dog     NDSSSSNRKA   SNSIGD....  ..SNLQWAAM  ALPAFFSLVI  GFAFGALYWK
Cat     NDSSSSSNRKX  TNPIED....  ..SSIQWAVM  ALPACFSLVI  GFAFGAFYWK
Cow     NDSSSSSNRKA  SNSIED....  ..SSLQWAAV  ALPAFFSLVI  GFAFGAFYWK
Rat     NDSSSSSNRKA  AKSPED....  ..PGLQWTAM  ALPALISLVI  GFAFGALYWK
Mouse   NDSSSSSNRKA  AKAPED....  ..SGLQWTAM  ALPALISLVI  GFAFGALYWK
Chicken NDSIGNTSS    NSNKEALGFI  SSSSLQGISI  ALTSLLSLLI  GFILGAIYWK
Scfpep  NDSssSNrka   .n..ed....  ..sslqwaam  ALpalfSLvi  GFafGALYWK 214
Human   KRQPSLTRAV  ENIQIN...E  EDNEISMLQE  KEREFQEV    248
Monkey  KRQPSLTRAV  ENIQIN...E  DDNEISMLQE  KEREFQEV
Dog     KKQPNLTRTV  ENIQIN...E  EDNEISMLQE  KEREFQEV
Cat     KKQPNLTRTV  ENIQIN...E  EDNEISMLQE  KEREFQEV
Cow     KKQPNLTRTV  ENRQIN...E  EDNEISMLQE  KEREFQEV
Rat     KKQSSLTRAV  ENIQIN...E  EDNEISMLQQ  KEREFQEV
Mouse   KKQSSLTRAV  ENIQIN...E  EDNEISMLQQ  KEREFQEV
Chicken KTHPKSRPES  NETIQCHGCQ  EENEISMLQQ  KEKEHLQV
Scfpep  Kkqpsltrav  eniqin...e  edNEISMLQe  KErEfqeV
```

FIG. 16D

EcoRI
```
           ta  a  t  t    ta a        t  t  c        g      t  a
GAATTCTTCCGTATCTTCAACCGTTCCATCGACGCTTTCAAAGACTTCGTT
 E    F    F    R    I    F    N    R    S    I    D    A    F    K    D    F    V
```

```
    g     a   t          ta gt    t    g        t      a    at a ag    t    g
GTTGCTTCCGAAACCTCCGACTGCGTTGTTTCCTCCACCCTGTCTCCGGAA
 V    A    S    E    T    S    D    C    V    V    S    S    T    L    S    P    E
```

BstEII
```
         t    a a  ca gt    c    a        a  t    t  a c  t  .  a
AAAGACTCCCGTGTTTCGGTTACCAAACCGTTCATGCTGCCGCCGGTTGCT
 K    D    S    R    V    S    V    T    K    P    F    M    L    P    P    V    A
```

```
  c ag         t ag  t       ag  ag t ag ag t     tag t    g       a    t
GCTTCCTCCCTGCGTAACGACTCCTCCTCCTCCAACTCCAAATACATCTAC
 A    S    S    L    R    N    D    S    S    S    S    N    S    K    Y    I    Y
```

BamHI
```
    t
CTGATCTAATAGGATCC
 L    I    *    *
```

FIG 16E

```
BstEII                                              BamHI
GGTTACCAAACCGTTCATGCTGCCGCCGGTTGCTGCTTAATAGGATCC
 V  T  K  P  F  M  L  P  P  V  A  A  *  *
```

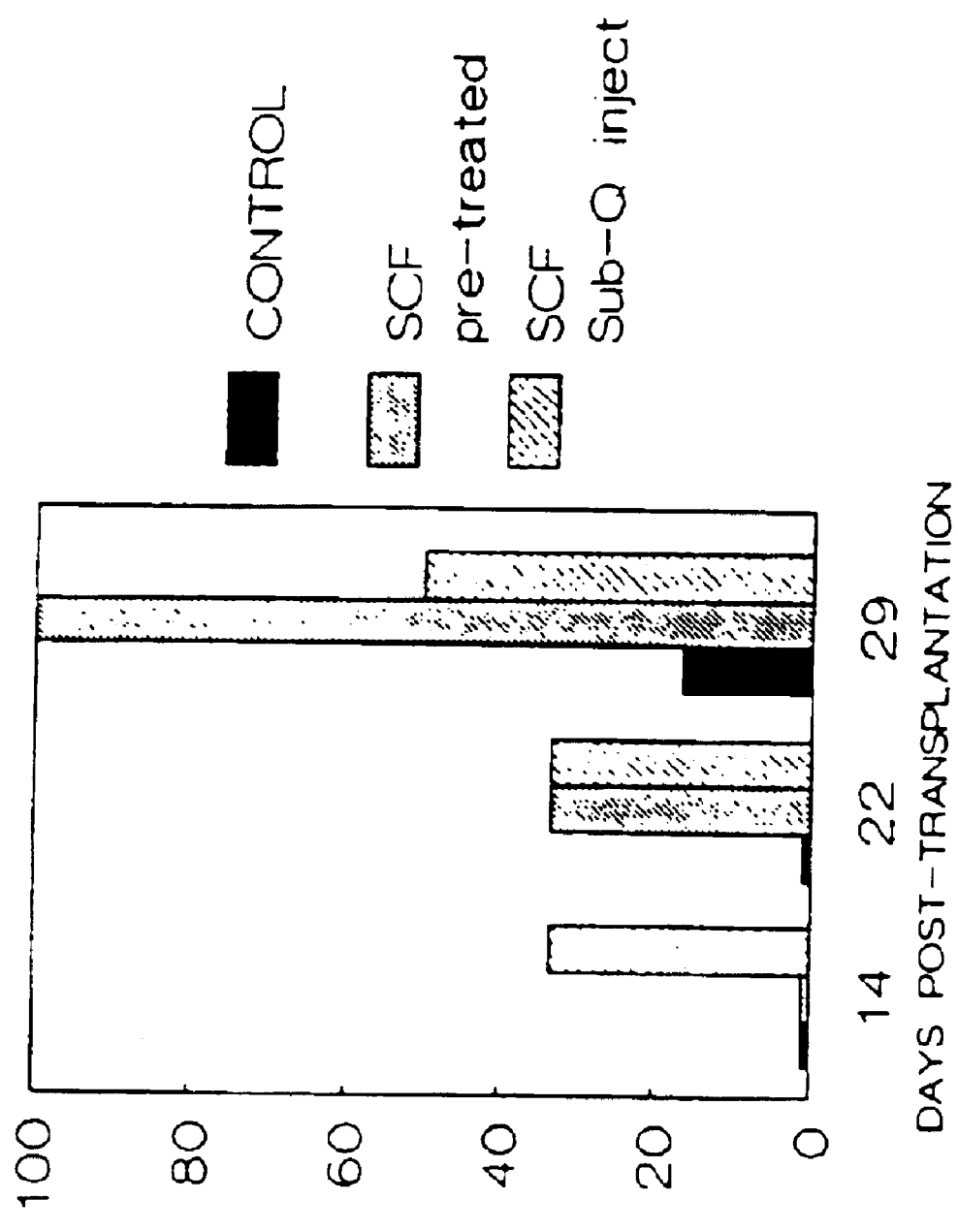

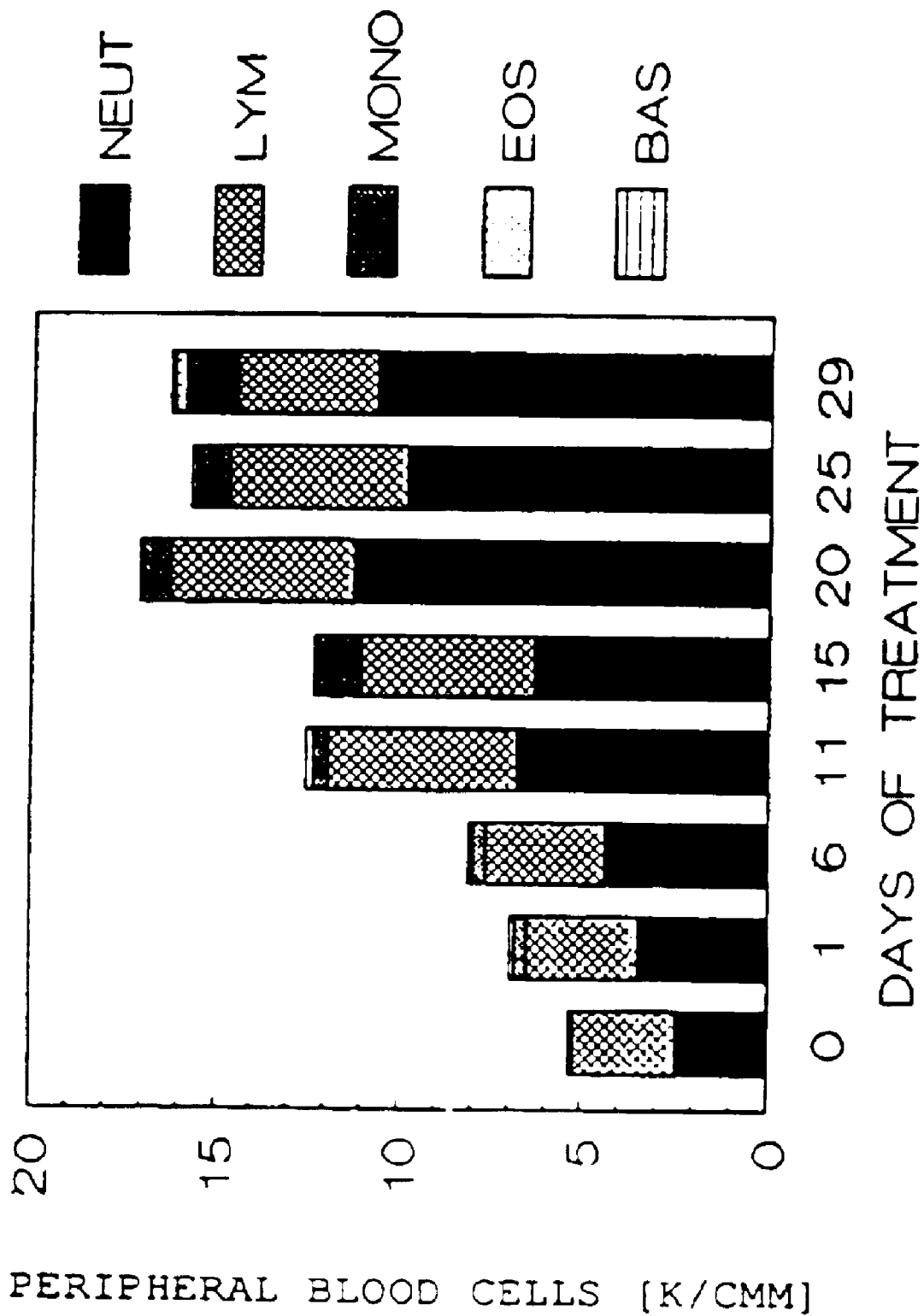

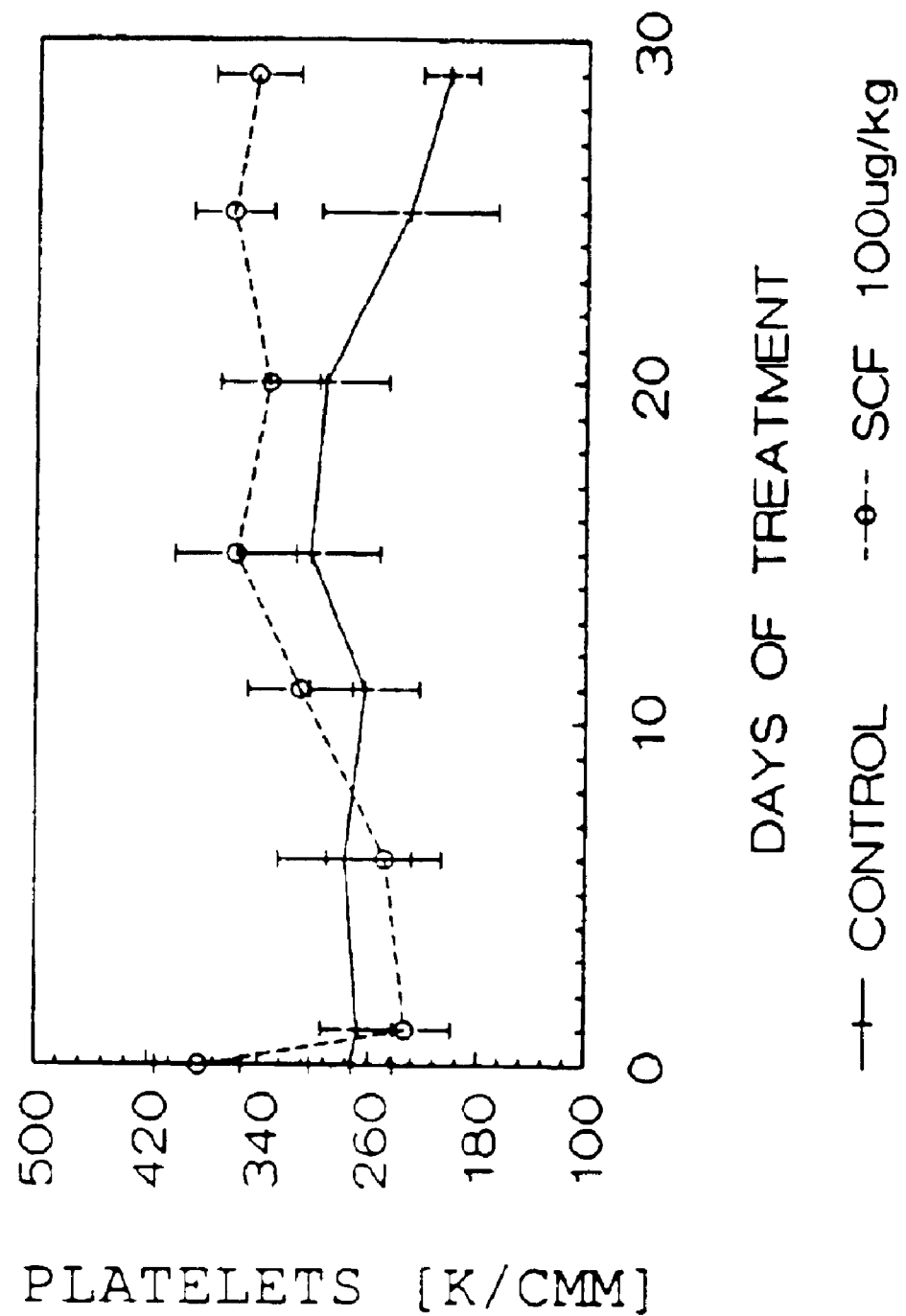

FIG. 42A

```
CCGCCTCGCGCCGAGACTAGAAGCGCTGCGGGAAGCAGGACAGTGGAGAGGCGCTGCGC    61

TCGGGCTACCCAATGCGTGGACTATCTGCCGCCGCTGTTCGTGCAATATGCTGGAGCTCCA   122

GAACAGCTAAACGGAGTCGCCACACCACTGTTTGTGCTGGATCGCAGCGCTGCCTTTCCTT   183

-25              -20
      Met Lys Lys Thr Gln Thr Trp Ile Leu Thr Cys Ile Tyr Leu Gln
      ATG AAG AAG ACA CAA ACT TGG ATT CTC ACT TGC ATT TAT CTT CAG    228

-10                                1
      Leu Leu Phe Asn Pro Leu Val Lys Thr Glu Gly Ile Cys Arg
      CTG CTC CTA TTT AAT CCT CTC GTC AAA ACT GAA GGG ATC TGC AGG    273

10                                            20
      Asn Arg Val Thr Asn Asn Val Lys Asp Val Thr Lys Leu Val Ala
      AAT CGT GTG ACT AAT AAT GTA AAA GAC GTC ACT AAA TTG GTG GCA    318

30
      Asn Leu Pro Lys Asp Tyr Met Ile Thr Leu Lys Tyr Val Pro Gly
      AAT CTT CCA AAA GAC TAC ATG ATA ACC CTC AAA TAT GTC CCC GGG    363

40                                            50
      Met Asp Val Leu Pro Ser His Cys Trp Ile Ser Glu Met Val Val
      ATG GAT GTT TTG CCA AGT CAT TGT TGG ATA AGC GAG ATG GTA GTA    408

60
      Gln Leu Ser Asp Ser Leu Thr Asp Leu Leu Asp Lys Phe Ser Asn
      CAA TTG TCA GAC AGC TTG ACT GAT CTT CTG GAC AAG TTT TCA AAT    453
```

FIG. 42B

```
                        70                              80
Ile Ser Glu Gly Leu Ser Asn Tyr Ser Ile Ile Asp Lys Leu Val
ATT TCT GAA GGC TTG AGT AAT TAT TCC ATC ATA GAC AAA CTT GTG    498

90
Asn Ile Val Asp Asp Leu Val Glu Cys Val Lys Glu Asn Ser Ser
AAT ATA GTG GAT GAC CTT GTG GAG TGC GTG AAA GAA AAC TCA TCT    543

100                             110
Lys Asp Leu Lys Lys Ser Phe Lys Ser Pro Glu Pro Arg Leu Phe
AAG GAT CTA AAA AAA TCA TTC AAG AGC CCA GAA CCC AGG CTC TTT    588

120
Thr Pro Glu Phe Phe Arg Ile Phe Asn Arg Ser Ile Asp Ala
ACT CCT GAA GAA TTC TTT AGA ATT TTT AAT AGA TCC ATT GAT GCC    633

130                             140
Phe Lys Asp Phe Val Val Ala Ser Glu Thr Ser Asp Cys Val Val
TTC AAG GAC TTT GTA GTG GCA TCT GAA ACT AGT GAT TGT GTG GTT    678

150
Ser Ser Thr Leu Ser Pro Glu Lys Asp Ser Arg Val Ser Val Thr
TCT TCA ACA TTA AGT CCT GAG AAA GAT TCC AGA GTC AGT GTC ACA    723
```

FIG. 42C

```
                             160                            170
Lys Pro Phe Met Leu Pro Pro Val Ala Ala Ser Ser Leu Arg Asn
AAA CCA TTT ATG TTA CCC CCT GTT GCA GCC AGC TCC CTT AGG AAT    768

180
Asp Ser Ser Ser Asn Arg Lys Ala Lys Asn Pro Pro Gly Asp
GAC AGC AGT AGC AGT AAT AGG AAG GCC AAA AAT CCC CCT GGA GAC    813

190                                     200
Ser Ser Leu His Trp Ala Ala Met Ala Leu Pro Ala Leu Phe Ser
TCC AGC CTA CAC TGG GCA GCA ATG GCC ATG TTG CCA GCA TTG TTT TCT    858

210
Leu Ile Ile Gly Phe Ala Phe Gly Ala Leu Tyr Trp Lys Lys Arg
CTT ATA ATT GGC TTT GCT TTT GGA GCC TTA TAC TGG AAG AAG AGA    903

220                                     230
Gln Pro Ser Leu Thr Arg Ala Val Glu Asn Ile Gln Ile Asn Glu
CAG CCA AGT CTT ACA AGG GCA GTT GAA AAT ATA CAA ATT AAT GAA    948

240
Glu Asp Asn Glu Ile Ser Met Leu Gln Glu Lys Glu Arg Glu Phe
GAG GAT AAT GAG ATT AGT ATG TTG CAA GAG AAA GAG AGA GAG TTT    993

248
Gln Glu Val End
CAA GAA GTG TAA TTGTGGCTTGTATCAACACTGTTACTTTCGTACATTGGC    1044
```

FIG. 42D

TGGTAACAGTTCATGTTTGCTTCATAAATGAAGCAGCTTTAAACAAATTCATATTCTGTC 1104
TGGAGTGACAGACCACATCTTTATCTGTTCTTGCTACCCATGACTTTATATGGATGATTC 1164
AGAAATTGGAACAGAATGTTTTACTGTGAAACTGGCACTGAATTAATCATCTATAAAGAA 1224
GAACTTGCATGGAGCAGGACTCTATTTAAGGACTGCGGGACTTGGGTCTCATTTAGAAC 1284
TTGCAGCTGATGTTGGAAGAGAAAGCACGTGTCTCAGACTGCATGTACCATTGCATGGC 1344
TCCAGAAATGTCTAAATGCTGAAAAAACACCTAGCTTTATTCTTCAGATACAAACTGCAG 1404

FIG. 44A

```
                                    AGCAGGGACAGTGGAGAGGGCGCTGCGCTC    30
GGGCTACCCAATGCGTGGACTATCTGCCGCCGCTGTTCGTGCAATATGCTGGAGCTCCAG          90
AACAGCTAAACGGAGTCGCCACCACTGTTTGTGCTGGATCGCAGCCGCTGCCTTTCCTT         150

-25
    Met Lys Lys Thr Gln Thr Trp Ile Leu Thr Cys Ile Tyr Leu Gln        195
    ATG AAG AAG ACA CAA ACT TGG ATT CTC ACT TGC ATT TAT CTT CAG

-10                -20                                        1
Leu Leu Phe Asn Pro Leu Val Lys Thr Glu Gly Ile Cys Arg              240
CTG CTC CTA TTT AAT CCT CTC GTC AAA ACT GAA GGG ATC TGC AGG 10                            20
Asn Arg Val Thr Asn Asn Val Lys Asp Val Thr Lys Leu Val Ala          285
AAT CGT GTG ACT AAT AAT GTA AAA GAC GTC ACT AAA TTG GTG GCA

30
Asn Leu Pro Lys Asp Tyr Met Ile Thr Leu Lys Tyr Val Pro Gly          330
AAT CTT CCA AAA GAC TAC ATG ATA ACC CTC AAA TAT GTC CCC GGG 40                          50
Met Asp Val Leu Pro Ser His Cys Trp Ile Ser Glu Met Val Val          375
ATG GAT GTT TTG CCA AGT CAT TGT TGG ATA AGC GAG ATG GTA GTA
```

FIG. 44B

```
Gln Leu Ser Asp Ser Leu Thr Asp Leu Leu Asp Lys Phe Ser Asn
CAA TTG TCA GAC AGC TTG ACT GAT CTT CTG GAC AAG TTT TCA AAT   420
                              60                        80
Ile Ser Glu Gly Leu Ser Asn Tyr Ser Ile Ile Asp Lys Leu Val
ATT TCT GAA GGC TTG AGT AAT TAT TCC ATC ATA GAC AAA CTT GTG   465
             70
Asn Ile Val Asp Asp Leu Val Glu Cys Val Lys Glu Asn Ser Ser
AAT ATA GTG GAT GAC CTT GTG GAG TGC GTG AAA GAA AAC TCA TCT   510
                              90                       110
Lys Asp Leu Lys Ser Phe Lys Ser Pro Glu Pro Arg Leu Phe
AAG GAT CTA AAA TCA TTC AAG AGC CCA GAA CCC AGG CTC TTT       555
            100
Thr Pro Glu Glu Phe Phe Arg Ile Phe Asn Arg Ser Ile Asp Ala
ACT CCT GAA GAA TTC TTT AGA ATT TTT AAT AGA TCC ATT GAT GCC   600
                             120                       140
Phe Lys Asp Phe Val Val Ala Ser Glu Thr Ser Asp Cys Val Val
TTC AAG GAC TTT GTA GTG GCA TCT GAA ACT AGT GAT TGT GTG GTT   645
            130
Ser Ser Thr Leu Ser Pro Glu Lys Gly Lys Ala Lys Asn Pro Pro
TCT TCA ACA TTA AGT CCT GAG AAA GGG AAG GCC AAA AAT CCC CCT   690
                             150
```

FIG. 44C

```
                                 160                                    170
Gly Asp Ser Ser Leu His Trp Ala Ala Met Ala Leu Pro Ala Leu
GGA GAC TCC AGC CTA CAC TGG GCA GCC ATG GCA TTG CCA GCA TTG      735

180
Phe Ser Leu Ile Ile Gly Phe Ala Phe Gly Ala Leu Tyr Trp Lys
TTT TCT CTT ATA ATT GGC TTT GCT TTT GGA GCC TTA TAC TGG AAG      780

190                                    200
Lys Arg Gln Pro Ser Leu Thr Arg Ala Val Glu Asn Ile Gln Ile
AAG AGA CAG CCA AGT CTT ACA AGG GCA GTT GAA AAT ATA CAA ATT      825

210
Asn Glu Glu Asp Asn Glu Ile Ser Met Leu Gln Glu Lys Glu Arg
AAT GAA GAG GAT AAT GAG ATA AGT ATG TTG CAA GAG AAA GAG AGA      870

220
Glu Phe Gln Glu Val End
GAG TTT CAA GAA GTG TAA     TTGTGGCTTGTATCAACACTGTTACTTTCGTA      920

CATTGGCTGGTAACAGTTCATGTTTGCTTCATAAATGAAGCAGCTTTAAACAAATTCATA     980

TTCTGTCTGGAGTGACAGACCACATCTTTATCTGTTCTTGCTACCCATGACTTTATATGG   1040

ATGATTCAGAAATTGGAACAGAATGTTTACTGTGAAACTGGCACTGA                1088
```

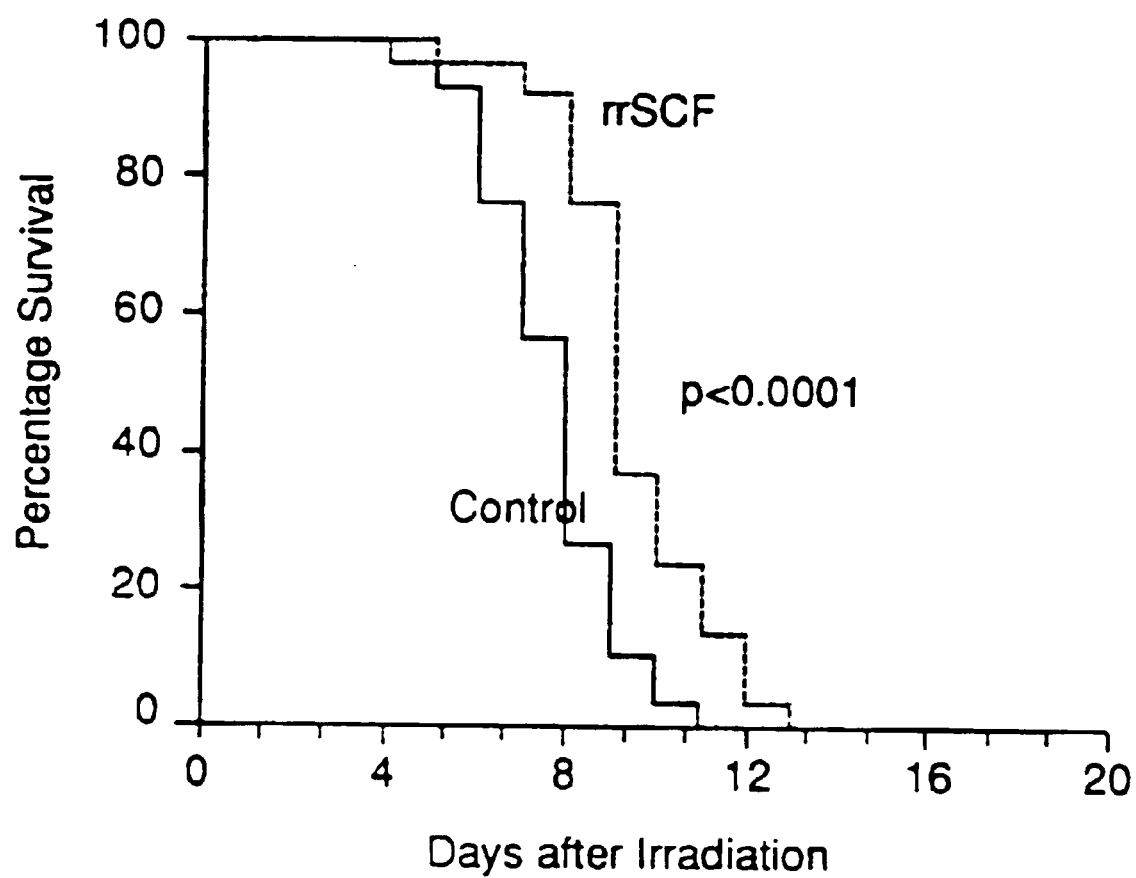

850 RADS; 5% of femur transplanted

FIG. 56
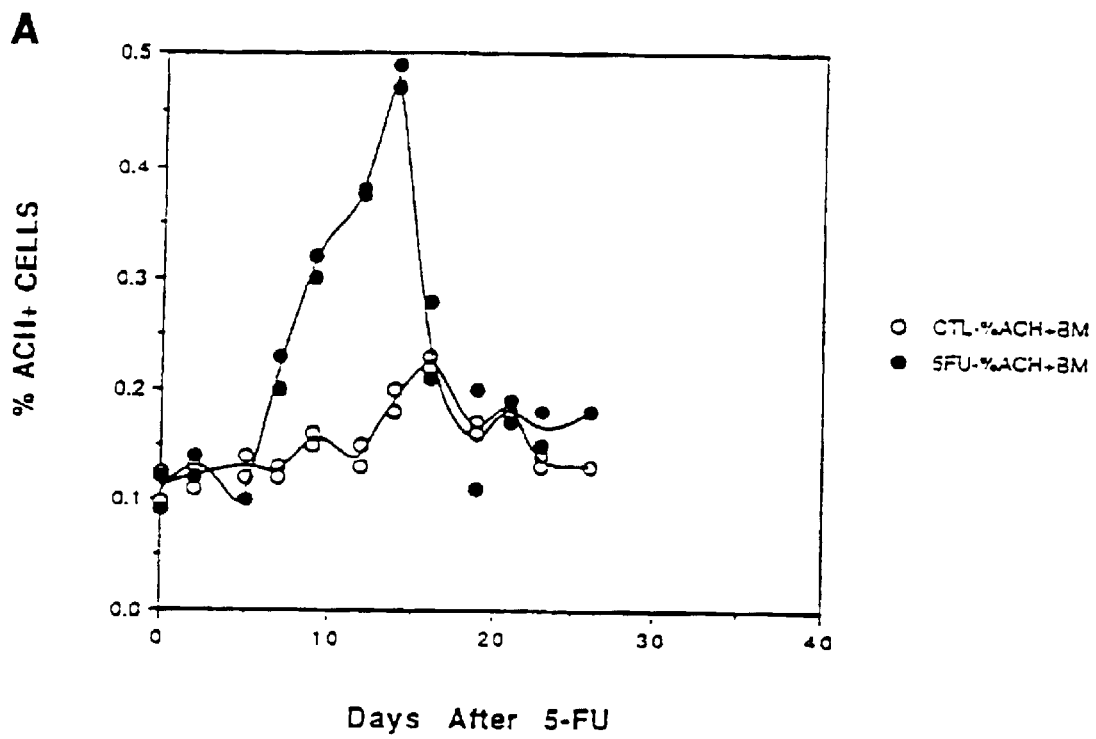
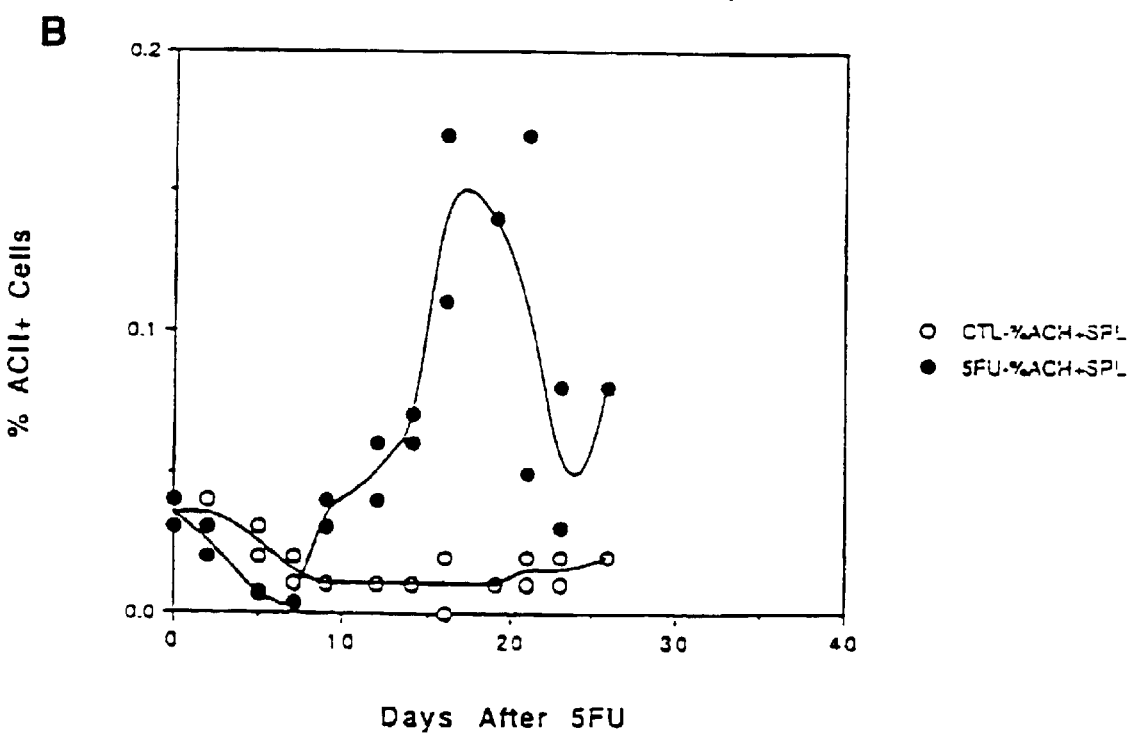

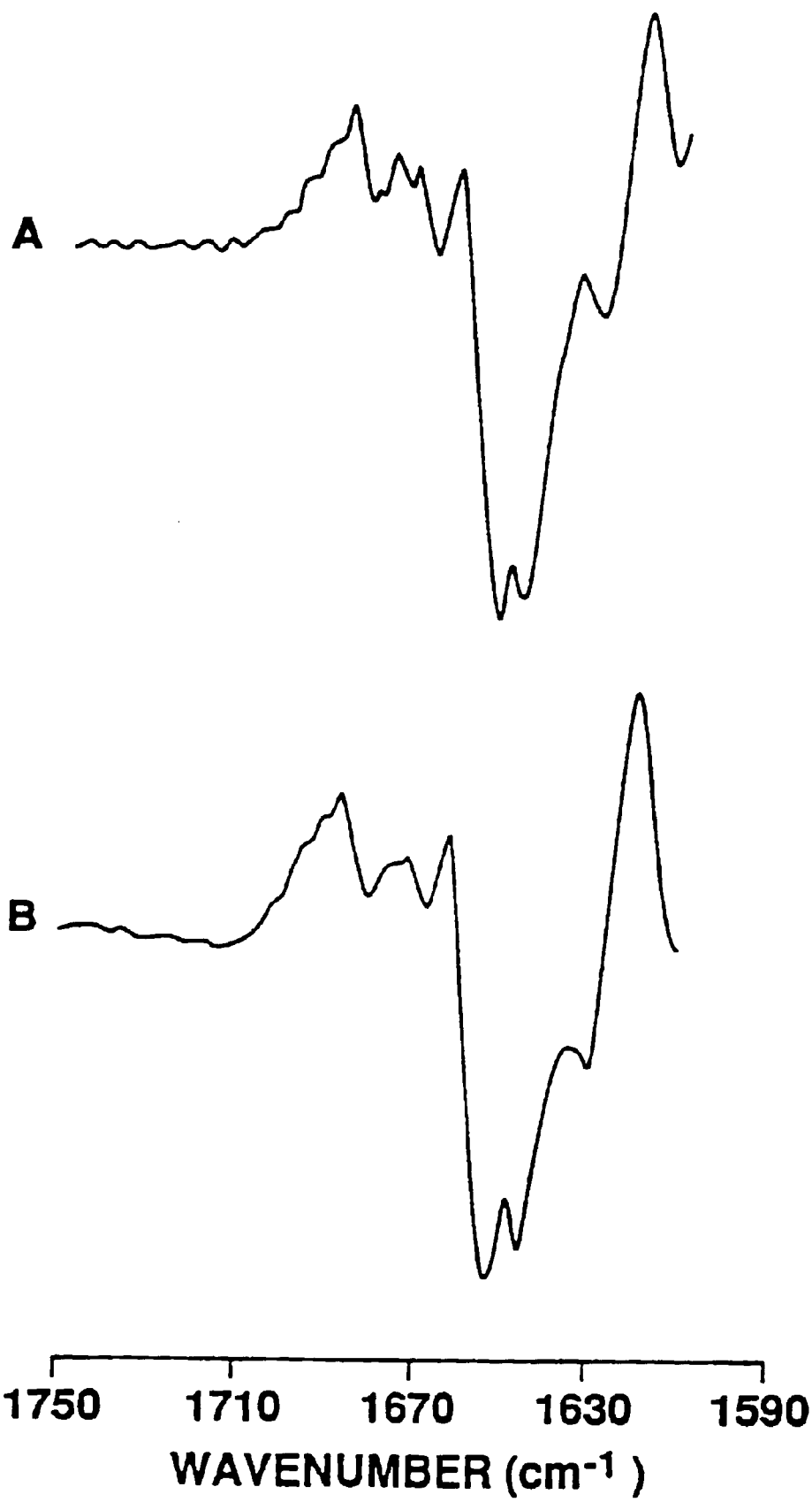

SEQUENCE LISTING (1) GENERAL INFORMATION:

(iii) NUMBER OF SEQUENCES: 104

(2) INFORMATION FOR SEQ ID NO:1:

(i) SEQUENCE CHARACTERISTICS:
      (A) LENGTH: 165 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Glu Glu Ile Cys Arg Asn Pro Val Thr Asp Asn Val Lys Asp Ile Thr
1               5                  10                  15

Lys Leu Val Ala Asn Leu Pro Asn Asp Tyr Met Ile Thr Leu Asn Tyr
                20                  25                  30

Val Ala Gly Met Asp Val Leu Pro Ser His Cys Trp Leu Arg Asp Met
            35                  40                  45

Val Thr His Leu Ser Val Ser Leu Thr Thr Leu Leu Asp Lys Phe Ser
        50                  55                  60

Asn Ile Ser Glu Gly Leu Ser Asn Tyr Ser Ile Ile Asp Lys Leu Gly
65                  70                  75                  80

Lys Ile Val Asp Asp Leu Val Ala Cys Met Glu Glu Asn Ala Pro Lys
                85                  90                  95
```

```
Asn Val Lys Glu Ser Leu Lys Lys Pro Glu Thr Arg Asn Phe Thr Pro
            100                 105                 110

Glu Glu Phe Phe Ser Ile Phe Asn Arg Ser Ile Asp Ala Phe Lys Asp
            115                 120                 125

Phe Met Val Ala Ser Asp Thr Ser Asp Cys Val Leu Ser Ser Thr Leu
        130                 135                 140

Gly Pro Glu Lys Asp Ser Arg Val Ser Val Thr Lys Pro Phe Met Leu
145                 150                 155                 160

Pro Pro Val Ala Ala
                165

(2) INFORMATION FOR SEQ ID NO:2:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 9
        (D) OTHER INFORMATION: /mod_base= Inosine (xi) SEQUENCE DESCRIPTION: SEQ ID NO:2:

ACRTTYTTNG GNGCRTTYTC YTCCAT                                          26

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION:12 and 15
        (D) OTHER INFORMATION: /mod_base= Inosine (xi) SEQUENCE DESCRIPTION: SEQ ID NO:3:

AARAAYTCYT CNGGNGTRAA RTT                                             23

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GTYTCNGGYT TYTT                                                       14

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:5:

ATGGARGARA AYGCCCCCAA RAAYGT                                26

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CCNAAYGAYT AYATGWTMAC                                      20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GGNGGNARCA TRAANGGYTT                                      20

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

ACCAKAARAT CTTYAAANCG ATC                                  23

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GTATTTTCAA TAGATCCATT GA                                   22

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

-continued

CCAACTATGT CGCC                                                          14

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GTAGTCAAGC TGACTGATAA G                                                  21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TAACCAACAA TGACTAGGCA A                                                  21

(2) INFORMATION FOR SEQ ID NO:13:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

TTCCAGAGTC AGTGTC                                                        16

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GCGAAGCTTG CCTTTCCTTA TGAAGAAGA                                          29

(2) INFORMATION FOR SEQ ID NO:15:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GCGCCGCGGT TACGGTGGTA ACATGAAGGG CTTTGTGA                                38

(2) INFORMATION FOR SEQ ID NO:16:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:16:

GATAAATGCA AGTGATAATC C                                       21

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GCGGTCGACC CGCGGAACTT TAAGTCCATG CAACAC                       36

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

CACCCGCGGT TATGCAACAG GGGGTAACAT AAATGG                       36

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

CACCCGCGGT TAGGCTGCAA CAGGGGGTAA CATAAA                       36

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

CTTAATGTTG AAGAAACC                                           18

(2) INFORMATION FOR SEQ ID NO:21:

(i) SEQUENCE CHARACTERISTICS:
        (A) LENGTH: 22 base pairs
        (B) TYPE: nucleic acid

```
        (C) STRANDEDNESS: single
        (D) TOPOLOGY: linear (ii) MOLECULE TYPE: DNA (xi) SEQUENCE DESCRIPTION: SEQ ID NO:21:

GATGGTAGTA CAATTGTCAG AC                                              22

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

GTCTGACAAT TGTACTACCA TC                                              22

(2) INFORMATION FOR SEQ ID NO:23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

CAATTTAGTG ACGTCTTTTA CA                                              22

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

TTAGATGAGT TTTCTTTCAC GCAC                                            24

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

AAATCATTCA AGAGCCCAGA ACCC                                            24

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:26:

AACATCCATC CCGGGGAC                                            18

(2) INFORMATION FOR SEQ ID NO:27:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

CTGGCAATAT TTTAAGTCTC AAGAAGACC                                29

(2) INFORMATION FOR SEQ ID NO:28:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

GCGCCGCGGC TCCTATAGGT GCTAATTGG                                29

(2) INFORMATION FOR SEQ ID NO:29:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

CCTCACCACT GTTTGTGCTG GATCGCA                                  27

(2) INFORMATION FOR SEQ ID NO:30:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

GGTGTCTAGA CTTGTGTCTT CTTCATAAGG A                             31

(2) INFORMATION FOR SEQ ID NO:31:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

CCCCCCCHGG                                                     10

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

TTTTTTTTTT TTTTTTTTGG                                                         20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

TTTTTTTTTT TTTTTTTTAG                                                         20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

TTTTTTTTTT TTTTTTTTCG                                                         20

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

TTCGGCCGAT CAGGCCCCCC CCCC                                           24

(2) INFORMATION FOR SEQ ID NO:36:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

TTCGGCCGGA TAGGCCTTTT TTTTTTTTTT                               30

(2) INFORMATION FOR SEQ ID NO:37:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:37:

GGCCGGATAG GCCTCACNNN NNNT                                              24

(2) INFORMATION FOR SEQ ID NO:38:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:38:

GGCCGGATAG GCCTCAC                                                      17

(2) INFORMATION FOR SEQ ID NO:39:

(i) SEQUENCE CHARACTERISTICS:
       (A) LENGTH: 4673 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: CDS
       (B) LOCATION: join(660..773, 1184..1246, 2053..2223, 2837..
           2993, 3692..3774)

(ix) FEATURE:
       (A) NAME/KEY: mat_peptide
       (B) LOCATION: join(720..773, 1184..1246, 2053..2223, 2837..
           2993, 3692..3774)

(xi) SEQUENCE DESCRIPTION: SEQ ID NO:39:

AAAGTATCTT TCTATTGGCG AAGGACATGT TTTCCCATAA GTGGTAAACA AACTGTCTGC        60

ACATAATAAT TATCTTGCTG CCGTAAAGAT TAGGTTAAAT TCTGCCTTCG ATCTAAAAAC       120

ACACCCTTCT GTCAATCCGA GGAGCAGTGT GCTAGTCTAG AGGTCTAAAT GAAGGCTCCT       180

TTCACGGTTG TATTTCTGCT CCCCAAATTG TCCACATTTA AAAGGAGAGT GCTTCTTTTC       240

AGCCTTAGGC TCTGAATTTC ATGCATTCCT CCATTTTCCG AGGTCCCCCC CAAGTGATAA       300

TTCTGTTACA CGTTGCTACA AGTTCATCCC TAATTGCCGT CAAGAAACTG ACTGTAGAAG       360

GCTTACCACA GACGTTGTAA CCGACAGTAA AGCCATTGAA AGAGTAATTC AAACAGGATG       420

GAAGCCAGGA GTATTTTGTG GCTGTTGCTC TTTTTCTTTT CAGTTTGGTG AGAGCAGCTT       480

GAATGCTTAA CATTTAAGCC ATCAGCTTAA AACAAACAA AACAAACAA AAAAAACCC         540

CGCTCTGGCA TATTTGCACT TAACACATAC GGTATAAGGT GTTACTGGTT TGCATAGTTC       600

TGGATTTTTT TTTTTTAAAA ACTGATGGAC ACCAAGAAAT GTTTCTGTTC TTTGTTTAG        659

ACT TGG ATT ATC ACT TGC ATT TAT CTT CAA CTG CTC CTA TTT AAT CCT        707
Thr Trp Ile Ile Thr Cys Ile Tyr Leu Gln Leu Leu Leu Phe Asn Pro
-20                 -15                 -10                 -5

CTC GTC AAA ACT CAG GAG ATC TGC AGG AAT CCT GTG ACT GAT AAT GTA        755
Leu Val Lys Thr Gln Glu Ile Cys Arg Asn Pro Val Thr Asp Asn Val
                1                   5                   10

```
AAA GAC ATT ACA AAA CTG GTAAGTAAAG AATGATTTTG GCATCTATAA            803
Lys Asp Ile Thr Lys Leu
         15

GTCTTCCCTG TGCTTGCTGA CCACATAGGT TCAGGGCACT CCCGACAGGA GTTCCCAGCT   863

TTCTAAGATA AGGAATCACT GTACGAGTCT GAAGTGCTTC TTCTGGGCAA ATGGGAGATG   923

CTTAGGTCAT GGAGGGTTTA TCTGTATAAC TGGCCCTTTG CACACCAACA AAGTGACTGA   983

CTGGCTTTTG CCTGTTACCT ACTGTCTCCA GTCCTGGGCA TGGTATATAC TTAGGCACCC  1043

AAGATTGGAT TTACAACTCA AGCATTATAT ATTGGACAAC ACGGGTATG AGATATTAAT  1103

GATATGTCAG GTTGGATGGA TGAGTTTTCT CAAGAAATTC TCTTGTATTT ACTCACGTTT  1163

TCATTTCTTG GTCTCTGTAG GTG GCG AAT CTT CCA AAT GAC TAT ATG ATA     1213
                       Val Ala Asn Leu Pro Asn Asp Tyr Met Ile
                                    20                  25

ACC CTC AAC TAT GTC GCC GGG ATG GAT GTT TTG GTATGTAGTC CACACACTTC  1266
Thr Leu Asn Tyr Val Ala Gly Met Asp Val Leu
      30                  35

TGAGTTGCCT TTTAGTAGCT AATGGGTGAC CTGTGCTTAT TCACATTGAA GACATTATTT  1326

GCTCTTTGTC GTTTTTAGAT GTTGACCTAT AATTTTTCCT TCAAGCTGCT GCTAAGATTA  1386

TCAGTGAGCA TTTCAGTATG TGTTTTAAGC CTACTCATTA AAAGGAAATG GCTCATCTTA  1446

GACGTAGCAA CCGATGTTAA TTTTTCCCCA GGCATCTCTC AGAGGGACTT GAATGTTAAA  1506

ATCATGTTAA ATTTCCTCCT TGGCTATGTT ATTTCTCATG GCTATGTTAT TCCTATTCGT  1566

ATTTCATTTA AAGGGACGGA ATATTTATTG TATTTCTGAA CTTTTTCAGG CATGCATCCG  1626

GGTCTTTGAA TAAAACACTA AGACTCCTTC TAGTAATGTT TGTAATCCTG TCTGTATCGA  1686

ATGTCTTTGA AAACGCAGTG ACTAAGCCAT AAATAATCTT CCACAGAACG TCCAGTGGTT  1746

CATGAACTTT GTATGTGGGG GTGGGGCAAG AATTGTCTCA CTATTGGTCA AGGAAGAGAA  1806

GGTAAGGTAT GCAAGGGTGG TTTAATCTTC TTCCGTGGAA GGACAAAATC ATCTATCATT  1866

TCCTCTGATC TCTATGCATT TGTTTGTTTT GAACTGAATC TGACTTGAGC AAGAGTTGGC  1926

GTCCTGTGTT CTGAGGAAAC TCTTTGTCCT GCAGTCAGTG ACTAAAAGTG CTGAGAGATC  1986

TGAAGAGCAC TCTGAATCTG CCATATTTTT AATAGATGCT TTGTCTTCTC TTTGAATTTC  2046

TTCCAG CCT AGT CAT TGT TGG TTA CGA GAT ATG GTA ACA CAC TTA TCA   2094
       Pro Ser His Cys Trp Leu Arg Asp Met Val Thr His Leu Ser
           40                  45                  50

GTC AGC TTG ACT ACT CTT CTG GAC AAG TTT TCA AAT ATT TCT GAA GGC   2142
Val Ser Leu Thr Thr Leu Leu Asp Lys Phe Ser Asn Ile Ser Glu Gly
         55                  60                  65

TTG AGT AAT TAT TCC ATC ATA GAC AAA CTT GGG AAA ATA GTG GAT GAC   2190
Leu Ser Asn Tyr Ser Ile Ile Asp Lys Leu Gly Lys Ile Val Asp Asp
 70                  75                  80                  85

CTC GTG GCA TGT ATG GAA GAA AAT GCA CCT AAG GTAACTTGGT ATTCATCAGA  2243
Leu Val Ala Cys Met Glu Glu Asn Ala Pro Lys
              90                  95

ATTATTTTTC TTATACTGAG CTCATGATGA GCAATTCACA ACCACTTGTA ATTCCAGCTC  2303

CAGAGGACAT TATCCCCTCT TTGGATGCCA TAGGAATCTG CTCTCAAATA TGTAGATACC  2363

ACCTCTGCCA CCTCAGCACA TACATACACA TAATTAAAAA ATAGAAACAT TAAAGGAGTT  2423

CCAATCAATC CTTATTCTTT TCTGTATTCA GTATGCCCAG ATGTAAATTC TAGGAATATG  2483

TTTTAAAGGC TAATTCTTAT TTTGTAATAA GCAGCTTTAA AATTCTTAAT TGTTTTTTCG  2543

GGTCACTTTA TTGTCCTATT GCCACGACAT TGTCCTGTCC CATTGTCTGT TATTCCTTCT  2603
```

```
GTTTTGTTTA TTGTTCCCTA GTTACTTTGA TCATGAGATT GACCTGTTAC CCGTTGTTAT    2663

TCTCTGTAGC CATTTTGAGT TGTGTCTATT AGAACAGCTG TTAAATTACT TGAATCATTG    2723

AGGACATAGT CAATAATCTA TTATGCTGAT CCAGTCAAGT CTATGAGTTA TTTGAAAACT    2783

AGAATCTTTG TTAATTATTT GTTTGCTTGT TTGTTTGTTT ATTATTTGTC TAG AAT       2839
                                                           Asn

GTA AAA GAA TCA CTG AAG AAG CCA GAA ACT AGA AAC TTT ACT CCT GAA      2887
Val Lys Glu Ser Leu Lys Lys Pro Glu Thr Arg Asn Phe Thr Pro Glu
            100                 105                 110

GAA TTC TTT AGT ATT TTC AAT AGA TCC ATT GAT GCC TTC AAG GAC TTC      2935
Glu Phe Phe Ser Ile Phe Asn Arg Ser Ile Asp Ala Phe Lys Asp Phe
    115                 120                 125

ATG GTG GCA TCT GAC ACT AGT GAT TGT GTG CTC TCT TCA ACA TTA GGT      2983
Met Val Ala Ser Asp Thr Ser Asp Cys Val Leu Ser Ser Thr Leu Gly
130                 135                 140                 145

CCT GAG AAA G GTAAGGCTTT TAAGCATTTC TTGTTTAAAT GTACATAGAA            3033
Pro Glu Lys

AGCCTGAACT TCTGTAAGCC TCTACTGCTG AATCAACTAA ATGTGTTGCT GTAGAAAGAA    3093

CGTGTGGGTT TTTCTGATAA AAACAAAAAG CAAATATCAA TGACTACCAA TGATTATTAT    3153

CTAGCTTGAG AGATATGCCC TAAGACAGCG ATTCTCGATA TTTCTAAATT AAAGAATTGT    3213

GTGATGGTGG CTCACATATT TTCTAACTGT GATATTTGCC AGGAGAGTAG AATAATGTTA    3273

TTCTTCATCC CCAGAATTCC TAAGATTTCA CGTCTCATGT CTTTTCCATA AGGTTCAAAC    3333

TCTGAGACTT GAGTTCTGAG CCTCAGCAGG TCATTCTGAA TCCCCACTCT CCCCGAGCTG    3393

GGTCCCTATG GGGAACTAAC TTCATTGCT TTCTTTTAAA ACATGACGAG TTACCAACAG     3453

CTCCTCGCTA TTATAAACAT GTTCCTAAGC ATGTCTGTGC ATGCAATAAG CCTTCACTCT    3513

ACAAGACAGT TATGGTGTAT CGCTTGACAA AACTGAGCAG CCAAGCTGAG TATGAAATAA    3573

TAATCTAGAC TTGGGAGGCA GACCCAGCAC CTACTGTGAT ATTGCACTTC GCCTTTGGGG    3633

GACTCTATGA TTCAAAAGTT CACCATGTAA CACTGACACA TTATTGCTTT CTATTTAG AT  3693
                                                                 Asp

TCC AGA GTC AGT GTC AGA AAA CCA TTT ATG TTA CCC CCT GTT GCA GCC      3741
Ser Arg Val Ser Val Arg Lys Pro Phe Met Leu Pro Pro Val Ala Ala
150                 155                 160                 165

AGT TCC CTT AGG AAT GAC AGC AGT AGC AGT AAT AGTAAGTACA CATATCTGAT    3794
Ser Ser Leu Arg Asn Asp Ser Ser Ser Ser Asn
                170                 175

TTACTGCATG CATGGCTCCA AGTATCCTCT ATAGGAGTGT TGCATGGACT TAAAGTTTAT    3854

AAATCACTAC TAATAATGCT GTTCTGTCAC TGTTATTCCT TGTATGGGCT TCCTGACAAT    3914

TAAATATCTG GTTTGTAGAA TCGGATCTCC TTAGAGGTTA AGATGACCAT GACAAAATTA    3974

GGCCAATCAA CTTTCTGCGA AGGTTATTTT AAATAAGGCA CGAAATTAAT TGAAGGAAAA    4034

AAAAATACAA GCAAGGCCTT ATTTTGAATC ATGGTAGGCT TAAAATAGAC TTTGTGGAGA    4094

ATGTCCCTGA TCAAAGTGGA GTTTTCAGAT TTCAAGTGCA TGTGCTAACT CTCCACAATG    4154

TCAAGGCTAT TTTCAGTTTT GTGTCTCCAT ATTTACTACT GCATGTTTGG AAATTTGCTG    4214

ATGCTGTTAG ATTACCTAAG AATGTATGTT GAAGAAGAAT GGACTTCTTT CCCTAAAATT    4274

TCTGTCCTCT TTGCCCAAGA ACCCACGTTC CTGGAAGACT ATCTTATTTT CATGTCTGTG    4334

CAATGATCAT TATAAAGATT ATTGAATATA CTGGGAATAC TCTGGTTTCT GTTTTTACAG    4394

ATTCATAATA GCTTATTCAG TCTTTAAAGA AAGTTCTCTG AAGTCCATGC TTAGAATGT     4454

TTCTCTATCA AAACTTGACC TGGACCTTAA ATAAAGCTAT ATTTAGTCTT TTTATCCCTG    4514
```

```
AAAAATATAT TTCACAGTGT AGACATTTGA TATACATCTA AGGGAAGGAT GCTGCCAGAA      4574

TGCTCGGGCT GGCAGTCTAC AAAGTCCACT GCTCTCAGGA TGGACTTCTG AAAGCGGAAA      4634

TTGTGAACTG CATGCATATA ACATATCAGA TCCTCGAGC                             4673

(2) INFORMATION FOR SEQ ID NO:40:

(i) SEQUENCE CHARACTERISTICS:
        (A) LENGTH: 196 amino acids
        (B) TYPE: amino acid
        (D) TOPOLOGY: linear (ii) MOLECULE TYPE: protein (xi) SEQUENCE DESCRIPTION: SEQ ID NO:40:

Thr Trp Ile Ile Thr Cys Ile Tyr Leu Gln Leu Leu Phe Asn Pro
-20              -15                 -10                 -5

Leu Val Lys Thr Gln Glu Ile Cys Arg Asn Pro Val Thr Asp Asn Val
             1                   5                   10

Lys Asp Ile Thr Lys Leu Val Ala Asn Leu Pro Asn Asp Tyr Met Ile
             15                  20                  25

Thr Leu Asn Tyr Val Ala Gly Met Asp Val Leu Pro Ser His Cys Trp
         30                  35                  40

Leu Arg Asp Met Val Thr His Leu Ser Val Ser Leu Thr Thr Leu Leu
45                   50                  55                  60

Asp Lys Phe Ser Asn Ile Ser Glu Gly Leu Ser Asn Tyr Ser Ile Ile
                 65                  70                  75

Asp Lys Leu Gly Lys Ile Val Asp Asp Leu Val Ala Cys Met Glu Glu
             80                  85                  90

Asn Ala Pro Lys Asn Val Lys Glu Ser Leu Lys Lys Pro Glu Thr Arg
             95                  100                 105

Asn Phe Thr Pro Glu Glu Phe Phe Ser Ile Phe Asn Arg Ser Ile Asp
    110                 115                 120

Ala Phe Lys Asp Phe Met Val Ala Ser Asp Thr Ser Asp Cys Val Leu
125                 130                 135                 140

Ser Ser Thr Leu Gly Pro Glu Lys Asp Ser Arg Val Ser Val Arg Lys
                145                 150                 155

Pro Phe Met Leu Pro Pro Val Ala Ala Ser Ser Leu Arg Asn Asp Ser
                160                 165                 170

Ser Ser Ser Asn
        175

(2) INFORMATION FOR SEQ ID NO:41:

(i) SEQUENCE CHARACTERISTICS:
        (A) LENGTH: 849 base pairs
        (B) TYPE: nucleic acid
        (C) STRANDEDNESS: single
        (D) TOPOLOGY: linear (ii) MOLECULE TYPE:DNA (ix) FEATURE:
        (A) NAME/KEY: CDS
        (B) LOCATION: 26..844

(ix) FEATURE:
        (A) NAME/KEY: mat_peptide
        (B) LOCATION: 101..844

(xi) SEQUENCE DESCRIPTION: SEQ ID NO:41:

CTGGATCGCA GCGCTGCCTT TCCTT ATG AAG AAG ACA CAA ACT TGG ATT ATC      52
```

```
                    Met Lys Lys Thr Gln Thr Trp Ile Ile
                        -25             -20

ACT TGC ATT TAT CTT CAA CTG CTC CTA TTT AAT CCT CTC GTC AAA ACT      100
Thr Cys Ile Tyr Leu Gln Leu Leu Leu Phe Asn Pro Leu Val Lys Thr
    -15             -10              -5

CAG GAG ATC TGC AGG AAT CCT GTG ACT GAT AAT GTA AAA GAC ATT ACA      148
Gln Glu Ile Cys Arg Asn Pro Val Thr Asp Asn Val Lys Asp Ile Thr
 1           5                  10                  15

AAA CTG GTG GCG AAT CTT CCA AAT GAC TAT ATG ATA ACC CTC AAC TAT      196
Lys Leu Val Ala Asn Leu Pro Asn Asp Tyr Met Ile Thr Leu Asn Tyr
             20              25                  30

GTC GCC GGG ATG GAT GTT TTG CCT AGT CAT TGT TGG TTA CGA GAT ATG      244
Val Ala Gly Met Asp Val Leu Pro Ser His Cys Trp Leu Arg Asp Met
         35              40              45

GTA ACA CAC TTA TCA GTC AGC TTG ACT ACT CTT CTG GAC AAG TTT TCA      292
Val Thr His Leu Ser Val Ser Leu Thr Thr Leu Leu Asp Lys Phe Ser
     50              55              60

AAT ATT TCT GAA GGC TTG AGT AAT TAT TCC ATC ATA GAC AAA CTT GGG      340
Asn Ile Ser Glu Gly Leu Ser Asn Tyr Ser Ile Ile Asp Lys Leu Gly
 65              70              75              80

AAA ATA GTG GAT GAC CTC GTG GCA TGT ATG GAA GAA AAT GCA CCT AAG      388
Lys Ile Val Asp Asp Leu Val Ala Cys Met Glu Glu Asn Ala Pro Lys
                 85              90              95

AAT GTA AAA GAA TCA CTG AAG AAG CCA GAA ACT AGA AAC TTT ACT CCT      436
Asn Val Lys Glu Ser Leu Lys Lys Pro Glu Thr Arg Asn Phe Thr Pro
             100             105             110

GAA GAA TTC TTT AGT ATT TTC AAT AGA TCC ATT GAT GCC TTC AAG GAC      484
Glu Glu Phe Phe Ser Ile Phe Asn Arg Ser Ile Asp Ala Phe Lys Asp
         115             120             125

TTC ATG GTG GCA TCT GAC ACT AGT GAT TGT GTG CTC TCT TCA ACA TTA      532
Phe Met Val Ala Ser Asp Thr Ser Asp Cys Val Leu Ser Ser Thr Leu
     130             135             140

GGT CCT GAG AAA GAT TCC AGA GTC AGT GTC ACA AAA CCA TTT ATG TTA      580
Gly Pro Glu Lys Asp Ser Arg Val Ser Val Thr Lys Pro Phe Met Leu
145             150             155             160

CCC CCT GTT GCA GCC AGT TCC CTT AGG AAT GAC AGC AGT AGC AGT AAT      628
Pro Pro Val Ala Ala Ser Ser Leu Arg Asn Asp Ser Ser Ser Ser Asn
             165             170             175

AGG AAA GCC GCA AAG TCC CCT GAA GAC CCA GGC CTA CAA TGG ACA GCA      676
Arg Lys Ala Ala Lys Ser Pro Glu Asp Pro Gly Leu Gln Trp Thr Ala
         180             185             190

ATG GCA CTG CCG GCT CTC ATT TCG CTT GTA ATT GGC TTT GCT TTT GGA      724
Met Ala Leu Pro Ala Leu Ile Ser Leu Val Ile Gly Phe Ala Phe Gly
     195             200             205

GCC TTA TAC TGG AAG AAG AAA CAG TCA AGT CTT ACA AGG GCA GTT GAA      772
Ala Leu Tyr Trp Lys Lys Lys Gln Ser Ser Leu Thr Arg Ala Val Glu
     210             215             220

AAT ATA CAG ATT AAT GAA GAG GAT AAT GAG ATA AGT ATG TTG CAA CAG      820
Asn Ile Gln Ile Asn Glu Glu Asp Asn Glu Ile Ser Met Leu Gln Gln
225             230             235             240

AAA GAG AGA GAG TTT CAA GAG GTG TAATT                                849
Lys Glu Arg Glu Phe Gln Glu Val
                245
```

(2) INFORMATION FOR SEQ ID NO:42:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:42:

```
Met Lys Lys Thr Gln Thr Trp Ile Ile Thr Cys Ile Tyr Leu Gln Leu
-25             -20             -15             -10

Leu Leu Phe Asn Pro Leu Val Lys Thr Gln Glu Ile Cys Arg Asn Pro
            -5                   1               5

Val Thr Asp Asn Val Lys Asp Ile Thr Lys Leu Val Ala Asn Leu Pro
        10              15                  20

Asn Asp Tyr Met Ile Thr Leu Asn Tyr Val Ala Gly Met Asp Val Leu
        25              30                  35

Pro Ser His Cys Trp Leu Arg Asp Met Val Thr His Leu Ser Val Ser
40              45              50                  55

Leu Thr Thr Leu Leu Asp Lys Phe Ser Asn Ile Ser Glu Gly Leu Ser
                60              65                  70

Asn Tyr Ser Ile Ile Asp Lys Leu Gly Lys Ile Val Asp Asp Leu Val
            75              80                  85

Ala Cys Met Glu Glu Asn Ala Pro Lys Asn Val Lys Glu Ser Leu Lys
            90              95                  100

Lys Pro Glu Thr Arg Asn Phe Thr Pro Glu Glu Phe Phe Ser Ile Phe
105                 110                 115

Asn Arg Ser Ile Asp Ala Phe Lys Asp Phe Met Val Ala Ser Asp Thr
120                 125                 130                 135

Ser Asp Cys Val Leu Ser Ser Thr Leu Gly Pro Glu Lys Asp Ser Arg
            140                 145                 150

Val Ser Val Thr Lys Pro Phe Met Leu Pro Pro Val Ala Ala Ser Ser
            155                 160                 165

Leu Arg Asn Asp Ser Ser Ser Asn Arg Lys Ala Ala Lys Ser Pro
            170                 175                 180

Glu Asp Pro Gly Leu Gln Trp Thr Ala Met Ala Leu Pro Ala Leu Ile
    185                 190                 195

Ser Leu Val Ile Gly Phe Ala Phe Gly Ala Leu Tyr Trp Lys Lys Lys
200                 205                 210                 215

Gln Ser Ser Leu Thr Arg Ala Val Glu Asn Ile Gln Ile Asn Glu Glu
                220                 225                 230

Asp Asn Glu Ile Ser Met Leu Gln Gln Lys Gly Arg Glu Phe Gln Glu
            235                 240                 245

Val
```

(2) INFORMATION FOR SEQ ID NO:43:

(i) SEQUENCE CHARACTERISTICS:
        (A) LENGTH: 3807 base pairs
        (B) TYPE: nucleic acid
        (C) STRANDEDNESS: single
        (D) TOPOLOGY: linear (ii) MOLECULE TYPE:DNA (ix) FEATURE:
        (A) NAME/KEY: CDS
        (B) LOCATION: join(905..1018, 1914..1976, 2572..2742, 3152
          ..3307, 3513..3595)

(ix) FEATURE:
        (A) NAME/KEY: mat_peptide
        (B) LOCATION: join(965..1018, 1914..1976, 2572..2742, 3152
          ..3307, 3513..3595)

(xi) SEQUENCE DESCRIPTION: SEQ ID NO:43:

```
CACAAGTGAG TAGGGCGCGC CCGGGAGCTC CCAGGCTCTC CAGGAAAAAT CGCGCCCGGT    60

GCCCCGGGGA AGCCGGCGCT CCCTGGGACT TGCAGCTGGG GCGTGCAGGG CTGTGCCTGC   120

CGGGTGAGAT ACTACAAAGA TAAATCAGTT GCACAAGTTC TTGAAACTCT ACAGTGTAAT   180

AAGGAAAAAT AAGTCATGCA TAAAAGCAAC TATAATACAT AATAGAAAAT GTTATTTTCA   240

AGCCGATGTG TAGGTTATGT GTGTTCGAGA GAGAGAGAGA GAAGACAGAT TACTTTCTGC   300

TAGGGTTCAA GAATGCCTTC CTGTTGGCTA AGGAAATATT TTCCTTAAGT GGCTAAAAAG   360

CTGTGTTTCA AAATATTCTT TTGATGTCTC ACAAATTCAG TGGAATTCTC TTAGGTCTAA   420

AAATATACAT CTCTCTCACT TTAACTTGGT GTGCTATTGT AGATTATTGG ATTAAAGCAC   480

TGCTCAGGGA TTATGCTGCT TCTTGCCAAG CAGTCTACAT TTAAAGTAGA AATAAGATGT   540

TTCTTTTGGT GCCATAAGGT ATACATTTTA TGCATTCTCT AGTTTTTAGA AGATACCCTA   600

AGGGCTAAGT CTTTAACATG CTGCTACAAG TTTATTCCTA ATTGCCATTG GGAAATTGGC   660

TGAAGAAAGT TTTTAACAAA AGTTAACAAT ATTGTCATTG AGAGAATAAT TCAAAATGGA   720

TTTTAACTAA AAGCTTTTAA AAACTTTGGT GAGCATAGCT TGAATGCGTA ATATTTAATT   780

GCATTTAAGC CAATAACATA TATTAGACTG GTCTTTTTGT GCATCAAGGC ATTAGATGTT   840

AAAAGTTTGA ATGATTACAG ATCTTAACTG ATGATCACCA AGCAATTTTT CTGTTTTCAT   900

TTAG ACT TGG ATT CTC ACT TGC ATT TAT CTT CAG CTG CTC CTA TTT AAT   949
     Thr Trp Ile Leu Thr Cys Ile Tyr Leu Gln Leu Leu Leu Phe Asn
         -20             -15             -10

CCT CTC GTC AAA ACT GAA GGG ATC TGC AGG AAT CGT GTG ACT AAT AAT    997
Pro Leu Val Lys Thr Glu Gly Ile Cys Arg Asn Arg Val Thr Asn Asn
 -5              1               5                  10

GTA AAA GAC GTC ACT AAA TTG GTAAGTAAGG AATGCTTTAC CGTGCTGTGT       1048
Val Lys Asp Val Thr Lys Leu
                15

AAAAAAGAGC TGTGGCTCTT TTTCCTGTGC TTGTTGATAA AAGATTTAGA TTTTTCTTGC  1108

CCCAAAGTAA TGTTTTCCTA AAGTGGGGAA AGTAATCACT GGGTTACAAT AAAGGGTTTA  1168

TAGAAAGCAG GTAGTGAGAT ATTTAGGGTC ATGGATAATT TGTTGGTAAA ACTGGCTAGT  1228

TGCACACCAC TGCTGTGACT GCTTCTTTGC TGGTCTTCTC CCCATCCTTC ATAGGCAGTG  1288

AAGGACCTTG GAGAGTTCGC TGTGTGCTGA TGGGCTTGCC CCAGCTTGTT CCCCATAATC  1348

TCTCCAGTGG GTTTCCCAGC ATGTTCTATT CCCCTTCACA TGTCTTCCTA CTCTTCTTTA  1408

AAAAGCCTAA CGAAAGGAAA TCTGAAATGG CTATTCTCCC AATTCAATCA GCAGGAAGAC  1468

CCTGTCACAT GTCAGTGGGT GTTTGCTCCT TCAGGGAACA TAGAGAGGTG ATTCATTGCC  1528

CACATGTTGA AGGGACTCAT CTCCCTGGTT TGTCACATTG AACTCTTCCC TCAGCGAAAG  1588

CATTTGCATT GCTTCCCGAA TTCCAAGATC ACAGGTGGAA GCTGAAATTC AGATCATGTT  1648

TCCAAAACTC AGTAGGTTAT ACCTAGCCAG GCATAACTGA ATTTGGAGTC TAAAAGATCT  1708

GTATTATCAC TTTTTTATTT TGAAGGATGC CTTTTGATTA CAGAGGGAAA TCAAGGATTA  1768

AAAATCAATA TACATGTAAA TATTGAAATT CATTGGTAAC TTTAAAAAGC ACAACAGTTT  1828

TGTGTGCTTT TCTCCAAAGC ACTACAAATA TGATTAATTG ATGTATAAGA ATTTTCTTAT  1888

GGAATTTTTT TTTTTGTCTC TGTAG GTG GCA AAT CTT CCA AAA GAC TAC ATG   1940
                             Val Ala Asn Leu Pro Lys Asp Tyr Met
                                 20                  25

ATA ACC CTC AAA TAT GTC CCC GGG ATG GAT GTT TTG GTATGTAAAC        1986
Ile Thr Leu Lys Tyr Val Pro Gly Met Asp Val Leu
     30                  35
```

```
TACATTTCTG AGTTTCATTT TAGTAGCTCA TAGAAGAAAT GGGATCATTC ATATTGAGAT    2046

AGTACACTAG CTGCTATTTA GGAGCTTGCT TATTGTCAGG ATTTGAAGAA TTTATCTTTG    2106

GAATTTGACT TGCAGGCTTT TTTTTCCCCC TCTTCCTGTT ACAAGAGTCC CTCCTCCTAT    2166

TACAATAGTC CCTCCTCCTC CTGTCACACT AGTCCCTTCT CTTCCTGTTA CAATAACCCC    2226

TGTCCTCCTA TTACAACATT TTAAGTAATG TAATATTAAT TTTAAAAATC TGGCCAGGCA    2286

CGGTGGTTCA TGCTTGTAAT CCCAGCACAT TGGGAAGCTG AGACGGGTGG ATCATTTGAG    2346

GTCAGGAAGT TTGAGACAGC CTGGCCAACA TGGTGAAACT TCCTCTCTAC TAAAAATAAA    2406

AAAGTAGCCA GGCATGGTGG CAGGCACTTG TAATCTGAGC TACTCGAGAG GCTGAGGCAG    2466

GAGAATCACT TGAGTAACTA AAACGATAGC TTTGAAGAGT ACTCCGAGTT TTATGGCACT    2526

TACTTATTAA AATAGCTGTT TTGTCTCTTT TTTCATATCT TGCAG CCA AGT CAT        2580
                                                Pro Ser His
                                                 40

TGT TGG ATA AGC GAG ATG GTA GTA CAA TTG TCA GAC AGC TTG ACT GAT     2628
Cys Trp Ile Ser Glu Met Val Val Gln Leu Ser Asp Ser Leu Thr Asp
         45                  50                  55

CTT CTG GAC AAG TTT TCA AAT ATT TCT GAA GGC TTG AGT AAT TAT TCC     2676
Leu Leu Asp Lys Phe Ser Asn Ile Ser Glu Gly Leu Ser Asn Tyr Ser
     60                  65                  70

ATC ATA GAC AAA CTT GTG AAT ATA GTG GAT GAC CTT GTG GAG TGC GTG     2724
Ile Ile Asp Lys Leu Val Asn Ile Val Asp Asp Leu Val Glu Cys Val
 75                  80                  85                  90

AAA GAA AAC TCA TCT AAG GTAACTTTGT GTTCATTGGG ATTATTTTTC             2772
Lys Glu Asn Ser Ser Lys
             95

ATTACGCTTC TCTAAAAACC CATGCTTCTT GGTGCTGTTG GGGAAAATGA GGCACCTTTA    2832

TTTATGATAT TTTGATTGTA TAAACTTCAA ATTTAAAAAT CTTGTTCAGA TGAGCAAAGA    2892

AAACAAGTAT TTGCAGTTAT ACTGCAATAC TGAAGTGCAC ATTCTTGTGT TCACTGCCCC    2952

AGATTCAACT TGTGATCCCA CTGGGATCAC TACCCTGCAT TACCAATCTG AATTACATAC    3012

GTTAAAACAG CCATCTAAAA GTGCTAGTTG TAAGAGTCTA ATACTTGAA TCTTTGAGAG     3072

ACATATTTAT AGTCCATTAT CTTCACCTCA GTTAAGTCTG AAGACTATTT GAAAAATGTA    3132

ATCCTATTTT TTCTTCTAG GAT CTA AAA AAA TCA TTC AAG AGC CCA GAA CCC   3184
                     Asp Leu Lys Lys Ser Phe Lys Ser Pro Glu Pro
                                    100                 105

AGG CTC TTT ACT CCT GAA GAA TTC TTT AGA ATT TTT AAT AGA TCC ATT     3232
Arg Leu Phe Thr Pro Glu Glu Phe Phe Arg Ile Phe Asn Arg Ser Ile
         110                 115                 120

GAT GCC TTC AAG GAC TTT GTA GTG GCA TCT GAA ACT AGT GAT TGT GTG     3280
Asp Ala Phe Lys Asp Phe Val Val Ala Ser Glu Thr Ser Asp Cys Val
     125                 130                 135

GTT TCT TCA ACA TTA AGT CCT GAG AAA GGTAAGACAT GTAAGCATTT           3327
Val Ser Ser Thr Leu Ser Pro Glu Lys
140                 145

CCAGTTCAAA TGTAAACAAC AAACTTAAAT CTTCCCTATG TAGTAAGAAT CTACCTCTGT    3387

GTTAAGCTGT AGCAAGATAC ATGCATGTAC GTCTAATAAA AAAGCAGATA TCAATAGCAC    3447

AGAAGAAACT CTATAACTCA TACAAATCAC CATATAACAC TGACACATTA TTGCTTTCTA    3507

TTTAG ATT CCA GAG TCA GTG TCA CAA AAC CAT TTA TGT TAC CCC CTG       3554
      Ile Pro Glu Ser Val Ser Gln Asn His Leu Cys Tyr Pro Leu
             150                 155                 160

TTG CAG CCA GCT CCC TTA GGA ATG ACA GCA GTA GCA GTA ATAGTAAGTA      3603
Leu Gln Pro Ala Pro Leu Gly Met Thr Ala Val Ala Val
             165                 170                 175
```

```
CATATATCTG ATTTAATGCA TGCATGGCTC CAATTAGCAC CTATAGGAGT ATTGCATGGG    3663

CTTTCAAGGA AACTTCTACA TTTATTATTA TTGATACTGT TCTGTTACTG TTATTCCTTT    3723

TATGGTCTTC TTGAGACTTA AGTTTGTAGA ATTAAATTTC CCTAGAGCTG GAGATAATGT    3783

TTAGAGAATT AGGCCAATAA ATTT                                          3807
```

(2) INFORMATION FOR SEQ ID NO:44:

(i) SEQUENCE CHARACTERISTICS:
        (A) LENGTH: 195 amino acids
        (B) TYPE: amino acid
        (D) TOPOLOGY: linear (ii) MOLECULE TYPE: protein (xi) SEQUENCE DESCRIPTION: SEQ ID NO:44:

```
Thr Trp Ile Leu Thr Cys Ile Tyr Leu Gln Leu Leu Phe Asn Pro
-20             -15                 -10                  -5

Leu Val Lys Thr Glu Gly Ile Cys Arg Asn Arg Val Thr Asn Asn Val
              1               5                   10

Lys Asp Val Thr Lys Leu Val Ala Asn Leu Pro Lys Asp Tyr Met Ile
             15                  20                  25

Thr Leu Lys Tyr Val Pro Gly Met Asp Val Leu Pro Ser His Cys Trp
         30                  35                  40

Ile Ser Glu Met Val Val Gln Leu Ser Asp Ser Leu Thr Asp Leu Leu
 45                  50                  55                  60

Asp Lys Phe Ser Asn Ile Ser Glu Gly Leu Ser Asn Tyr Ser Ile Ile
                  65                  70                  75

Asp Lys Leu Val Asn Ile Val Asp Asp Leu Val Glu Cys Val Lys Glu
             80                  85                  90

Asn Ser Ser Lys Asp Leu Lys Lys Ser Phe Lys Ser Pro Glu Pro Arg
             95                 100                 105

Leu Phe Thr Pro Glu Glu Phe Phe Arg Ile Phe Asn Arg Ser Ile Asp
         110                 115                 120

Ala Phe Lys Asp Phe Val Val Ala Ser Glu Thr Ser Asp Cys Val Val
125                 130                 135                 140

Ser Ser Thr Leu Ser Pro Glu Lys Ile Pro Glu Ser Val Ser Gln Asn
                145                 150                 155

His Leu Cys Tyr Pro Leu Leu Gln Pro Ala Pro Leu Gly Met Thr Ala
             160                 165                 170

Val Ala Val
     175
```

(2) INFORMATION FOR SEQ ID NO:45:

(i) SEQUENCE CHARACTERISTICS:
        (A) LENGTH: 820 base pairs
        (B) TYPE: nucleic acid
        (C) STRANDEDNESS: single
        (D) TOPOLOGY: linear (ii) MOLECULE TYPE:DNA (ix) FEATURE:
        (A) NAME/KEY: CDS
        (B) LOCATION: 17..640

(ix) FEATURE:
        (A) NAME/KEY: mat_peptide
        (B) LOCATION: 92..640

(xi) SEQUENCE DESCRIPTION: SEQ ID NO:45:

```
AAGCTTGCCT TTCCTT ATG AAG AAG ACA CAA ACT TGG ATT CTC ACT TGC              49
                  Met Lys Lys Thr Gln Thr Trp Ile Leu Thr Cys
                  -25             -20                 -15

ATT TAT CTT CAG CTG CTC CTA TTT AAT CCT CTC GTC AAA ACT GAA GGG             97
Ile Tyr Leu Gln Leu Leu Leu Phe Asn Pro Leu Val Lys Thr Glu Gly
            -10                 -5                   1

ATC TGC AGG AAT CGT GTG ACT AAT AAT GTA AAA GAC GTC ACT AAA TTG            145
Ile Cys Arg Asn Arg Val Thr Asn Asn Val Lys Asp Val Thr Lys Leu
        5                   10                  15

GTG GCA AAT CTT CCA AAA GAC TAC ATG ATA ACC CTC AAA TAT GTC CCC            193
Val Ala Asn Leu Pro Lys Asp Tyr Met Ile Thr Leu Lys Tyr Val Pro
    20                  25                  30

GGG ATG GAT GTT TTG CCA AGT CAT TGT TGG ATA AGC GAG ATG GTA GTA            241
Gly Met Asp Val Leu Pro Ser His Cys Trp Ile Ser Glu Met Val Val
35                  40                  45                  50

CAA TTG TCA GAC AGC TTG ACT GAT CTT CTG GAC AAG TTT TCA AAT ATT            289
Gln Leu Ser Asp Ser Leu Thr Asp Leu Leu Asp Lys Phe Ser Asn Ile
                55                  60                  65

TCT GAA GGC TTG AGT AAT TAT TCC ATA ATA GAC AAA CTT GTG AAT ATA            337
Ser Glu Gly Leu Ser Asn Tyr Ser Ile Ile Asp Lys Leu Val Asn Ile
            70                  75                  80

GTG GAT GAC CTT GTG GAG TGC GTG AAA GAA AAC TCA TCT AAG GAT CTA            385
Val Asp Asp Leu Val Glu Cys Val Lys Glu Asn Ser Ser Lys Asp Leu
        85                  90                  95

AAA AAA TCA TTC AAG AGC CCA GAA CCC AGG CTC TTT ACT CCT GAA GAA            433
Lys Lys Ser Phe Lys Ser Pro Glu Pro Arg Leu Phe Thr Pro Glu Glu
    100                 105                 110

TTC TTT AGA ATT TTT AAT AGA TCC ATT GAT GCC TTC AAG GAC TTT GTA            481
Phe Phe Arg Ile Phe Asn Arg Ser Ile Asp Ala Phe Lys Asp Phe Val
115                 120                 125                 130

GTG GCA TCT GAA ACT AGT GAT TGT GTG GTT TCT TCA ACA TTA AGT CCT            529
Val Ala Ser Glu Thr Ser Asp Cys Val Val Ser Ser Thr Leu Ser Pro
                135                 140                 145

GAG AAA GAT TCC AGA GTC AGT GTC ACA AAA CCA TTT ATG TTA CCC CCT            577
Glu Lys Asp Ser Arg Val Ser Val Thr Lys Pro Phe Met Leu Pro Pro
            150                 155                 160

GTT GCA GCC AGC TCC CTT AGG AAT GAC AGC AGT AGC AGT AAT AGT AAG            625
Val Ala Ala Ser Ser Leu Arg Asn Asp Ser Ser Ser Ser Asn Ser Lys
        165                 170                 175

TAC ATA TAT CTG ATT TAATGCATGC ATGGCTCCAA TTAGCACCTA TAGGAGTATT            680
Tyr Ile Tyr Leu Ile
    180

GCATGGGCTT TCAAGGAAAC TTCTACATTT ATTATTATTG ATACTGTTCT GTTACTGTTA          740

TTCCTTTTAT GGTCTTCTTG AGACTTAAGT TTGTAGAATT AAATTTCCCT AGAGCTGGAG          800

ATAATGTTTA GAGAATTAGG                                                      820
```

(2) INFORMATION FOR SEQ ID NO:46:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO:46:

```
Met Lys Lys Thr Gln Thr Trp Ile Leu Thr Cys Ile Tyr Leu Gln Leu
-25                 -20                 -15                 -10
```

```
Leu Leu Phe Asn Pro Leu Val Lys Thr Glu Gly Ile Cys Arg Asn Arg
            -5                  1                   5

Val Thr Asn Asn Val Lys Asp Val Thr Lys Leu Val Ala Asn Leu Pro
        10                  15                  20

Lys Asp Tyr Met Ile Thr Leu Lys Tyr Val Pro Gly Met Asp Val Leu
    25                  30                  35

Pro Ser His Cys Trp Ile Ser Glu Met Val Val Gln Leu Ser Asp Ser
40                  45                  50                  55

Leu Thr Asp Leu Leu Asp Lys Phe Ser Asn Ile Ser Glu Gly Leu Ser
                60                  65                  70

Asn Tyr Ser Ile Ile Asp Lys Leu Val Asn Ile Val Asp Asp Leu Val
            75                  80                  85

Glu Cys Val Lys Glu Asn Ser Ser Lys Asp Leu Lys Lys Ser Phe Lys
            90                  95                  100

Ser Pro Glu Pro Arg Leu Phe Thr Pro Glu Glu Phe Phe Arg Ile Phe
    105                 110                 115

Asn Arg Ser Ile Asp Ala Phe Lys Asp Phe Val Val Ala Ser Glu Thr
120                 125                 130                 135

Ser Asp Cys Val Val Ser Ser Thr Leu Ser Pro Glu Lys Asp Ser Arg
                140                 145                 150

Val Ser Val Thr Lys Pro Phe Met Leu Pro Pro Val Ala Ala Ser Ser
            155                 160                 165

Leu Arg Asn Asp Ser Ser Ser Ser Asn Ser Lys Tyr Ile Tyr Leu Ile
        170                 175                 180

(2) INFORMATION FOR SEQ ID NO:47:

(i) SEQUENCE CHARACTERISTICS:
        (A) LENGTH: 5864 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: join(565..579, 1684..1797, 2693..2755, 3351..
            3521, 3932..4088, 4314..4397, 4778..4887, 5208..5275,
            5677..5713)

(ix) FEATURE:
        (A) NAME/KEY: mat_peptide
        (B) LOCATION: join(1744..1797, 2693..2755, 3351..3521, 3932
            ..4088, 4314..4397, 4778..4887, 5208..5275, 5677
            ..5713)

(xi) SEQUENCE DESCRIPTION: SEQ ID NO:47:

GAGCTCCGAG CCCTCTCTGG CGCGCGAGGT ATTTCGTCTG TNCCCGGGGG TGCCAGGTGA      60

GCCCCAGCGG ATCCGGGAGG GTAAGCTGGG ACTCCTCGCG AGCAGTAGCT GCAGGGTACC     120

AAGCTTCGCC CTCTGCGTCC CCGCGCCTTC GCGGTCTCCC GCCAGTGCAG GTCCGGGGCC     180

CCCAGGCGAG CGGACAAGGT TGGCCTAATC TGCCAAACTT CTGGGGCATT TACCGTGCTC     240

TGGCCGCCCT CCCGATTCTT CCCTCCGCGC CCTTGCCTGC TTCTCGCCTA CCCCGGGCTC     300

CGGAAGGGAA GGAGGCGTGT CCGGAGCAGG CGGGCGGGAA CTGTATAAAA GCGCCGGCGG     360

CTCAGCAGCC GGCTTCGCTC GCCGCCTCGC GCCGAGACTA GAAGCGCTGC GGGAAGCAGG     420

GACAGTGGAG AGGGCGCTGC GCTCGGGCTA CCCAATGCGT GGACTATCTG CCGCCGCTGT     480

TCGTGCAATA TGCTGGAGCT CCAGAACAGC TAAACGGAGT CGCCACACCA CTGTTTGTGC     540
```

```
                                                    -continued

TGGATCGCAC CGCTGCCTTT CCTT ATG AAG AAG ACA CAA GTGAGTAGGG           589
                         Met Lys Lys Thr Gln
                             -25

CGCGCCCGGG AGCTCCCAGG CTCTCCAGGA AAAATCGCGC CCGGTGCCCC GGGGAAGCCG   649

GCGCTCCCTG GGACTTGCAG CTGGGGCGTG CAGGGCTGTG CCTGCCGGGT GAGACAAGAG   709

GATGCGGGGG AGGCCGGCGT GGTGTGTGAT CCCGAGCCGA GCCGNNTGAG CCAGGGAGAA   769

AAGGAGTGGG AGTACTGAGA GGGAGCCAGT GTCAAGTTTG GAGCCTCAGC AGTTAAGTTT   829

TGAGCTGTCA GTCGGAAACC GTAATTCCCG TCTGGTGGAA AGATTGGCTT TTNGNCCACG   889

GAATGTAAGT TATCACAGAT ACTACAAAGA TAAATCAGTT GCACAAGTTC TTGAAACTCT   949

ACAGTGTAAT AAGGAAAAAT AAGTCATGCA TAAAAGCAAC TATAATACAT AATAGAAAAT  1009

GTTATTTTCA AGCCGATGTG TAGGTTATGT GTGTTCGAGA GAGAGAGAGA GAAGACAGAT  1069

TACTTTCTGC TAGGGTTCAA GAATGCCTTC CTGTTGGCTA AGGAAATATT TTCCTTAAGT  1129

GGCTAAAAAG CTGTGTTTCA AAATATTCTT TTGATGTCTC ACAAATTCAG TGGAATTCTC  1189

TTAGGTCTAA AAATATACAT CTCTCTCACT TTAACTTGGT GTGCTATTGT AGATTATTGG  1249

ATTAAAGCAC TGCTCAGGGA TTATGCTGCT TCTTGCCAAG CAGTCTACAT TTAAAGTAGA  1309

AATAAGATGT TTCTTTTGGT GCCATAAGGT ATACATTTTA TGCATTCTCT AGTTTTTAGA  1369

AGATACCCTA AGGGCTAAGT CTTTAACATG CTGCTACAAG TTTATTCCTA ATTGCCATTG  1429

GGAAATTGGC TGAAGAAAGT TTTAACAAA AGTTAACAAT ATTGTCATTG AGAGAATAAT  1489

TCAAAATGGA TTTTAACTAA AAGCTTTTAA AAACTTTGGT GAGCATAGCT TGAATGCGTA  1549

ATATTTAATT GCATTTAAGC CAATAACATA TATTAGACTG GTCTTTTTGT GCATCAAGGC  1609

ATTAGATGTT AAAAGTTTGA ATGATTACAG ATCTTAACTG ATGATCACCA AGCAATTTTT  1669

CTGTTTTCAT TTAG ACT TGG ATT CTC ACT TGC ATT TAT CTT CAG CTG CTC   1719
                Thr Trp Ile Leu Thr Cys Ile Tyr Leu Gln Leu Leu
                    -20                 -15                 -10

CTA TTT AAT CCT CTC GTC AAA ACT GAA GGG ATC TGC AGG AAT CGT GTG   1767
Leu Phe Asn Pro Leu Val Lys Thr Glu Gly Ile Cys Arg Asn Arg Val
            -5                  1                   5

ACT AAT AAT GTA AAA GAC GTC ACT AAA TTG GTAAGTAAGG AATGCTTTAC      1817
Thr Asn Asn Val Lys Asp Val Thr Lys Leu
    10                  15

CGTGCTGTGT AAAAAAGAGC TGTGGCTCTT TTTCCTGTGC TTGTTGATAA AAGATTTAGA  1877

TTTTTCTTGC CCCAAAGTAA TGTTTTCCTA AAGTGGGGAA AGTAATCACT GGGTTACAAT  1937

AAAGGGTTTA TAGAAAGCAG GTAGTGAGAT ATTTAGGGTC ATGGATAATT TGTTGGTAAA  1997

ACTGGCTAGT TGCACACCAC TGCTGTGACT GCTTCTTTGC TGGTCTTCTC CCCATCCTTC  2057

ATAGGCAGTG AAGGACCTTG GAGAGTTCGC TGTGTGCTGA TGGGCTTGCC CCAGCTTGTT  2117

CCCCATAATC TCTCCAGTGG GTTTCCCAGC ATGTTCTATT CCCCTTCACA TGTCTTCCTA  2177

CTCTTCTTTA AAAAGCCTAA CGAAAGGAAA TCTGAAATGG CTATTCTCCC AATTCAATCA  2237

GCAGGAAGAC CCTGTCACAT GTCAGTGGGT GTTTGCTCCT TCAGGAACA TAGAGAGGTG   2297

ATTCATTGCC CACATGTTGA AGGGACTCAT CTCCCTGGTT TGTCACATTG AACTCTTCCC  2357

TCAGCGAAAG CATTTGCATT GCTTCCCGAA TTCCAAGATC ACAGGTGGAA GCTGAAATTC  2417

AGATCATGTT TCCAAAACTC AGTAGGTTAT ACCTAGCCAG GCATAACTGA ATTTGGAGTC  2477

TAAAAGATCT GTATTATCAC TTTTTTATTT TGAAGGATGC CTTTTGATTA CAGAGGGAAA  2537

TCAAGGATTA AAAATCAATA TACATGTAAA TATTGAAATT CATTGGTAAC TTTAAAAAGC  2597

ACAACAGTTT TGTGTGCTTT TCTCCAAAGC ACTACAAATA TGATTAATTG ATGTATAAGA  2657
```

```
ATTTTCTTAT GGAATTTTTT TTTTTGTCTC TGTAG GTG GCA AAT CTT CCA AAA         2710
                                      Val Ala Asn Leu Pro Lys
                                                        20

GAC TAC ATG ATA ACC CTC AAA TAT GTC CCC GGG ATG GAT GTT TTG            2755
Asp Tyr Met Ile Thr Leu Lys Tyr Val Pro Gly Met Asp Val Leu
 25                  30                  35

GTATGTAAAC TACATTTCTG AGTTTCATTT TAGTAGCTCA TAGAAGAAAT GGGATCATTC      2815

ATATTGAGAT AGTACACTAG CTGCTATTTA GGAGCTTGCT TATTGTCAGG ATTTGAAGAA      2875

TTTATCTTTG GAATTTGACT TGCAGGCTTT TTTTTCCCCC TCTTCCTGTT ACAAGAGTCC      2935

CTCCTCCTAT TACAATAGTC CCTCCTCCTC CTGTCACACT AGTCCCTTCT CTTCCTGTTA      2995

CAATAACCCC TGTCCTCCTA TTACAACATT TTAAGTAATG TAATATTAAT TTTAAAAATC      3055

TGGCCAGGCA CGGTGGTTCA TGCTTGTAAT CCCAGCACAT GGGAAGCTG AGACGGGTGG       3115

ATCATTTGAG GTCAGGAAGT TTGAGACAGC CTGGCCAACA TGGTGAAACT TCCTCTCTAC      3175

TAAAAATAAA AAAGTAGCCA GGCATGGTGG CAGGCACTTG TAATCTGAGC TACTCGAGAG      3235

GCTGAGGCAG GAGAATCACT TGAGTAACTA AAACGATAGC TTTGAAGAGT ACTCCGAGTT      3295

TTATGGCACT TACTTATTAA AATAGCTGTT TTGTCTCTTT TTTCATATCT TGCAG CCA       3353
                                                             Pro
                                                              40

AGT CAT TGT TGG ATA AGC GAG ATG GTA GTA CAA TTG TCA GAC AGC TTG        3401
Ser His Cys Trp Ile Ser Glu Met Val Val Gln Leu Ser Asp Ser Leu
             45                  50                  55

ACT GAT CTT CTG GAC AAG TTT TCA AAT ATT TCT GAA GGC TTG AGT AAT        3449
Thr Asp Leu Leu Asp Lys Phe Ser Asn Ile Ser Glu Gly Leu Ser Asn
             60                  65                  70

TAT TCC ATC ATA GAC AAA CTT GTG AAT ATA GTG GAT GAC CTT GTG GAG        3497
Tyr Ser Ile Ile Asp Lys Leu Val Asn Ile Val Asp Asp Leu Val Glu
         75                  80                  85

TGC GTG AAA GAA AAC TCA TCT AAG GTAACTTTGT GTTCATTGGG ATTATTTTC        3551
Cys Val Lys Glu Asn Ser Ser Lys
         90                  95

ATTACGCTTC TCTAAAAACC CATGCTTCTT GGTGCTGTTG GGAAAATGA GGCACCTTTA       3611

TTTATGATAT TTTGATTGTA TAAACTTCAA ATTTAAAAAT CTTGTTCAGA TGAGCAAAGA      3671

AAACAAGTAT TTGCAGTTAT ACTGCAATAC TGAAGTGCAC TATTCTTGTG TTCACTGCCC      3731

CAGATTCAAC TTGTGATCCC ACTGGGATCA CTACCCTGCA TTACCAATCT GAATTACATA      3791

CGTTAAAACA GCCATCTAAA AGTGCTAGTT GTAAGAGTCT AAATACTTGA ATCTTTGAGA      3851

GACATATTTA TAGTCCATTA TCTTCACCTC AGTTAAGTCT GAAGACTATT TGAAAAATGT      3911

AATCCTATTT TTTCTTCTAG GAT CTA AAA AAA TCA TTC AAG AGC CCA GAA          3961
                       Asp Leu Lys Lys Ser Phe Lys Ser Pro Glu
                                        100                 105

CCC AGG CTC TTT ACT CCT GAA GAA TTC TTT AGA ATT TTT AAT AGA TCC        4009
Pro Arg Leu Phe Thr Pro Glu Glu Phe Phe Arg Ile Phe Asn Arg Ser
             110                 115                 120

ATT GAT GCC TTC AAG GAC TTT GTA GTG GCA TCT GAA ACT AGT GAT TGT        4057
Ile Asp Ala Phe Lys Asp Phe Val Val Ala Ser Glu Thr Ser Asp Cys
         125                 130                 135

GTG GTT TCT TCA ACA TTA AGT CCT GAG AAA G GTAAGACATG TAAGCATTTC        4108
Val Val Ser Ser Thr Leu Ser Pro Glu Lys
         140                 145

CAGTTCAAAT GTAAACAACA AACTTAAATC TTCCCTATGT AGTAAGAATC TACCTCTGTG      4168

TTAAGCTGTA GCAAGATACA TGCATGTACG TCTAAAAAAA AGCAGATATC AATAGCACAG      4228
```

| | | |
|---|---|---|
| AAGAAACTAA TGATTGTAGA TTTGTGGGCT CTATAACTCA TACAAATCAC CATATAACAC | | 4288 |
| TGACACATTA TTGCTTTCTA TTTAG AT TCC AGA GTC AGT GTC ACA AAA CCA<br>                                                 Asp Ser Arg Val Ser Val Thr Lys Pro<br>                                                        150                  155 | | 4339 |
| TTT ATG TTA CCC CCT GTT GCA GCC AGC TCC CTT AGG AAT GAC AGC AGT<br>Phe Met Leu Pro Pro Val Ala Ala Ser Ser Leu Arg Asn Asp Ser Ser<br>          160                  165                    170 | | 4387 |
| AGC AGT AAT A GTAAGTACAT ATATCTGATT TAATGCATGC ATGGCTCCAA<br>Ser Ser Asn<br>        175 | | 4437 |
| TTAGCACCTA TAGGAGTATT GCATGGGCTT TCAAGGAAAC TTCTACATTT ATTATTATTG | | 4497 |
| ATACTGTTCT GTTACTGTTA TTCCTTTTAT GGTCTTCTTG AGACTTAAGT TTGTAGAATT | | 4557 |
| AAATTTCCCT AGAGCTGGAG ATAATGTTTA GAGAATTAGG CCAATAAATT TTCTGCTGAG | | 4617 |
| GTTATTTTAA ATAAGACATA AAATTAATTT TAGAAATATG ATTTATGCCT TTGTTGAAT | | 4677 |
| CATTAACATA TATACAGAAA CAGTTAAAAC AACCACAGCA TAAGAGAAAA ACTTCTAGAA | | 4737 |
| TGGATATGCT GTATTCATCA GTGTGTTCTT TAAATTATAG GG AAG GCC AAA AAT<br>                                                     Arg Lys Ala Lys Asn<br>                                                                      180 | | 4791 |
| CCC CCT GGA GAC TCC AGC CTA CAC TGG CCA GCC ATG GCA TTG CCA GCA<br>Pro Pro Gly Asp Ser Ser Leu His Trp Pro Ala Met Ala Leu Pro Ala<br>          185                  190                    195 | | 4839 |
| TTG TTT TCT CTT ATA ATT GGC TTT GCT TTT GGA GCC TTA TAC TGG AAG<br>Leu Phe Ser Leu Ile Ile Gly Phe Ala Phe Gly Ala Leu Tyr Trp Lys<br>          200                  205                    210 | | 4887 |
| GTAAGTGGTA CCATTCCTTT TTTTAAAAAT ATGCTATGTT TACATAAATT ATCATCTTTT | | 4947 |
| TTTCCTCAAG AAATGATCCT TTAAGAAAAC AGTGAATCTA CCTTAGCTTA TACTAAACAA | | 5007 |
| AATTTAAATT TTATAAAGTT TCCTGTTTCT CATTATGTCT GGAGACAATC CCTCTAGCTG | | 5067 |
| ATAATTCACG CTTAAGAATT AGGAACTAAA ACTGTTATTG GAGTTATTGC CATAAAAGAT | | 5127 |
| AAAAGTGGAG TCCACTTACC TCTTAAATAT TAGACCATTC ATTGATTATT TTACAGTATA | | 5187 |
| TGTCTTTCTT CTTTTTCCAG AAG AGA CAG CCA AGT CTT ACA AGG GCA GTT<br>                                     Lys Arg Gln Pro Ser Leu Thr Arg Ala Val<br>                                                215                  220 | | 5237 |
| GAA AAT ATA CAA ATT AAT GAA GAG GAT AAT GAG ATA AG GTATTTTGTT<br>Glu Asn Ile Gln Ile Asn Glu Glu Asp Asn Glu Ile Ser<br>          225                  230                    235 | | 5285 |
| TTGCTAAATG TGTGCCCAAT CAAGCATGAC ATTGCCATTT CACACACTGT GTACCTGCCC | | 5345 |
| ATAATGTCTT TAAGAAGTCC TTCACTCATG ACAGTAGCTC CTAACCAGTG AGTCCCAACT | | 5405 |
| CTATCCATGT TTCTGATGTC TCACTCTCTC TTCGTATGTG TATATGCATA TACAGAGAAA | | 5465 |
| GAAATGTTTT AACTACTTGG AAAGACTACC TTAAGACAAA TGAAGTCTTC CCTCTTCCCT | | 5525 |
| ATAGTAATAA GAAGGTAGGC TCCCCCATTC AATTTTGCAA TCTTCTGCTA CTATATTTAC | | 5585 |
| AGAAAAGCTG CCTTTTACAA TGCCGAGATC ATGGTGTACC TCAGAATCTC TGACCAAGAG | | 5645 |
| CAAATAAGCA TTTTTTCTTA TTGTTTTTCA G T ATG TTG CAA GAG AAA GAG AGA<br>                                         Met Leu Gln Glu Lys Glu Arg<br>                                                      240 | | 5698 |
| GAG TTT CAA GAA GTG TAATTGTGGC TTGTATCAAC ACTGTTACTT TCGTACATTG<br>Glu Phe Gln Glu Val<br>          245 | | 5753 |
| GTAAGTTTTT TTCTTCTTTC CTTTTTTTTT CTTTTTTTTA TTATACTTTA AGTTCTAGGG | | 5813 |
| TACATGTGCA CAATGTGCAG GTTTGTTACG TATGTTTACA TGTGCCATGT T | | 5864 |

(2) INFORMATION FOR SEQ ID NO:48:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:48:

```
Met Lys Lys Thr Gln Thr Trp Ile Leu Thr Cys Ile Tyr Leu Gln Leu
-25                 -20                 -15                 -10

Leu Leu Phe Asn Pro Leu Val Lys Thr Glu Gly Ile Cys Arg Asn Arg
                -5                   1                   5

Val Thr Asn Asn Val Lys Asp Val Thr Lys Leu Val Ala Asn Leu Pro
            10                  15                  20

Lys Asp Tyr Met Ile Thr Leu Lys Tyr Val Pro Gly Met Asp Val Leu
        25                  30                  35

Pro Ser His Cys Trp Ile Ser Glu Met Val Val Gln Leu Ser Asp Ser
40                  45                  50                  55

Leu Thr Asp Leu Leu Asp Lys Phe Ser Asn Ile Ser Glu Gly Leu Ser
                60                  65                  70

Asn Tyr Ser Ile Ile Asp Lys Leu Val Asn Ile Val Asp Asp Leu Val
            75                  80                  85

Glu Cys Val Lys Glu Asn Ser Ser Lys Asp Leu Lys Lys Ser Phe Lys
            90                  95                  100

Ser Pro Glu Pro Arg Leu Phe Thr Pro Glu Gly Phe Phe Arg Ile Phe
105                 110                 115

Asn Arg Ser Ile Asp Ala Phe Lys Asp Phe Val Val Ala Ser Glu Thr
120                 125                 130                 135

Ser Asp Cys Val Val Ser Ser Thr Leu Ser Pro Glu Lys Asp Ser Arg
                140                 145                 150

Val Ser Val Thr Lys Pro Phe Met Leu Pro Pro Val Ala Ala Ser Ser
            155                 160                 165

Leu Arg Asn Asp Ser Ser Ser Ser Asn Arg Lys Ala Lys Asn Pro Pro
            170                 175                 180

Gly Asp Ser Ser Leu His Trp Pro Ala Met Ala Leu Pro Ala Leu Phe
185                 190                 195

Ser Leu Ile Ile Gly Phe Ala Phe Gly Ala Leu Tyr Trp Lys Lys Arg
200                 205                 210                 215

Gln Pro Ser Leu Thr Arg Ala Val Glu Asn Ile Gln Ile Asn Glu Glu
                220                 225                 230

Asp Asn Glu Ile Ser Met Leu Gln Glu Lys Glu Arg Glu Phe Gln Glu
            235                 240                 245

Val
```

(2) INFORMATION FOR SEQ ID NO:49:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

```
Met Lys Lys Thr Gln Thr Trp Ile Leu Thr Cys Ile Tyr Leu Gln Leu
1               5                   10                  15
```

```
Leu Leu Phe Asn Pro Leu Val Lys Thr Glu Gly Ile Cys Arg Asn Arg
             20                  25                  30

Val Thr Asn Asn Val Lys Asp Val Thr Lys Leu Val Ala Asn Leu Pro
             35                  40                  45

Lys Asp Tyr Met Ile Thr Leu Lys Tyr Val Pro Gly Met Asp Val Leu
 50                  55                  60

Pro Ser His Cys Trp Ile Ser Glu Met Val Val Gln Leu Ser Asp Ser
 65                  70                  75                  80

Leu Thr Asp Leu Leu Asp Lys Phe Ser Asn Ile Ser Glu Gly Leu Ser
             85                  90                  95

Asn Tyr Ser Ile Ile Asp Lys Leu Val Asn Ile Val Asp Asp Leu Val
            100                 105                 110

Glu Cys Val Lys Glu Asn Ser Lys Asp Leu Lys Lys Ser Phe Lys
            115                 120                 125

Ser Pro Glu Pro Arg Leu Phe Thr Pro Glu Glu Phe Phe Arg Ile Phe
130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
            180                 185                 190

Leu Arg Asn Asp Ser Ser Ser Asn Arg Lys Ala Lys Asn Pro Pro
            195                 200                 205

Gly Asp Ser Ser Leu His Trp Ala Ala Met Ala Leu Pro Ala Leu Phe
    210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
                260                 265                 270

Val (2) INFORMATION FOR SEQ ID NO:50:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

Met Lys Lys Thr Gln Thr Trp Ile Leu Thr Cys Ile Tyr Leu Gln Leu
 1                   5                  10                  15

Leu Leu Phe Asn Pro Leu Val Lys Thr Glu Gly Ile Cys Arg Asn Arg
             20                  25                  30

Val Thr Asn Asn Val Lys Asp Val Thr Lys Leu Val Ala Asn Leu Pro
             35                  40                  45

Lys Asp Tyr Met Ile Thr Leu Lys Tyr Val Pro Gly Met Asp Val Leu
 50                  55                  60

Pro Ser His Cys Trp Ile Ser Glu Met Val Val Gln Leu Ser Asp Ser
 65                  70                  75                  80
```

-continued

```
Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Asp Leu Val
                100                 105                 110

Glu Cys Val Lys Glu Asn Ser Ser Lys Asp Leu Lys Lys Ser Phe Lys
                115                 120                 125

Ser Pro Glu Pro Arg Leu Phe Thr Pro Glu Glu Phe Arg Ile Phe
        130                 135                 140

Asn Arg Ser Ile Asp Ala Phe Lys Asp Phe Ala Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
                180                 185                 190

Leu Arg Asn Asp Ser Ser Ser Asn Arg Lys Ala Lys Asn Pro Thr
            195                 200                 205

Gly Asp Ser Ser Leu His Trp Ala Ala Met Ala Leu Pro Ala Phe Phe
        210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Gly Lys Glu Arg Glu Phe Gln Glu
                260                 265                 270

Val
```

(2) INFORMATION FOR SEQ ID NO:51:

(i) SEQUENCE CHARACTERISTICS:
        (A) LENGTH: 274 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:51:

```
Met Lys Lys Thr Gln Thr Trp Ile Ile Thr Cys Ile Tyr Leu Gln Leu
1               5                   10                  15

Leu Leu Phe Asn Pro Leu Val Lys Thr Lys Gly Ile Cys Gly Lys Arg
                20                  25                  30

Val Thr Asp Asp Val Lys Asp Val Thr Lys Leu Val Ala Asn Leu Pro
                35                  40                  45

Lys Asp Tyr Lys Ile Ala Leu Lys Tyr Val Pro Gly Met Asp Val Leu
        50                  55                  60

Pro Ser His Cys Trp Ile Ser Val Met Val Glu Gln Leu Ser Val Ser
65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Lys Ile Val Asp Asp Leu Val
                100                 105                 110

Glu Cys Thr Glu Gly Tyr Ser Phe Glu Asn Val Lys Lys Ala Pro Lys
                115                 120                 125

Ser Pro Glu Leu Arg Leu Phe Thr Pro Glu Glu Phe Arg Ile Phe
        130                 135                 140

Asn Arg Ser Ile Asp Ala Phe Lys Asp Leu Glu Thr Val Ala Ser Lys
```

```
            145                 150                 155                 160
    Ser Ser Glu Cys Val Val Ser Ser Thr Leu Ser Pro Asp Lys Asp Ser
                    165                 170                 175

Arg Val Ser Val Thr Lys Pro Phe Met Leu Pro Pro Val Ala Ala Ser
                    180                 185                 190

Ser Leu Arg Asn Asp Ser Ser Ser Asn Arg Lys Ala Ser Asn Ser
                    195                 200                 205

Ile Gly Asp Ser Asn Leu Gln Trp Ala Ala Met Ala Leu Pro Ala Phe
                    210                 215                 220

Phe Ser Leu Val Ile Gly Phe Ala Phe Gly Ala Leu Tyr Trp Lys Lys
    225                 230                 235                 240

Lys Gln Pro Asn Leu Thr Arg Thr Val Glu Asn Ile Gln Ile Asn Glu
                    245                 250                 255

Glu Asp Asn Glu Ile Ser Met Leu Gln Glu Lys Glu Arg Glu Phe Gln
                    260                 265                 270

Glu Val (2) INFORMATION FOR SEQ ID NO:52:

(i) SEQUENCE CHARACTERISTICS:
        (A) LENGTH: 271 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:52:

Met Lys Thr Gln Thr Trp Ile Val Thr Cys Ile Tyr Leu Gln Leu Leu
    1               5                   10                  15

Phe Asn Pro Leu Val Lys Thr Lys Gly Leu Cys Arg Asn Arg Val Thr
                    20                  25                  30

Asp Asp Val Lys Asp Val Thr Lys Leu Val Ala Asn Leu Pro Lys Asp
                    35                  40                  45

Tyr Lys Ile Ala Leu Lys Tyr Val Pro Gly Met Asp Val Leu Pro Ser
    50                  55                  60

His Cys Trp Ile Ser Val Met Val Glu Gln Leu Ser Val Ser Leu Thr
    65                  70                  75                  80

Asp Leu Leu Asp Lys Phe Ser Asn Ile Ser Glu Gly Leu Ser Asn Tyr
                    85                  90                  95

Ser Ile Ile Asp Lys Leu Val Lys Ile Val Asp Asp Leu Val Glu Cys
                    100                 105                 110

Val Glu Gly His Ser Ser Glu Asn Val Lys Lys Ser Ser Lys Ser Pro
                    115                 120                 125

Glu Pro Arg Leu Phe Thr Pro Glu Glu Phe Phe Arg Ile Phe Asn Arg
                    130                 135                 140

Ser Ile Asp Ala Phe Lys Asp Leu Glu Met Val Ala Ser Lys Thr Ser
    145                 150                 155                 160

Glu Cys Val Val Ser Ser Thr Leu Ser Pro Glu Lys Asp Ser Arg Val
                    165                 170                 175

Ser Val Thr Lys Pro Phe Met Leu Pro Pro Val Ala Ala Ser Ser Leu
                    180                 185                 190

Arg Asn Asp Ser Ser Ser Asn Arg Lys Thr Asn Pro Ile Glu Asp
                    195                 200                 205

Ser Ser Ile Gln Trp Ala Val Met Ala Leu Pro Ala Cys Phe Ser Leu
    210                 215                 220
```

```
Val Ile Gly Phe Ala Phe Gly Ala Phe Tyr Trp Lys Lys Gln Pro
225                 230                 235                 240

Asn Leu Thr Arg Thr Val Glu Asn Ile Gln Ile Asn Glu Glu Asp Asn
                245                 250                 255

Glu Ile Ser Met Leu Gln Glu Lys Glu Arg Glu Phe Gln Glu Val
            260                 265                 270
```

(2) INFORMATION FOR SEQ ID NO:53:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

```
Met Lys Lys Thr Gln Thr Trp Ile Ile Thr Cys Ile Tyr Leu Gln Leu
1               5                   10                  15

Leu Leu Phe Asn Pro Leu Val His Thr Gln Gly Ile Cys Ser Asn Arg
            20                  25                  30

Val Thr Asp Asp Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
    50                  55                  60

Pro Ser His Cys Trp Ile Ser Glu Met Val Glu Gln Leu Ser Val Ser
65                  70                  75                  80

Leu Thr Asp Leu Leu Asp Lys Phe Ser Asn Ile Ser Glu Gly Leu Ser
                85                  90                  95

Asn Tyr Cys Ile Ile Asp Lys Leu Val Lys Ile Val Asp Asp Leu Val
            100                 105                 110

Glu Cys Met Glu His Ser Ser Glu Asn Val Lys Lys Ser Ser Lys Ser
            115                 120                 125

Pro Glu Pro Arg Gln Phe Thr Pro Glu Lys Phe Gly Ile Phe Asn
    130                 135                 140

Lys Ser Ile Asp Ala Phe Lys Asp Leu Glu Ile Val Ala Ser Lys Met
145                 150                 155                 160

Ser Glu Cys Val Ile Ser Ser Thr Ser Ser Pro Glu Lys Asp Ser Arg
            165                 170                 175

Val Ser Val Thr Lys Pro Phe Met Leu Pro Pro Val Ala Ala Ser Ser
            180                 185                 190

Leu Arg Asn Asp Ser Ser Ser Ser Asn Arg Lys Ala Ser Asn Ser Ile
        195                 200                 205

Glu Asp Ser Ser Leu Gln Trp Ala Ala Val Ala Leu Pro Ala Phe Phe
    210                 215                 220

Ser Leu Val Ile Gly Phe Ala Phe Gly Ala Phe Tyr Trp Lys Lys Lys
225                 230                 235                 240

Gln Pro Asn Leu Thr Arg Thr Val Glu Asn Arg Gln Ile Asn Glu Glu
                245                 250                 255

Asp Asn Glu Ile Ser Met Leu Gln Glu Lys Glu Arg Glu Phe Gln Glu
            260                 265                 270

Val
```

(2) INFORMATION FOR SEQ ID NO:54:

(i) SEQUENCE CHARACTERISTICS:
    (A) LENGTH: 273 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:54:

```
Met Lys Lys Thr Gln Thr Trp Ile Ile Thr Cys Ile Tyr Leu Gln Leu
1               5                   10                  15

Leu Leu Phe Asn Pro Leu Val Lys Thr Gln Glu Ile Cys Arg Asn Pro
            20                  25                  30

Val Thr Asp Asn Val Lys Asp Ile Thr Lys Leu Val Ala Asn Leu Pro
        35                  40                  45

Asn Asp Tyr Met Ile Thr Leu Asn Tyr Val Ala Gly Met Asp Val Leu
    50                  55                  60

Pro Ser His Cys Trp Leu Arg Asp Met Val Thr His Leu Ser Val Ser
65                  70                  75                  80

Leu Thr Thr Leu Leu Asp Lys Phe Ser Asn Ile Ser Glu Gly Leu Ser
                85                  90                  95

Asn Tyr Ser Ile Ile Asp Lys Leu Gly Lys Ile Val Asp Asp Leu Val
            100                 105                 110

Ala Cys Met Glu Glu Asn Ala Pro Leu Asn Val Lys Glu Ser Leu Lys
        115                 120                 125

Lys Pro Glu Thr Arg Asn Phe Thr Pro Glu Glu Phe Phe Ser Ile Phe
    130                 135                 140

Asn Arg Ser Ile Asp Ala Phe Lys Asp Phe Met Val Ala Ser Asp Thr
145                 150                 155                 160

Ser Asp Cys Val Leu Ser Ser Thr Leu Gly Pro Glu Lys Asp Ser Arg
                165                 170                 175

Val Ser Val Thr Lys Pro Phe Met Leu Pro Pro Val Ala Ala Ser Ser
            180                 185                 190

Leu Arg Asn Asp Ser Ser Ser Asn Arg Lys Ala Ala Lys Ser Pro
    195                 200                 205

Glu Asp Pro Gly Leu Gln Trp Thr Ala Met Ala Leu Pro Ala Leu Ile
    210                 215                 220

Ser Leu Val Ile Gly Phe Ala Phe Gly Ala Leu Tyr Trp Lys Lys Lys
225                 230                 235                 240

Gln Ser Ser Leu Thr Arg Ala Val Glu Asn Ile Gln Ile Asn Glu Glu
                245                 250                 255

Asp Asn Glu Ile Ser Met Leu Gln Gln Lys Glu Arg Glu Phe Gln Glu
            260                 265                 270

Val
```

(2) INFORMATION FOR SEQ ID NO:55:

(i) SEQUENCE CHARACTERISTICS:
    (A) LENGTH: 273 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:55:

```
Met Lys Lys Thr Gln Thr Trp Ile Ile Thr Cys Ile Tyr Leu Gln Leu
1               5                   10                  15
```

-continued

```
Leu Leu Phe Asn Pro Leu Val Lys Thr Lys Glu Ile Cys Gly Asn Pro
             20                  25                  30

Val Thr Asp Asn Val Lys Asp Ile Thr Lys Leu Val Ala Asn Leu Pro
         35                  40                  45

Asn Asp Tyr Met Ile Thr Leu Asn Tyr Val Ala Gly Met Asp Val Leu
 50                  55                  60

Pro Ser His Cys Trp Leu Arg Asp Met Val Ile Gln Leu Ser Leu Ser
 65                  70                  75                  80

Leu Thr Thr Leu Leu Asp Lys Phe Ser Asn Ile Ser Glu Gly Leu Ser
                 85                  90                  95

Asn Tyr Ser Ile Ile Asp Lys Leu Gly Lys Ile Val Asp Asp Leu Val
                100                 105                 110

Leu Cys Met Glu Glu Asn Ala Pro Lys Asn Ile Lys Glu Ser Pro Lys
             115                 120                 125

Arg Pro Glu Thr Arg Ser Phe Thr Pro Glu Glu Phe Phe Ser Ile Phe
130                 135                 140

Asn Arg Ser Ile Asp Ala Phe Lys Asp Phe Met Val Ala Ser Asp Thr
145                 150                 155                 160

Ser Asp Cys Val Leu Ser Ser Thr Leu Gly Pro Glu Lys Asp Ser Arg
                165                 170                 175

Val Ser Val Thr Lys Pro Phe Met Leu Pro Pro Val Ala Ala Ser Ser
            180                 185                 190

Leu Arg Asn Asp Ser Ser Ser Asn Arg Lys Ala Ala Lys Ala Pro
                195                 200                 205

Glu Asp Ser Gly Leu Gln Trp Thr Ala Met Ala Leu Pro Ala Leu Ile
        210                 215                 220

Ser Leu Val Ile Gly Phe Ala Phe Gly Ala Leu Tyr Trp Lys Lys Lys
225                 230                 235                 240

Gln Ser Ser Leu Thr Arg Ala Val Glu Asn Ile Gln Ile Asn Glu Glu
                245                 250                 255

Asp Asn Glu Ile Ser Met Leu Gln Gln Lys Glu Arg Glu Phe Gln Glu
                260                 265                 270

Val
```

(2) INFORMATION FOR SEQ ID NO:56:

(i) SEQUENCE CHARACTERISTICS:
      (A) LENGTH: 282 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:56:

```
Thr Trp Ile Ile Thr Cys Phe Cys Leu Gln Leu Leu Leu Leu Asn Pro
 1               5                  10                  15

Leu Val Lys Ala Gln Ser Ser Cys Gly Asn Pro Val Thr Asp Asp Val
             20                  25                  30

Asn Asp Ile Ala Lys Leu Val Gly Asn Leu Pro Asn Asp Tyr Leu Ile
             35                  40                  45

Thr Leu Lys Tyr Val Pro Lys Met Asp Ser Leu Pro Asn His Cys Trp
 50                  55                  60

Leu His Leu Met Val Pro Glu Phe Ser Arg Ser Leu His Asn Leu Leu
 65                  70                  75                  80

Gln Lys Phe Ser Asp Ile Ser Asp Met Ser Asp Val Leu Ser Asn Tyr
```

```
                85                  90                  95
Ser Ile Ile Asn Asn Leu Thr Arg Ile Ile Asn Asp Leu Met Ala Cys
            100                 105                 110

Leu Ala Phe Asp Lys Asn Lys Asp Phe Ile Lys Glu Asn Gly Leu His
            115                 120                 125

Tyr Glu Glu Asp Arg Phe Ile Pro Glu Asn Phe Phe Arg Leu Phe Asn
            130                 135                 140

Ser Thr Ile Glu Val Tyr Lys Glu Phe Ala Asp Ser Leu Asp Lys Asn
145                 150                 155                 160

Asp Cys Ile Met Pro Ser Thr Val Glu Thr Pro Glu Asn Asp Ser Arg
            165                 170                 175

Val Ala Val Thr Lys Thr Ile Ser Phe Pro Pro Val Ala Ala Ser Ser
            180                 185                 190

Leu Arg Asn Asp Ser Ile Gly Ser Asn Thr Ser Ser Asn Ser Asn Lys
            195                 200                 205

Glu Ala Leu Gly Phe Ile Ser Ser Ser Leu Gln Gly Ile Ser Ile
            210                 215                 220

Ala Leu Thr Ser Leu Leu Ser Leu Leu Ile Gly Phe Ile Leu Gly Ala
225                 230                 235                 240

Ile Tyr Trp Lys Lys Thr His Pro Lys Ser Arg Pro Glu Ser Asn Glu
            245                 250                 255

Thr Ile Gln Cys His Gly Cys Gln Glu Glu Asn Glu Ile Ser Met Leu
            260                 265                 270

Gln Gln Lys Glu Lys Glu His Leu Gln Val
            275                 280

(2) INFORMATION FOR SEQ ID NO:57:

(i) SEQUENCE CHARACTERISTICS:
        (A) LENGTH: 266 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:57:

Met Lys Lys Thr Gln Thr Trp Ile Ile Thr Cys Ile Tyr Leu Gln Leu
1               5                   10                  15

Leu Leu Phe Asn Pro Leu Val Lys Thr Gly Ile Cys Arg Asn Arg Val
            20                  25                  30

Thr Asp Val Lys Asp Val Thr Lys Leu Val Ala Asn Leu Pro Lys Asp
            35                  40                  45

Tyr Met Ile Thr Leu Lys Tyr Val Pro Gly Met Asp Val Leu Pro Ser
            50                  55                  60

His Cys Trp Ile Ser Glu Met Val Gln Leu Ser Val Ser Leu Thr
65                  70                  75                  80

Asp Leu Leu Asp Lys Phe Ser Asn Ile Ser Glu Gly Leu Ser Asn Tyr
            85                  90                  95

Ser Ile Ile Asp Lys Leu Val Lys Ile Val Asp Asp Leu Val Glu Cys
            100                 105                 110

Glu Glu Asn Ser Ser Lys Asn Val Lys Lys Ser Lys Ser Pro Glu Pro
            115                 120                 125

Arg Leu Phe Thr Pro Glu Glu Phe Phe Arg Ile Phe Asn Arg Ser Ile
            130                 135                 140

Asp Ala Phe Lys Asp Phe Met Val Ala Ser Lys Thr Ser Asp Cys Val
```

```
                145                 150                 155                 160
            Val Ser Ser Thr Leu Ser Pro Glu Lys Asp Ser Arg Val Ser Val Thr
                            165                 170                 175
            Lys Pro Phe Met Leu Pro Pro Val Ala Ala Ser Ser Leu Arg Asn Asp
                        180                 185                 190
            Ser Ser Ser Asn Arg Lys Ala Asn Glu Asp Ser Ser Leu Gln Trp
                    195                 200                 205
            Ala Ala Met Ala Leu Pro Ala Leu Phe Ser Leu Val Ile Gly Phe Ala
                210                 215                 220
            Phe Gly Ala Leu Tyr Trp Lys Lys Lys Gln Pro Ser Leu Thr Arg Ala
            225                 230                 235                 240
            Val Glu Asn Ile Gln Ile Asn Glu Glu Asp Asn Glu Ile Ser Met Leu
                            245                 250                 255
            Gln Glu Lys Glu Arg Glu Phe Gln Glu Val
                        260                 265

(2) INFORMATION FOR SEQ ID NO:58:

(i) SEQUENCE CHARACTERISTICS:
        (A) LENGTH: 269 base pairs
        (B) TYPE: nucleic acid
        (C) STRANDEDNESS: single
        (D) TOPOLOGY: linear (ii) MOLECULE TYPE:DNA (ix) FEATURE:
        (A) NAME/KEY: CDS
        (B) LOCATION: join(1..210, 223..258)

(xi) SEQUENCE DESCRIPTION: SEQ ID NO:58:

GAA TTC TTC CGT ATC TTC AAC CGT TCC ATC GAC GCT TTC AAA GAC TTC       48
Glu Phe Phe Arg Ile Phe Asn Arg Ser Ile Asp Ala Phe Lys Asp Phe
  1               5                  10                  15

GTT GTT GCT TCC GAA ACC TCC GAC TGC GTT GTT TCC TCC ACC CTG TCT       96
Val Val Ala Ser Glu Thr Ser Asp Cys Val Val Ser Ser Thr Leu Ser
                 20                  25                  30

CCG GAA AAA GAC TCC CGT GTT TCG GTT ACC AAA CCG TTC ATG CTG CCG      144
Pro Glu Lys Asp Ser Arg Val Ser Val Thr Lys Pro Phe Met Leu Pro
             35                  40                  45

CCG GTT GCT GCT TCC TCC CTG CGT AAC GAC TCC TCC TCC TCC AAC TCC      192
Pro Val Ala Ala Ser Ser Leu Arg Asn Asp Ser Ser Ser Ser Asn Ser
         50                  55                  60

AAA TAC ATC TAC CTG ATC TAATAGGATC CG GTT ACC AAA CCG TTC ATG        240
Lys Tyr Ile Tyr Leu Ile             Val Thr Lys Pro Phe Met
 65              70                                  75

CTG CCG CCG GTT GCT GCT TAATAGGATC C                                 269
Leu Pro Pro Val Ala Ala
             80

(2) INFORMATION FOR SEQ ID NO:59:

(i) SEQUENCE CHARACTERISTICS:
        (A) LENGTH: 82 amino acids
        (B) TYPE: amino acid
        (D) TOPOLOGY: linear (ii) MOLECULE TYPE: protein (xi) SEQUENCE DESCRIPTION: SEQ ID NO:59:

Glu Phe Phe Arg Ile Phe Asn Arg Ser Ile Asp Ala Phe Lys Asp Phe
  1               5                  10                  15
```

```
Val Val Ala Ser Glu Thr Ser Asp Cys Val Ser Ser Thr Leu Ser
            20                  25                  30

Pro Glu Lys Asp Ser Arg Val Ser Val Thr Lys Pro Phe Met Leu Pro
        35                  40                  45

Pro Val Ala Ala Ser Ser Leu Arg Asn Asp Ser Ser Ser Asn Ser
    50                  55                  60

Lys Tyr Ile Tyr Leu Ile Val Thr Lys Pro Phe Met Leu Pro Pro Val
65                  70                  75                  80

Ala Ala (2) INFORMATION FOR SEQ ID NO:60:

(i) SEQUENCE CHARACTERISTICS:
        (A) LENGTH: 1404 base pairs
        (B) TYPE: nucleic acid
        (C) STRANDEDNESS: single
        (D) TOPOLOGY: linear (ii) MOLECULE TYPE:DNA (ix) FEATURE:
        (A) NAME/KEY: CDS
        (B) LOCATION: 184..1002

(ix) FEATURE:
        (A) NAME/KEY: mat_peptide
        (B) LOCATION: 259..1002

(xi) SEQUENCE DESCRIPTION: SEQ ID NO:60:
```

| | |
|---|---|
| CCGCCTCGCG CCGAGACTAG AAGCGCTGCG GGAAGCAGGG ACAGTGGAGA GGGCGCTGCG | 60 |
| CTCGGGCTAC CCAATGCGTG GACTATCTGC CGCCGCTGTT CGTGCAATAT GCTGGAGCTC | 120 |
| CAGAACAGCT AAACGGAGTC GCCACACCAC TGTTTGTGCT GGATCGCAGC GCTGCCTTTC | 180 |

```
CTT ATG AAG AAG ACA CAA ACT TGG ATT CTC ACT TGC ATT TAT CTT CAG      228
    Met Lys Lys Thr Gln Thr Trp Ile Leu Thr Cys Ile Tyr Leu Gln
    -25                 -20                 -15

CTG CTC CTA TTT AAT CCT CTC GTC AAA ACT GAA GGG ATC TGC AGG AAT      276
Leu Leu Leu Phe Asn Pro Leu Val Lys Thr Glu Gly Ile Cys Arg Asn
-10                 -5                  1                   5

CGT GTG ACT AAT AAT GTA AAA GAC GTC ACT AAA TTG GTG GCA AAT CTT      324
Arg Val Thr Asn Asn Val Lys Asp Val Thr Lys Leu Val Ala Asn Leu
                10                  15                  20

CCA AAA GAC TAC ATG ATA ACC CTC AAA TAT GTC CCC GGG ATG GAT GTT      372
Pro Lys Asp Tyr Met Ile Thr Leu Lys Tyr Val Pro Gly Met Asp Val
            25                  30                  35

TTG CCA AGT CAT TGT TGG ATA AGC GAG ATG GTA GTA CAA TTG TCA GAC      420
Leu Pro Ser His Cys Trp Ile Ser Glu Met Val Val Gln Leu Ser Asp
        40                  45                  50

AGC TTG ACT GAT CTT CTG GAC AAG TTT TCA AAT ATT TCT GAA GGC TTG      468
Ser Leu Thr Asp Leu Leu Asp Lys Phe Ser Asn Ile Ser Glu Gly Leu
55                  60                  65                  70

AGT AAT TAT TCC ATC ATA GAC AAA CTT GTG AAT ATA GTG GAT GAC CTT      516
Ser Asn Tyr Ser Ile Ile Asp Lys Leu Val Asn Ile Val Asp Asp Leu
                75                  80                  85

GTG GAG TGC GTG AAA GAA AAC TCA TCT AAG GAT CTA AAA AAA TCA TTC      564
Val Glu Cys Val Lys Glu Asn Ser Ser Lys Asp Leu Lys Lys Ser Phe
            90                  95                  100

AAG AGC CCA GAA CCC AGG CTC TTT ACT CCT GAA GAA TTC TTT AGA ATT      612
Lys Ser Pro Glu Pro Arg Leu Phe Thr Pro Glu Glu Phe Phe Arg Ile
        105                 110                 115

TTT AAT AGA TCC ATT GAT GCC TTC AAG GAC TTT GTA GTG GCA TCT GAA      660
Phe Asn Arg Ser Ile Asp Ala Phe Lys Asp Phe Val Val Ala Ser Glu
```

-continued

```
             120                 125                 130
ACT AGT GAT TGT GTG GTT TCT TCA ACA TTA AGT CCT GAG AAA GAT TCC        708
Thr Ser Asp Cys Val Val Ser Ser Thr Leu Ser Pro Glu Lys Asp Ser
135                 140                 145                 150

AGA GTC AGT GTC ACA AAA CCA TTT ATG TTA CCC CCT GTT GCA GCC AGC        756
Arg Val Ser Val Thr Lys Pro Phe Met Leu Pro Pro Val Ala Ala Ser
                155                 160                 165

TCC CTT AGG AAT GAC AGC AGT AGC AGT AAT AGG AAG GCC AAA AAT CCC        804
Ser Leu Arg Asn Asp Ser Ser Ser Ser Asn Arg Lys Ala Lys Asn Pro
            170                 175                 180

CCT GGA GAC TCC AGC CTA CAC TGG GCA GCC ATG GCA TTG CCA GCA TTG        852
Pro Gly Asp Ser Ser Leu His Trp Ala Ala Met Ala Leu Pro Ala Leu
        185                 190                 195

TTT TCT CTT ATA ATT GGC TTT GCT TTT GGA GCC TTA TAC TGG AAG AAG        900
Phe Ser Leu Ile Ile Gly Phe Ala Phe Gly Ala Leu Tyr Trp Lys Lys
    200                 205                 210

AGA CAG CCA AGT CTT ACA AGG GCA GTT GAA AAT ATA CAA ATT AAT GAA        948
Arg Gln Pro Ser Leu Thr Arg Ala Val Glu Asn Ile Gln Ile Asn Glu
215                 220                 225                 230

GAG GAT AAT GAG ATA AGT ATG TTG CAA GAG AAA GAG AGA GAG TTT CAA        996
Glu Asp Asn Glu Ile Ser Met Leu Gln Glu Lys Glu Arg Glu Phe Gln
                235                 240                 245

GAA GTG TAATTGTGGC TTGTATCAAC ACTGTTACTT TCGTACATTG GCTGGTAACA        1052
Glu Val
GTTCATGTTT GCTTCATAAA TGAAGCAGCT TTAAACAAAT TCATATTCTG TCTGGAGTGA     1112

CAGACCACAT CTTTATCTGT TCTTGCTACC CATGACTTTA TATGGATGAT TCAGAAATTG    1172

GAACAGAATG TTTTACTGTG AAACTGGCAC TGAATTAATC ATCTATAAAG AAGAACTTGC    1232

ATGGAGCAGG ACTCTATTTT AAGGACTGCG GGACTTGGGT CTCATTTAGA ACTTGCAGCT    1292

GATGTTGGAA GAGAAAGCAC GTGTCTCAGA CTGCATGTAC CATTTGCATG GCTCCAGAAA    1352

TGTCTAAATG CTGAAAAAAC ACCTAGCTTT ATTCTTCAGA TACAAACTGC AG            1404
```

(2) INFORMATION FOR SEQ ID NO:61:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:61:

```
Met Lys Lys Thr Gln Thr Trp Ile Leu Thr Cys Ile Tyr Leu Gln Leu
-25                 -20                 -15                 -10

Leu Leu Phe Asn Pro Leu Val Lys Thr Glu Gly Ile Cys Arg Asn Arg
            -5                   1                   5

Val Thr Asn Asn Val Lys Asp Val Thr Lys Leu Val Ala Asn Leu Pro
        10                  15                  20

Lys Asp Tyr Met Ile Thr Leu Lys Tyr Val Pro Gly Met Asp Val Leu
    25                  30                  35

Pro Ser His Cys Trp Ile Ser Glu Met Val Val Gln Leu Ser Asp Ser
40                  45                  50                  55

Leu Thr Asp Leu Leu Asp Lys Phe Ser Asn Ile Ser Glu Gly Leu Ser
            60                  65                  70

Asn Tyr Ser Ile Ile Asp Lys Leu Val Asn Ile Val Asp Asp Leu Val
        75                  80                  85

Glu Cys Val Lys Glu Asn Ser Ser Lys Asp Leu Lys Lys Ser Phe Lys
    90                  95                  100
```

```
Ser Pro Glu Pro Arg Leu Phe Thr Pro Glu Glu Phe Arg Ile Phe
    105                 110                 115

Asn Arg Ser Ile Asp Ala Phe Lys Asp Phe Val Val Ala Ser Glu Thr
120                 125                 130                 135

Ser Asp Cys Val Val Ser Ser Thr Leu Ser Pro Glu Lys Asp Ser Arg
                140                 145                 150

Val Ser Val Thr Lys Pro Phe Met Leu Pro Pro Val Ala Ala Ser Ser
                155                 160                 165

Leu Arg Asn Asp Ser Ser Ser Asn Arg Lys Ala Lys Asn Pro Pro
                170                 175                 180

Gly Asp Ser Ser Leu His Trp Ala Ala Met Ala Leu Pro Ala Leu Phe
185                 190                 195

Ser Leu Ile Ile Gly Phe Ala Phe Gly Ala Leu Tyr Trp Lys Lys Arg
200                 205                 210                 215

Gln Pro Ser Leu Thr Arg Ala Val Glu Asn Ile Gln Ile Asn Glu Glu
                220                 225                 230

Asp Asn Glu Ile Ser Met Leu Gln Glu Lys Glu Arg Glu Phe Gln Glu
                235                 240                 245

Val (2) INFORMATION FOR SEQ ID NO:62:

(i) SEQUENCE CHARACTERISTICS:
        (A) LENGTH: 1088 base pairs
        (B) TYPE: nucleic acid
        (C) STRANDEDNESS: single
        (D) TOPOLOGY: linear (ii) MOLECULE TYPE: protein (ix) FEATURE:
        (A) NAME/KEY: CDS
        (B) LOCATION: 151..885

(ix) FEATURE:
        (A) NAME/KEY: mat_peptide
        (B) LOCATION: 226..885

(xi) SEQUENCE DESCRIPTION: SEQ ID NO:62:

AGCAGGGACA GTGGAGAGGG CGCTGCGCTC GGGCTACCCA ATGCGTGGAC TATCTGCCGC        60

CGCTGTTCGT GCAATATGCT GGAGCTCCAG AACAGCTAAA CGGAGTCGCC ACACCACTGT       120

TTGTGCTGGA TCGCAGCGCT GCCTTTCCTT ATG AAG AAG ACA CAA ACT TGG ATT       174
                                 Met Lys Lys Thr Gln Thr Trp Ile
                                     -25                 -20

CTC ACT TGC ATT TAT CTT CAG CTG CTC CTA TTT AAT CCT CTC GTC AAA        222
Leu Thr Cys Ile Tyr Leu Gln Leu Leu Leu Phe Asn Pro Leu Val Lys
        -15                 -10                  -5

ACT GAA GGG ATC TGC AGG AAT CGT GTG ACT AAT AAT GTA AAA GAC GTC        270
Thr Glu Gly Ile Cys Arg Asn Arg Val Thr Asn Asn Val Lys Asp Val
      1               5                  10                  15

ACT AAA TTG GTG GCA AAT CTT CCA AAA GAC TAC ATG ATA ACC CTC AAA        318
Thr Lys Leu Val Ala Asn Leu Pro Lys Asp Tyr Met Ile Thr Leu Lys
                20                  25                  30

TAT GTC CCC GGG ATG GAT GTT TTG CCA AGT CAT TGT TGG ATA AGC GAG        366
Tyr Val Pro Gly Met Asp Val Leu Pro Ser His Cys Trp Ile Ser Glu
                35                  40                  45

ATG GTA GTA CAA TTG TCA GAC AGC TTG ACT GAT CTT CTG GAC AAG TTT        414
Met Val Val Gln Leu Ser Asp Ser Leu Thr Asp Leu Leu Asp Lys Phe
        50                  55                  60
```

-continued

```
TCA AAT ATT TCT GAA GGC TTG AGT AAT TAT TCC ATC ATA GAC AAA CTT        462
Ser Asn Ile Ser Glu Gly Leu Ser Asn Tyr Ser Ile Ile Asp Lys Leu
 65                  70                  75

GTG AAT ATA GTG GAT GAC CTT GTG GAG TGC GTG AAA GAA AAC TCA TCT        510
Val Asn Ile Val Asp Asp Leu Val Glu Cys Val Lys Glu Asn Ser Ser
 80                  85                  90                  95

AAG GAT CTA AAA AAA TCA TTC AAG AGC CCA GAA CCC AGG CTC TTT ACT        558
Lys Asp Leu Lys Lys Ser Phe Lys Ser Pro Glu Pro Arg Leu Phe Thr
                    100                 105                 110

CCT GAA GAA TTC TTT AGA ATT TTT AAT AGA TCC ATT GAT GCC TTC AAG        606
Pro Glu Glu Phe Phe Arg Ile Phe Asn Arg Ser Ile Asp Ala Phe Lys
                115                 120                 125

GAC TTT GTA GTG GCA TCT GAA ACT AGT GAT TGT GTG GTT TCT TCA ACA        654
Asp Phe Val Val Ala Ser Glu Thr Ser Asp Cys Val Val Ser Ser Thr
            130                 135                 140

TTA AGT CCT GAG AAA GGG AAG GCC AAA AAT CCC CCT GGA GAC TCC AGC        702
Leu Ser Pro Glu Lys Gly Lys Ala Lys Asn Pro Pro Gly Asp Ser Ser
145                 150                 155

CTA CAC TGG GCA GCC ATG GCA TTG CCA GCA TTG TTT TCT CTT ATA ATT        750
Leu His Trp Ala Ala Met Ala Leu Pro Ala Leu Phe Ser Leu Ile Ile
160                 165                 170                 175

GGC TTT GCT TTT GGA GCC TTA TAC TGG AAG AAG AGA CAG CCA AGT CTT        798
Gly Phe Ala Phe Gly Ala Leu Tyr Trp Lys Lys Arg Gln Pro Ser Leu
                180                 185                 190

ACA AGG GCA GTT GAA AAT ATA CAA ATT AAT GAA GAG GAT AAT GAG ATA        846
Thr Arg Ala Val Glu Asn Ile Gln Ile Asn Glu Glu Asp Asn Glu Ile
                195                 200                 205

AGT ATG TTG CAA GAG AAA GAG AGA GAG TTT CAA GAA GTG TAATTGTGGC        895
Ser Met Leu Gln Glu Lys Glu Arg Glu Phe Gln Glu Val
                210                 215                 220

TTGTATCAAC ACTGTTACTT TCGTACATTG GCTGGTAACA GTTCATGTTT GCTTCATAAA     955

TGAAGCAGCT TTAAACAAAT TCATATTCTG TCTGGAGTGA CAGACCACAT CTTTATCTGT    1015

TCTTGCTACC CATGACTTTA TATGGATGAT TCAGAAATTG GAACAGAATG TTTTACTGTG    1075

AAACTGGCAC TGA                                                       1088
```

(2) INFORMATION FOR SEQ ID NO:63:

(i) SEQUENCE CHARACTERISTICS:
        (A) LENGTH: 245 amino acids
        (B) TYPE: amino acid
        (D) TOPOLOGY: linear (ii) MOLECULE TYPE: protein (xi) SEQUENCE DESCRIPTION: SEQ ID NO:63:

```
Met Lys Lys Thr Gln Thr Trp Ile Leu Thr Cys Ile Tyr Leu Gln Leu
-25                 -20                 -15                 -10

Leu Leu Phe Asn Pro Leu Val Lys Thr Glu Gly Ile Cys Arg Asn Arg
                 -5                   1                   5

Val Thr Asn Asn Val Lys Asp Val Thr Lys Leu Val Ala Asn Leu Pro
             10                  15                  20

Lys Asp Tyr Met Ile Thr Leu Lys Tyr Val Pro Gly Met Asp Val Leu
         25                  30                  35

Pro Ser His Cys Trp Ile Ser Glu Met Val Val Gln Leu Ser Asp Ser
 40                  45                  50                  55

Leu Thr Asp Leu Leu Asp Lys Phe Ser Asn Ile Ser Glu Gly Leu Ser
                 60                  65                  70

Asn Tyr Ser Ile Ile Asp Lys Leu Val Asn Ile Val Asp Asp Leu Val
```

```
                    75                  80                  85
Glu Cys Val Lys Glu Asn Ser Ser Lys Asp Leu Lys Lys Ser Phe Lys
            90                  95                 100
Ser Pro Glu Pro Arg Leu Phe Thr Pro Glu Glu Phe Phe Arg Ile Phe
        105                 110                 115
Asn Arg Ser Ile Asp Ala Phe Lys Asp Phe Val Val Ala Ser Glu Thr
120                 125                 130                 135
Ser Asp Cys Val Val Ser Ser Thr Leu Ser Pro Glu Lys Gly Lys Ala
                140                 145                 150
Lys Asn Pro Pro Gly Asp Ser Ser Leu His Trp Ala Ala Met Ala Leu
            155                 160                 165
Pro Ala Leu Phe Ser Leu Ile Ile Gly Phe Ala Phe Gly Ala Leu Tyr
        170                 175                 180
Trp Lys Lys Arg Gln Pro Ser Leu Thr Arg Ala Val Glu Asn Ile Gln
185                 190                 195
Ile Asn Glu Glu Asp Asn Glu Ile Ser Met Leu Gln Glu Lys Glu Arg
200                 205                 210                 215
Glu Phe Gln Glu Val
                220
```

(2) INFORMATION FOR SEQ ID NO:64:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:64:

```
Glu Glu Ile Cys Arg Asn Pro Val Thr Asp Asn Val Lys Asp Ile Thr
1               5                  10                  15
Lys Leu Val Ala Asn Leu Pro Asn Asp Tyr Met Ile Thr Leu Asn Tyr
            20                  25                  30
Val Ala Gly Met Asp Val Leu Pro Ser His Xaa Trp Leu Arg Asp
        35                  40                  45
```

(2) INFORMATION FOR SEQ ID NO:65:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

```
Ile Thr Thr Leu Asn Tyr Val Ala Gly Met
1               5                  10
```

(2) INFORMATION FOR SEQ ID NO:66:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

-continued

```
Val Ala Ser Asp Thr Ser Asp Cys Val Leu Ser Xaa Xaa Leu Gly Pro
1               5                   10                  15

Glu Lys Asp Ser Arg Val Ser Val Xaa Lys
            20                  25
```

(2) INFORMATION FOR SEQ ID NO:67:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

```
Asp Val Leu Pro Ser His Cys Trp Leu Arg Asp Met
1               5                   10
```

(2) INFORMATION FOR SEQ ID NO:68:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:68:

```
Glu Glu Asn Ala Pro Lys Asn Val Glu Ser Leu Lys Lys Pro Thr Arg
1               5                   10                  15

Asn Phe Thr Pro Glu Glu Phe Phe Ser Ile Phe Asp Arg Ser Ile Asp
            20                  25                  30

Ala
```

(2) INFORMATION FOR SEQ ID NO:69:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:69:

```
Glu Ser Leu Lys Lys Pro Glu Thr Arg
1               5
```

(2) INFORMATION FOR SEQ ID NO:70:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:70:

```
Val Ser Val Xaa Lys
1               5
```

(2) INFORMATION FOR SEQ ID NO:71:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:71:

Ile Val Asp Asp Leu Val Ala Ala Met Glu Glu Asn Ala Pro Lys
 1               5                  10                  15

(2) INFORMATION FOR SEQ ID NO:72:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:72:

Asn Phe Thr Pro Glu Glu Phe Phe Ser Ile Phe Xaa Arg
 1               5                  10

(2) INFORMATION FOR SEQ ID NO:73:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:73:

Leu Val Ala Asn Leu Pro Asn Asp Tyr Met Ile Thr Leu Asn Tyr Val
 1               5                  10                  15

Ala Gly Asp Asp Val Leu Pro Ser His Cys Trp Leu Arg
                20                  25

(2) INFORMATION FOR SEQ ID NO:74:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:74:

Ser Ile Asp Ala Phe Lys Asp Phe Met Val Ala Ser Asp Thr Ser Asp
 1               5                  10                  15

Cys Val Leu Ser Xaa Xaa Leu Gly
                20

(2) INFORMATION FOR SEQ ID NO:75:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:75:

```
Glu Ser Leu Lys Lys Pro Glu Thr Arg Asn Phe Thr Pro Glu Glu Phe
 1               5                  10                  15

Phe Ser Ile Phe Xaa Arg
                20
```

(2) INFORMATION FOR SEQ ID NO:76:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:76:

```
Glu Ser Leu Lys Lys Pro Glu Thr Arg Asn Phe Thr Pro Glu Glu Phe
 1               5                  10                  15

Phe Ser Ile Phe Asp Arg
                20
```

(2) INFORMATION FOR SEQ ID NO:77:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

```
Asn Ala Pro Lys Asn Val Lys Glu
 1               5
```

(2) INFORMATION FOR SEQ ID NO:78:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

```
Ser Arg Val Ser Val Xaa Lys Pro Phe Met Leu Pro Pro Val Ala Ala
 1               5                  10                  15
```

(2) INFORMATION FOR SEQ ID NO:79:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

```
Ser Leu Lys Lys Pro Glu Thr Arg Asn Phe Thr Pro Glu Glu Phe Phe
 1               5                  10                  15

Ser Ile Phe Asn Arg Ser Ile Asp Ala Phe Lys Asp Phe Met Val Ala
                20                  25                  30

Ser Asp
```

(2) INFORMATION FOR SEQ ID NO:80:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:80:

```
Ser Leu Lys Lys Pro Glu Thr Arg Asn Phe Thr Pro Glu Glu Phe Phe
1               5                   10                  15

Ser Ile Phe Asn Arg Ser Ile Asp Ala Phe Lys Asp Phe Met Val Ala
            20                  25                  30

Ser Asp Thr Ser Asp
        35
```

(2) INFORMATION FOR SEQ ID NO:81:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:81:

```
Leu Arg Asp Met Val Thr His Leu Ser Val Ser Leu Thr Thr Leu Leu
1               5                   10                  15

Asp Lys Phe Ser Asn Ile Ser Glu Gly Leu Ser Asn Tyr Ser Ile Ile
            20                  25                  30

Asp Lys Leu Gly Lys Ile Val Asp
        35                  40
```

(2) INFORMATION FOR SEQ ID NO:82:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:82:

```
Ser Arg Val Ser Val Thr Lys Pro Phe Met Leu Pro Pro Val Ala Ala
1               5                   10                  15
```

(2) INFORMATION FOR SEQ ID NO:83:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:83:

```
Pro Val Ala Ala
1
```

(2) INFORMATION FOR SEQ ID NO:84:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:84:

CCTGAGAAAG ATTCCAGAGTC                                                      21

(2) INFORMATION FOR SEQ ID NO:85:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:85:

CTGCAGTTTG TATCTGAAG                                                        19

(2) INFORMATION FOR SEQ ID NO:86:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:86:

CATATAAAGT CATGGGTAG                                                        19

(2) INFORMATION FOR SEQ ID NO:87:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:87:

ACTTGTGTCT TCTTCATAAG GAAAGGC                                               27

(2) INFORMATION FOR SEQ ID NO:88:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:88:

TGTACGAAAG TAACAGTGTT G                                                     21

(2) INFORMATION FOR SEQ ID NO:89:

(i) SEQUENCE CHARACTERISTICS:
            (A) LENGTH: 22 base pairs
            (B) TYPE: nucleic acid
            (C) STRANDEDNESS: single (D) TOPOLOGY: linear (ii) MOLECULE TYPE: DNA (xi) SEQUENCE DESCRIPTION: SEQ ID NO:89:

ACTGCTCCTA TTTAATCCTC TC                                        22

(2) INFORMATION FOR SEQ ID NO:90:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:90:

CACTGACTCT GGAATCTTTC TCA                                       23

(2) INFORMATION FOR SEQ ID NO:91:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:91:

TCGACCCGGA TCCCC                                                15

(2) INFORMATION FOR SEQ ID NO:92:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:92:

TCGAGGGGAT CCGGG                                                15

(2) INFORMATION FOR SEQ ID NO:93:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:93:

TCTTCTTCAT GGCGGCGGCA AGCTT                                     25

(2) INFORMATION FOR SEQ ID NO:94:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:94:

Asp Ser Arg Val Ser Val Xaa Lys Pro Phe Phe Met Leu Pro Pro Val
1               5                   10                  15

Ala Ala (2) INFORMATION FOR SEQ ID NO:95:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:95:

Asp Ser Arg Val Ser Val Thr Lys Pro Phe Phe Met Leu Pro Pro Val
1               5                   10                  15

Ala Ala (2) INFORMATION FOR SEQ ID NO:96:

(i) SEQUENCE CHARACTERISTICS:
            (A) LENGTH: 55 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:96:

CGATTTGATT CTAGAAGGAG GAATAACATA TGGTTAACGC GTTGGAATTC GGTAC          55

(2) INFORMATION FOR SEQ ID NO:97:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:97:

CGAATTCCAA CGCGTTAACC ATATGTTATT CCTCCTTCTA GAATCAAAT                 49

(2) INFORMATION FOR SEQ ID NO:98:

(i) SEQUENCE CHARACTERISTICS:
            (A) LENGTH: 9 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:98:

TATGCAGGA                                                              9

(2) INFORMATION FOR SEQ ID NO:99:

(i) SEQUENCE CHARACTERISTICS:
            (A) LENGTH: 11 base pairs
            (B) TYPE: nucleic acid
            (C) STRANDEDNESS: single
            (D) TOPOLOGY: linear -continued

```
        (ii) MOLECULE TYPE: DNA (xi) SEQUENCE DESCRIPTION: SEQ ID NO:99:

GATCTCCTGC A                                                          11

(2) INFORMATION FOR SEQ ID NO:100:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:100:

TATGGAAGGT ATCTGCA                                                    17

(2) INFORMATION FOR SEQ ID NO:101:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:101:

GATACCTTCC A                                                          11

(2) INFORMATION FOR SEQ ID NO:102:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:102:

TTTCCTTATG                                                            10

(2) INFORMATION FOR SEQ ID NO:103:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:103:

GCCGCCGCCA TG                                                         12

(2) INFORMATION FOR SEQ ID NO:104:

(i) SEQUENCE CHARACTERISTICS:
            (A) LENGTH: 25 base pairs
            (B) TYPE: nucleic acid
            (C) STRANDEDNESS: single
            (D) TOPOLOGY: linear
```

```
    (ii) MOLECULE TYPE: DNA (xi) SEQUENCE DESCRIPTION: SEQ ID NO:104:

TCTTCTTCAT GGCGGCGGCA AGCTT                                              25
```

STEM CELL FACTOR COMPOSITIONS

This is a divisional of U.S. application Ser. No. 09/005,893, filed Jan. 12, 1998, which is a divisional application of Ser. No. 08/449,653, which was filed May 24, 1995, now U.S. Pat. No. 6,248,319 issued June 19, 2001, which is a divisional application or U.S. application Ser. No. 08/172,329 filed Dec. 21, 1993, now U.S. Pat. No. 6,218,148 issued Apr. 17, 2001, which is a continuation of U.S. application Ser. No. 07/982,255 filed Nov. 25, 1992, now U.S. Pat. No. 6,204,363 issued Mar. 20, 2001, which is a continuation of U.S. application Ser. No. 07/684,535 filed Apr. 10, 1991, now abandoned, which is a continuation-in-part application of U.S. application Ser. No. 07/589,701 filed Oct. 1, 1990, now abandoned, which is a continuation-in-part application of U.S. application Ser. No. 07/573,616 filed Aug. 24, 1990, now abandoned, which is a continuation-in-part application of U.S. application Ser. No. 07/537,198 filed Jun. 11, 1990, now abandoned, which is a continuation-in-part application of U.S. application Ser. No. 07/422,383 filed Oct. 16, 1989, now abandoned, each of which are hereby incorporated by reference.

The present invention relates in general to novel factors which stimulate primitive progenitor cells including early hematopoietic progenitor cells, and to DNA sequences encoding such factors. In particular, the invention relates to these novel factors, to fragments and polypeptide analogs thereof and to DNA sequences encoding the same.

BACKGROUND OF THE INVENTION

The human blood-forming (hematopoietic) system is comprised of a variety of white blood cells (including neutrophils, macrophages, basophils, mast cells, eosinophils, T and B cells), red blood cells (erythrocytes) and clot-forming cells (megakaryocytes, platelets), It is believed that small amounts of certain hematopoietic growth factors account for the differentiation of a small number of "stem cells" into a variety of blood cell progenitors for the tremendous proliferation of those cells, and for the ultimate differentiation of mature blood cells from those lines. The hematopoietic regenerative system functions well under normal conditions. However, when stressed by chemotherapy, radiation, or natural myelodysplastic disorders, a resulting period during which patients are seriously leukopenic, anemic, or thrombocytopenic occurs. The development and the use of hematopoietic growth factors accelerates bone marrow regeneration during this dangerous phase.

In certain viral induced disorders, such as acquired autoimmune deficiency (AIDS) blood elements such as T cells may be specifically destroyed. Augmentation of T cell production may be therapeutic in such cases.

Because the hematopoietic growth factors are present in extremely small amounts, the detection and identification of these factors has relied upon an array of assays which as yet only distinguish among the different factors on the basis of stimulative effects on cultured cells under artificial conditions.

The application of recombinant genetic techniques has clarified the understanding of the biological activities of individual growth factors. For example, the amino acid and DNA sequences for human erythropoietin (EPO), which stimulates the production of erythrocytes, have been obtained. (See, Lin, U.S. Pat. No. 4,703,008, hereby incorporated by reference). Recombinant methods have also been applied to the isolation of cDNA for a human granulocyte colony-stimulating factor, G-CSF (See, Souza, U.S. Pat. No. 4,810,643, hereby incorporated by reference), and human granulocyte-macrophage colony stimulating factor (GM-CSF) [Lee, et al., *Proc. Natl. Acad. Sci. USA*, 82, 4360–4364 (1985); Wong, et al., Science, 228, 810–814 (1985)], murine G- and GM-CSF [Yokota, et al., *Proc. Natl. Acad. Sci. (USA)*, 81, 1070 (1984); Fung, et al., *Nature*, 307, 233 (1984); Gough, et al., *Nature*, 309, 763 (1984)], and human macrophage colony-stimulating factor (CSF-1) [Kawasaki, et al., *Science*, 230, 291 (1985)].

The High Proliferative Potential Colony Forming Cell (HPP-CFC) assay system tests for the action of factors on early hematopoietic progenitors [Zont, *J. Exp. Med.*, 159, 679–690 (1984)]. A number of reports exist in the literature for factors which are active in the HPP-CFC assay. The sources of these factors are indicated in Table 1. The most well characterized factors are discussed below.

An activity in human spleen conditioned medium has been termed synergistic factor (SF). Several human tissues and human and mouse cell lines produce an SF, referred to as SF-1, which synergizes with CSF-1 to stimulate the earliest HPP-CFC. SF-1 has been reported in media conditioned by human spleen cells, human placental cells, 5637 cells (a bladder carcinoma cell line), and EMT-6 cells (a mouse mammary carcinoma cell line). The identity of SF-1 has yet to be determined. Initial reports demonstrate overlapping activities of interleukin-1 with SF-1 from cell line 5637 [Zsebo et al., *Blood*, 71, 962–968 (1988)]. However, additional reports have demonstrated that the combination of interleukin-1 (IL-1) plus CSF-1 cannot stimulate the same colony formation as can be obtained with CSF-1 plus partially purified preparations of 5637 conditioned media [McNiece, *Blood*, 73, 919 (1989)].

The synergistic factor present in pregnant mouse uterus extract is CSF-1. WEHI-3 cells (murine myelomonocytic leukemia cell line) produce a synergistic factor which appears to be identical to IL-3. Both CSF-1 and IL-3 stimulate hematopoietic progenitors which are more mature than the target of SF-1.

Another class of synergistic factor has been shown to be present in conditioned media from TC-1 cells (bone marrow-derived stromal cells). This cell line produces a factor which stimulates both early myeloid and lymphoid cell types. It has been termed hemolymphopoietic growth factor 1 (HLGF-1). It has an apparent molecular weight of 120,000 [McNiece et al., *Exp. Hematol.*, 16, 383 (1988)].

Of the known interleukins and CSFS, IL-1, IL-3, and CSF-1 have been identified as possessing activity in the HPP-CFC assay. The other sources of synergistic activity mentioned in Table 1 have not been structurally identified. Based on the polypeptide sequence and biological activity profile, the present invention relates to a molecule which is distinct from IL-1, IL-3, CSF-1 and SF-1.

TABLE 1

Preparations Containing Factors Active in the HPP-CFC Assay

| Source[1] | Reference |
|---|---|
| Human Spleen CM | [Kriegler, Blood, 50, 503(1982)] |
| Mouse Spleen CM | [Bradley, Exp. Hematol. Today Baum, ed., 285 (1980)] |
| Rat Spleen CM | [Bradley, supra, (1980)] |
| Mouse lung CM | [Bradley, supra, (1980)] |
| Human Placental CM | [Kriegler, supra (1982)] |

TABLE 1-continued

Preparations Containing Factors Active
in the HPP-CFC Assay

| Source[1] | Reference |
| --- | --- |
| Pregnant Mouse Uterus | [Bradley, supra (1980)] |
| GTC-C CM | [Bradley, supra (1980)] |
| RH3 CM | [Bradley, supra (1980)] |
| PHA PBL | [Bradley, supra (1980)] |
| WEHI-38 CM | [McNiece, Cell Biol. Int. Rep., 6, 243(1982)] |
| EMT-6 CM | [McNiece, Exp. Hematol., 15, 854 (1987)] |
| L- Cell CM | [Kriegler, Exp. Hematol., 12, 844 (1984)] |
| 5637 CM | [Stanley, Cell, 45, 667 (1986)] |
| TC-1 CM | [Song, Blood, 66, 273 (1985)] |

[1]CM = Conditioned media.

When administered parenterally, proteins are often cleared rapidly from the circulation and may therefore elicit relatively short-lived pharmacological activity. Consequently, frequent injections of relatively large doses of bioactive proteins may be required to sustain therapeutic efficacy. Proteins modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified proteins [Abuchowski et al., In: "Enzymes as Drugs", Holcenberg et al., eds. Wiley-Interscience, New York, N.Y., 367–383 (1981), Newmark et al., J. Appl. Biochem. 4:185–189 (1982), and Katre et al., Proc. Natl. Acad. Sci. USA 84, 1487–1491 (1987)]. Such modifications may also increase the protein's solubility in aqueous solution, eliminate aggregation, enhance the physical and chemical stability of the protein, and greatly reduce the immunogenicity and antigenicity of the protein. As a result, the desired in vivo biological activity may be achieved by the administration of such polymer-protein adducts less frequently or in lower doses than with the unmodified protein.

Attachment of polyethylene glycol (PEG) to proteins is particularly useful because PEG has very low toxicity in mammals [Carpenter et al., Toxicol. Appl. Pharmacol., 18, 35–40 (1971)]. For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous proteins. For example, a PEG adduct of a human protein might be useful for the treatment of disease in other mammalian species without the risk of triggering a severe immune response.

Polymers such as PEG may be conveniently attached to one or more reactive amino acid residues in a protein such as the alpha-amino group of the amino-terminal amino acid, the epsilon amino groups of lysine side chains, the sulfhydryl groups of cysteine side chains, the carboxyl groups of aspartyl and glutamyl side chains, the alpha-carboxyl group of the carboxyl-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino, hydrazine or hydrazide groups are useful for reaction with aldehydes generated by periodate oxidation of carbohydrate groups in proteins.

It is an object of the present invention to provide a factor causing growth of early hematopoietic progenitor cells.

SUMMARY OF THE INVENTION

According to the present invention, novel factors, referred to herein as "stem cell factors" (SCF) having the ability to stimulate growth of primitive progenitors including early hematopoietic progenitor cells are provided. These SCFs also are able to stimulate non-hematopoietic stem cells such as neural stem cells and primordial germ stem cells. Such factors include purified naturally-occurring stem cell factors. The invention also relates to non-naturally-occurring polypeptides having amino acid sequences sufficiently duplicative of that of naturally-occurring stem cell factor to allow possession of a hematopoietic biological activity of naturally occurring stem cell factor.

The present invention also provides isolated DNA sequences for use in securing expression in procaryotic or eukaryotic host cells of polypeptide products having amino acid sequences sufficiently duplicative of that of naturally-occurring stem cell factor to allow possession of a hematopoietic biological activity of naturally occurring stem cell factor. Such DNA sequences include:

(a) DNA sequences set out in FIGS. 14B, 14C, 15B, 15C, 15D, 42 and 44 or their complementary strands;

(b) DNA sequences which hybridize to the DNA sequences defined in (a) or fragments thereof; and (c) DNA sequences which, but for the degeneracy of the genetic code, would hybridize to the DNA sequences defined in (a) and (b).

Also provided are vectors containing such DNA sequences, and host cells transformed or transfected with such vectors. Also comprehended by the invention are methods of producing SCF by recombinant techniques, and methods of treating disorders. Additionally, pharmaceutical compositions including SCF and antibodies specifically binding SCF are provided.

The invention also relates to a process for the efficient recovery of stem cell factor from a material containing SCF, the process comprising the steps of ion exchange chromatographic separation and/or reverse phase liquid chromatographic separation.

The present invention also provides a biologically-active adduct having prolonged in vivo half-life and enhanced potency in mammals, comprising SCF covalently conjugated to a water-soluble polymer such as polyethylene glycol or copolymers of polyethylene glycol and polypropylene glycol, wherein said polymer is unsubstituted or substituted at one end with an alkyl group. Another aspect of this invention resides in a process for preparing the adduct described above, comprising reacting the SCF with a water-soluble polymer having at least one terminal reactive group and purifying the resulting adduct to produce a product with extended circulating half-life and enhanced biological activity.

BRIEF DESCRIPTION OF THE DRAWINGS

FIG. 11 shows the amino acid sequence (SEQ ID NO. 1) of mammalian SCF derived from protein sequencing.

FIG. 12

A. oligonucleotides for rat SCF cDNA (SEQ ID NOS.: 2–19)

B. oligonucleotides for human SCF DNA (SEQ ID NOS.: 20–30)

C. universal oligonucleotides (SEQ ID NOS.: 31–38).

FIG. 13 shows

A. a scheme for polymerase chain reaction (PCR) amplification of rat SCF cDNA

B. a scheme for PCR amplification of human SCF cDNA.

FIG. 14 shows

A. sequencing strategy for rat genomic DNA

B. the nucleic acid sequence of rat (SEQ ID NOS.: 39 and 40) genomic DNA.

C. the nucleic acid sequence of rat SCF cDNA and amino acid sequence of rat SCF protein. (SEQ ID NOS.: 41 and 42).

FIG. 15 shows

A. the strategy for sequencing human genomic DNA

B. the nucleic acid sequence of human (SEQ ID NO).: 43 and 44) genomic DNA

C. the composite nucleic acid sequence of (SEQ ID NOS.: 45 and 46) human SCF cDNA and amino acid sequence of SCF protein.

D. the nucleic acid sequence of genomic DNA and amino acid sequence of human SCF protein, including (SEQ ID NOS.: 47 and 48) flanking regions and introns.

FIGS. 16A and B shows the aligned amino acid sequences of human, monkey, dog, mouse, and rat (SEQ ID NOS.: 49–57) SCF protein.

Figure 16C:
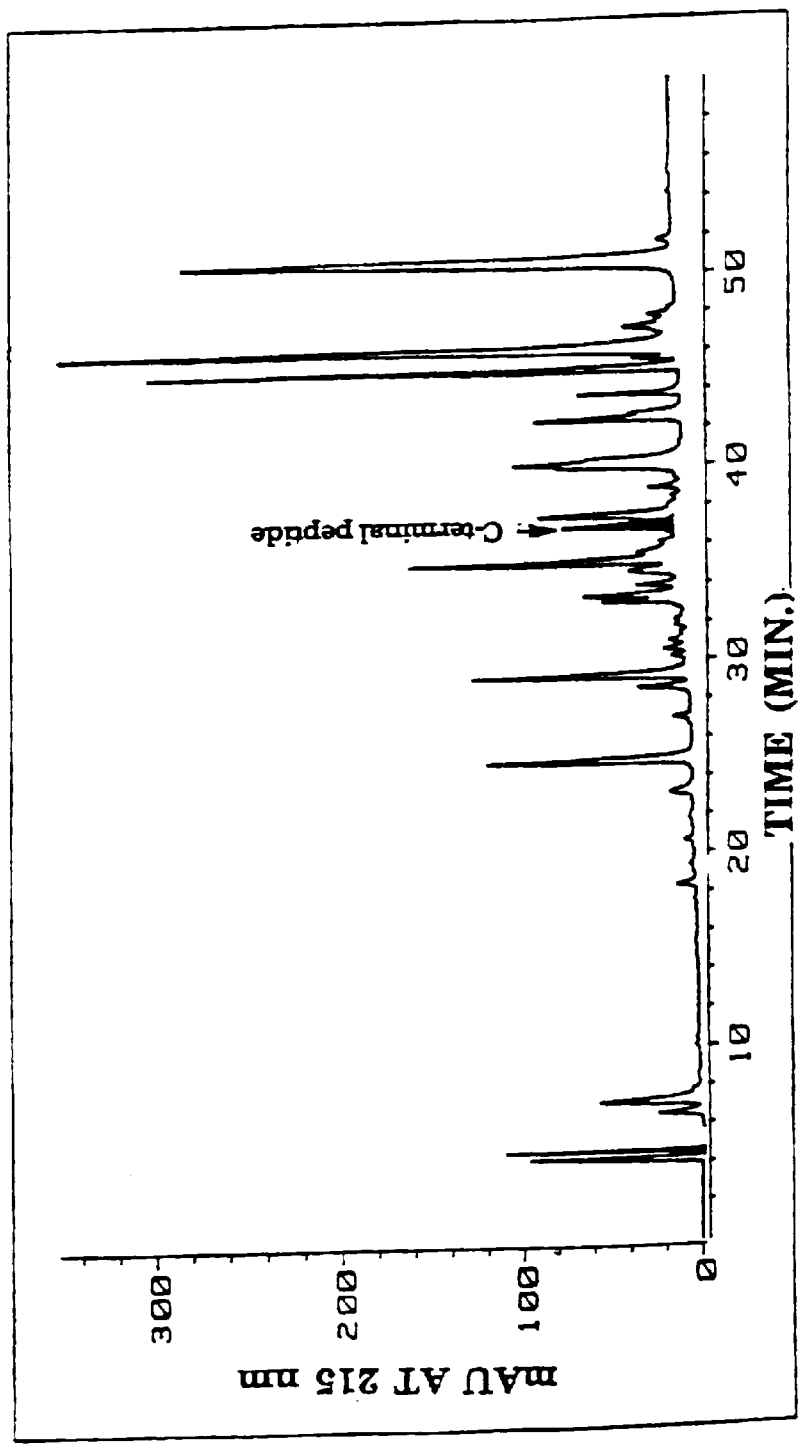

FIG. 16C shows an elution profile of $hSCF^{1-248}$ from CHO cells after AspN peptidase digestion and HPLC.

FIG. 16D shows the nucleotide sequence of the 221 base pair EcoRI-BamIII fragment constructed from (SEQ ID NOS.: 58 and 59) oligonucleotides that were used in creating the plasmid for human [Met$^{-1}$ ]SCF$^{1-165}$. Uppercase letters below the nucleotide sequence represent the amino acid sequence. Lowercase letters above the nucleotide sequence show nucleotides in the original hSCF$^{1-183}$ sequence that were altered to generate codons most frequently used by $E.$ $coli.$ FIG. 16E shows the 39 base pair BstEII-BamHI fragment used in creating the plasmid for human [Met$^{-1}$] SCF$^{1-165}$ with optimized C-terminal codons.

Figure 17:
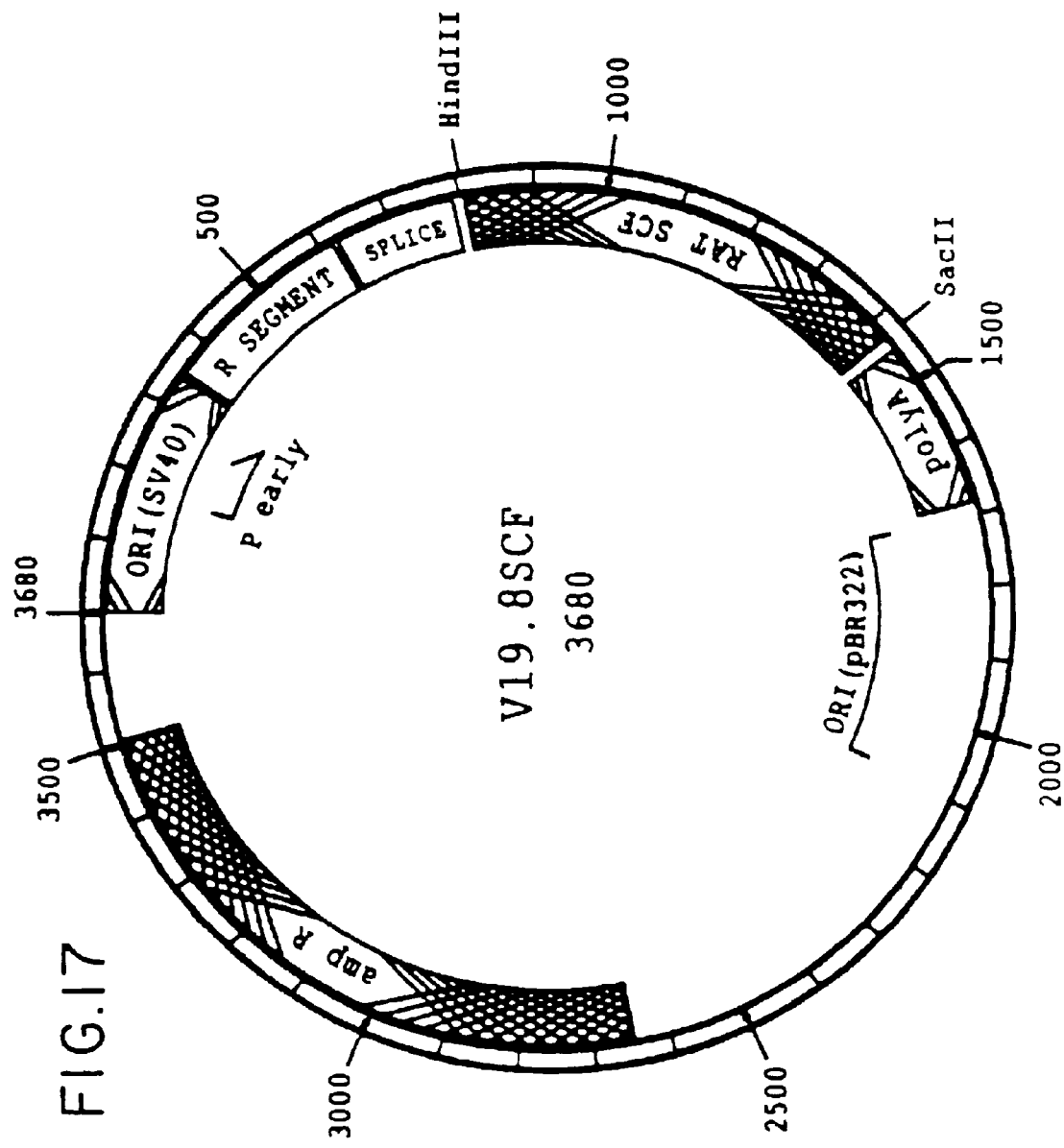

FIG. 17 shows the structure of mammalian cell expression vector V19.8 SCF.

Figure 18:
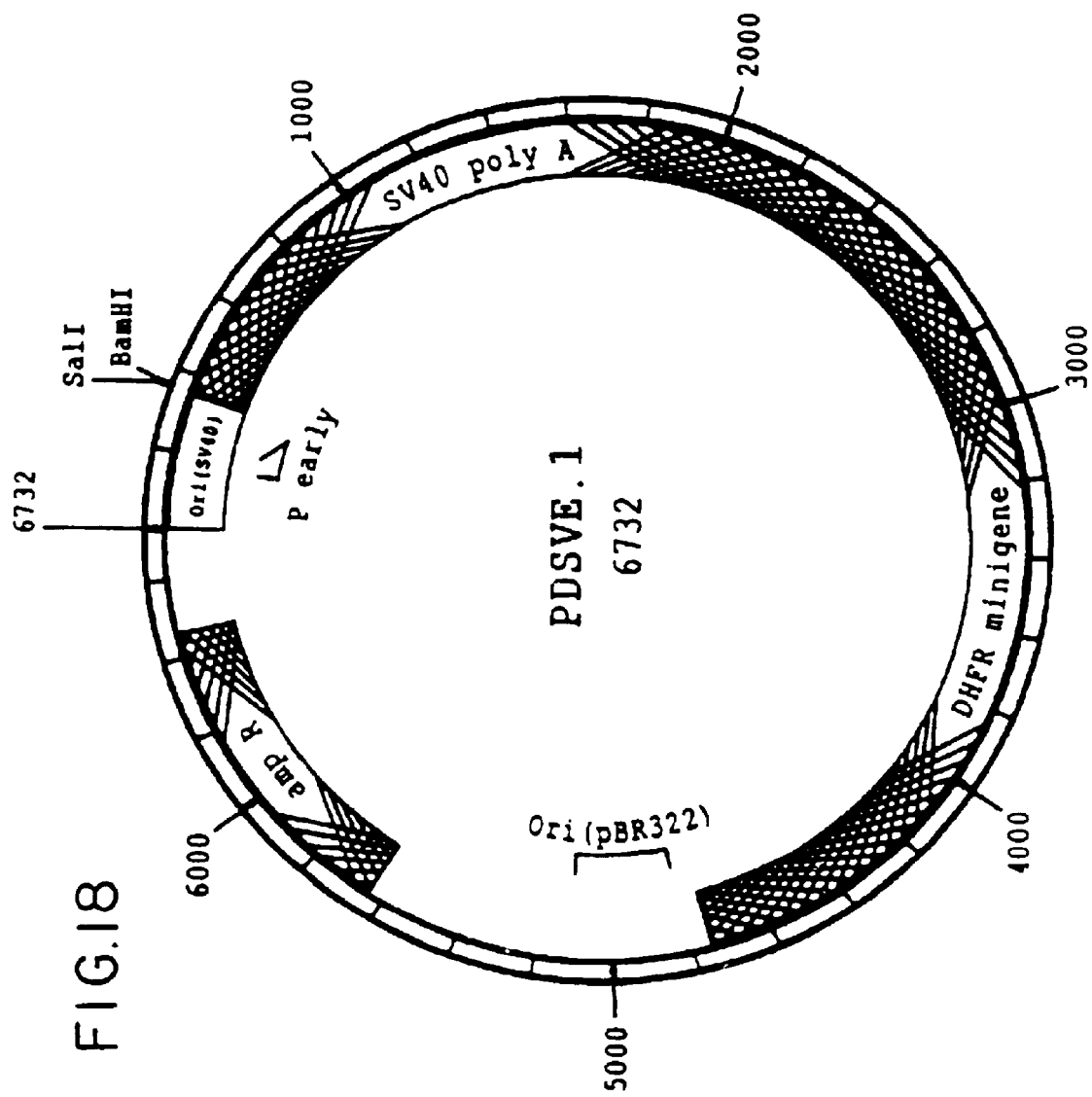

FIG. 18 shows the structure of mammalian CHO cell expression vector pDSVE.1.

Figure 19:
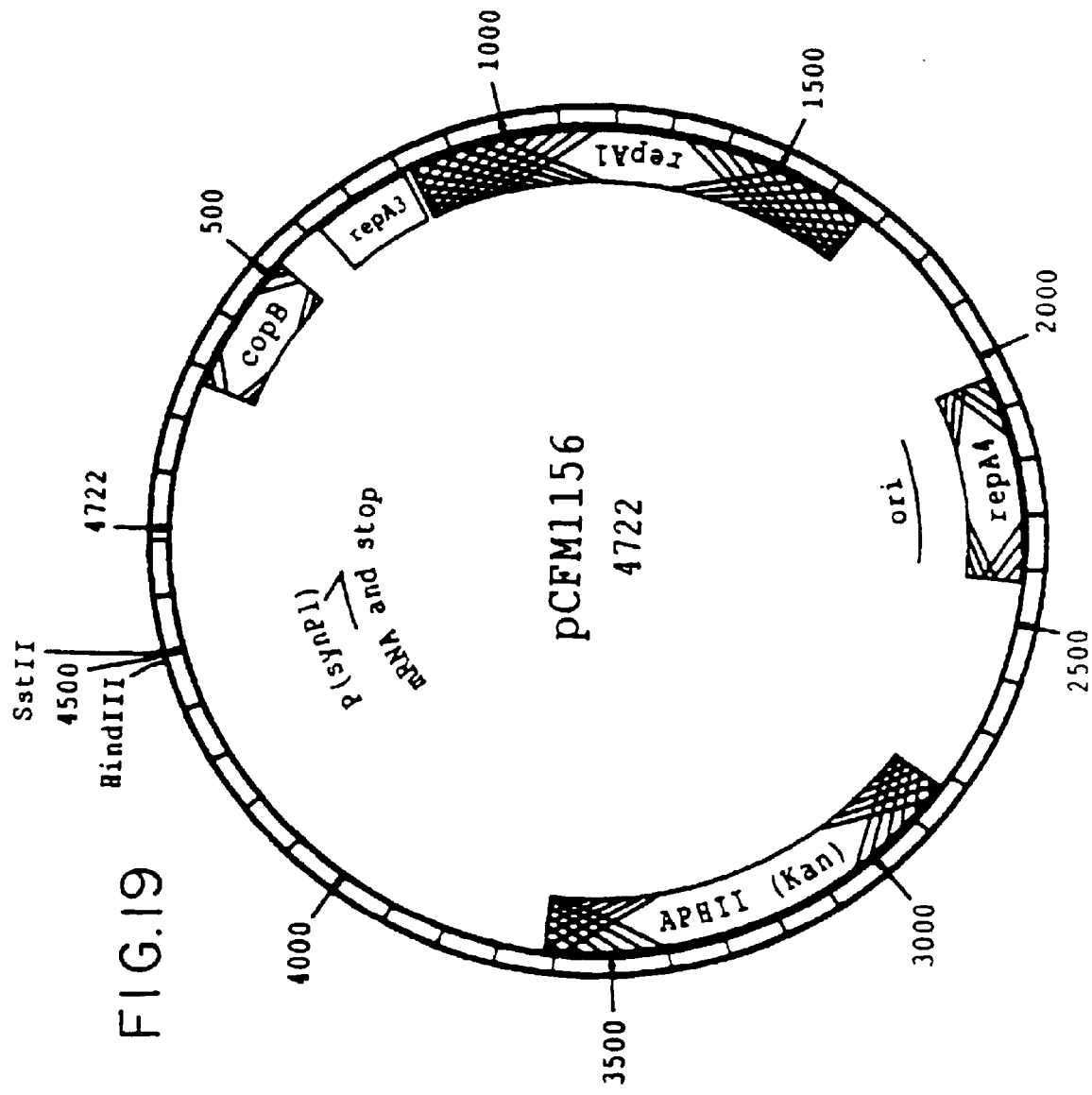

FIG. 19 shows the structure of $E.$ $coli$ expression vector pCFM1156.

FIG. 20 shows

A. a radioimmunoassay of mammalian SCF

B. SDS-PAGE of immune-precipitated mammalian SCF.

Figure 21:
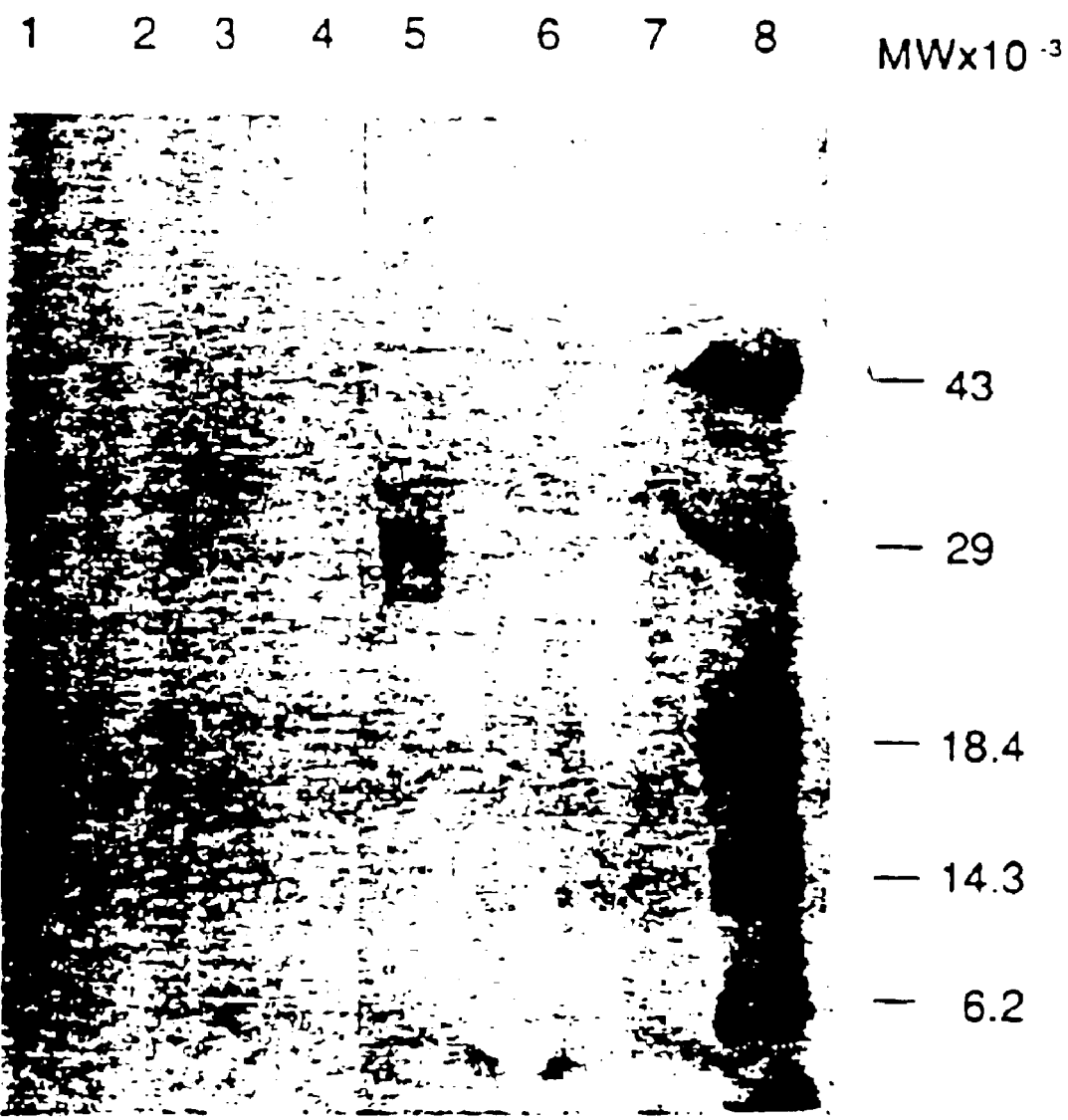

FIG. 21 shows Western analysis of recombinant human SCF.

Figure 22:

FIG. 22 shows Western analysis of recombinant rat SCF.

Figure 22A:
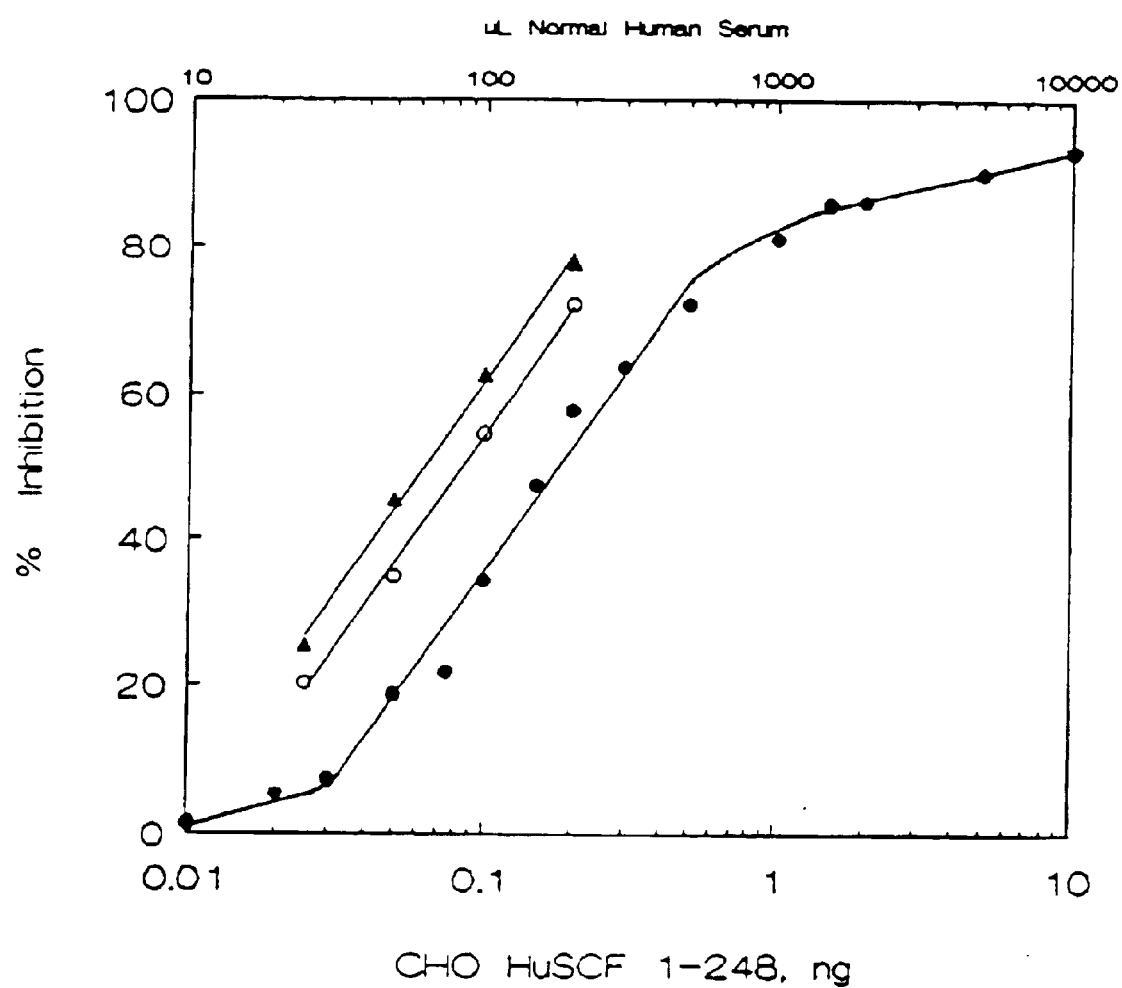

FIG. 22A shows radioimmune assay determination of SCF in Human Serum. The percent inhibition of $^{125}$I-human SCF binding produced was determined for various doses of an unlabeled standard of CHO HuSCF$^{1-248}$ (solid circles); a sample of NHS Lot 500080713 (open circles); and NHS Lot 500081015 (solid triangle).

FIG. 23 is a bar graph showing the effect of COS-1 cell-produced recombinant rat SCF on bone marrow transplantation.

Figure 24A:
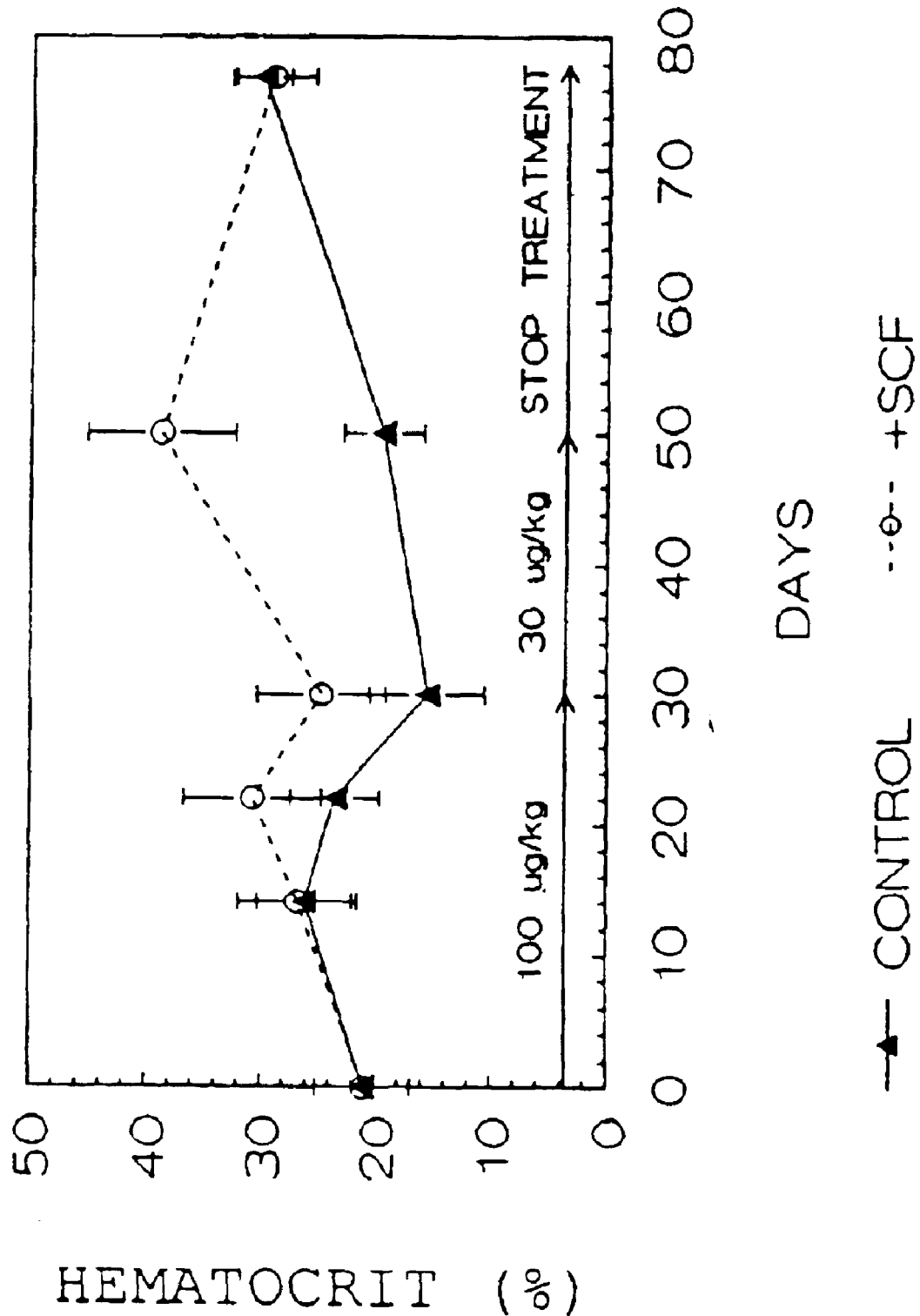
Figure 24B:
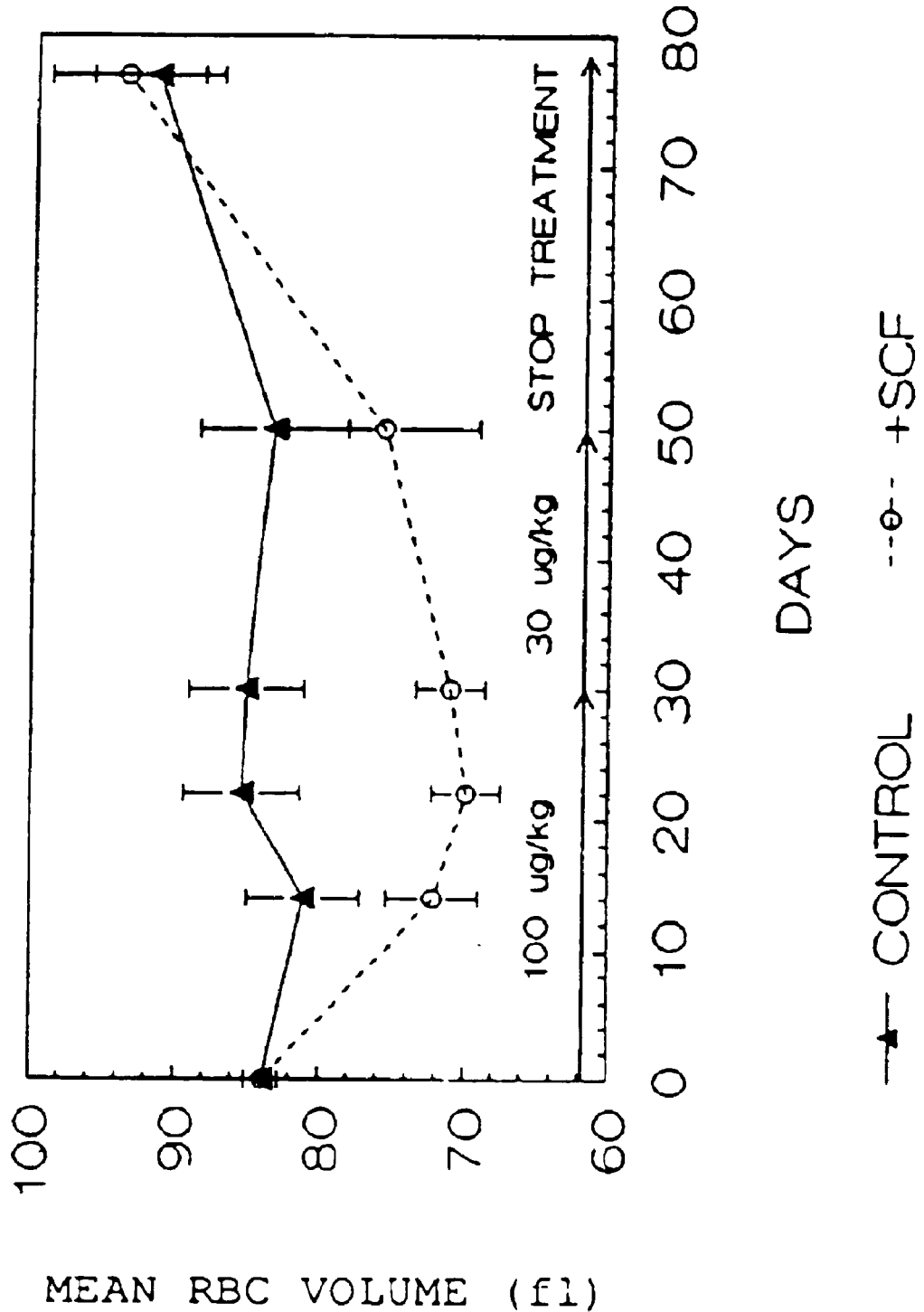

FIG. 24 shows the effect of recombinant rat SCF on curing the macrocytic anemia of Steel mice, as assessed by hematocrit analysis (24A) or mean red blood cell volume (24B).

Figure 25:
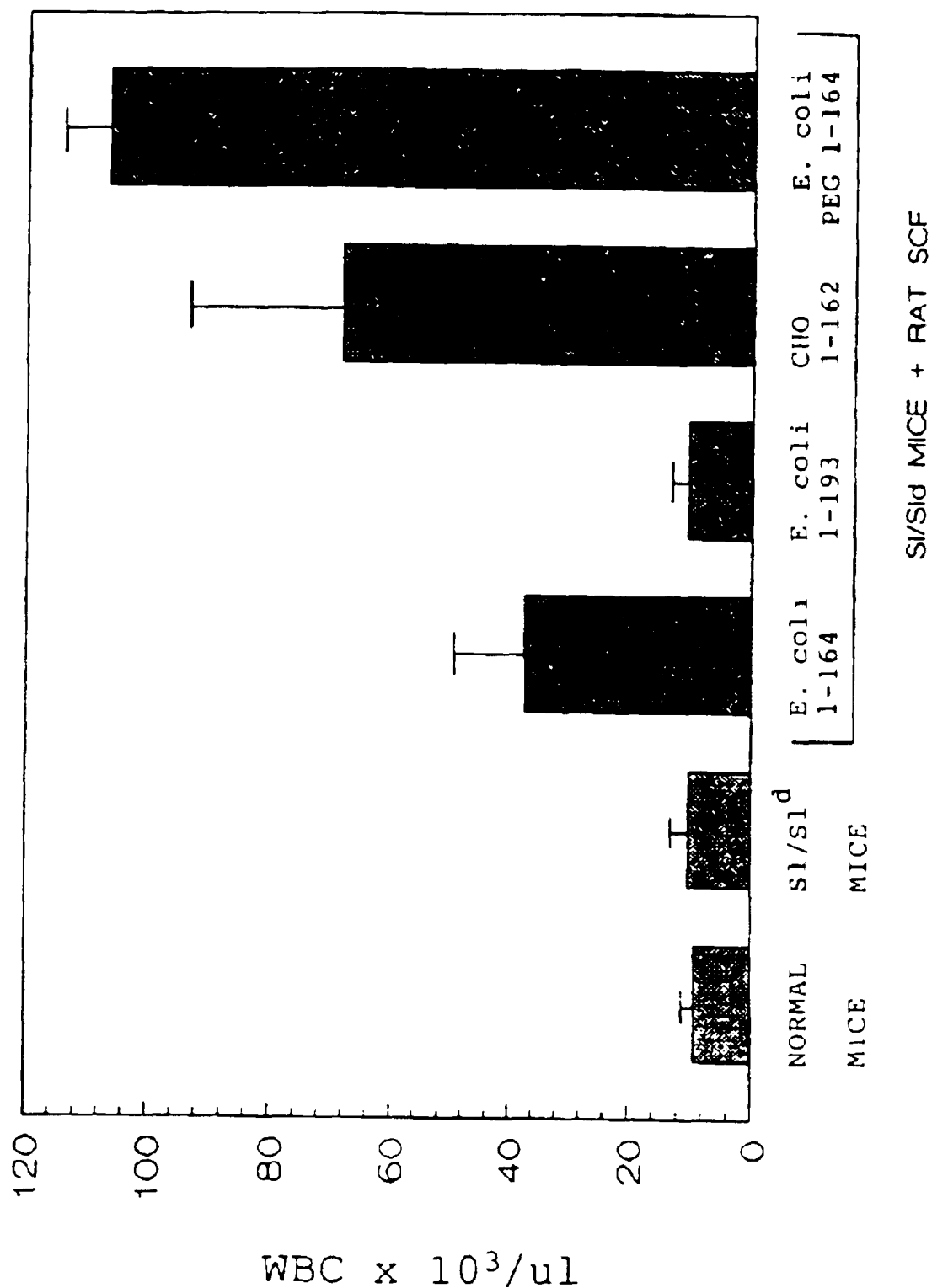

FIG. 25 shows the peripheral white blood cell count (WBC) of Steel mice treated with recombinant rat SCF.

Figure 26:
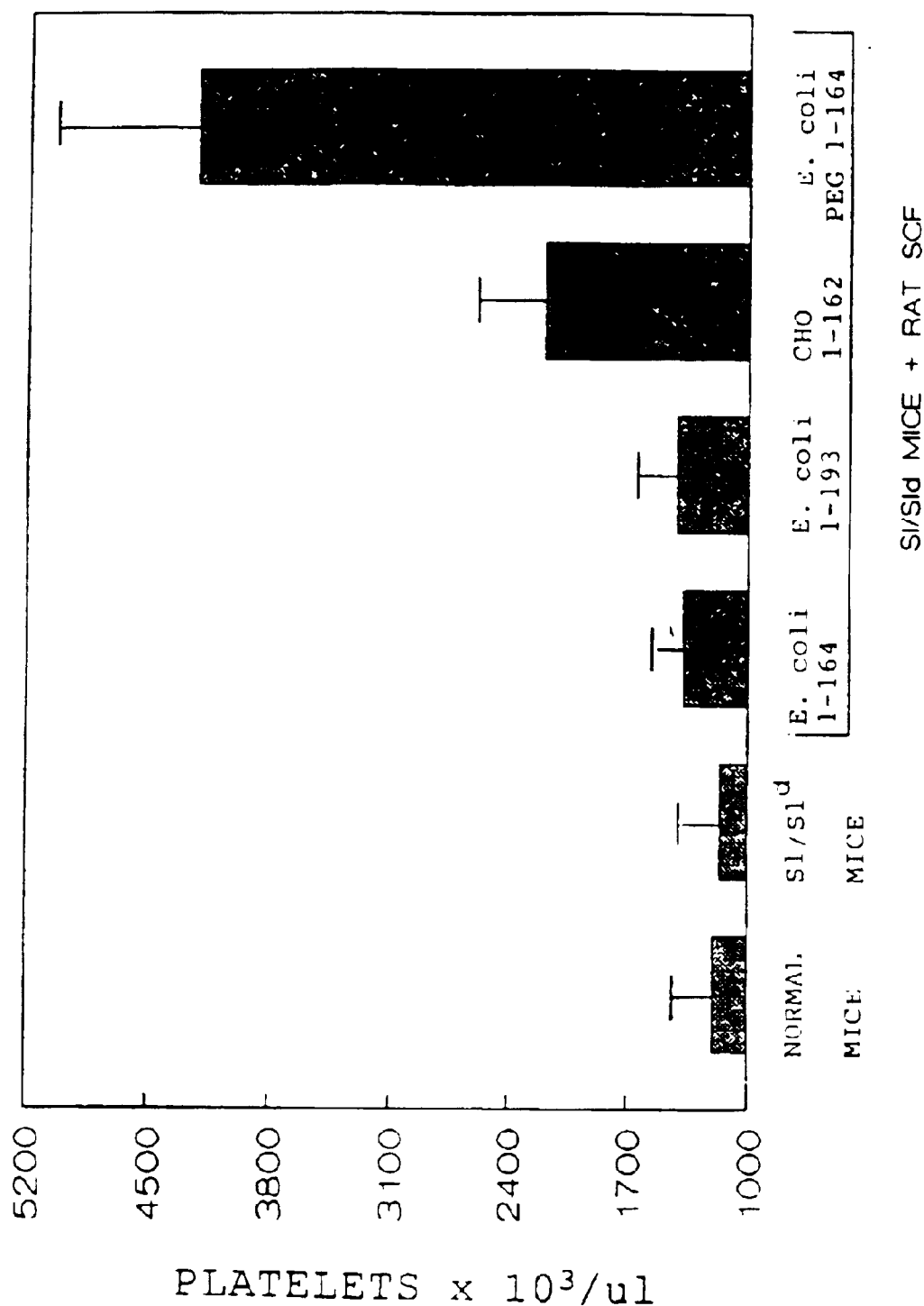

FIG. 26 shows the platelet counts of Steel mice treated with recombinant rat SCF.

Figure 27:
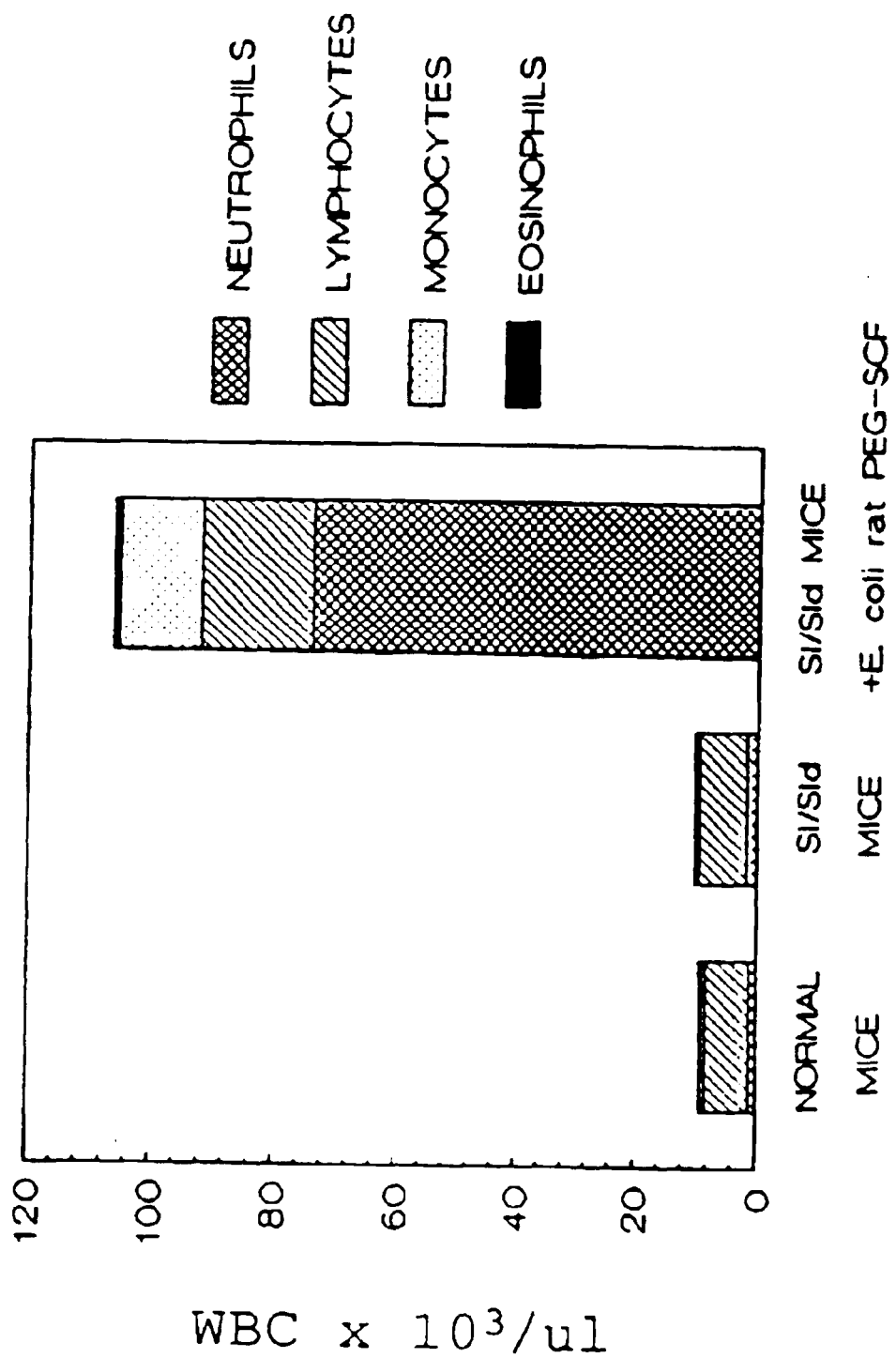

FIG. 27 shows the differential WBC count for Steel mice treated with recombinant rat SCF$^{1-164}$ PEG25.

Figure 28:
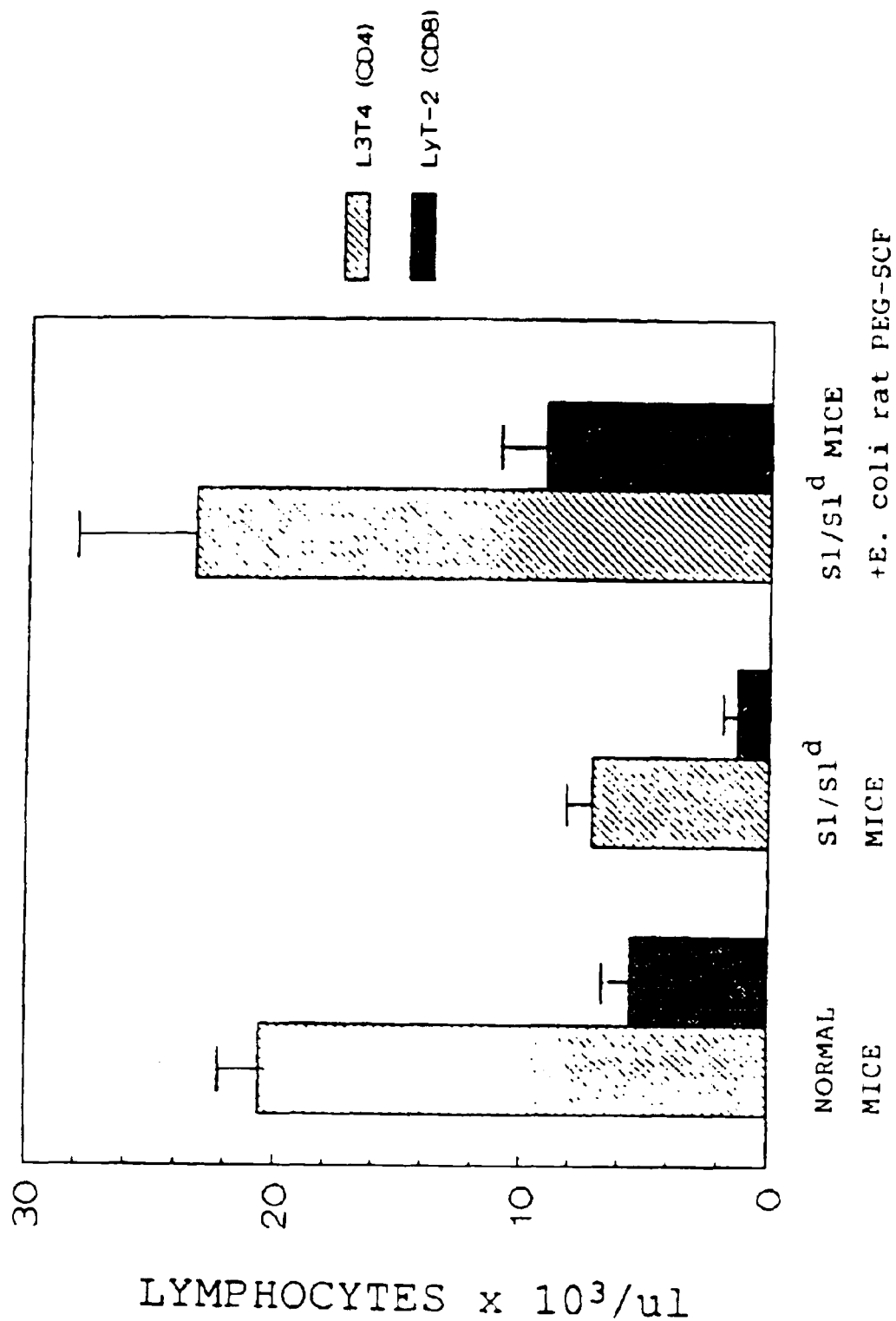

FIG. 28 shows the lymphocyte subsets for Steel mice treated with recombinant rat SCF$^{1-164}$ PEG25.

Figure 29A:
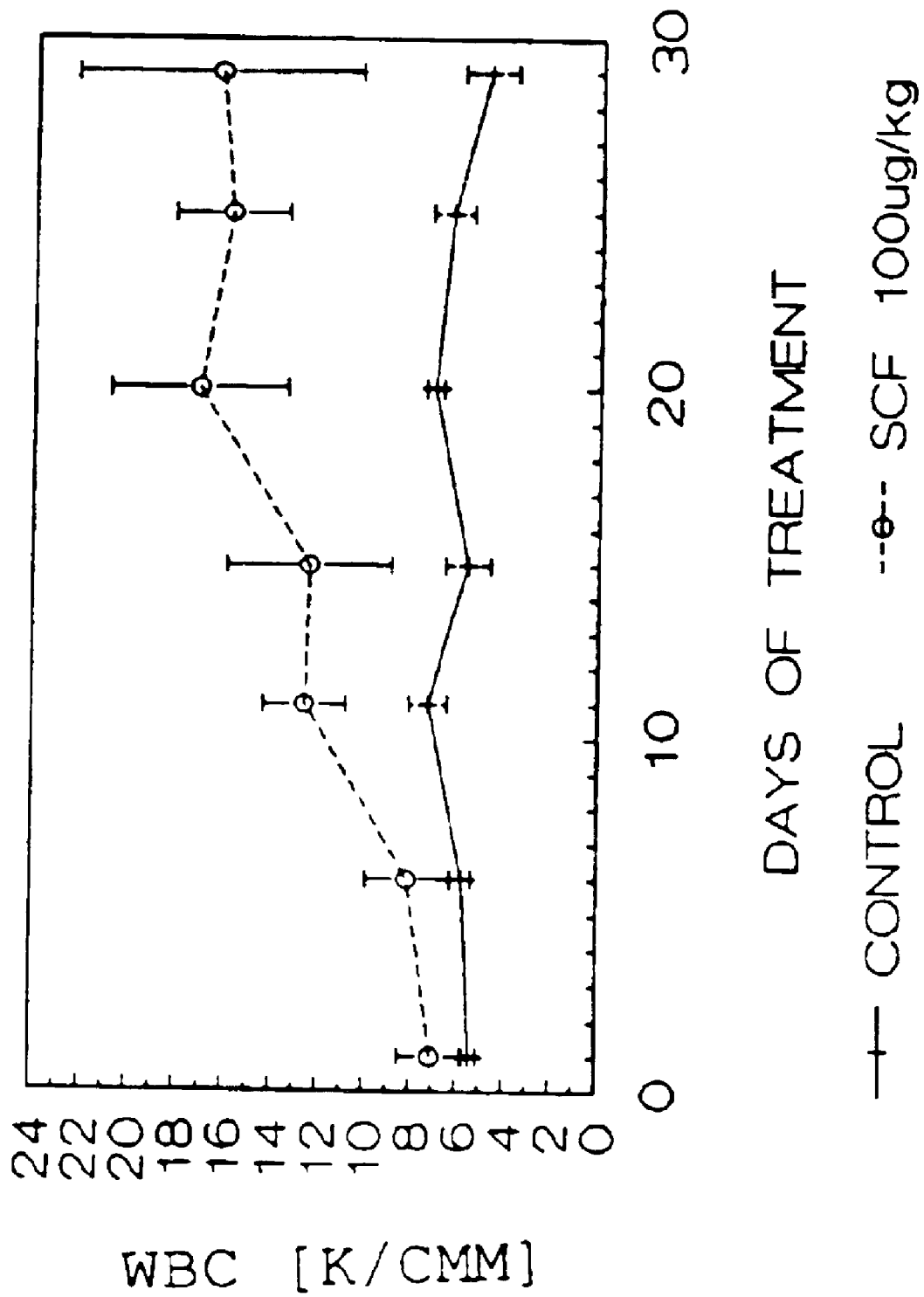

FIG. 29 shows the effect of recombinant human sequence SCF treatment of normal primates in increasing WBC count. 29A. expressed as white blood cells in [K/cmm] 29B. expressed as peripheral blood cells in [K/cmm].

Figure 30B:
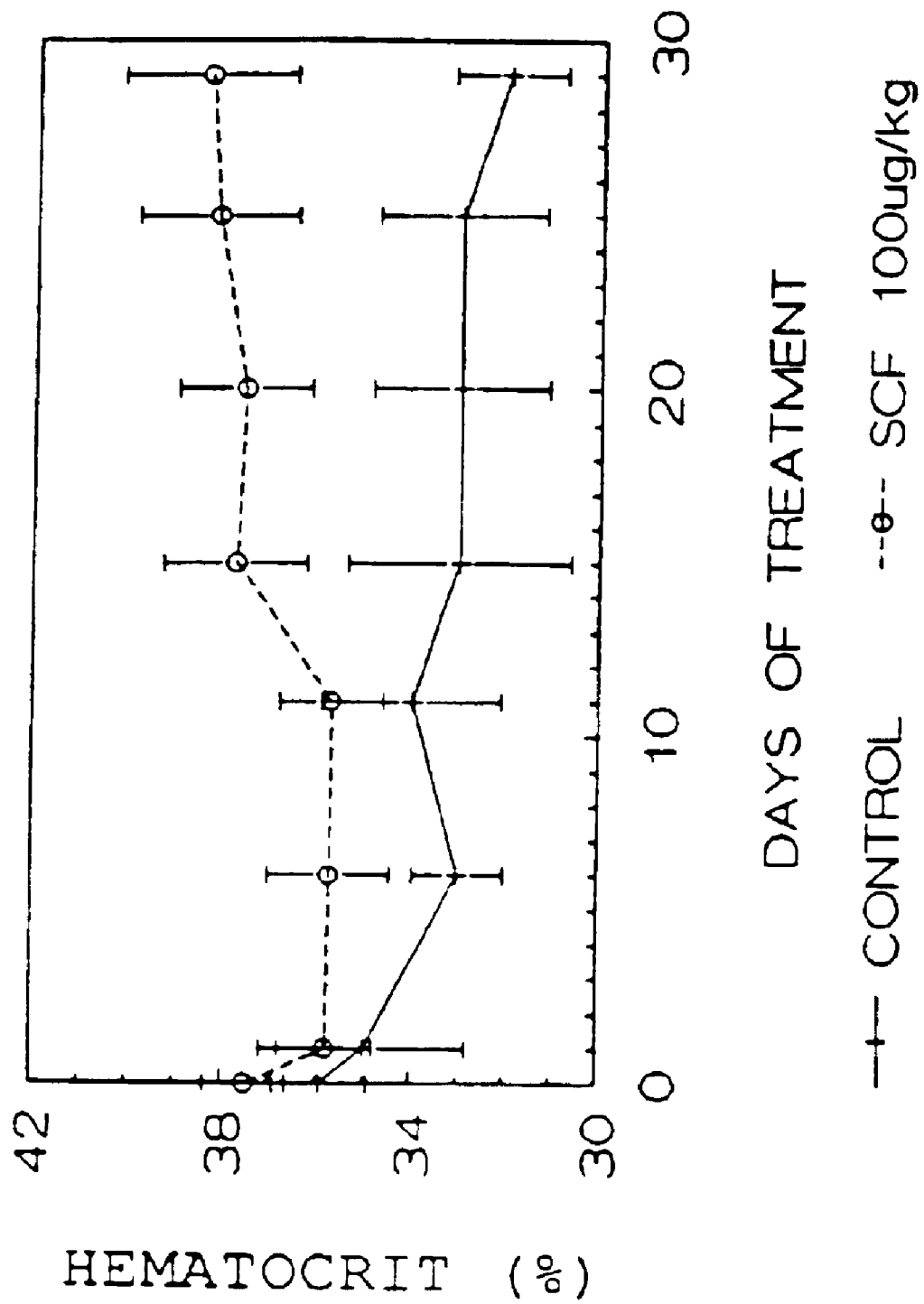

FIG. 30 shows the effect of recombinant human sequence SCF treatment of normal primates in increasing hematocrits (30B) and platelet numbers (30A ).

FIG. 31 shows photographs of

A. human bone marrow colonies stimulated by recombinant human SCF$^{1-162}$

B. Wright-Giemsa stained cells from colonies in FIG. 31A.

Figures 31A, 31B:
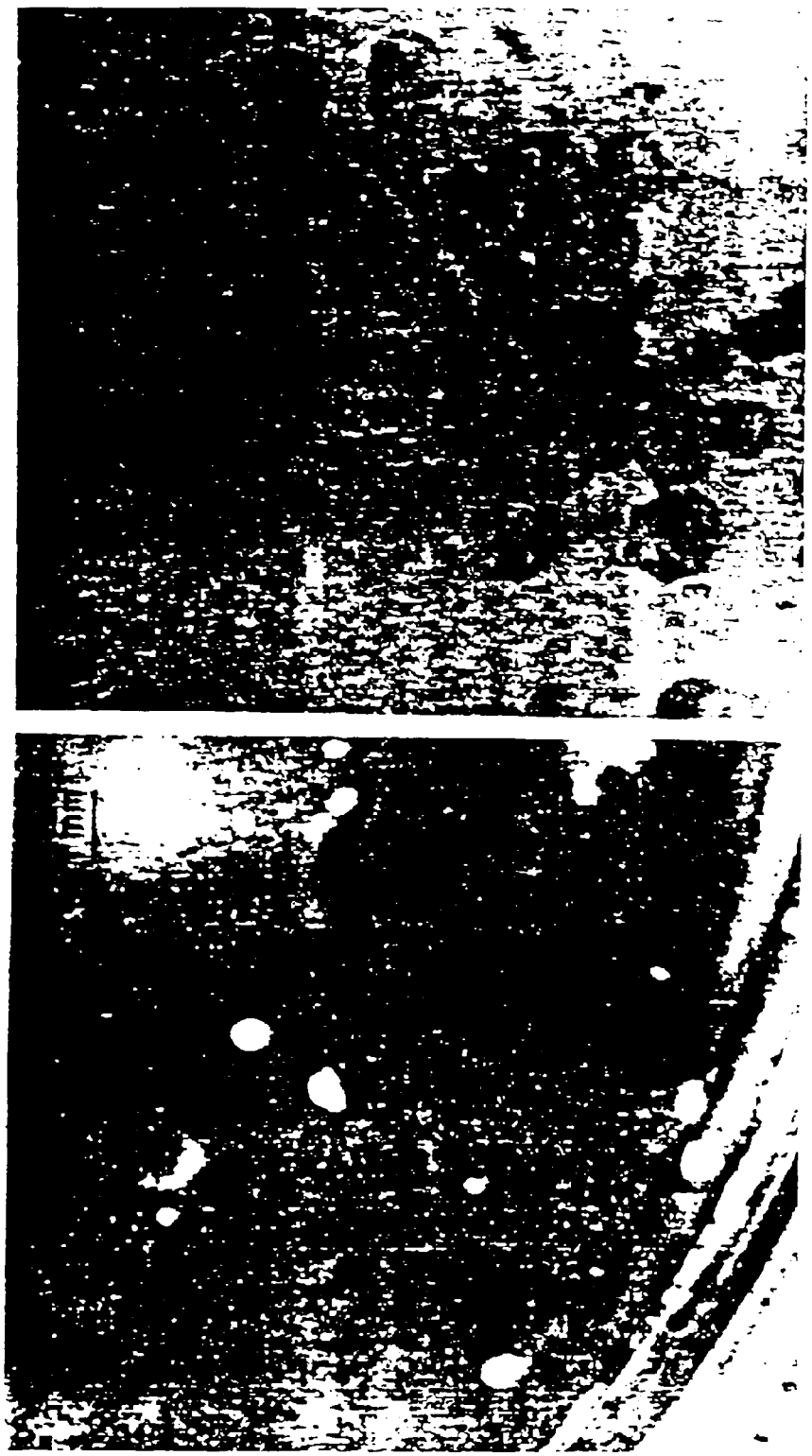
Figure 31C:
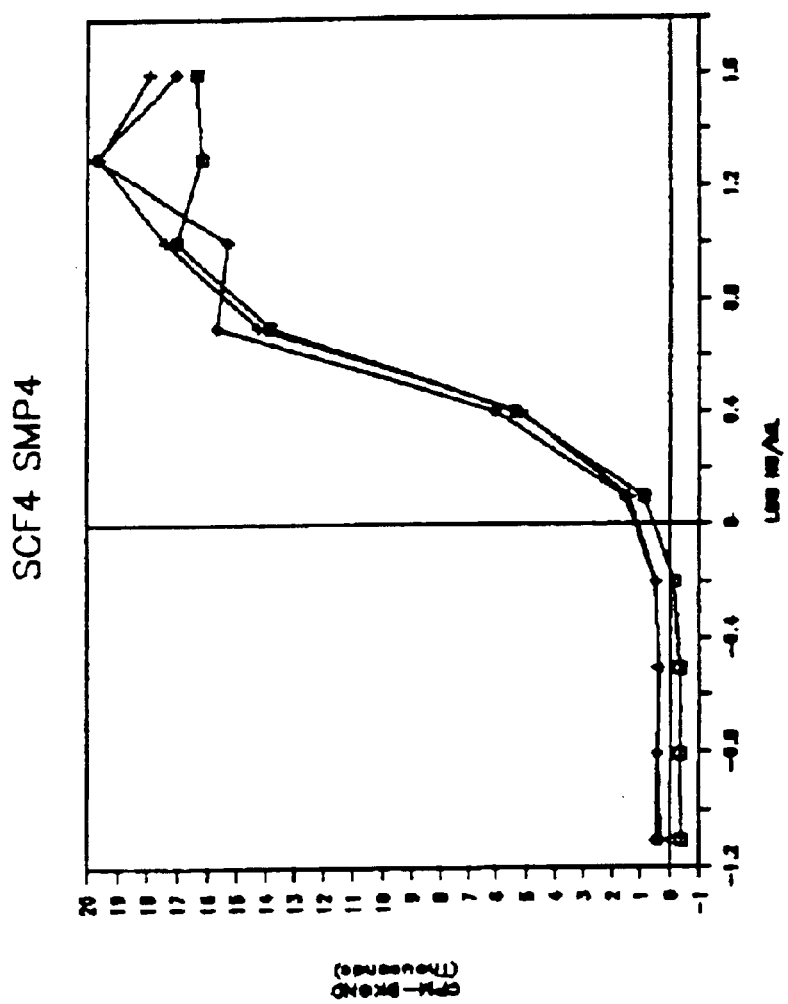

FIG. 31C shows proliferation of the UT-7 cell line by $E.$ $coli$ derived SCFs. Open squares are human [Met$^{-1}$]SCF$^{1-164}$ crosses and open diamonds are human [Met$^{-1}$]SCF$^{1-165}$.

Figure 32A:
Figure 32:
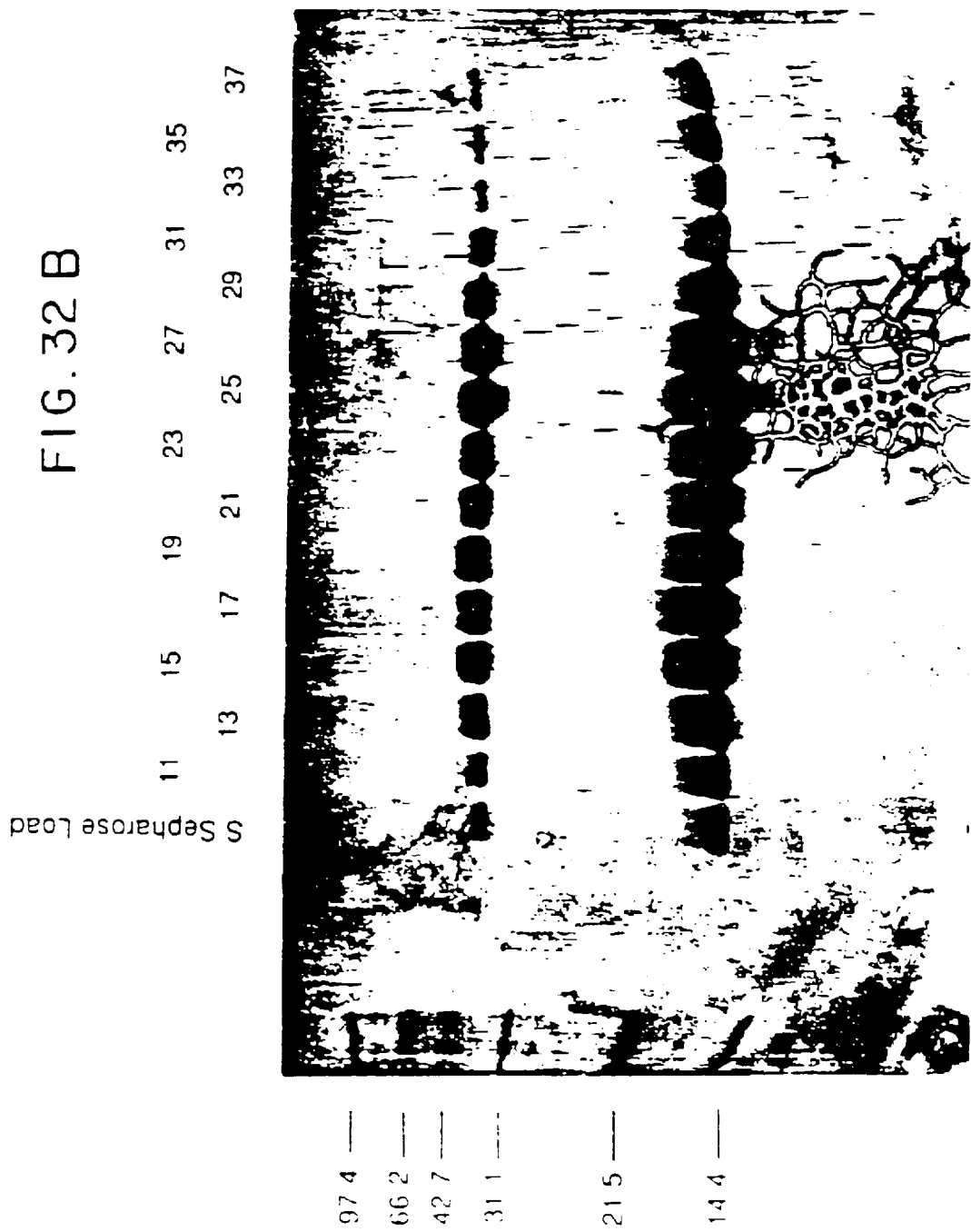
Figure 33:
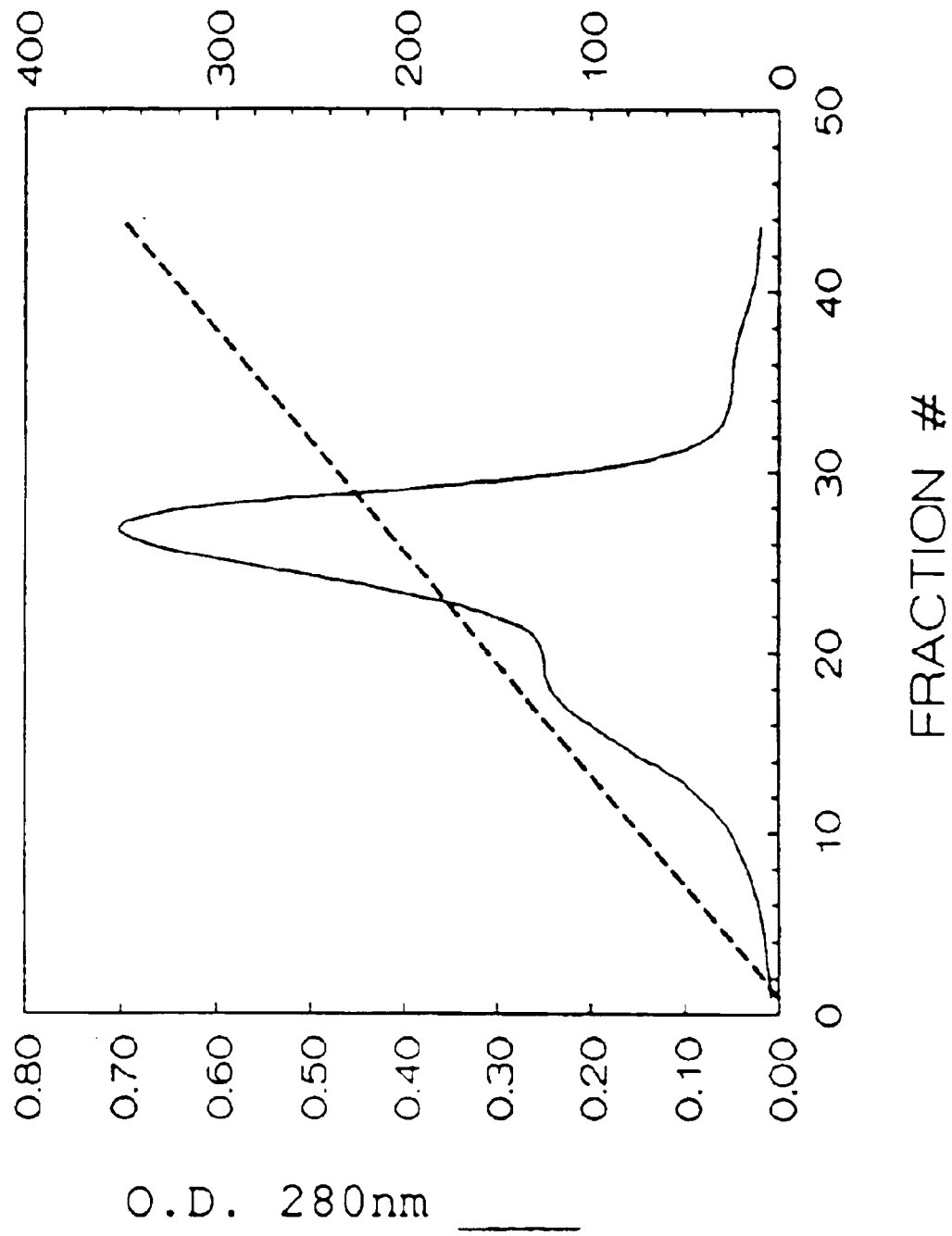

FIG. 32 shows SDS-PAGE of S-Sepharose column fractions from chromatogram shown in FIG. 33

A. with reducing agent

B. without reducing agent.

Figure 34A:
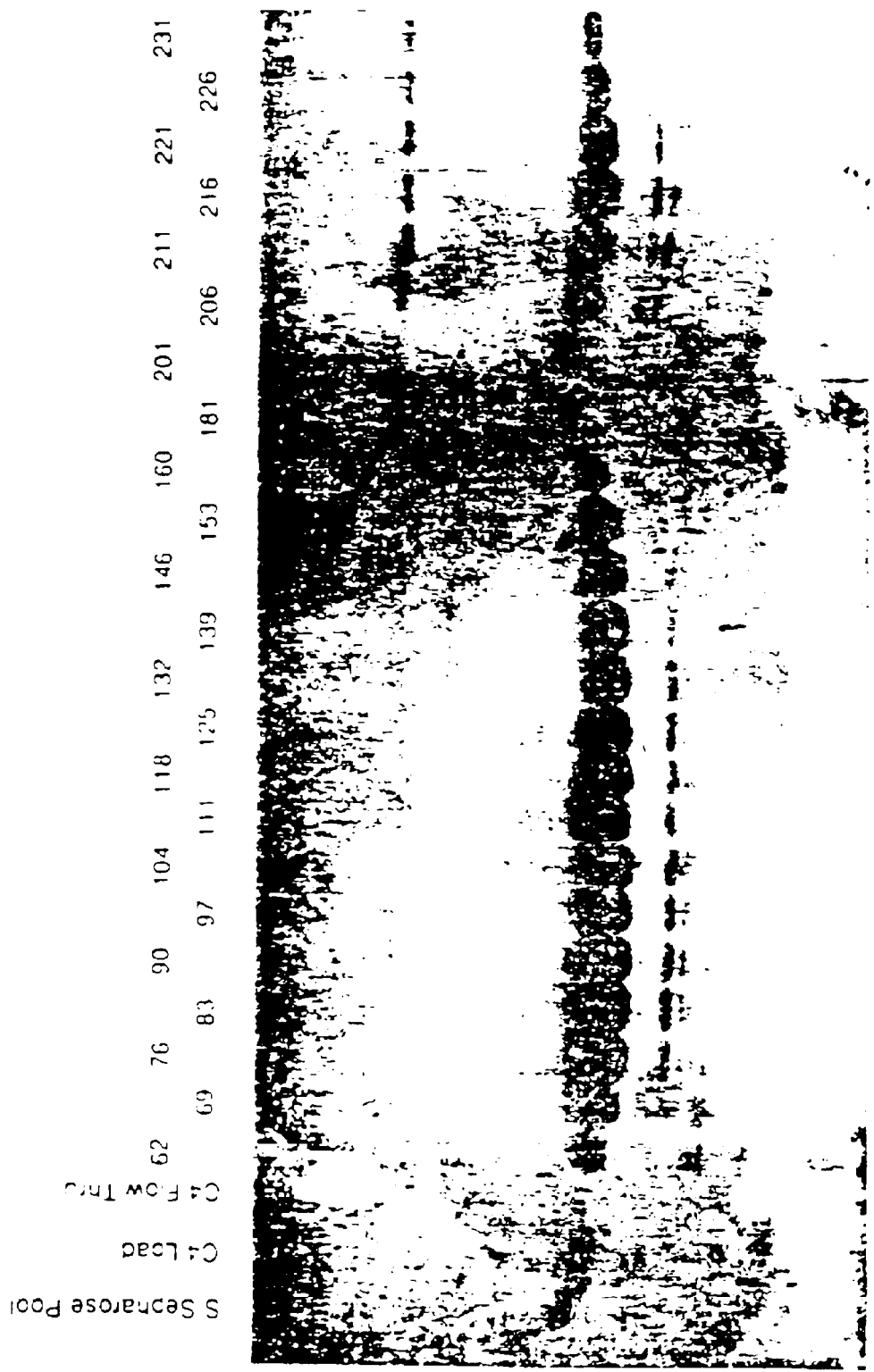
Figure 34B:
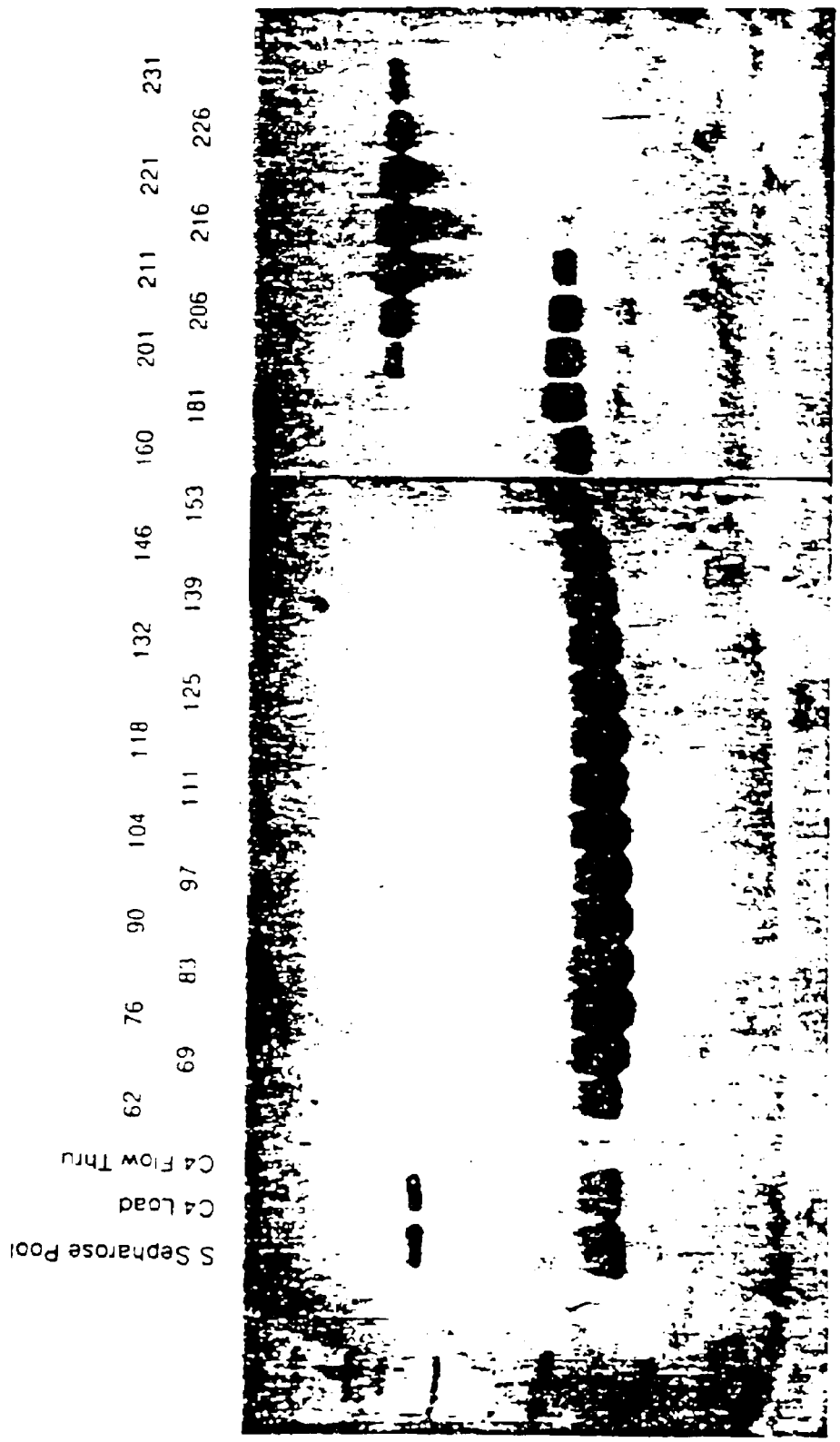
Figure 35:
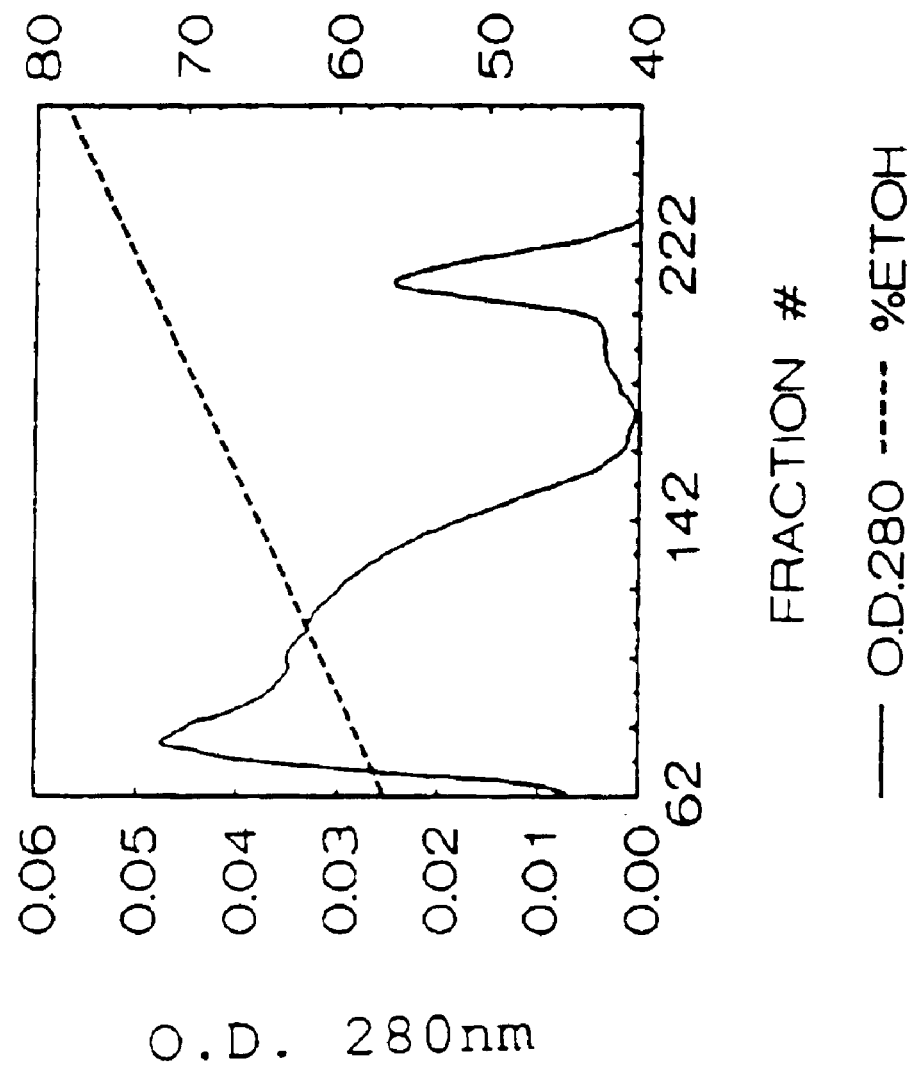

FIG. 33 is a chromatogram of an S-Sepharose column of $E.$ $coli$ $derived$ $recombinant$ $human$ $SCF.$ FIG. 34 shows SDS-PAGE of $C_4$ column fractions from chromatogram showing FIG. 35

A. with reducing agent

B. without reducing agent.

FIG. 35 is a chromatogram of a $C_4$ column of $E.$ $coli$ derived recombinant human SCF.

Figure 36:
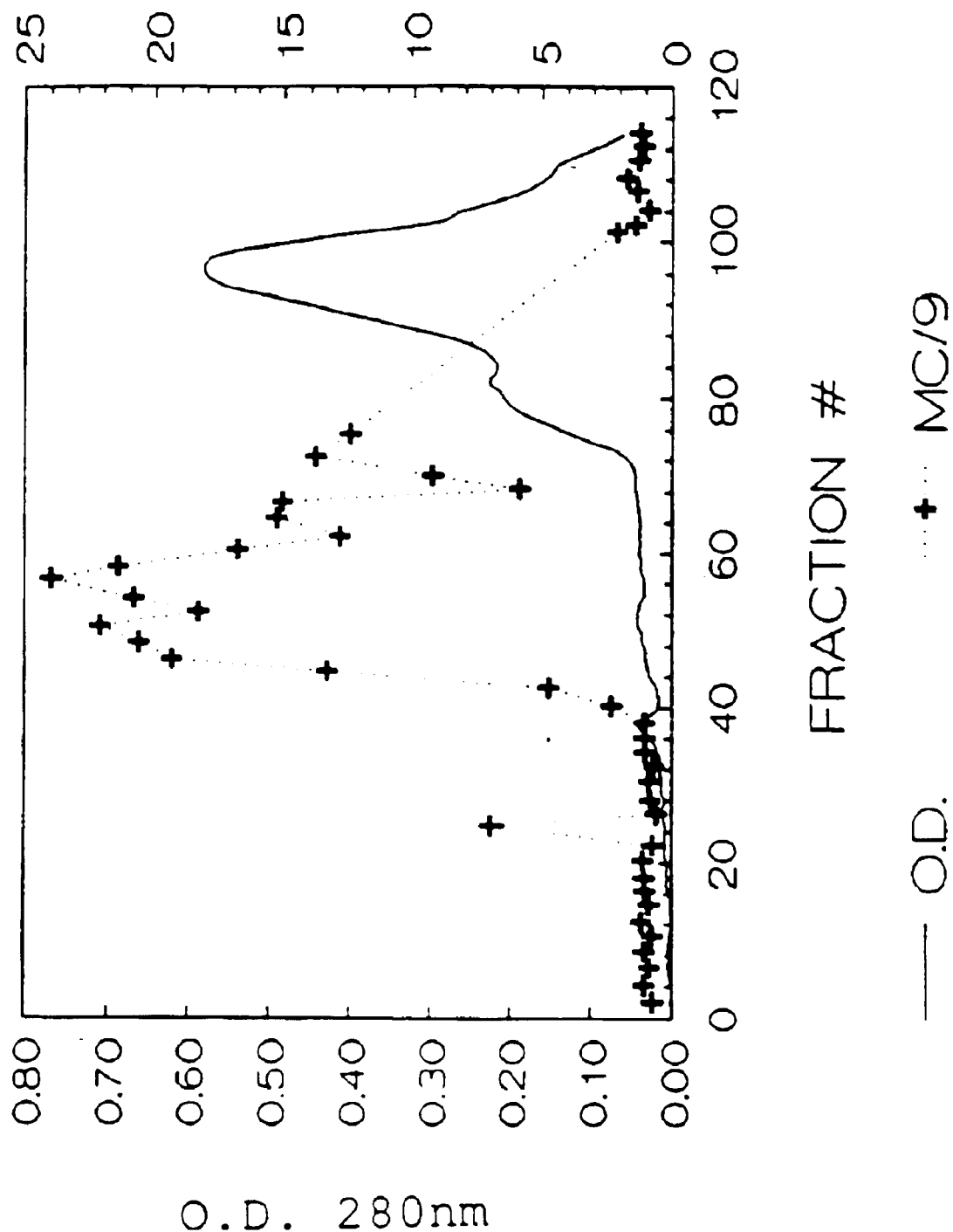

FIG. 36 is a chromatogram of a Q-Sepharose column of CHO derived recombinant rat SCF.

Figure 37:
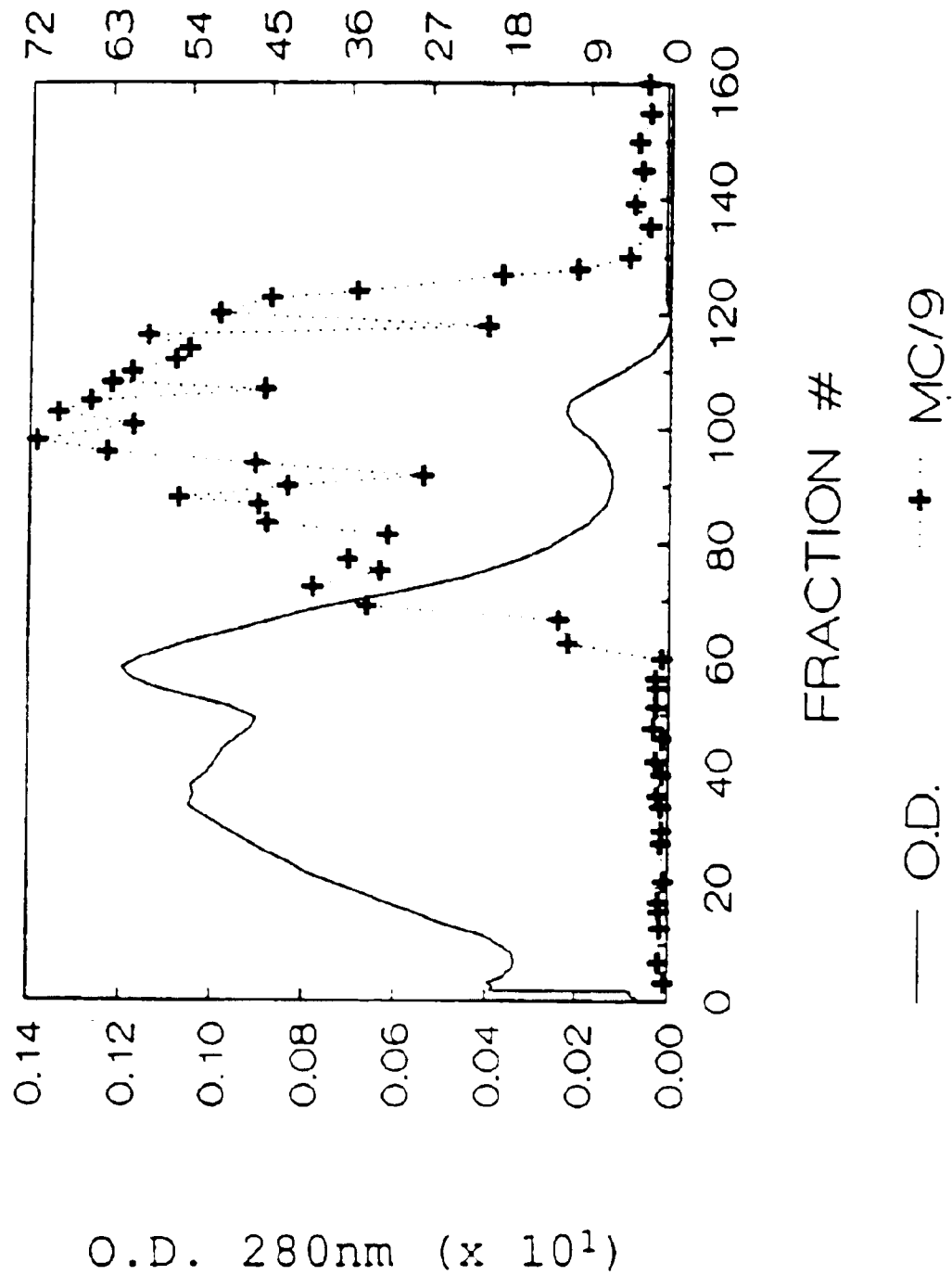

FIG. 37 is a chromatogram of a $C_4$ column of CHO derived recombinant rat SCF.

Figure 38:
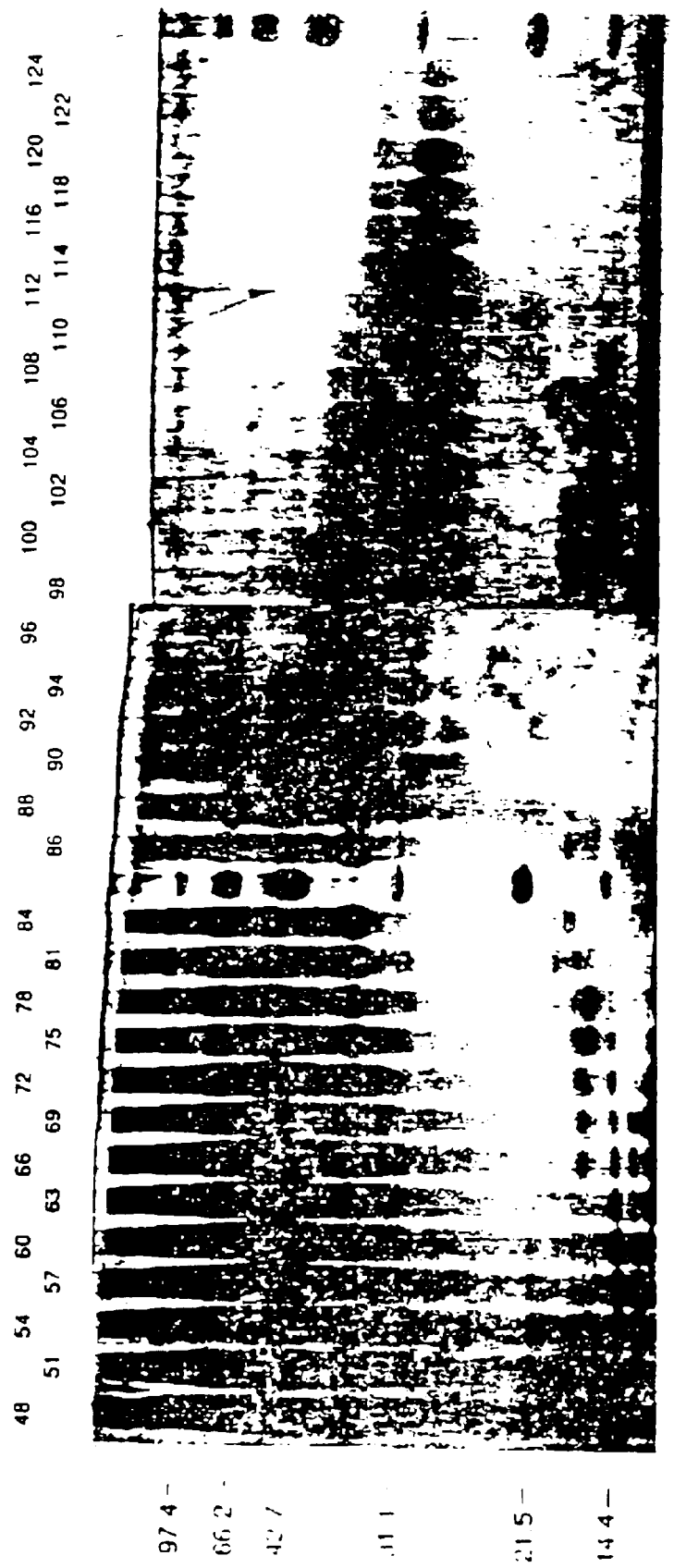

FIG. 38 shows SDS-PAGE of $C_4$ column fractions from chromatogram shown in FIG. 37.

Figure 39:
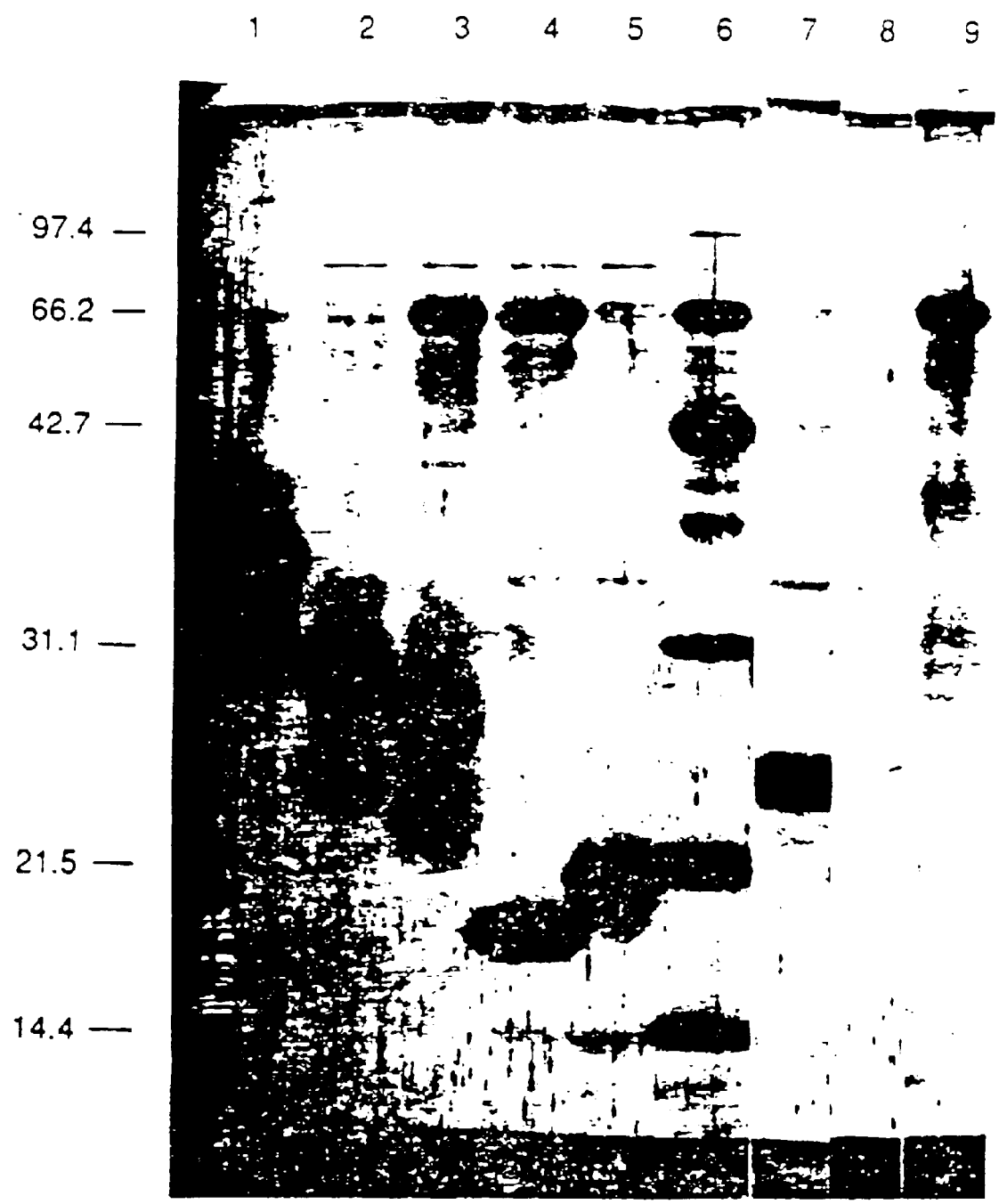

FIG. 39 shows SDS-PAGE of purified CHO derived recombinant rat SCF before and after de-glycosylation.

FIG. 40 shows
  A. gel filtration chromatography of recombinant rat pegylated $SCF^{1-164}$ reaction mixture
  B. gel filtration chromatography of recombinant rat $SCF^{1-164}$ unmodified.

Figure 41:
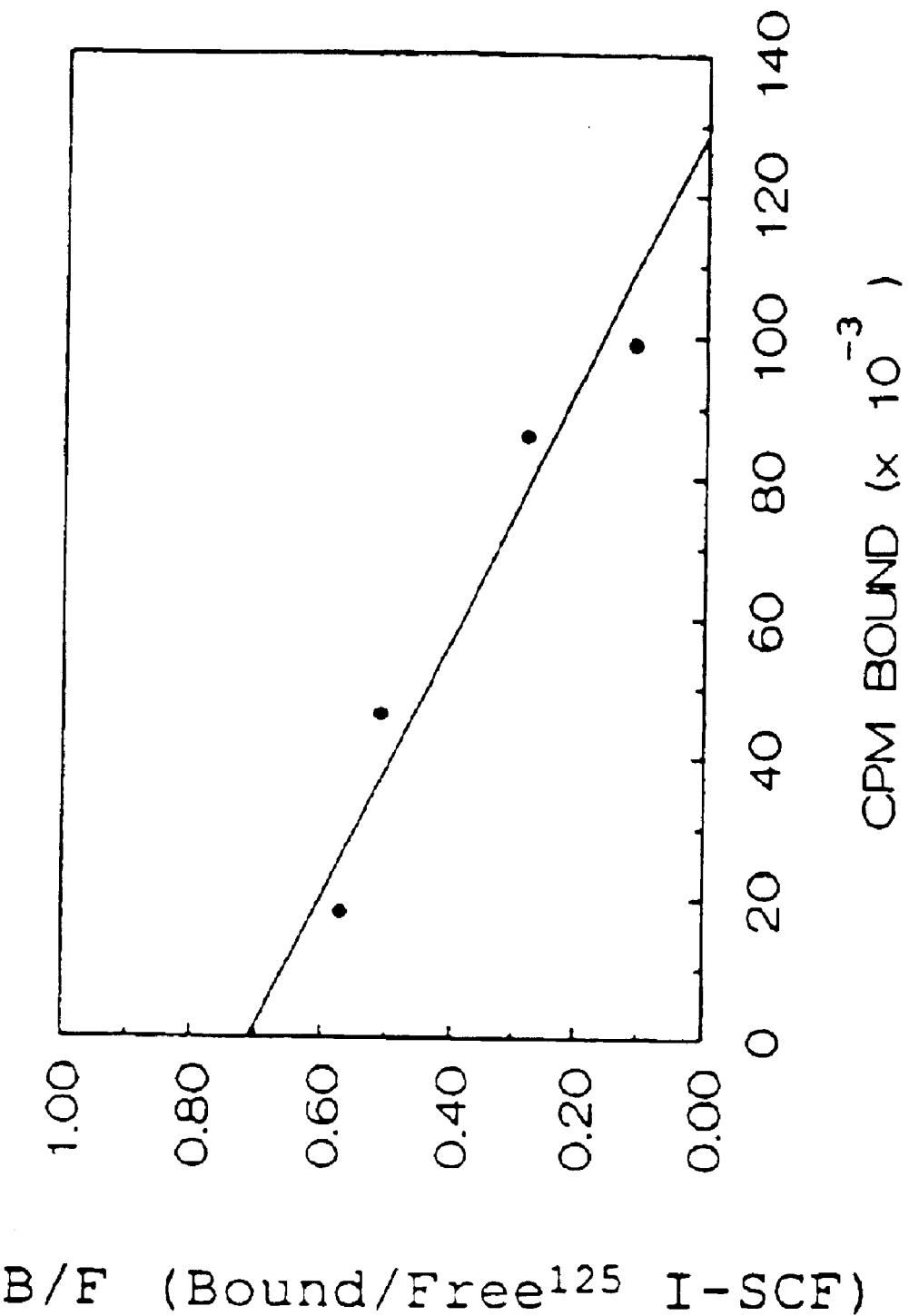

FIG. 41 shows labelled SCF binding to fresh leukemic blasts.

FIGS. 42A–42D shows human SCF cDNA sequence (SEQ ID NOs:60 AND 61)obtained from the HT1080 fibrosarcoma cell line.

Figure 43:
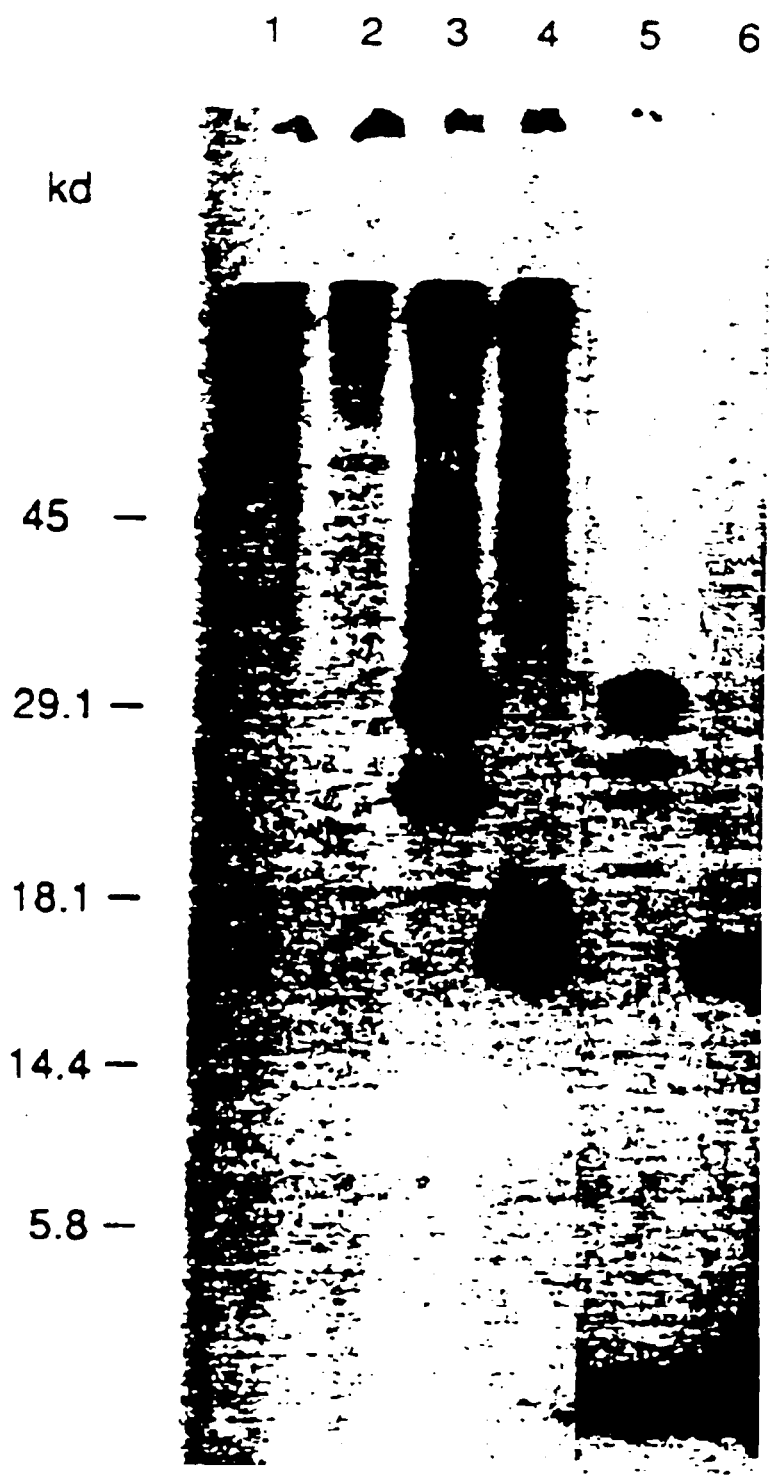

FIG. 43 shows an autoradiograph from COS-7 cells expressing human $SCF^{1-248}$ and CHO cells expressing human $SCF^{1-164}$.

FIGS. 44A–44C shows human SCF cDNA sequence (SEQ ID NOs:62 AND 63) obtained from the 5637 bladder carcinoma cell line.

FIG. 45 shows the enhanced survival of irradiated mice after SCF treatment.

Figure 46:
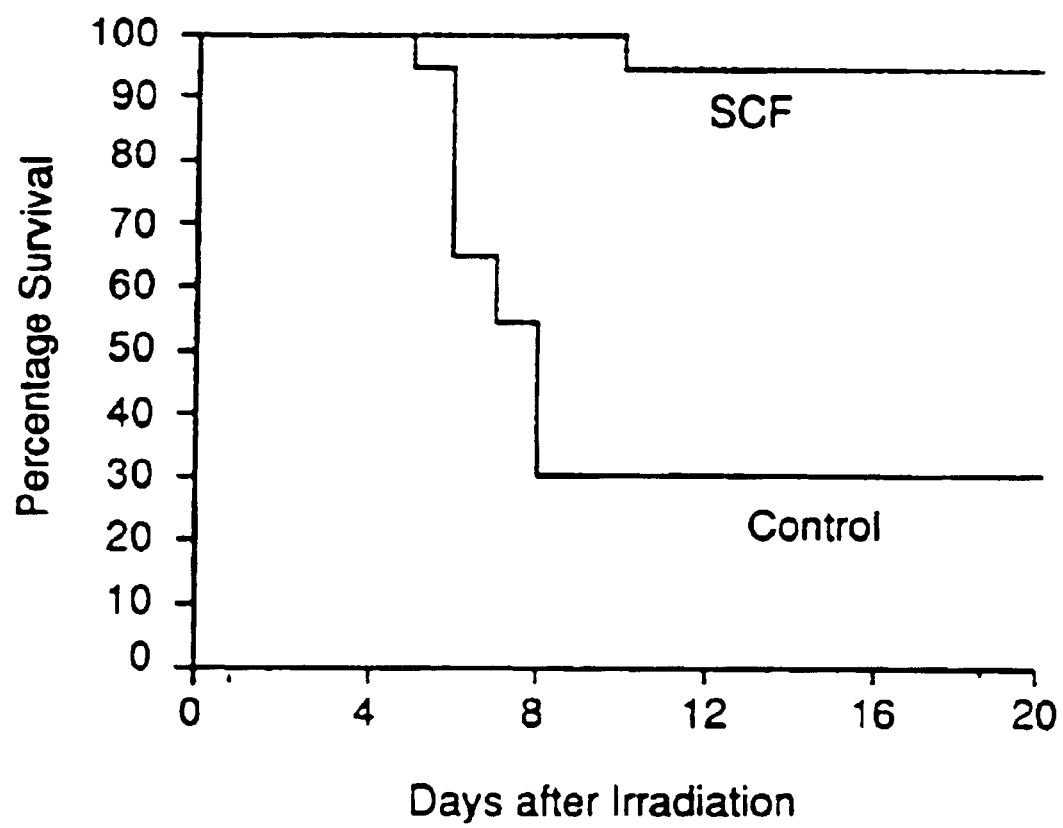

FIG. 46 shows the enhanced survival of irradiated mice after bone marrow transplantation with 5% of a femur and SCF treatment.

Figure 47:
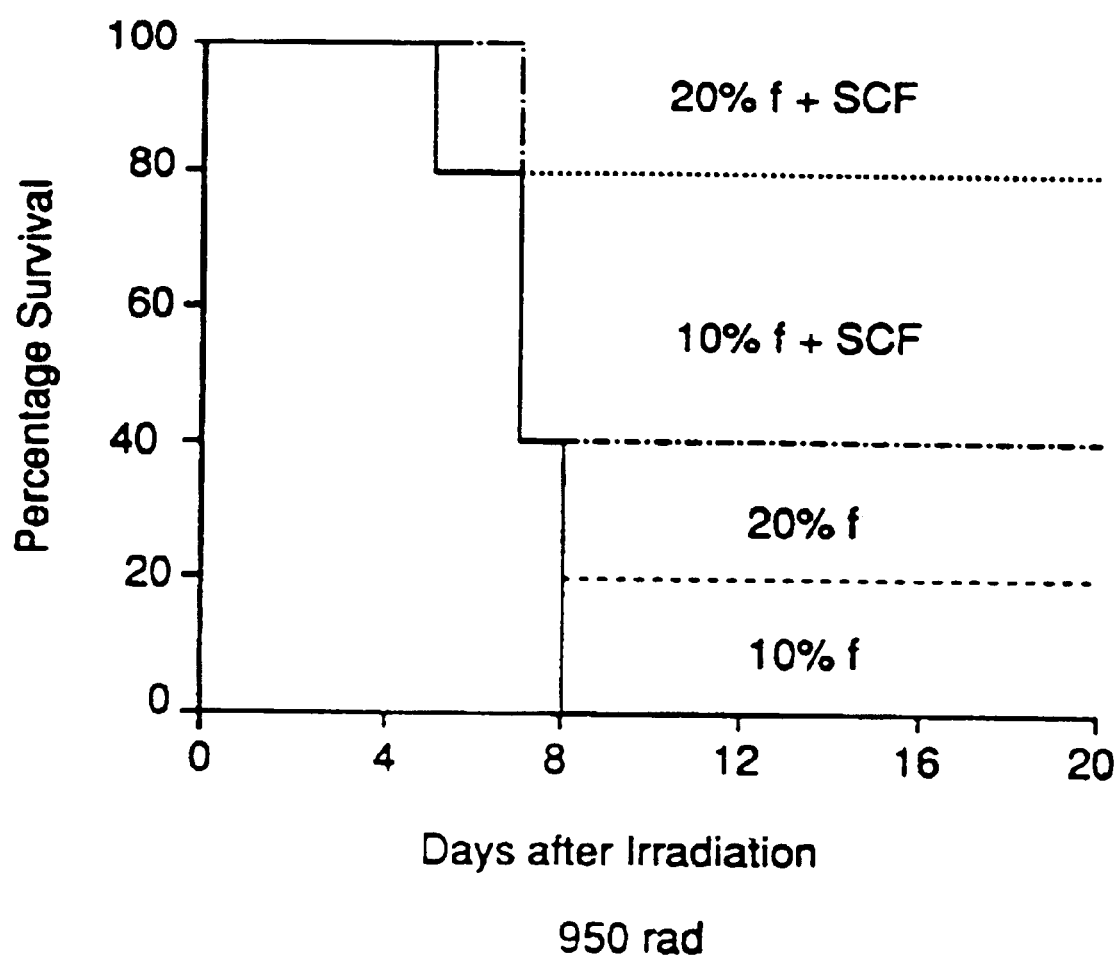

FIG. 47 shows the enhanced survival of irradiated mice after bone marrow transplantation with 0.1 and 20% of a femur and SCF treatment.

Figure 48:
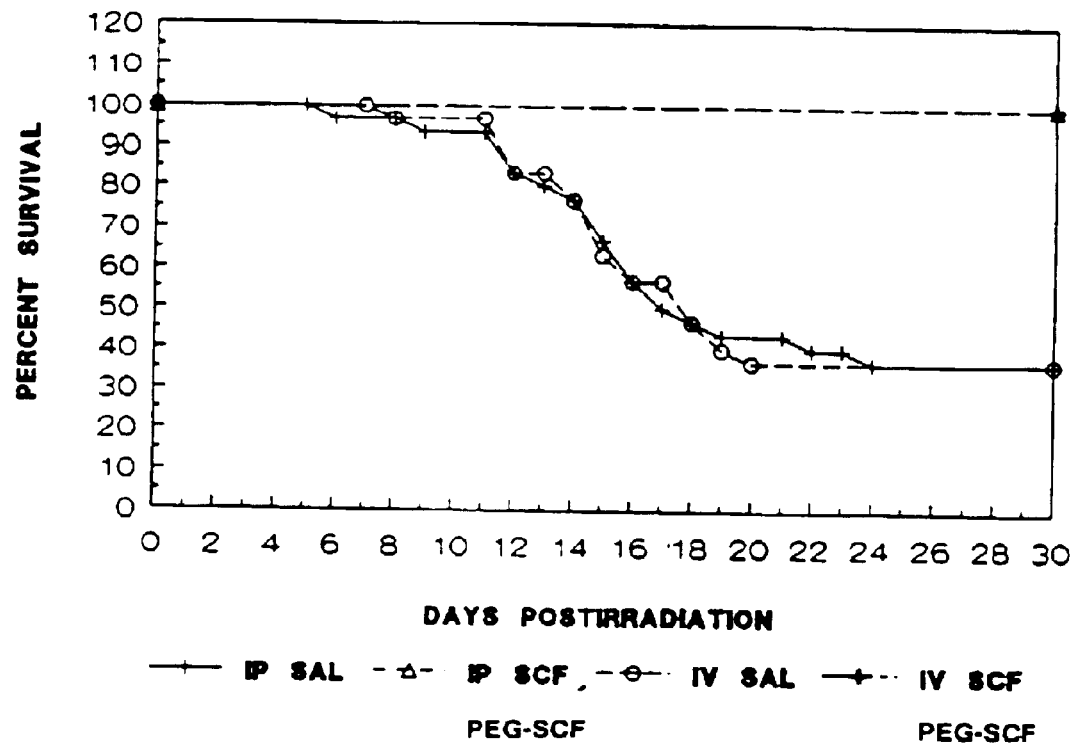

FIG. 48 shows radioprotection effects of rat SCF on survival of mice after irradiation.

Figure 49:
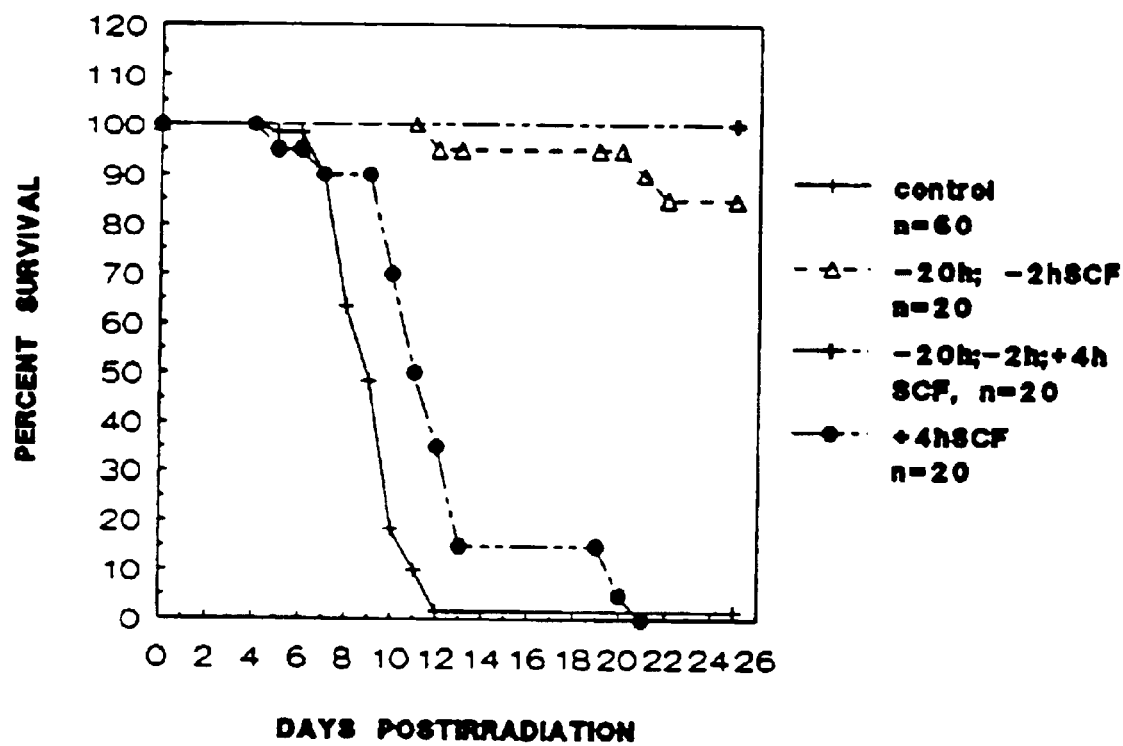

FIG. 49 shows radioprotection effects of rat SCF on survival of mice after irradiation.

Figure 50:
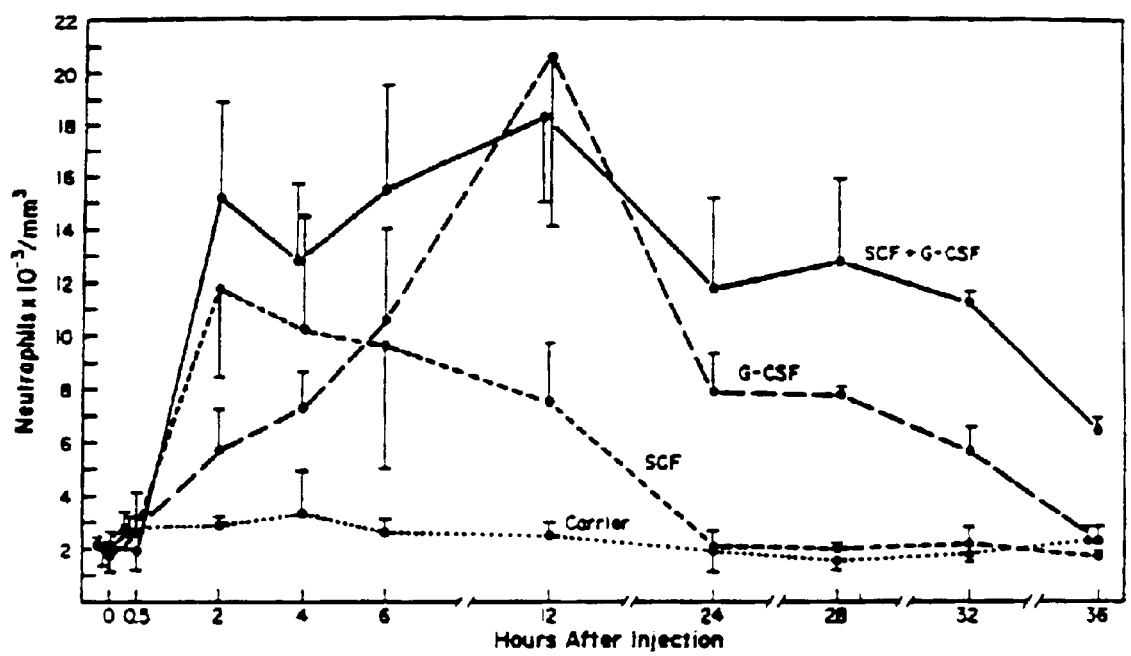

FIG. 50 shows a single coinjection of rrSCF plus G-CSF causes an increase in circulating neutrophils that is approximately additive as compared to the rrSCF alone- and G-CSF alone-induced neutrophilia. The kinetics of rrSCF plus G-CSF-induced neutrophilia reflect the combined effect of the differing kinetics of rrSCF-induced neutrophilia peaking at 6 hours and G-CSF-induced neutrophilia peaking at 12 hours.

Figure 51:
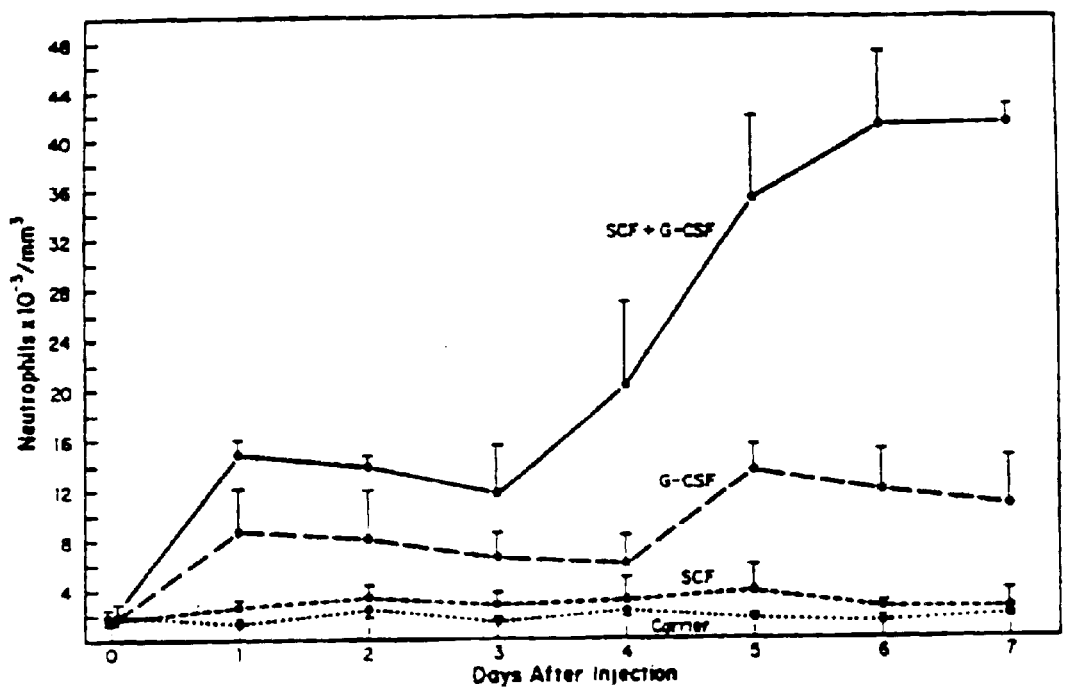

FIG. 51 shows daily coinjection of rrSCF and G-CSF for one week caused a highly synergistic increase in circulating neutrophils with a marked linear increase between day 4 and day 6.

Figure 52:
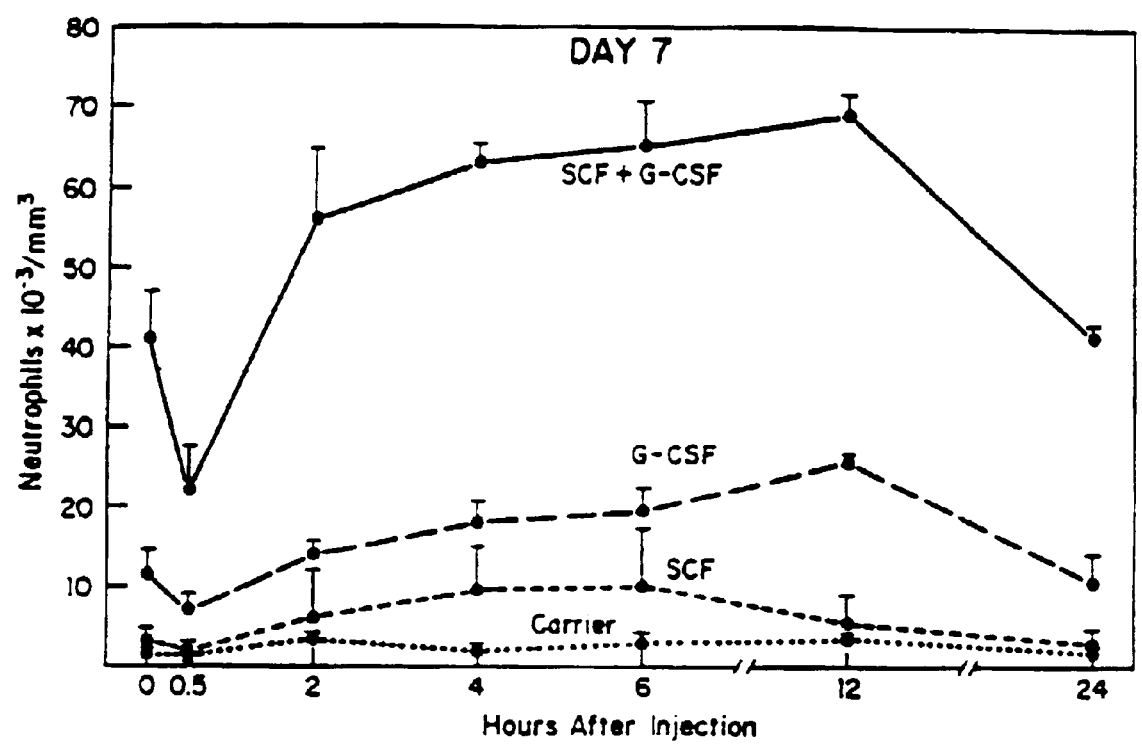

FIG. 52 shows a kinetic study of rrSCF plus G-CSF-induced neutrophilia after the seventh daily injection shows that the peak of circulating neutrophils occurs at 12 hours and reaches a level of $69 \times 10^3$ PMN/mm$^3$.

Figure 53:
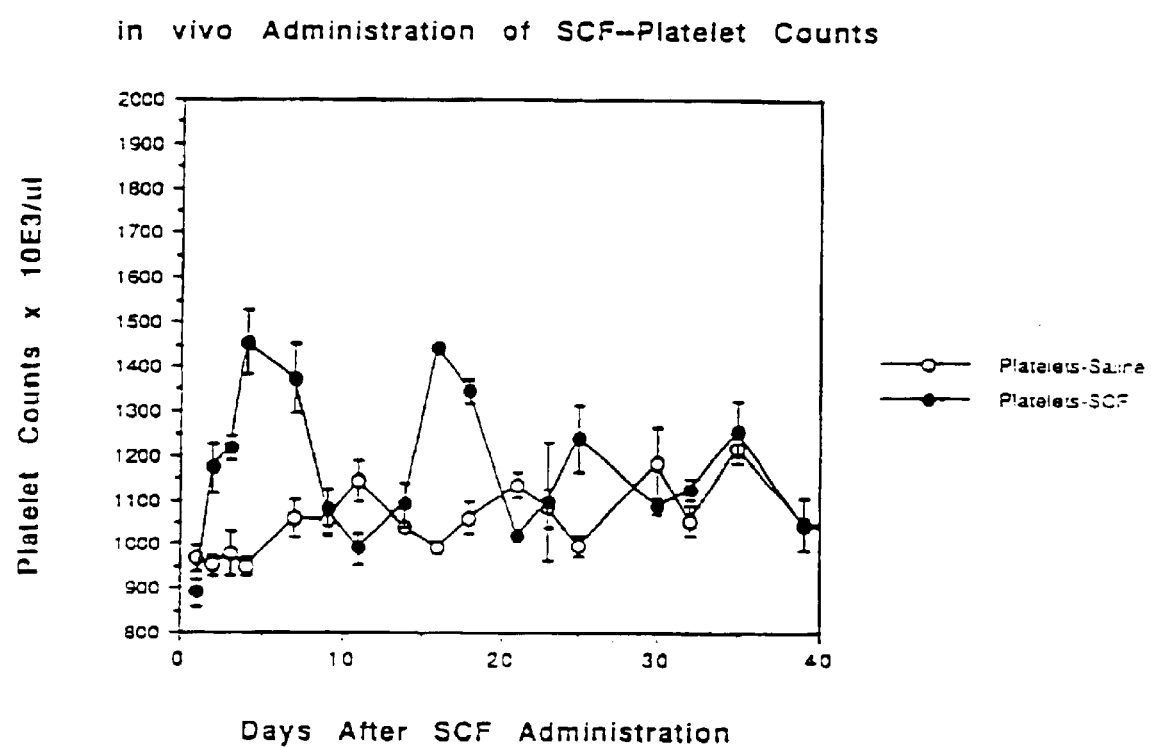

FIG. 53 shows in vivo administration of SCF-platelet counts.

Figure 54:
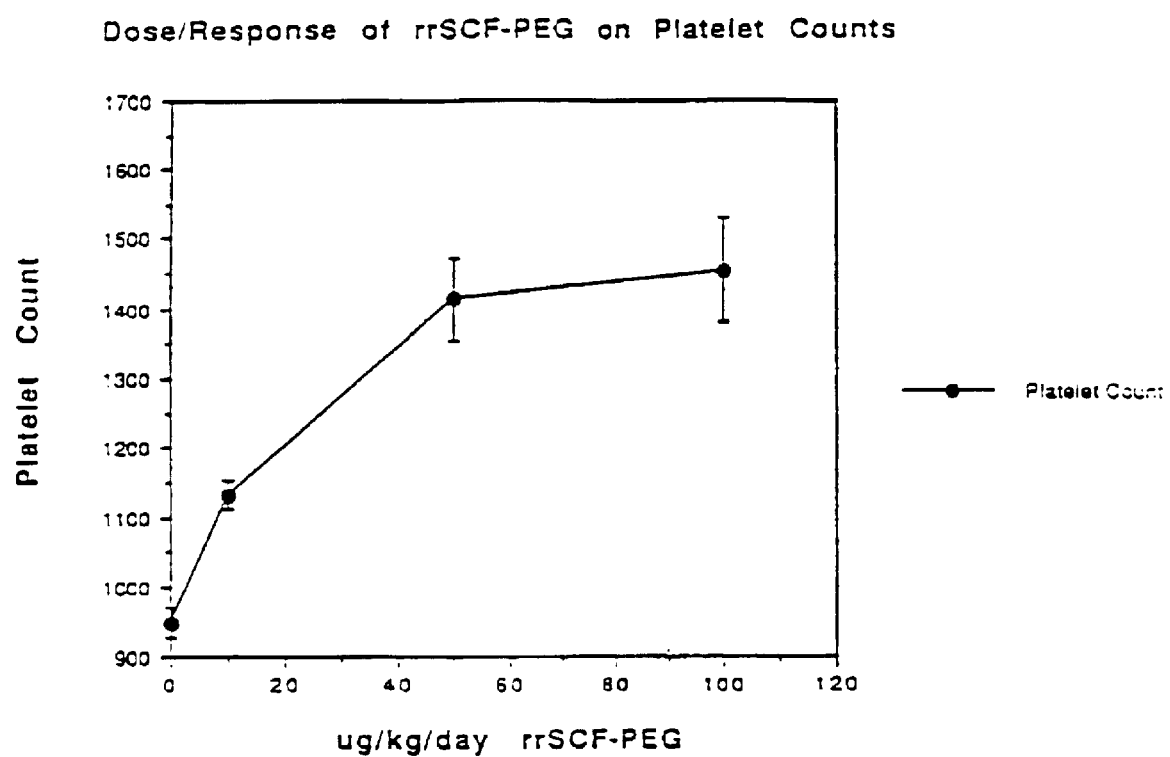

FIG. 54 shows dose response of rratSCF-PEG on platelet counts.

Figure 55:
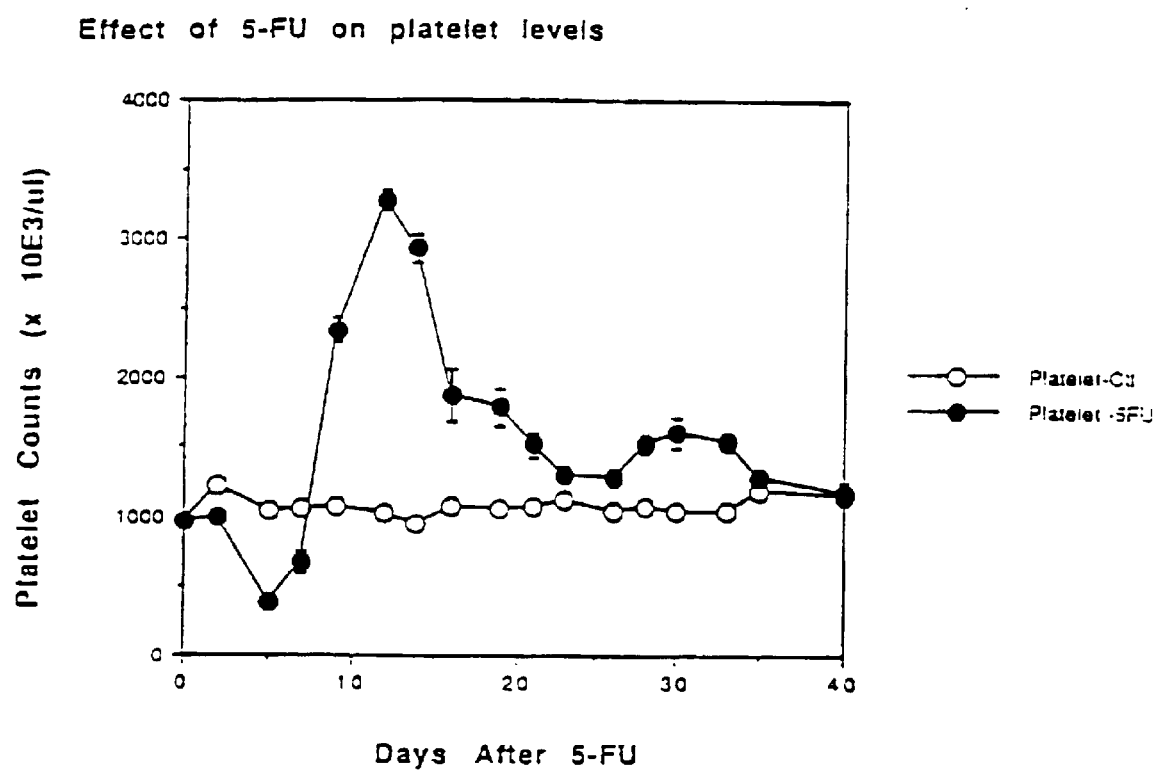

FIG. 55 shows effect of 5-FU on platelet levels.

FIG. 56 shows 5-FU effect on ACH+ cells in marrow (56A) and spleen (56B).

Figure 57:
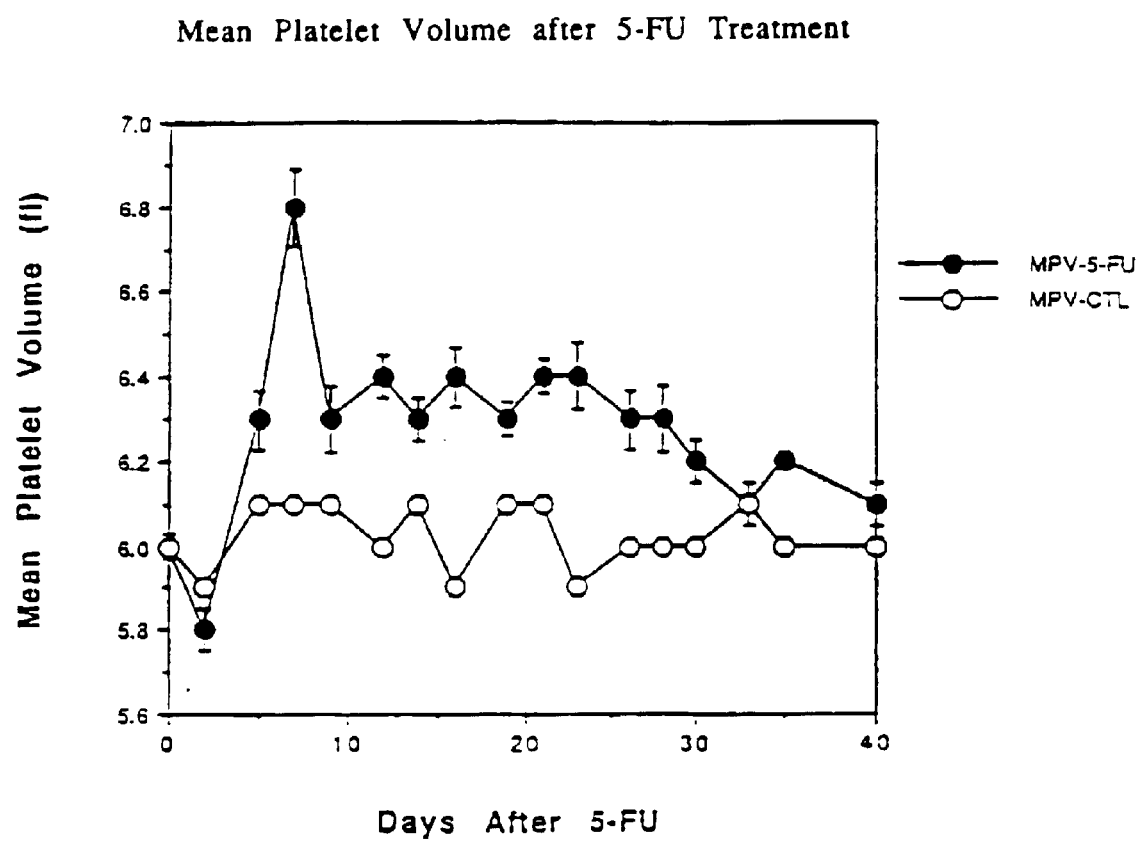

FIG. 57 shows mean platelet volume after 5-FU treatment.

Figure 58:
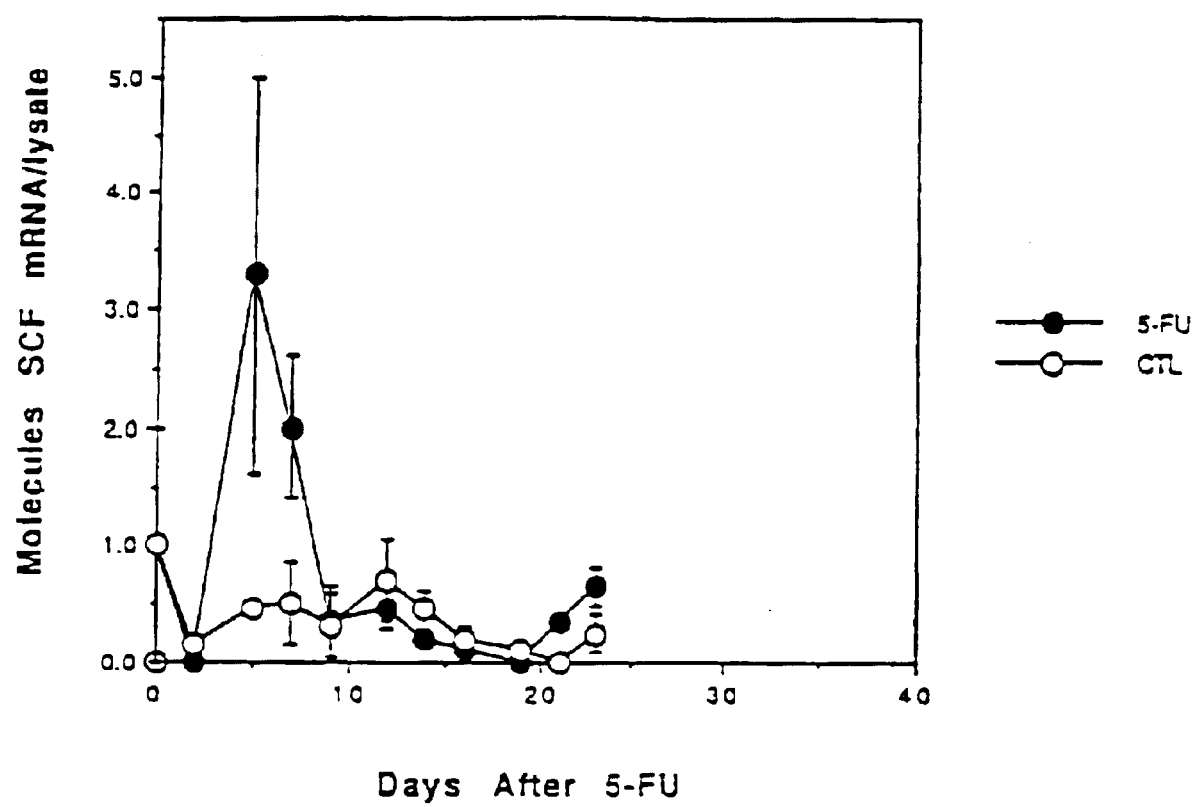

FIG. 58 shows SCF mRNA levels after 5-FU treatment. The data in this figure were Generated from the same marrow samples collected in FIG. 56. Data points are the values determined from individual mice.

Figure 59:
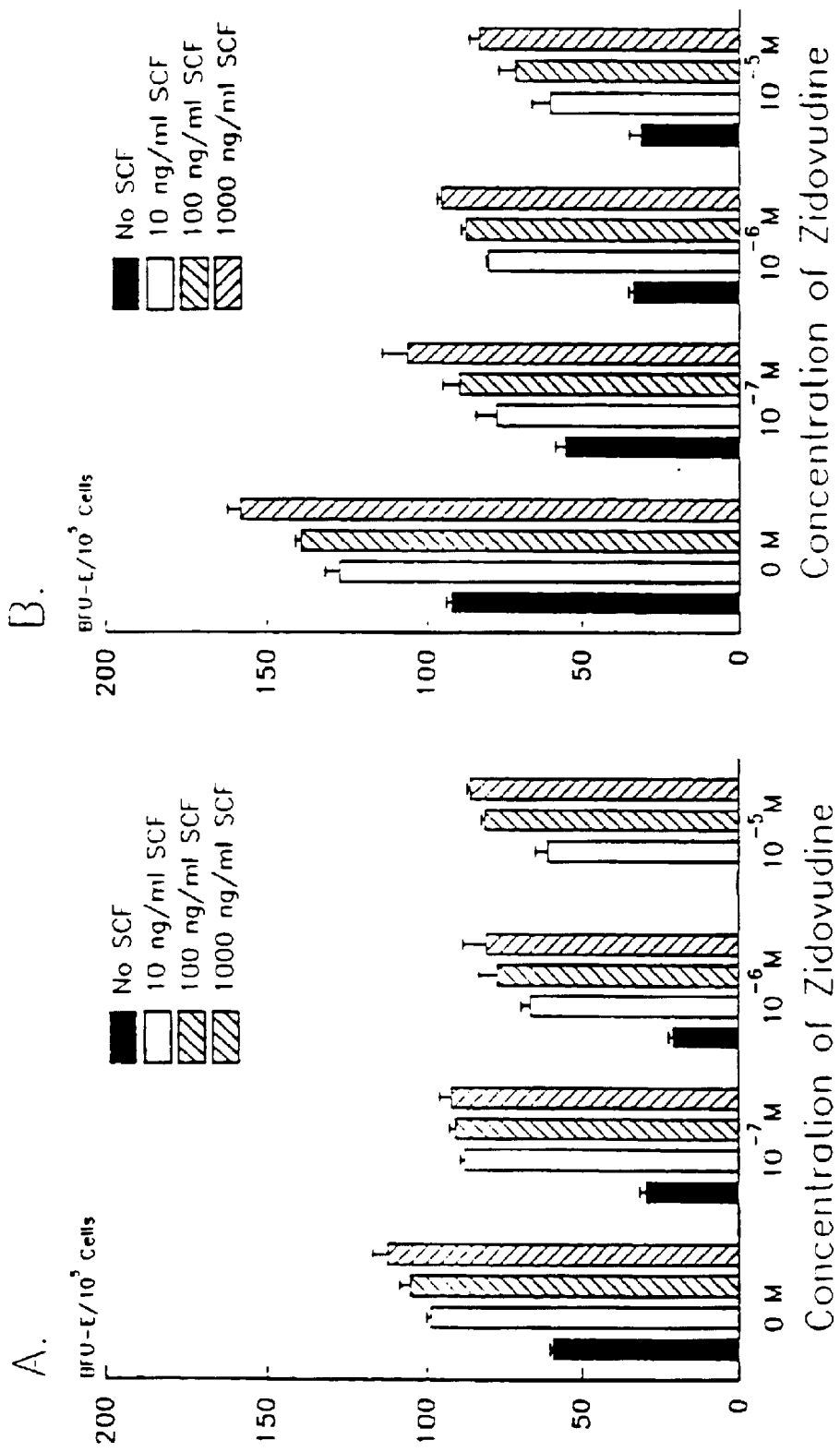

FIG. 59 shows the effects of HuSCF and zidovudine on peripheral blood BFU-E in normal donors. Light density cells were plated in duplicate in the presence of (A) 1 U/ml or (B) 4 U/ml of erythropoietin, four concentrations of zidovudine (0, $10^{-7}$ M, $10^{-6}$ M and $10^{-5}$ M) and four concentrations of HuSCF (0, 10 ng/ml, 100 ng/ml and 1000 ng/ml). The bars represent the mean±S.E.M. for the duplicate determinations of both normal donors. All of the increases for HuSCF are statistically significant (independent t-test, 2-tailed, p<0.01).

Figure 60:
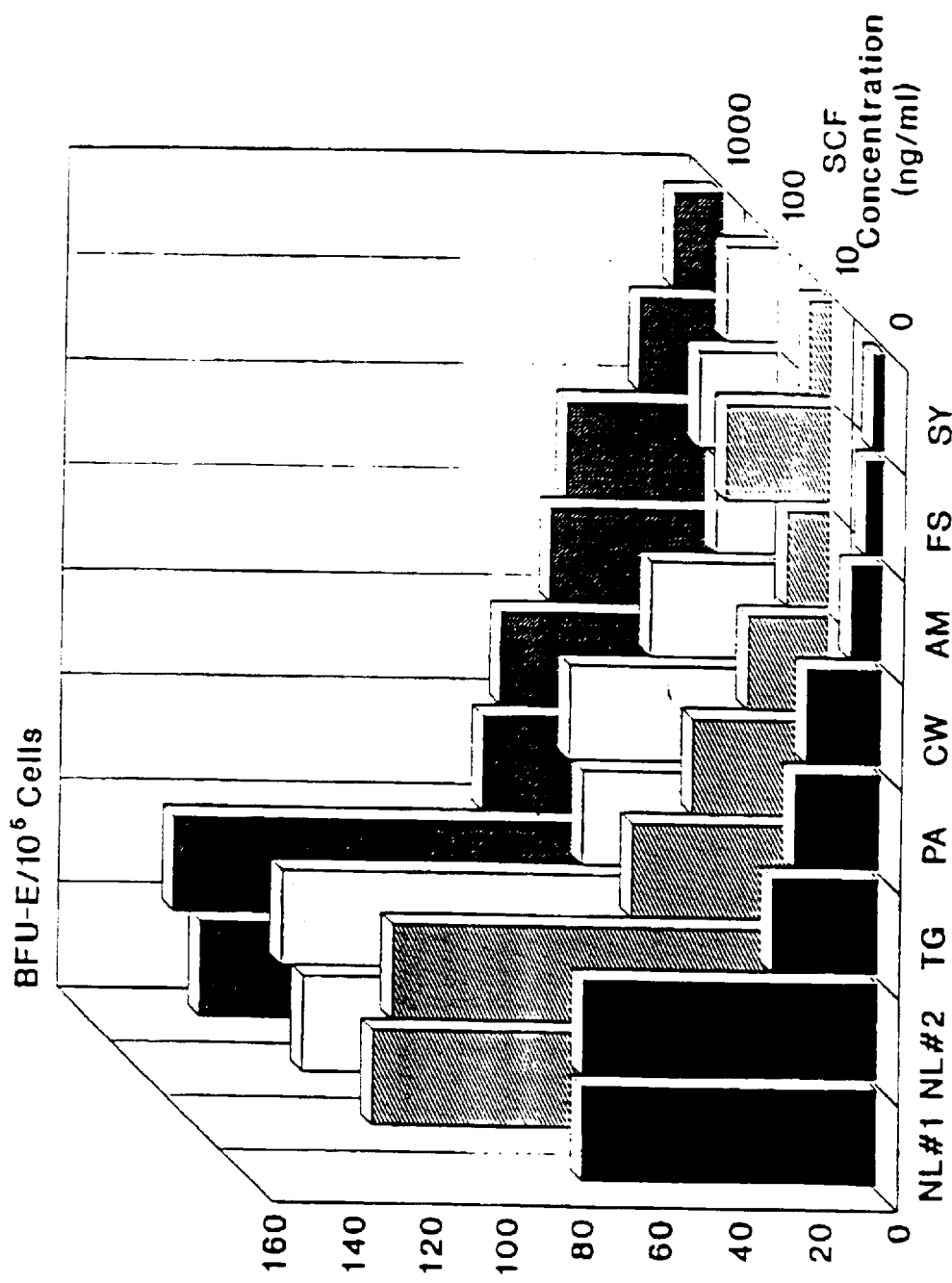

FIG. 60 shows the effects of HuSCF and zidovudine on peripheral blood BFU-E in normal and HIV-infected donors. Light density cells were plated in duplicate in the presence of 1 U/ml of erythropoietin and four concentrations of HuSCF (0, 10 ng/ml, 100 ng/ml and 1000 ng/ml). The bars represent the mean for the duplicate determinations.

Figure 61:
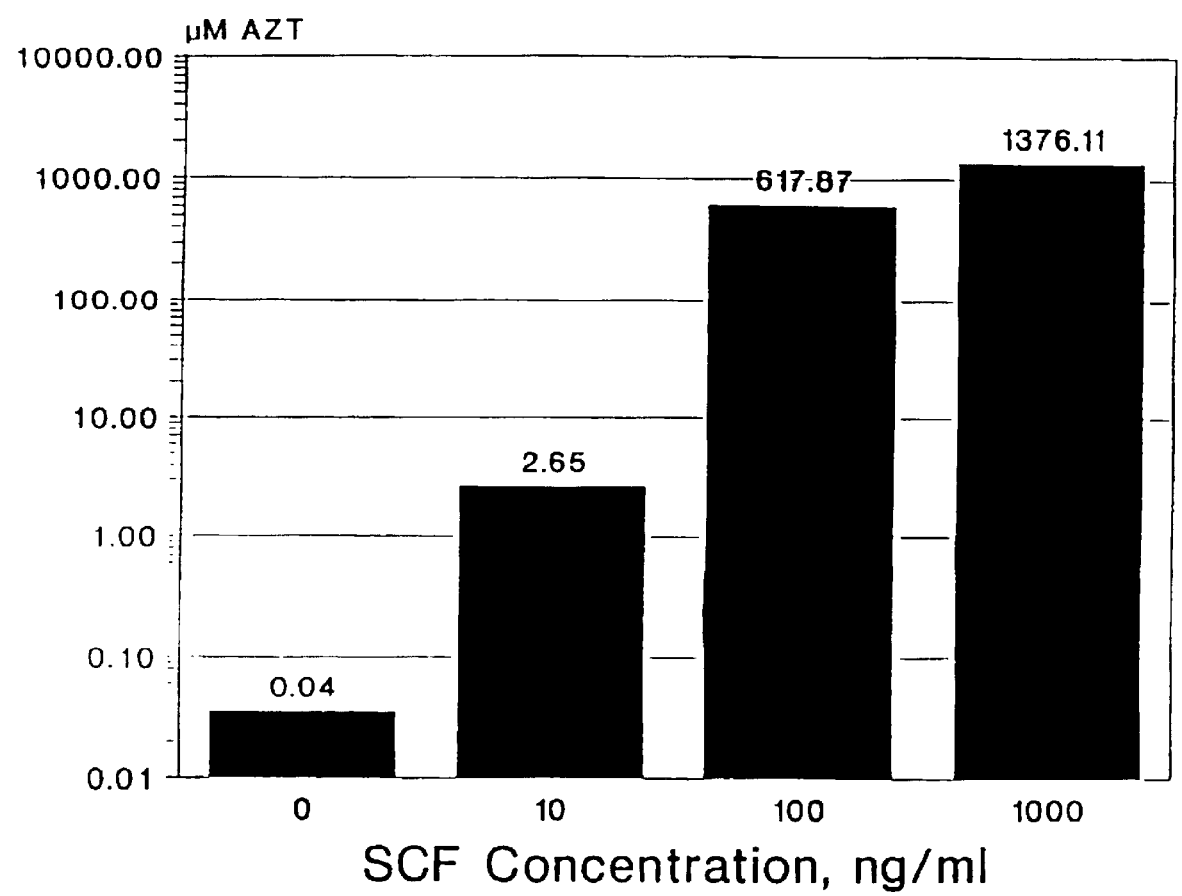

FIG. 61 shows alteration of the BFU-E $ID_{50}$ of zidovudine by HuSCF. The 50% inhibitory concentration for BFU-E for each level of HuSCF was calculated as described in the text. The bars represent the mean for the two normal donors.

Figure 62:
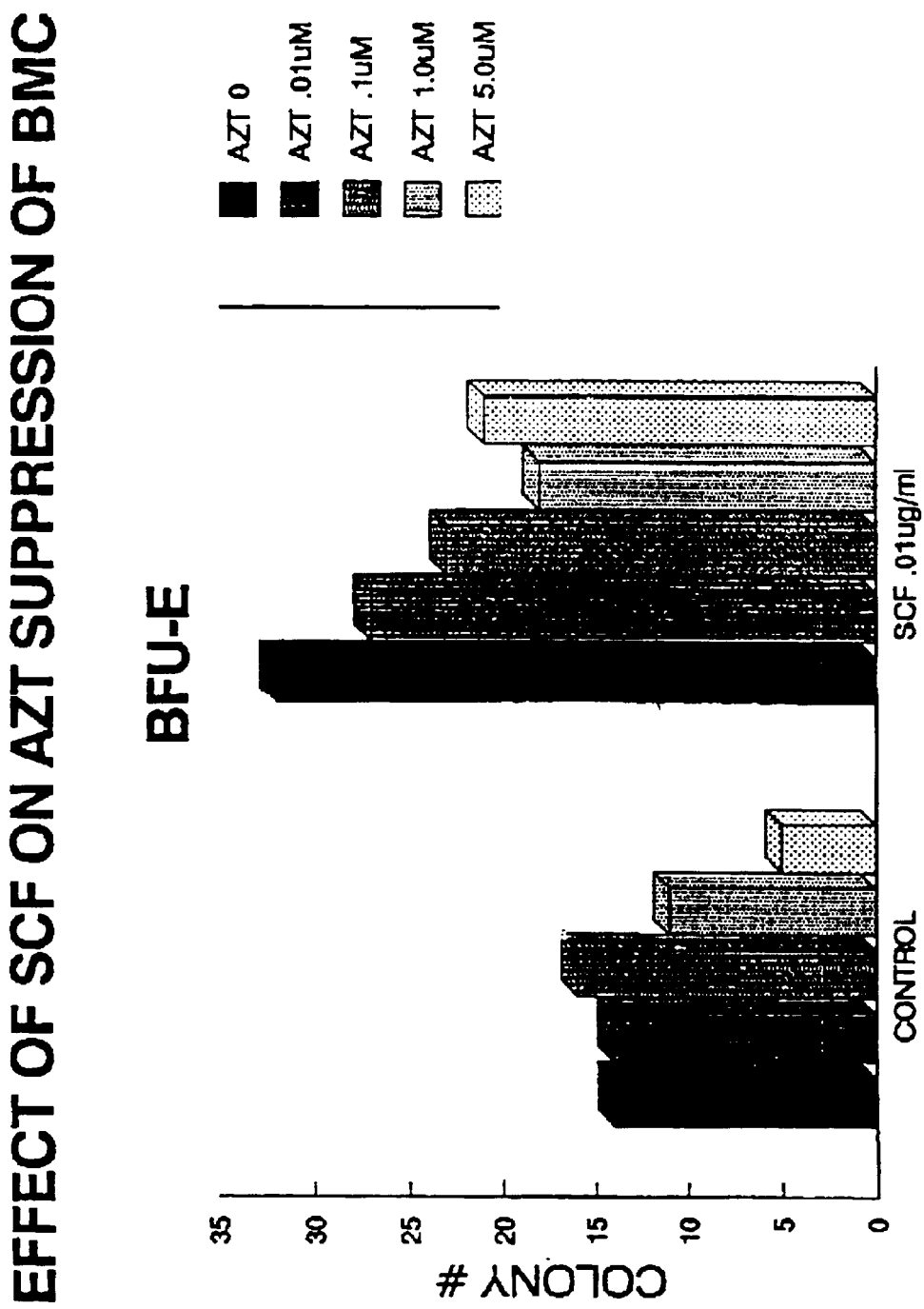

FIG. 62 shows effects of HuSCF on AZT suppression of bone marrow culture as measured by BFU-E.

Figure 63:
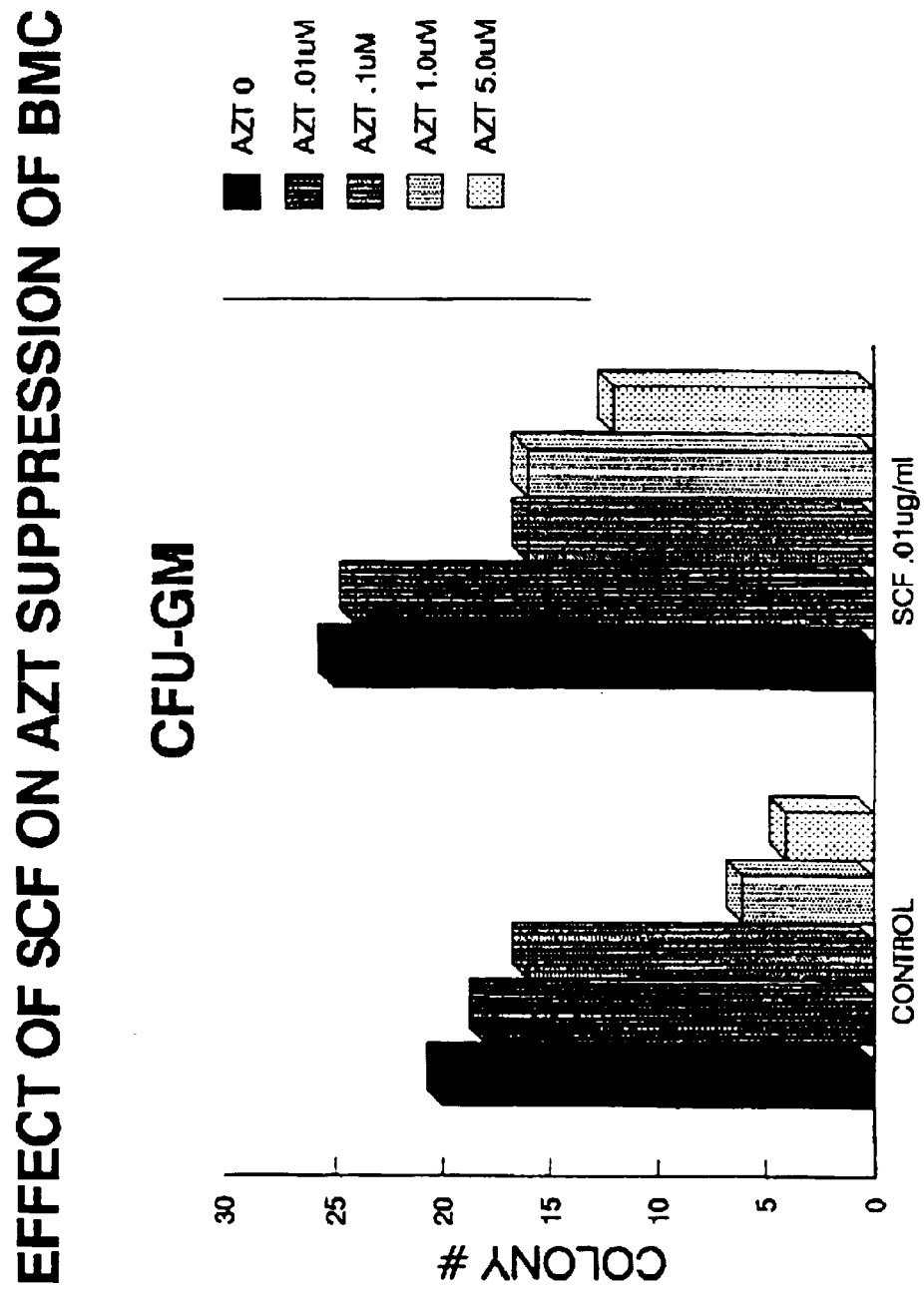

FIG. 63 shows effect of HuSCF on AZT suppression of bone marrow culture as measured by CFU-GM.

Figure 64:
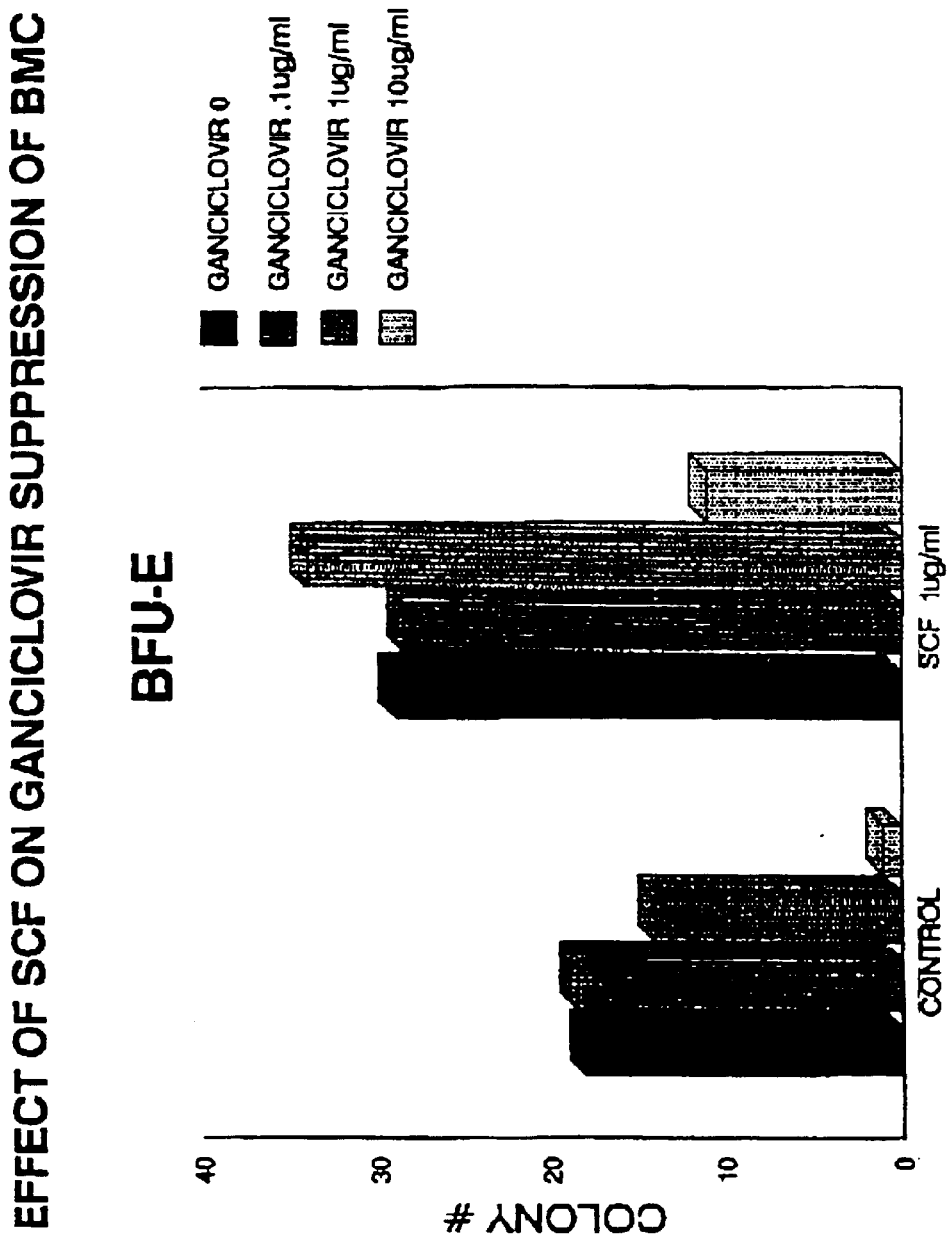

FIG. 64 shows effects of HuSCF on gancyclovir suppression of bone marrow culture as measured by BFU-E.

Figure 65:
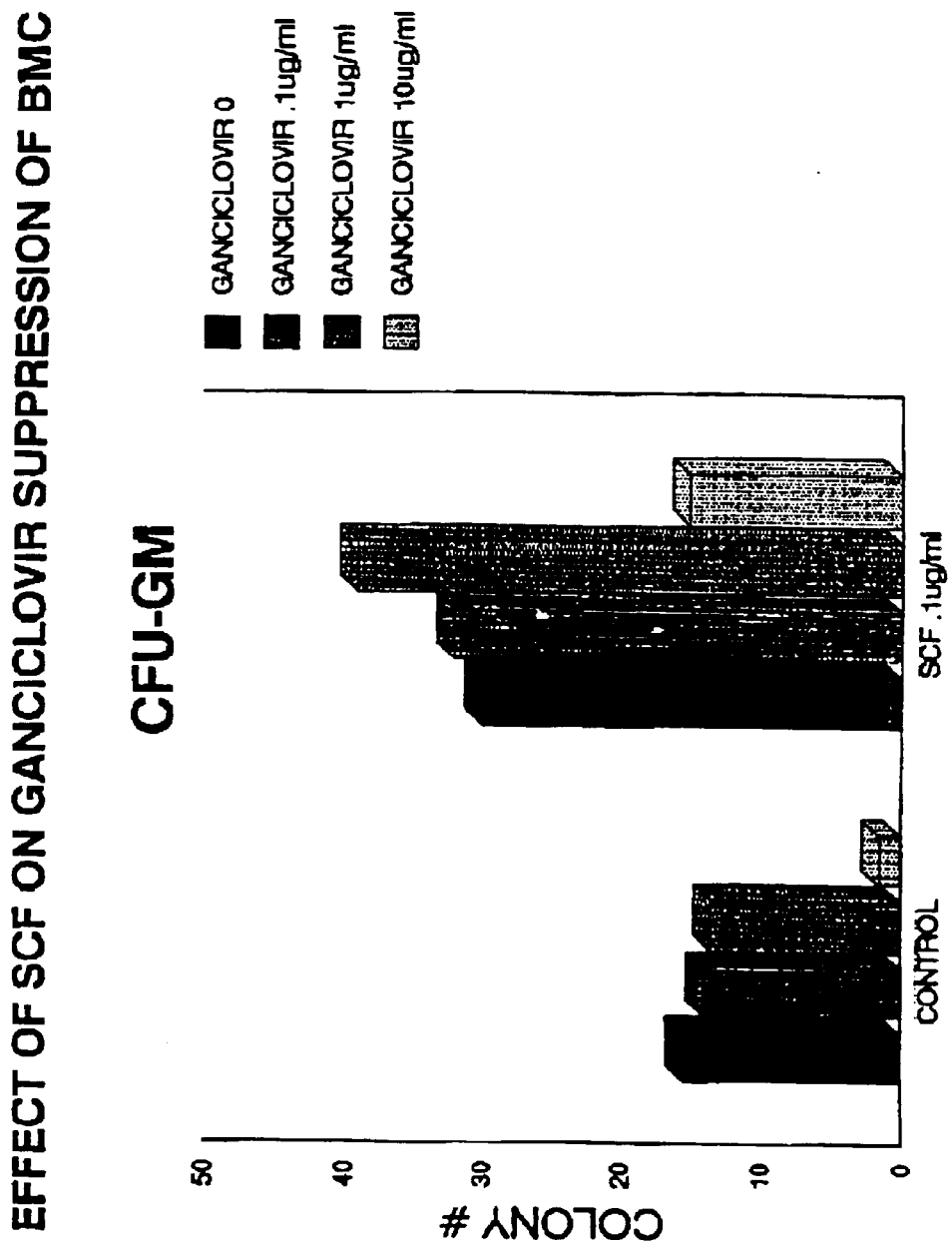

FIG. 65 shows effect of HuSCF on gancyclovir suppression of bone marrow culture as measured by CFU-GM.

Figure 66:

FIG. 66 shows effect of rat SCF alone and in combination with CFU-S number in a pre-CFU-S assay.

Figure 67:
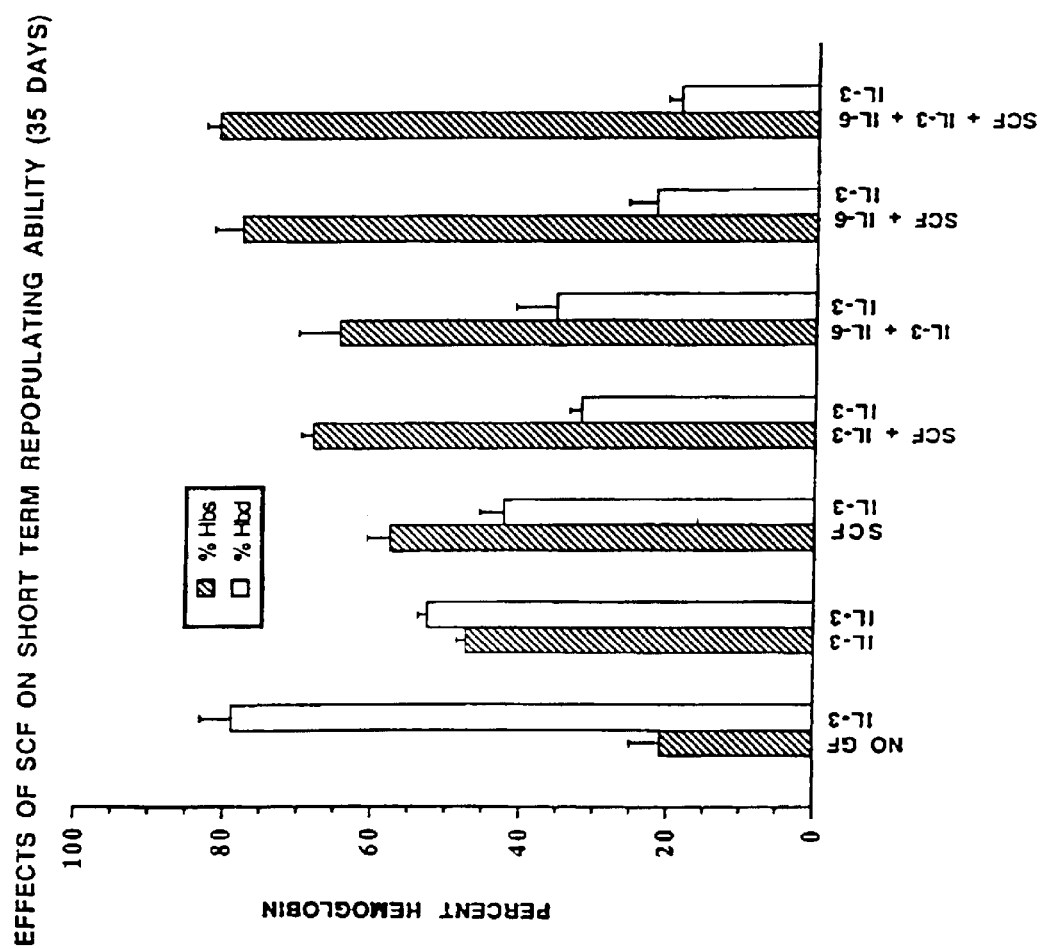

FIG. 67 shows effect of SCF alone and in combination on the recovery of hemaglobin.

Figure 68:
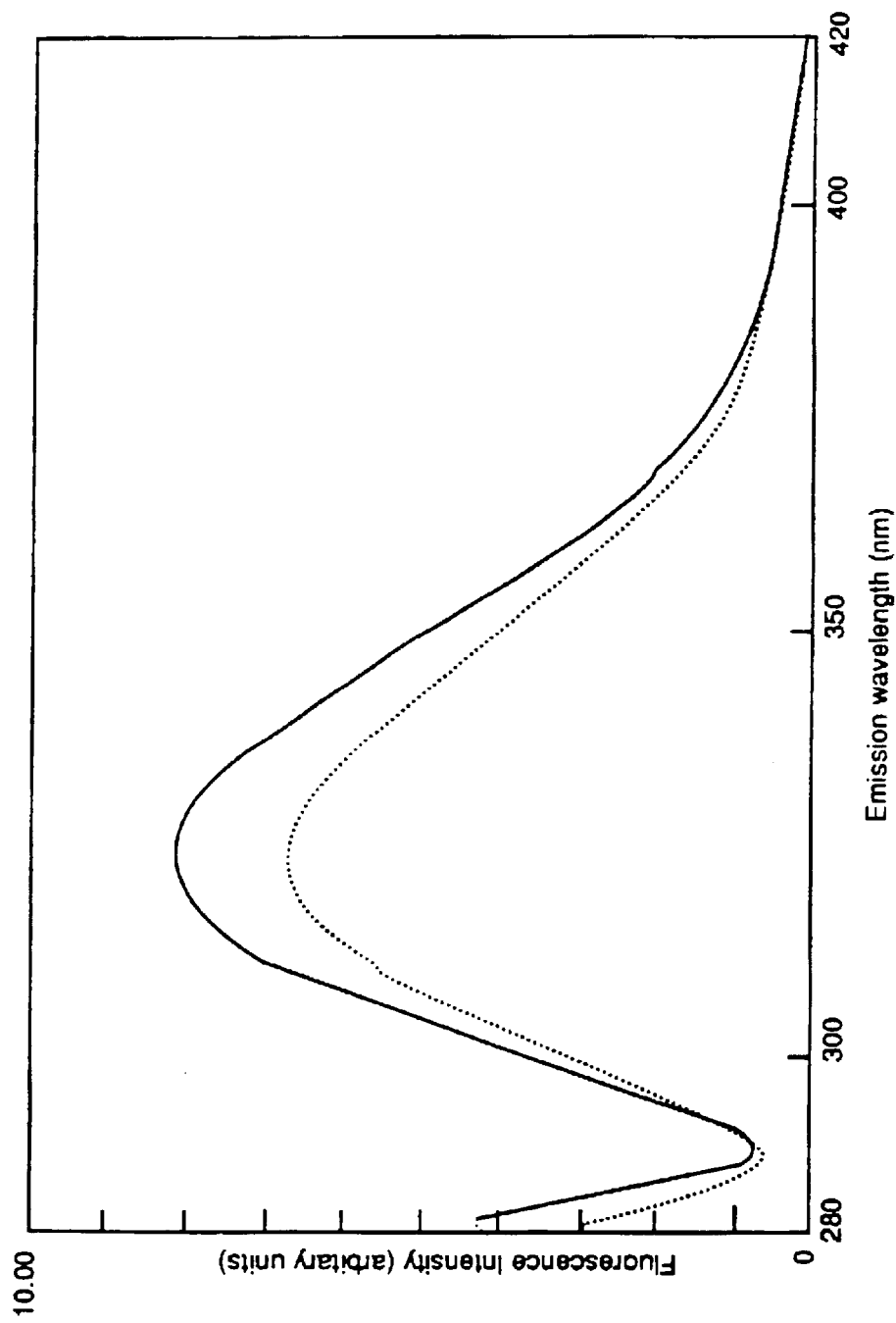

FIG. 68 shows fluorescence emission spectra of human $SCF^{1-164}$. Emission intensity is shown for CHO cell derived [Met$^{-1}$]$SCF^{1-162}$ (dotted line) and E. coli derived [Met$^{-1}$]$SCF^{1-164}$ (solid line).

Figure 69A:
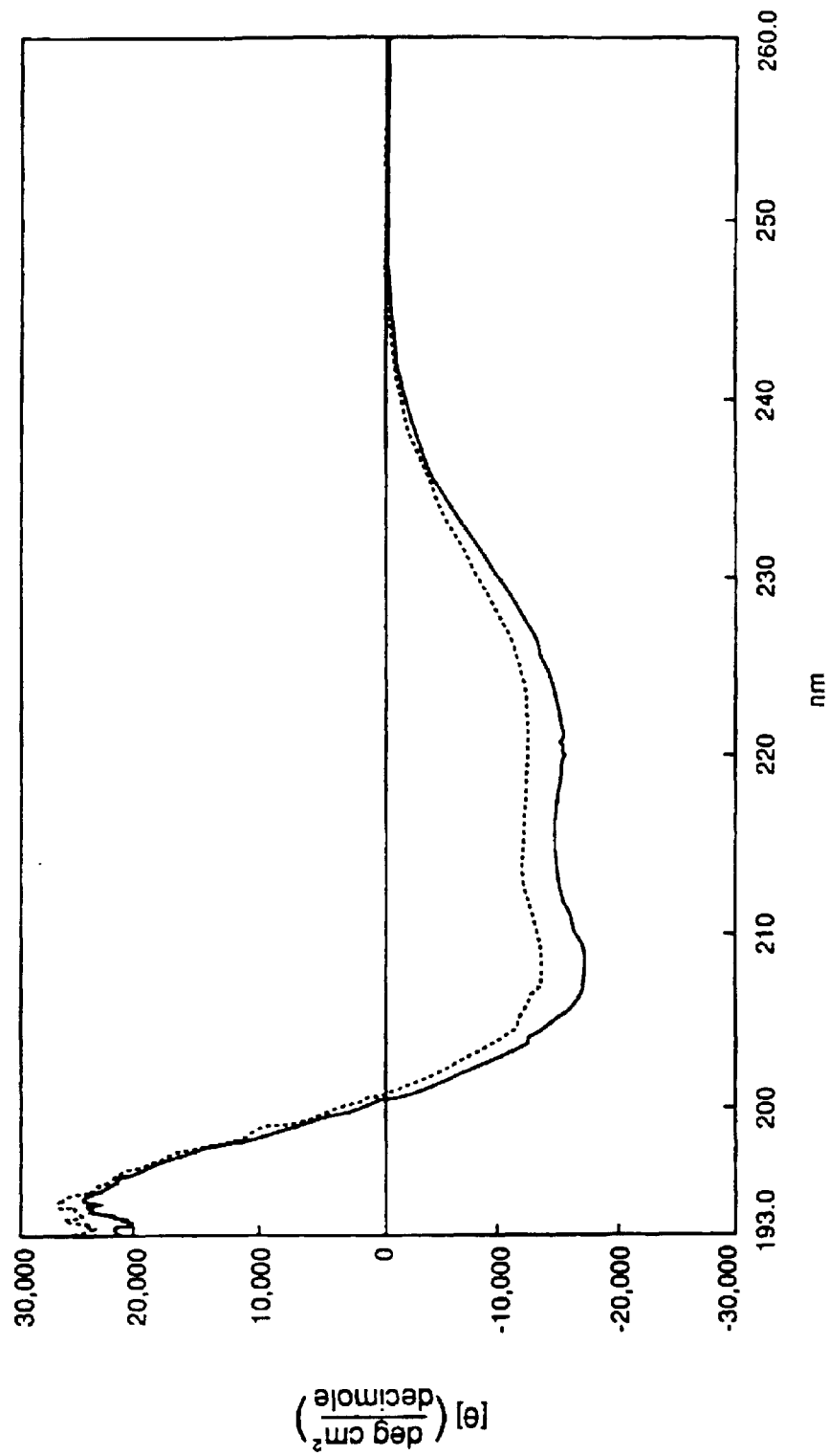
Figure 69B:
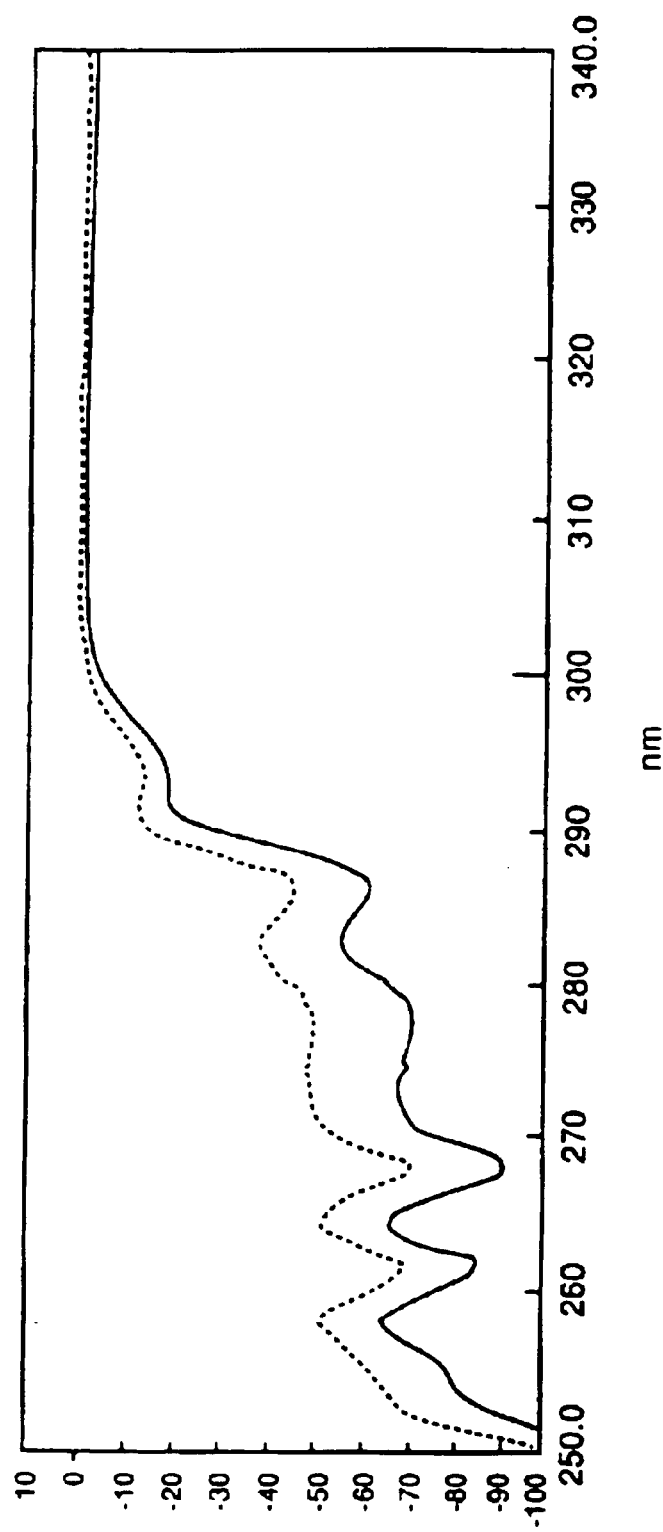

FIG. 69 shows circular dichroism of SCF. The far ultraviolet spectra (A) and near ultraviolet spectra (B) are shown for CHO cell-derived [Met$^{-1}$]$SCF^{1-162}$ (dotted line) and E. coli derived [Met$^{-1}$]$SCF^{1-164}$ (solid line).

FIG. 70 shows second derivative infrared spectra of SCF. The second derivative infrared spectra in the amide I region (1700–1620 cm$^{-1}$) for E. coli derived [Met$^{-1}$]$SCF^{1-164}$ (A) and CHO cell derived (Met$^{-1}SCF^{1-162}$ (B) are shown.

Numerous aspects and advantages of the invention will be apparent to those skilled in the art upon consideration of the following detailed description which provides illustrations of the practice of the invention in its presently-preferred embodiments.

DETAILED DESCRIPTION OF THE INVENTION

According to the present invention, novel stem cell factors and DNA sequences coding for all or part of such SCFs are provided. The term "stem cell factor" or "SCF" as used herein refers to naturally-occurring SCF (e.g. natural human SCF) as well as non-naturally occurring (i.e., different from naturally occurring) polypeptides having amino acid sequences and glycosylation sufficiently duplicative of that of naturally-occurring stem cell factor to allow possession of a hematopoietic biological activity of naturally-occurring stem cell factor. Stem cell factor has the ability to stimulate growth of early hematopoietic progenitors which are capable of maturing to erythroid, megakaryocyte, granulocyte, lymphocyte, and macrophage cells. SCF treatment of mammals results in absolute increases in hematopoietic cells of both myeloid and lymphoid lineages. One of the hallmark characteristics of stem cells is their ability to differentiate into both myeloid and lymphoid cells [Weissman, *Science*, 241, 58–62 (1988)]. Treatment of Steel mice (Example 8B) with recombinant rat SCF results in increases of granulocytes, monocytes, erythrocytes, lymphocytes, and platelets. Treatment of normal primates with recombinant human SCF results in increases in myeloid and lymphoid cells (Example 8C).

There is embryonic expression of SCF by cells in the migratory pathway and homing sites of melanoblasts, germ cells, hematopoietic cells, brain and spinal chord.

Early hematopoietic progenitor cells are enriched in bone marrow from mammals which has been treated with 5-Fluorouracil (5-FU). The chemotherapeutic drug 5-FU selectively depletes late hematopoietic progenitors. SCF is active on post 5-FU bone marrow.

The biological activity and pattern of tissue distribution of SCF demonstrates its central role in embryogenesis and hematopoiesis as well as its capacity for treatment of various stem cell deficiencies.

The present invention provides DNA sequences which include: the incorporation of codons "preferred" for expression by selected nonmammalian hosts; the provision of sites for cleavage by restriction endonuclease enzymes; and the provision of additional initial, terminal or intermediate DNA sequences which facilitate construction of readily-expressed vectors. The present invention also provides DNA sequences coding for polypeptide analogs or derivatives of SCF which differ from naturally-occurring forms in terms of the identity or location of one or more amino acid residues (i.e., deletion analogs containing less than all of the residues specified for SCF; substitution analogs, wherein one or more residues specified are replaced by other residues; and addition analogs wherein one or more amino acid residues is added to a terminal or medial portion of the polypeptide) and which share some or all the properties of naturally-occurring forms. The present invention specifically provides DNA sequences encoding the full length unprocessed amino acid sequence as well as DNA sequences encoding the processed form of SCF.

Novel DNA sequences of the invention include sequences useful in securing expression in procaryotic or eucaryotic host cells of polypeptide products having at least a part of the primary structural conformation and one or more of the biological properties of naturally-occurring SCF. DNA sequences of the invention specifically comprise: (a) DNA sequences set forth in FIGS. 14B, 14C, 15B, 15C, 15D, 42and 44 or their complementary strands; (b) DNA sequences which hybridize (under hybridization conditions disclosed in Example 3 or more stringent conditions) to the DNA sequences in FIGS. 14B, 14C, 15B, 15C, 15D, 42, and 44 or to fragments thereof; and (c) DNA sequences which, but for the degeneracy of the genetic code, would hybridize to the DNA sequences in FIGS. 14B, 14C, 15B, 15C, 15D, 42, and 44. Specifically comprehended in parts (b) and (c) are genomic DNA sequences encoding allelic variant forms of SCF and/or encoding SCF from other mammalian species, and manufactured DNA sequences encoding SCF, fragments of SCF, and analogs of SCF. The DNA sequences may incorporate codons facilitating transcription and translation of messenger RNA in microbial hosts. Such manufactured sequences may readily be constructed according to the methods of Alton et al., PCT published application WO 83/04053.

According to another aspect of the present invention, the DNA sequences described herein which encode polypeptides having SCF activity are valuable for the information which they provide concerning the amino acid sequence of the mammalian protein which have heretofore been unavailable. The DNA sequences are also valuable as products useful in effecting the large scale synthesis of SCF by a variety of recombinant techniques. Put another way, DNA sequences provided by the invention are useful in generating new and useful viral and circular plasmid DNA vectors, new and useful transformed and transfected procaryotic and eucaryotic host cells (including bacterial and yeast cells and mammalian cells grown in culture), and new and useful methods for cultured growth of such host cells capable of expression of SCF and its related products.

DNA sequences of the invention are also suitable materials for use as labeled probes in isolating human genomic DNA encoding SCF and other genes for related proteins as well as cDNA and genomic DNA sequences of other mammalian species. DNA sequences may also be useful in various alternative methods of protein synthesis (e.g., in insect cells) or in genetic therapy in humans and other mammals. DNA sequences of the invention are expected to be useful in developing transgenic mammalian species which may serve as eucaryotic "hosts" for production of SCF and SCF products in quantity. See, generally, Palmiter et al., Science 222, 809–814 (1983).

The present invention provides purified and isolated naturally-occurring SCF (i.e. purified from nature or manufactured such that the primary, secondary and tertiary conformation, and the glycosylation pattern are identical to naturally-occurring material) as well as non-naturally occurring polypeptides having a primary structural conformation (i.e., continuous sequence of amino acid residues) and glycosylation sufficiently duplicative of that-of naturally occurring stem cell factor to allow possession of a hematopoietic biological activity of naturally occurring SCF. Such polypetides include derivatives and analogs.

In a preferred embodiment, SCF is characterized by being the product of procaryotic or eucaryotic host expression (e.g., by bacterial, yeast, higher plant, insect and mammalian cells in culture) of exogenous DNA sequences obtained by genomic or cDNA cloning or by gene synthesis. That is, in a preferred embodiment, SCF is "recombinant SCF." The products of expression in typical yeast (e.g., *Saccharomyces cerevisiae*) or procaryote (e.g., *E. coli*) host cells are free of association with any mammalian proteins. The products of expression in vertebrate [e.g., non-human mammalian (e.g. COS or CHO) and avian] cells are free of association with any human proteins. Depending upon the host employed, polypeptides of the invention may be glycosylated with mammalian or other eucaryotic carbohydrates or may be non-glycosylated. The host cell can be altered using techniques such as those described in Lee et al. J. Biol. Chem. 264, 13848 (1989) hereby incorporated by reference. Polypeptides of the invention may also include an initial methionine amino acid residue (at position −1).

In addition to naturally-occurring allelic forms of SCF, the present invention also embraces other SCF products such as polypeptide analogs of SCF. Such analogs include fragments of SCF. Following the procedures of the above-noted published application by Alton et al. (WO 83/04053), one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives of SCF. Such products share at least one of the biological properties of SCF but may differ in others. As examples, products of the invention include those which are foreshortened by e.g., deletions; or those which are more stable to hydrolysis (and, therefore, may have more pronounced or longer-lasting effects than naturally-occurring); or which have been altered to delete or to add one or more potential sites for O-glycosylation and/or N-glycosylation or which have one or more cysteine residues deleted or replaced by, e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within SCF, which fragments may possess one property of SCF (e.g., receptor binding) and not others (e.g., early hematopoietic cell growth activity). It is noteworthy that activity is not necessary for any one or more of the products of the invention to have therapeutic utility [see, Weiland et al., *Blut,* 44, 173–175 (1982)] or utility in other contexts, such as in assays of SCF antagonism. Competitive antagonists may be quite useful in, for example, cases of overproduction of SCF or cases of human leukemias where the malignant cells overexpress receptors for SCF, as indicated by the overexpression of SCF receptors in leukemic blasts (Example 13).

Of applicability to polypeptide analogs of the invention are reports of the immunological property of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically-significant proteins such as viral antigens, polypeptide hormones, and the like. Included among the immune reactions of such polypeptides is the provocation of the formation of specific antibodies in immunologically-active animals [Lerner et al., *Cell,* 23, 309–310 (1981); Ross et al., *Nature,* 294, 654–656 (1981); Walter et al., *Proc. Natl. Acad. Sci. USA,* 77, 5197–5200 (1980); Lerner et al., *Proc. Natl. Acad. Sci. USA,* 78, 3403–3407 (1981); Walter et al., *Proc. Natl. Acad. Sci. USA,* 78, 4882–4886 (1981); Wong et al., *Proc. Natl. Acad. Sci. USA,* 79, 5322–5326 (1982); Baron et al., *Cell,* 28, 395–404 (1982); Dressman et al., *Nature,* 295, 185–160 (1982); and Lerner, *Scientific American,* 248, 66–74 (1983)]. See, also, Kaiser et al. [*Science,* 223, 249–255 (1984)] relating to biological and immunological properties of synthetic peptides which approximately share secondary structures of peptide hormones but may not share their primary structural conformation.

The present invention also includes that class of polypeptides coded for by portions of the DNA complementary to the protein-coding strand of the human cDNA or genomic DNA sequences of SCF, i.e., "complementary inverted proteins" as described by Tramontano et al. [*Nucleic Acid Res.,* 12, 5049–5059 (1984)].

Representative SCF polypeptides of the present invention include but are not limited to $SCF^{1-148}$, $SCF^{1-162}$, $SCF^{1-164}$, $SCF^{1-165}$ and $SCF^{1-183}$ in FIG. 15C; $SCF^{1-185}$, $SCF^{1-188}$, $SCF^{1-189}$ and $SCF^{1-248}$ in FIG. 42; and $SCF^{1-157}$, $SCF^{1-160}$, $SCF^{1-161}$ and $SCF^{1-220}$ in FIG. 44.

SCF can be purified using techniques known to those skilled in the art. The subject invention comprises a method of purifying SCF from an SCF containing material such as conditioned media or human urine, serum, the method comprising one or more of steps such as the following: subjecting the SCF containing material to ion exchange chromatography (either cation or anion exchange chromatography); subjecting the SCF containing material to reverse phase liquid chromatographic separation involving, for example, an immobilized $C_4$ or $C_6$ resin; subjecting the fluid to immobilized-lectin chromatography, i.e., binding of SCF to the immobilized lectin, and eluting with the use of a sugar that competes for this binding. Details in the use of these methods will be apparent from the descriptions given in Examples 1, 10, and 11 for the purification of SCF. The techniques described in Example 2 of the Lai et al. U.S. Pat. No. 4,667,016, hereby incorporated by reference are also useful in purifying stem cell factor.

Isoforms of SCF are isolated using standard techniques such as the techniques set forth in commonly owned U.S. Ser. No. 421,444, entitled Erythropoietin Isoforms, filed Oct. 13, 1989, now abandoned, hereby incorporated by reference.

Also comprehended by the invention are pharmaceutical compositions comprising therapeutically effective amounts of polypeptide products of the invention together with suitable diluents, preservatives, solubilizers, emulsifiers, adjuvants and/or carriers useful in SCF therapy. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent adsorption to surfaces, detergents (e.g., Tween 20, Tween 80, Pluronic F68, bile acid salts), solubilizing agents (e.g., glycerol, polyethylene glycol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein (described in Example 12 below), complexation with metal ions, or incorporation of the material into or onto particulate preparations of polymeric compounds such as polylactic acid, polglycolic acid, hydrogels, etc. or into liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of SCF. The choice of composition will depend on the physical and chemical properties of the protein having SCF activity. For example, a product derived from a membrane-bound form of SCF may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and SCF coupled to antibodies directed against tissue-specific receptors, ligands or antigens or coupled to ligands of tissue-specific receptors. Other embodiments of the compositions of the invention incorporate particulate forms, protective coatings, protease inhibitors or permeation enhancers for various routes of administration, including parenteral, pulmonary, nasal and oral.

The invention also comprises compositions including one or more additional hematopoietic factors such as EPO, G-CSF, GM-CSF, CSF-1, IL-1, IL-2, IL-3, IL-4, IL-5, IL-6, IL-7, IL-8, IL-9, IL-10, IL-11, IGF-I, or LIF (Leukemic Inhibitory Factor).

Polypeptides of the invention may be "labeled" by association with a detectable marker substance (e.g., radiolabeled with $^{125}I$ or biotinylated) to provide reagents useful in detection and quantification of SCF or its receptor bearing cells in solid tissue and fluid samples such as blood or urine.

Biotinylated SCF is useful in conjunction with immobilized streptavidin to purge leukemic blasts from bone marrow in autologous bone marrow transplantation. Biotinylated SCF is useful in conjunction with immobilized streptavidin to enrich for stem cells in autologous or allogeneic stem cells in autologous or allogeneic bone marrow transplantation. Toxin conjugates of SCF, such as ricin [Uhr, *Prog. Clin. Biol. Res.* 288, 403–412 (1989)] diptheria toxin [Moolten, *J. Natl. Con. Inst.,* 55, 473–477 (1975)], and radioisotopes are useful for direct anti-neoplastic therapy (Example 13) or as a conditioning regimen for bone marow transplantation.

Nucleic acid products of the invention are useful when labeled with detectable markers (such as radiolabels and non-isotopic labels such as biotin) and employed in hybridization processes to locate the human SCF gene position and/or the position of any related gene family in a chromosomal map. They are also useful for identifying human SCF gene disorders at the DNA level and used as gene markers for identifying neighboring genes and their disorders. The human SCF gene is encoded on chromosome 12, and the murine SCF gene maps to chromosome 10 at the S1 locus.

SCF is useful, alone or in combination with other therapy, in the treatment of a number of hematopoietic disorders. SCF can be used alone or with one or more additional hematopoietic factors such as EPO, G-CSF, GM-CSF, CSF-1, IL-1, IL-2, IL-3, IL-4, IL-5, IL-6, IL-7, IL-8, IL-9, IL-10, IL-11, IL-1, IGF-I or LIF in the treatment of hematopoietic disorders.

There is a group of stem cell disorders which are characterized by a reduction in functional marrow mass due to toxic, radiant, or immunologic injury and which may be treatable with SCF. Aplastic anemia is a stem cell disorder in which there is a fatty replacement of hematopoietic tissue and pancytopenia. SCF enhances hematopoietic proliferation and is useful in treating aplastic anemia (Example 8B). Steel mice are used as a model of human aplastic anemia [Jones, *Exp. Hematol.,* 11, 571–580 (1983)). Promising results have been obtained with the use of a related cytokine, GM-CSF in the treatment of aplastic anemia [Antin, et al., *Blood,* 70, 129a (1987)]. Paroxysmal nocturnal hemoglobinuria (PNH) is a stem cell disorder characterized by formation of defective platelets and granulocytes as well as abnormal erythrocytes.

There are many diseases which are treatable with SCF. These include the following: myelofibrosis, myelosclerosis, osteopetrosis, metastatic carcinoma, acute leukemia, multiple myeloma, Hodgkin's disease, lymphoma, Gaucher's disease, Niemann-Pick disease, Letterer-Siwe disease, refractory erythroblastic anemia, Di Guglielmo syndrome, congestive splenomegaly, Hodgkin's disease, Kala azar, sarcoidosis, primary splenic pancytopenia, miliary tuberculosis, disseminated fungus disease, Fulminating septicemia, malaria, vitamin $B_{12}$ and folic acid deficiency, pyridoxine deficiency, Diamond Blackfan anemia, hypopigmentation disorders such as piebaldism and vitiligo. The erythroid, megakaryocyte, and granulocytic stimulatory properties of SCF are illustrated in Example 8B and 8C.

Enhancement of growth in non-hematopoietic stem cells such as primordial germ cells, neural crest derived melanocytes, commissural axons originating from the dorsal spinal cord, crypt cells of the gut, mesonephric and metanephric kidney tubules, and olfactory bulbs is of benefit in states where specific tissue damage has occurred to these sites. SCF is useful for treating neurological damage and is a growth factor for nerve cells. SCF is useful during in vitro fertilization procedures or in treatment of infertility states. SCF is useful for treating intestinal damage resulting from irradiation or chemotherapy.

There are stem cell myeloproliferative disorders such as polycythemia vera, chronic myelogenous leukemia, myeloid mataplasia, primary thrombocythemia, and acute leukemias which are treatable with SCF, anti-SCF antibodies, or SCF-toxin conjugates.

There are numerous cases which document the increased proliferation of leukemic cells to the hematopoietic cell growth factors G-CSF, GM-CSF, and IL-3 [Delwel, et al., *Blood,* 72, 1944–1949 (1988)]. Since the success of many chemotherapeutic drugs depends on the fact that neoplastic cells cycle more actively than normal cells, SCF alone or in combination with other factors acts as a growth factor for neoplastic cells and sensitizes them to the toxic effects of chemotherapeutic drugs. The overexpression of SCF receptors on leukemic blasts is shown in Example 13.

A number of recombinant hematopoietic factors are undergoing investigation for their ability to shorten the leukocyte nadir resulting from chemotherapy and radiation regimens. Although these factors are very useful in this setting, there is an early hematopoietic compartment which is damaged, especially by radiation, and has to be repopulated before these later-acting growth factors can exert their optimal action. The use of SCF alone or in combination with these factors further shortens or eliminates the leukocyte and platelet nadir resulting from chemotherapy or radiation treatment. In addition, SCF allows for a dose intensification of the anti-neoplastic or irradiation regimen (Example 19).

SCF is useful for expanding early hematopoietic progenitors in syngeneic, allogeneic, or autologous bone marrow transplantation. The use of hematopoietic growth factors has been shown to decrease the time for neutrophil recovery after transplantation [Donahue, et al., *Nature,* 321, 872–875 (1986) and Welte et al., *J. Exp. Med.,* 165, 941–948, (1987)]. For bone marrow transplantation, the following three scenarios are used alone or in combination: a donor is treated with SCF alone or in combination with other hematopoietic factors prior to bone marrow aspiration or peripheral blood leucophoresis to increase the number of cells available for transplantation; the bone marrow is treated in vitro to activate or expand the cell number prior to transplantation; finally, the recipient is treated to enhance engraftment of the donor marrow.

SCF is useful for enhancing the efficiency of gene therapy based on transfecting (or infecting with a retroviral vector) hematopoietic stem cells. SCF permits culturing and multiplication of the early hematopoietic progenitor cells which are to be transfected. The culture can be done with SCF alone or in combination with IL-6, IL-3, or both. Once tranfected, these cells are then infused in a bone marrow transplant into patients suffering from genetic disorders. [Lim, *Proc. Natl. Acad. Sci,* 86, 8892–8896 (1989)]. Examples of genes which are useful in treating genetic disorders include adenosine deaminase, glucocerebrosidase, hemoglobin, and cystic fibrosis.

SCF is useful for treatment of acquired immune deficiency (AIDS) or severe combined immunodeficiency states (SCID) alone or in combination with other factors such as IL-7 (see Example 14). Illustrative of this effect is the ability of SCF therapy to increase the absolute level of circulating T-helper (CD4+, $OKT_4$+) lymphocytes. These cells are the primary cellular target of human immunodeficiency virus (HIV) leading to the immunodeficiency state in AIDS patients [Montagnier, in *Human T-Cell Leukemia/Lymphoma Virus,* ed. R. C. Gallo, Cold Spring Harbor, N.Y., 369-379 (1984)]. In addition, SCF is useful for combatting the myelosuppressive effects of anti-HIV drugs such as AZT [Gogu *Life Sciences,* 45, No. 4 (1989)].

SCF is useful for enhancing hematopoietic recovery after acute blood loss.

In vivo treatment with SCF is useful as a boost to the immune system for fighting neoplasia (cancer). An example of the therapeutic utility of direct immune function enhancement by a recently cloned cytokine (IL-2) is described in Rosenberg et al., *N. Eng. J. Med.,* 313 1485 (1987).

The administration of SCF with other agents such as one or more other hematopoietic factors, is temporally spaced or given together. Prior treatment with SCF enlarges a progenitor population which responds to terminally-acting hematopoietic factors such as G-CSF or EPO. The route of administration may be intravenous, intraperitoneal sub-cutaneous, or intramuscular.

The subject invention also relates to antibodies specifically binding stem cell factor. Example 7 below describes the production of polyclonal antibodies. A further embodiment of the invention is monoclonal antibodies specifically binding SCF (see Example 20). In contrast to conventional antibody (polyclonal) preparations which typically include different antibodies directed against different determinants (epitopes), each monoclonal antibody is directed against a single determinant on the antigen. Monoclonal antibodies are useful to improve the selectivity and specificity of diagnostic and analytical assay methods using antigen-antibody binding. Also, they are used to neutralize or remove SCF from serum. A second advantage of monoclonal antibodies is that they can be synthesized by hybridoma cells in culture, uncontaminated by other immunoglobulins. Monoclonal antibodies may be prepared from supernatants of cultured hybridoma cells or from ascites induced by intra-peritoneal inoculation of hybridoma cells into mice. The hybridoma technique described originally by Köhler and Milstein [*Eur. J. Immunol.* 6, 511–519 (1976)] has been widely applied to produce hybrid cell lines that secrete high levels of monoclonal antibodies against many specific antigens.

The following examples are offered to more fully illustrate the invention, but are not to be construed as limiting the scope thereof.

EXAMPLE 1

Purification/Characterization of Stem Cell Factor from Buffalo Rat Liver Cell Conditoned Medium
A. In Vitro Biological Assays
1. HPP-CFC Assay There are a variety of biological activities which can be attributed to the natural mammalian rat SCF as well as the recombinant rat SCF protein. One such activity is its effect on early hematopoietic cells. This activity can be measured in a High Proliferative Potential Colony Forming Cell (HPP-CFC) assay [Zsebo, et al., supra (1988)]. To investigate the effects of factors on early hematopoietic cells, the HPP-CFC assay system utilizes mouse bone marrow derived from animals 2 days after 5-fluorouracil (5-FU) treatment. The chemotherapeutic drug 5-FU selectively depletes late hematopoietic progenitors, allowing for detection of early progenitor cells and hence factors which act on such cells. The rat SCF is plated in the presence of CSF-1 or IL-6 in semi-solid agar cultures. The agar cultures contain McCoys complete medium (GIBCO), 20% fetal bovine serum, 0.3% agar, and $2 \times 10^5$ bone marrow cells/ml. The McCoys complete medium contains the following components: 1×McCoys medium supplemented with 0.1 mM pyruvate, 0.24× essential amino acids, 0.24× non-essential amino acids, 0.027% sodium bicarbonate, 0.24× vitamins, 0.72 mM glutamine, 25 µg/ml L-serine, and 12 µg/ml L-asparagine. The bone marrow cells are obtained from Balb/c mice injected i.v. with 150 mg/kg 5-FU. The femurs are harvested 2 days post 5-FU treatment of the mice and bone marrow is flushed out. The red blood cells are lysed with red blood cell lysing reagent (Becton Dickenson) prior to plating. Test substances are plated with the above mixture in 30 mm dishes. Fourteen days later the colonies (>1 mm in diameter) which contain thousands of cells are scored. This assay was used throughout the purification of natural mammalian cell-derived rat SCF.

In a typical assay, rat SCF causes the proliferation of approximately 50 HPP-CFC per 200,000 cells plated. The rat SCF has a synergistic activity on 5-FU treated mouse bone marrow cells; HPP-CFC colonies will not form in the presence of single factors but the combination of SCF and CSF-1 or SCF and IL-6 is active in this assay.

2. MC/9 Assay

Another useful biological activity of both naturally-derived and recombinant rat SCF is the ability to cause the proliferation of the IL-4 dependent murine mast cell line, MC/9 (ATCC CRL 8306). MC/9 cells are cultured with a source of IL-4 according to the ATCC CRL 8306 protocol. The medium used in the bioassay is RPMI 1640, 4% fetal bovine serum, $5 \times 10^{-5}$ M 2-mercaptoethanol, and 1× glutamine-pen-strep. The MC/9 cells proliferate in response to SCF without the requirement for other growth factors. This proliferation is measured by first culturing the cells for 24 h without growth factors, plating 5000 cells in each well of 96 well plates with test sample for 48 h, pulsing for 4 h with 0.5 uCi $^3$H-thymidine (specific activity 20 Ci/mmol), harvesting the solution onto glass fiber filters, and then measuring specifically-bound radioactivity. This assay was used in the purification of mammalian cell derived rat SCF after the ACA 54 gel filtration step, section C2 of this Example. Typically, SCF caused a 4-10 fold increase in CPM over background.

3. CFU-GM

The action of purified mammalian SCF, both naturally-derived and recombinant, free from interfering colony stimulating factors (CSFs), on normal undepleted mouse bone marrow has been ascertained. A CFU-GM assay [Broxmeyer et al. *Exp. Hematol.,* 5, 87 (1977)] is used to evaluate the effect of SCF on normal marrow. Briefly, total bone marrow cells after lysis of red blood cells are plated in semi-solid agar cultures containing the test substance. After 10 days, the colonies containing clusters of >40 cells are scored. The agar cultures can be dried down onto glass slides and the morphology of the cells can be determined via specific histological stains.

On normal mouse bone marrow, the purified mammalian rat SCF was a pluripotential CSF, stimulating the growth of colonies consisting of immature cells, neutrophils, macrophages, eosinophils, and megakaryo-cytes without the requirement for other factors. From 200,000 cells plated, over 100 such colonies grow over a 10 day period. Both rat and human recombinant SCF stimulate the production of erythroid cells in combination with EPO, see Example 9.

B. Conditioned Medium

Buffalo rat liver (BRL) 3A cells, from the American Type Culture Collection (ATCC CRL 1442), were grown on microcarriers in a 20 liter perfusion culture system for the production of SCF. This system utilizes a Biolafitte fermenter (Model ICC-20) except for the screens used for retention of microcarriers and the oxygenation tubing. The 75 micron mesh screens are kept free of microcarrier clogging by periodic back flushing achieved through a system of check valves and computer-controlled pumps. Each screen alternately acts as medium feed and harvest screen. This oscillating flow pattern ensures that the screens do not clog. Oxygenation was provided through a coil of silicone tubing (50 feet long, 0.25 inch ID, 0.03 inch wall). The growth medium used for the culture of BRL 3A cells was Minimal Essential Medium (with Earle's Salts) (GIBCO), 2 mM glutamine, 3 g/L glucose, tryptose phosphate (2.95 g/L), 5% fetal bovine serum and 5% fetal calf serum. The harvest medium was identical except for the omission of serum. The reactor contained Cytodex 2 microcarriers (Pharmacia) at a concentration of 5 g/L and was seeded with $3 \times 10^9$ BRL 3A cells grown in roller bottles and removed by trypsinization. The cells were allowed to attach to and grow on the microcarriers for eight days. Growth medium was perfused through the reactor as needed based on glucose consumption. The glucose concentration was maintained at approximately 1.5 g/L. After eight days, the reactor was perfused with six volumes of serum free medium to remove most of the serum (protein concentration <50 ug/ml). The reactor was then operated batchwise until the glucose concentration fell below 2 g/L. From this point onward, the reactor was operated at a continuous perfusion rate of approximately 10 L/day. The pH of the culture was maintained at 6.9±0.3 by adjusting the $CO_2$ flow rate. The dissolved oxygen was maintained higher than 20% of air saturation by supplementing with pure oxygen as necessary. The temperature was maintained at 37±0.5° C.

Approximately 336 liters of serum free conditioned medium was generated from the above system and was used as the starting material for the purification of natural mammalian cell-derived rat SCF.

C. Purification

All purification work was carried out at 4° C. unless indicated otherwise.

Figure 1:
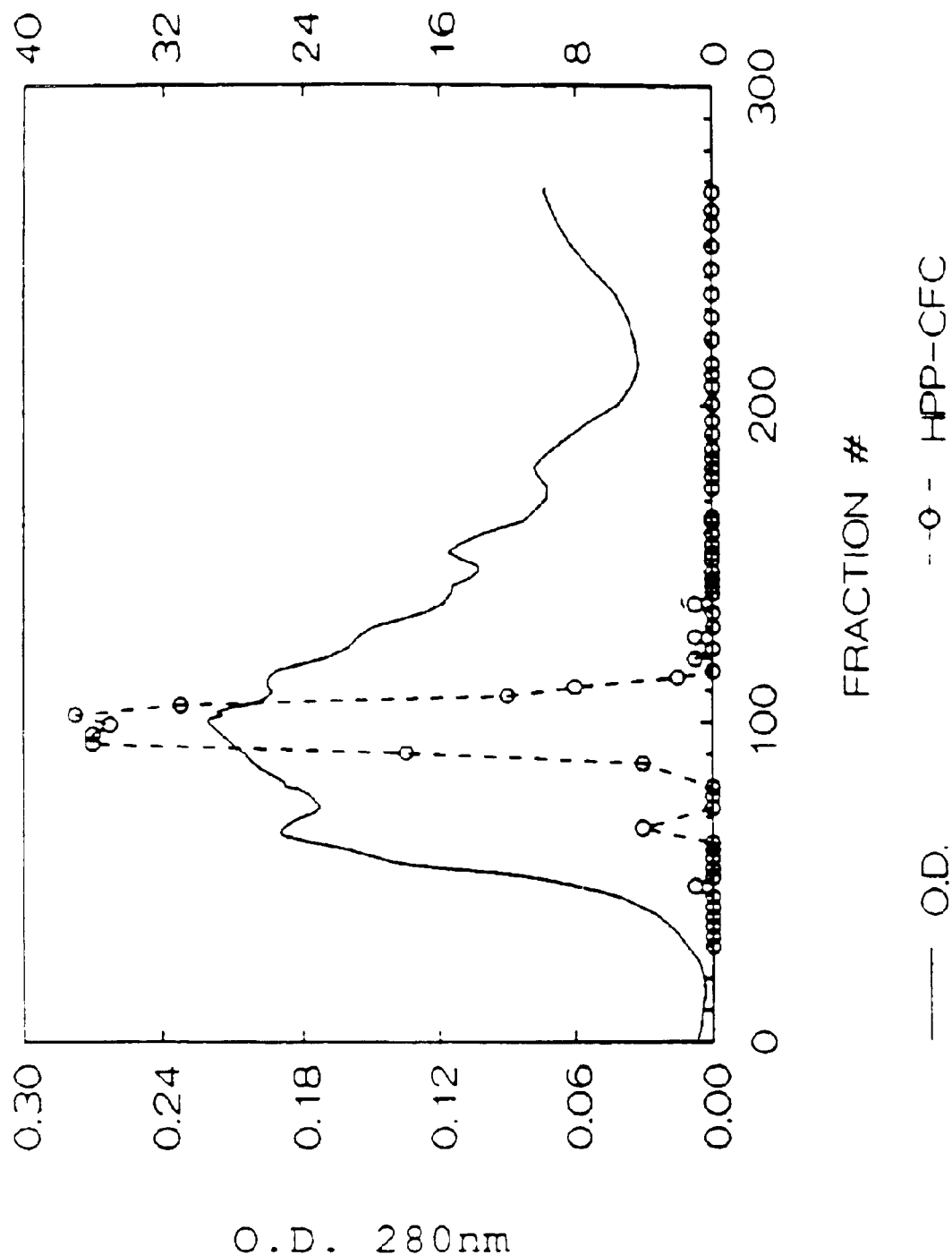
FIG. 1 is an anion exchange chromatogram from the purification of mammalian SCF.

1. DEAE-cellulose Anion Exchange Chromatography Conditioned medium generated by serum-free growth of BRL 3A cells was clarified by filtration through 0.45μ Sartocapsules (Sartorius). Several different batches (41 L, 27 L, 39 L, 30.2 L, 37.5 L, and 161 L) were separately subjected to concentration, diafiltration/buffer exchange, and DEAE-cellulose anion exchange chromatography, in similar fashion for each batch. The DEAE-cellulose pools were then combined and processed further as one batch in sections C2-5 of this Example. To illustrate, the handling of the 41 L batch was as follows. The filtered conditioned medium was concentrated to ~700 ml using a Millipore Pellicon tangential flow ultrafiltration apparatus with four 10,000 molecular weight cutoff polysulfone membrane cassettes (20 ft² total membrane area; pump rate ~1095 ml/min and filtration rate 250–315 ml/min). Diafiltration/buffer exchange in preparation for anion exchange chromatography was then accomplished by adding 500 ml of 50 mM Tris-HCl, pH 7.8 to the concentrate, reconcentrating to 500 ml using the tangential flow ultrafiltration apparatus, and repeating this six additional times. The concentrated/diafiltered preparation was finally recovered in a volume of 700 ml. The preparation was applied to a DEAE-cellulose anion exchange column (5×20.4 cm; Whatman DE-52 resin) which had been equilibrated with the 50 mM Tris-HCl, pH 7.8 buffer. After sample application, the column was washed with 2050 ml of the Tris-HCl buffer, and a salt gradient (0–300 mM NaCl in the Tris-HCl buffer; 4 L total volume) was applied. Fractions of 15 ml were collected at a flow rate of 167 ml/h. The chromatography is shown in FIG. 1. HPP-CFC colony number refers to biological activity in the HPP-CFC assay; 100 μl from the indicated fractions was assayed. Fractions collected during the sample application and wash are not shown in the Figure; no biological activity was detected in these fractions.

The behavior of all conditioned media batches subjected to the concentration, diafiltration/buffer exchange, and anion exchange chromatography was similar. Protein concentrations for the batches, determined by the method of Bradford [*Anal. Biochem.* 72, 248–254 (1976)] with bovine serum albumin as standard were in the range 30–50 μg/ml. The total volume of conditioned medium utilized for this preparation was about 336 L.

2. ACA 54 Gel Filtration Chromatography

Figure 2:
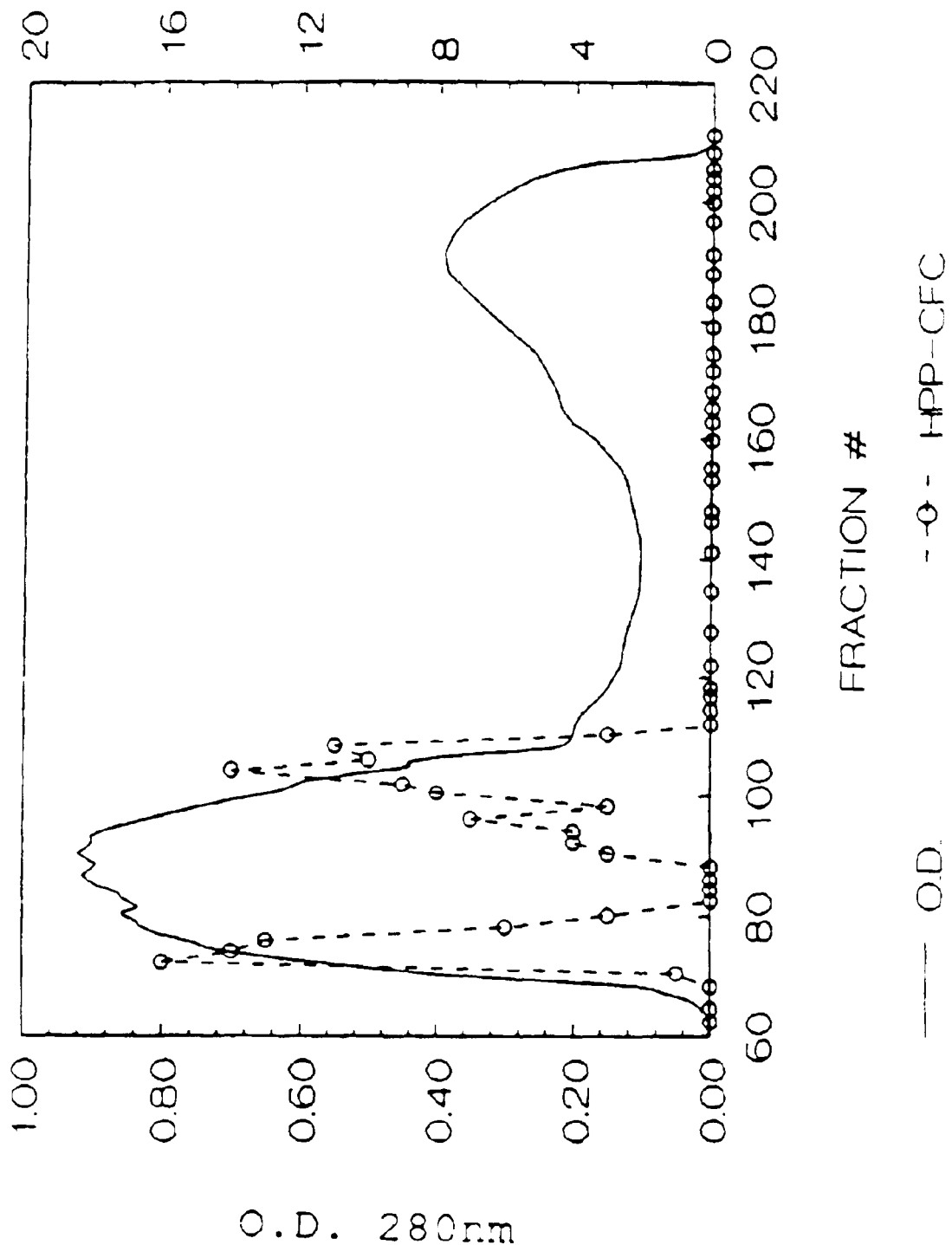
FIG. 2 is a gel filtration chromatogram from the purification of mammalian SCF.

Fractions having biological activity from the DEAE-cellulose columns run for each of the six conditioned media batches referred to above (for example, fractions 87-114 for the run shown in FIG. 1) were combined (total volume 2900 ml) and concentrated to a final volume of 74 ml with the use of Amicon stirred cells and YM10 membranes. This material was applied to an ACA 54 (LKB) gel filtration column (FIG. 2) equilibrated in 50 mM Tris-HCl, 50 mM NaCl, pH 7.4. Fractions of 14 ml were collected at a flow rate of 70 ml/h. Due to inhibitory factors co-eluting with the active fractions, the peak of activity (HPP-CFC colony number) appears split; however, based on previous chromatograms, the activity co-elutes with the major protein peak and therefore one pool of the fractions was made.

Figure 3:
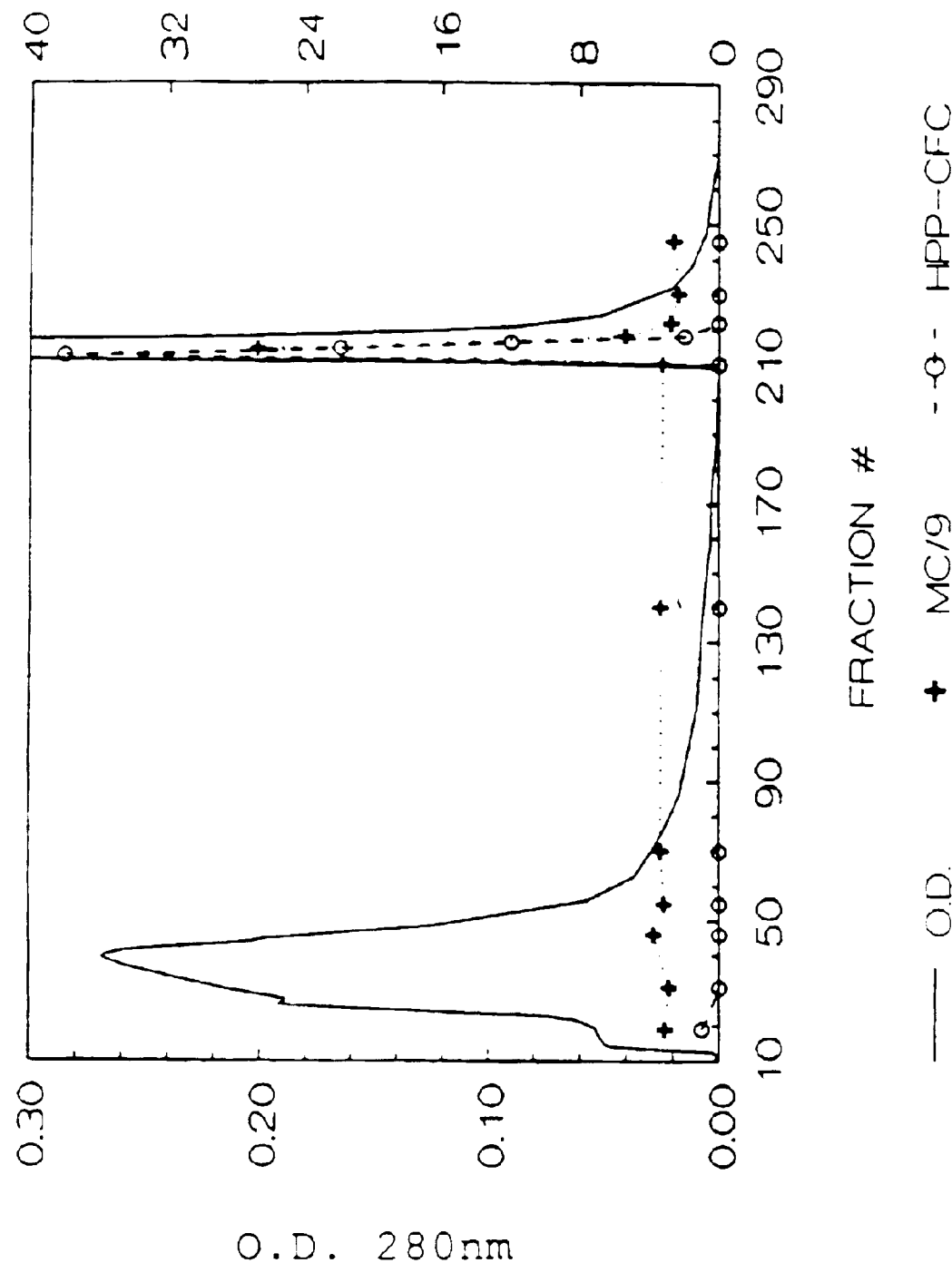
FIG. 3 is a wheat germ agglutinin-agarose chromatogram from the purification of mammalian SCF.

3. Wheat Germ Agglutinin-Agarose Chromatography Fractions 70-112 from the ACA 54 gel filtration column were pooled (500 ml). The pool was divided in half and each half subjected to chromatography using a wheat germ agglutinin-agarose column (5×24.5 cm; resin from E-Y Laboratories, San Mateo, Calif; wheat germ agglutinin recognizes certain carbohydrate structures) equilibrated in 20 mM Tris-HCl, 500 mM NaCl, pH 7.4. After the sample applications, the column was washed with about 2200 ml of the column buffer, and elution of bound material was then accomplished by applying a solution of 350 mM N-acetyl-D-glucosamine dissolved in the column buffer, beginning at fraction ~210 in FIG. 3. Fractions of 13.25 ml were collected at a flow rate of 122 ml/h. One of the chromatographic runs is shown in FIG. 3. Portions of the fractions to be assayed were dialyzed against phosphate-buffered saline; 5 ul of the dialyzed materials were placed into the MC/9 assay (cpm values in FIG. 3) and 10 μl into the HPP-CFC assay (colony number values in FIG. 3). It can be seen that the active material bound to the column and was eluted with the N-acetyl-D-glucosamine, whereas much of the contaminating material passed through the column during sample application and wash.

4. S-Sepharose Fast Flow Cation Exchange Chromatography

Figure 4:
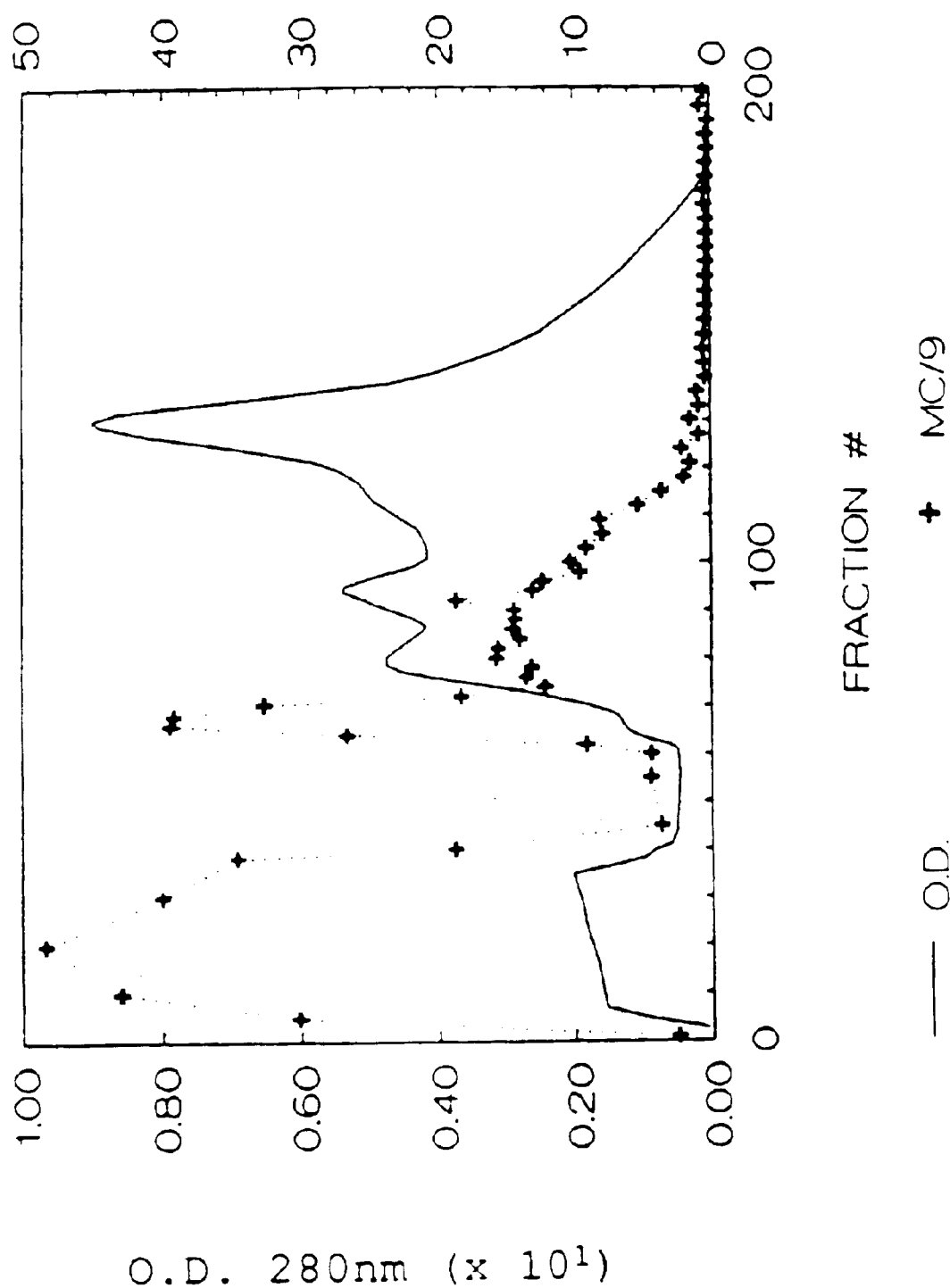
FIG. 4 is a cation exchange chromatogram from the purification of mammalian SCF.

Fractions 211-225 from the wheat germ agglutinin-agarose chromatography shown in FIG. 3 and equivalent fractions from the second run were pooled (375 ml) and dialyzed against 25 mM sodium formate, pH 4.2. To minimize the time of exposure to low pH, the dialysis was done over a period of 8 h, against 5 L of buffer, with four changes being made during the 8 h period. At the end of this dialysis period, the sample volume was 480 ml and the pH and conductivity of the sample were close to those of the dialysis buffer. Precipitated material appeared in the sample during dialysis. This was removed by centrifugation at 22,000×g for 30 min, and the supernatant from the centrifuged sample was applied to a S-Sepharose Fast Flow cation exchange column (3.3×10.25 cm; resin from Pharmacia) which had been equilibrated in the sodium formate buffer. Flow rate was 465 ml/h and fractions of 14.2 ml were collected. After sample application, the column was washed with 240 ml of column buffer and elution of bound material was carried out by applying a gradient of 0–750 mM NaCl (NaCl dissolved in column buffer; total gradient volume 2200 ml), beginning at fraction ~45 in FIG. 4. The elution profile is shown in FIG. 4. Collected fractions were adjusted to pH 7–7.4 by addition of 200 µl of 0.97 M Tris base. The cpm in FIG. 4 again refer to the results obtained in the MC/9 biological assay; portions of the indicated fractions were dialyzed against phosphate-buffered saline, and 20 µl placed into the assay. It can be seen in FIG. 4 that the majority of biologically active material passed through the column unbound, whereas much of the contaminating material bound and was eluted in the salt gradient.

5. Chromatography Using Silica-Bound Hydrocarbon Resin

Fractions 4-40 from the S-Sepharose column of FIG. 4 were pooled (540 ml). 450 ml of the pool was combined with an equal volume of buffer B (100 mM ammonium acetate, pH 6:isopropanol; 25:75) and applied at a flow rate of 540 ml/h to a $C_4$ column (Vydac Proteins $C_4$; 2.4×2 cm) equilibrated with buffer A (60 mM ammonium acetate, pH 6:isopropanol; 62.5:37.5). After sample application, the flow rate was reduced to 154 ml/h and the column was washed with 200 ml of buffer A. A linear gradient from buffer A to buffer B (total volume 140 ml) was then applied, and fractions of 9.1 ml were collected. Portions of the pool from S-Sepharose chromatography, the $C_4$ column starting sample, runthrough pool, and wash pool were brought to 40 µg/ml bovine serum albumin by addition of an appropriate volume of a 1 mg/ml stock solution, and dialyzed against phosphate-buffered saline in preparation for biological assay. Similarly, 40 µl aliquots of the gradient fractions were combined with 360 µl of phosphate-buffered saline containing 16 µg bovine serum albumin, and this was followed by dialysis against phosphate-buffered saline in preparation for biological assay. These various fractions were assayed by the MC/9 assay (6.3 µl aliquots of the prepared gradient fractions; cpm in FIG. 5). The assay results also indicated that about 75% of the recovered activity was in the runthrough and wash fractions, and 25% in the gradient fractions indicated in FIG. 5. SDS-PAGE [Laemmli, Nature, 227, 680–685 (1970); stacking gels contained 4% (w/v) acrylamide and separating gels contained 12.5% (w/v) acrylamide] of aliquots of various fractions is shown in FIG. 6. For the gel shown, sample aliquots were dried under vacuum and then redissolved using 20 µl sample treatment buffer (nonreducing, i.e., without 2-mercaptoethanol) and boiled for 5 min prior to loading onto the gel. Lanes A and B represent column starting material (75 µl out of 890 ml) and column runthrough (75 µl out of 880 ml), respectively; the numbered marks at the left of the Figure represent migration positions (reduced) of markers having molecular weights of $10^3$ times the indicated numbers, where the markers are phosphorylase b ($M_r$ of 97,400), bovine serum albumin ($M_r$ of 66,200), ovalbumin ($M_r$ of 42,700), carbonic anhydrase ($M_r$ of 31,000), soybean trypsin inhibitor ($M_r$ of 21,500), and lysozyme ($M_r$ of 14,400); lanes 4-9 represent the corresponding fractions collected during application of the gradient (60 µl out of 9.1 ml). The gel was silver-stained [Morrissey, Anal. Biochem., 117, 307–310 (1981)]. It can be seen by comparing lanes A and B that the majority of stainable material passes through the column. The stained material in fractions 4-6 in the regions just above and below the $M_r$ 31,000 standard position coincides with the biological activity detected in the gradient fractions (FIG. 5) and represents the biologically active material. It should be noted that this material is visualized in lanes 4-6, but not in lanes A and/or B, because a much larger proportion of the total volume (0.66% of the total for fractions 4-6 versus 0.0084% of the total for lanes A and B) was loaded for the former. Fractions 4-6 from this column were pooled.

Figure 5:
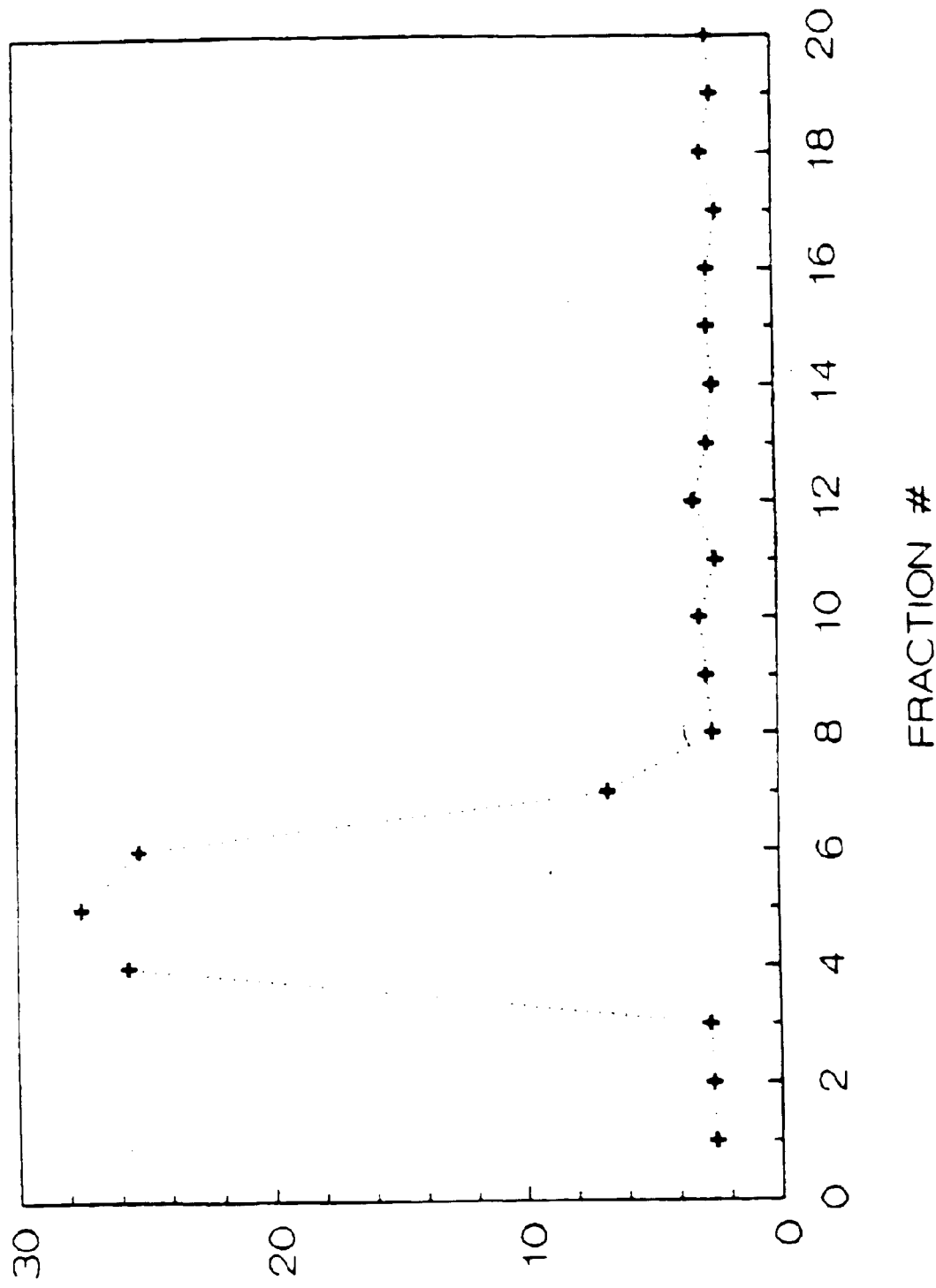
FIG. 5 is a $C_4$ chromatogram from the purification of mammalian SCF.
Figure 6:
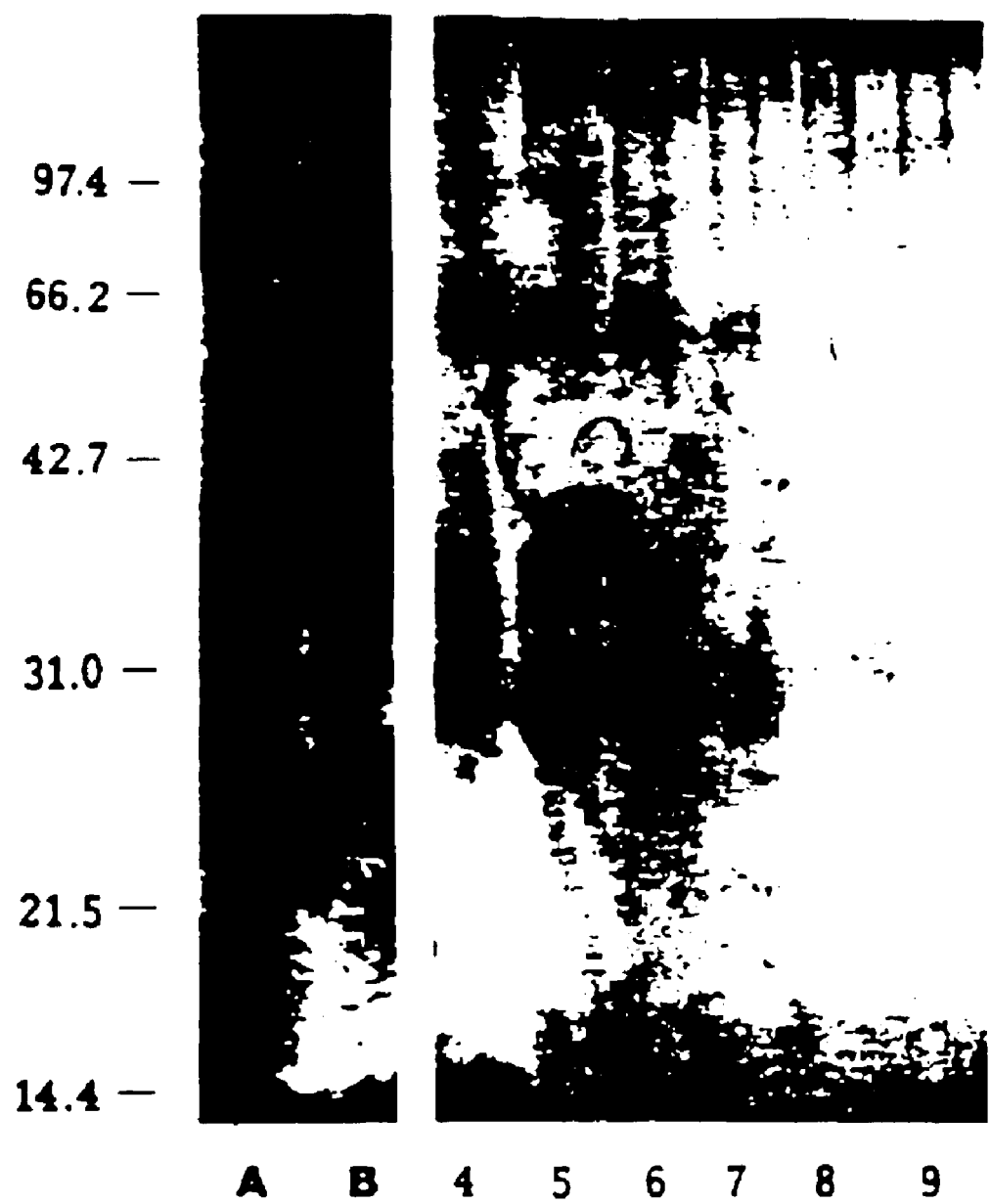
FIG. 6 shows sodium dodecyl sulfate (SDS)-polyacrylamide gel electrophoresis (PAGE) (SDS-PAGE) of $C_4$ column fractions from FIG. 5.

As mentioned above, roughly 75% of the recovered activity ran through the $C_4$ column of FIG. 5. This material was rechromatographed using $C_4$ resin essentially as described above, except that a larger column (1.4×7.8 cm) and slower flow rate (50–60 ml/h throughout) were used. Roughly 50% of recovered activity was in the runthrough, and 50% in gradient fractions showing similar appearance on SDS-PAGE to that of the active gradient fractions in FIG. 6. Active fractions were pooled (29 ml).

Figure 7:
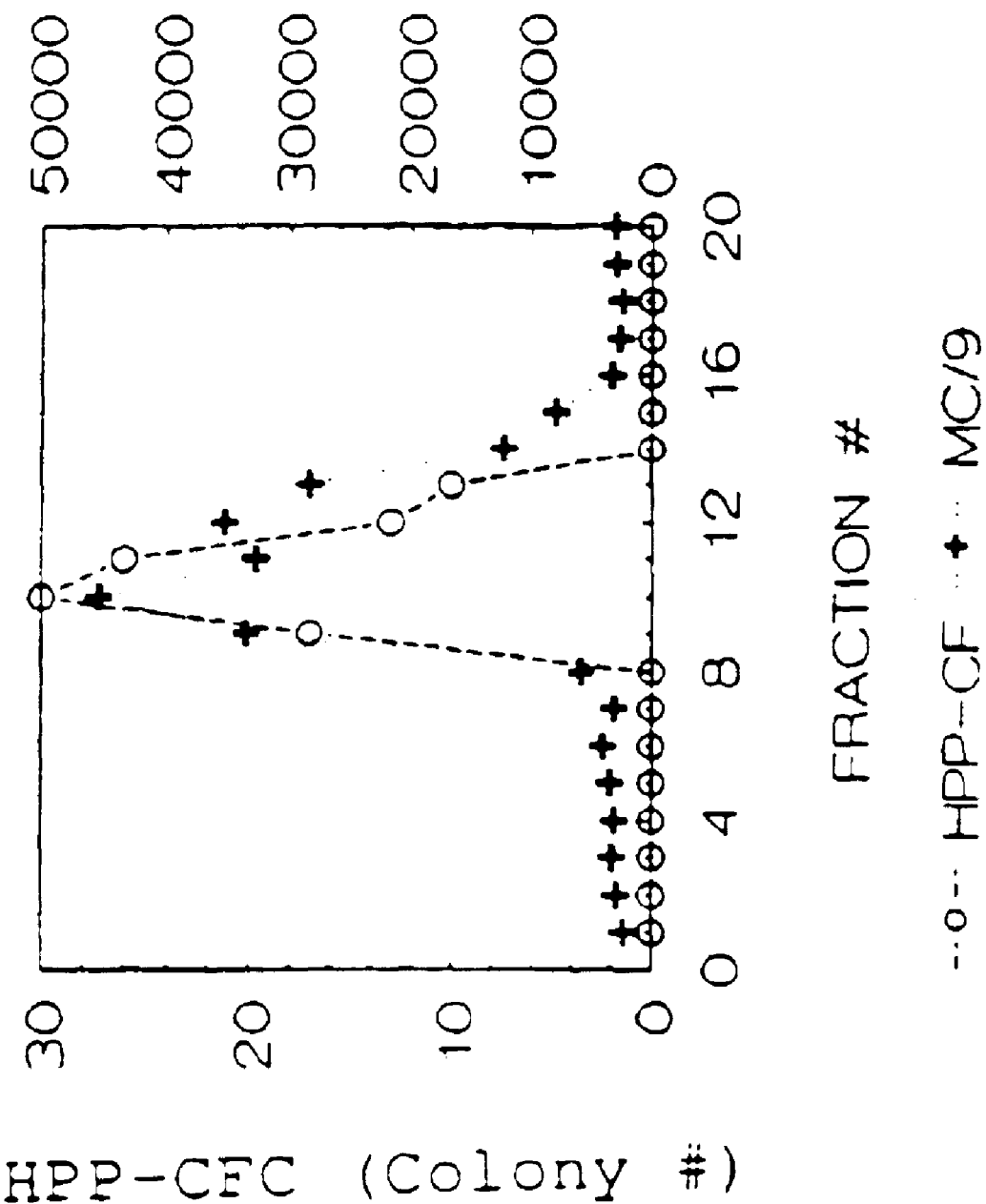
FIG. 7 is an analytical $C_4$ chromatogram of mammalian SCF.
Figure 8:
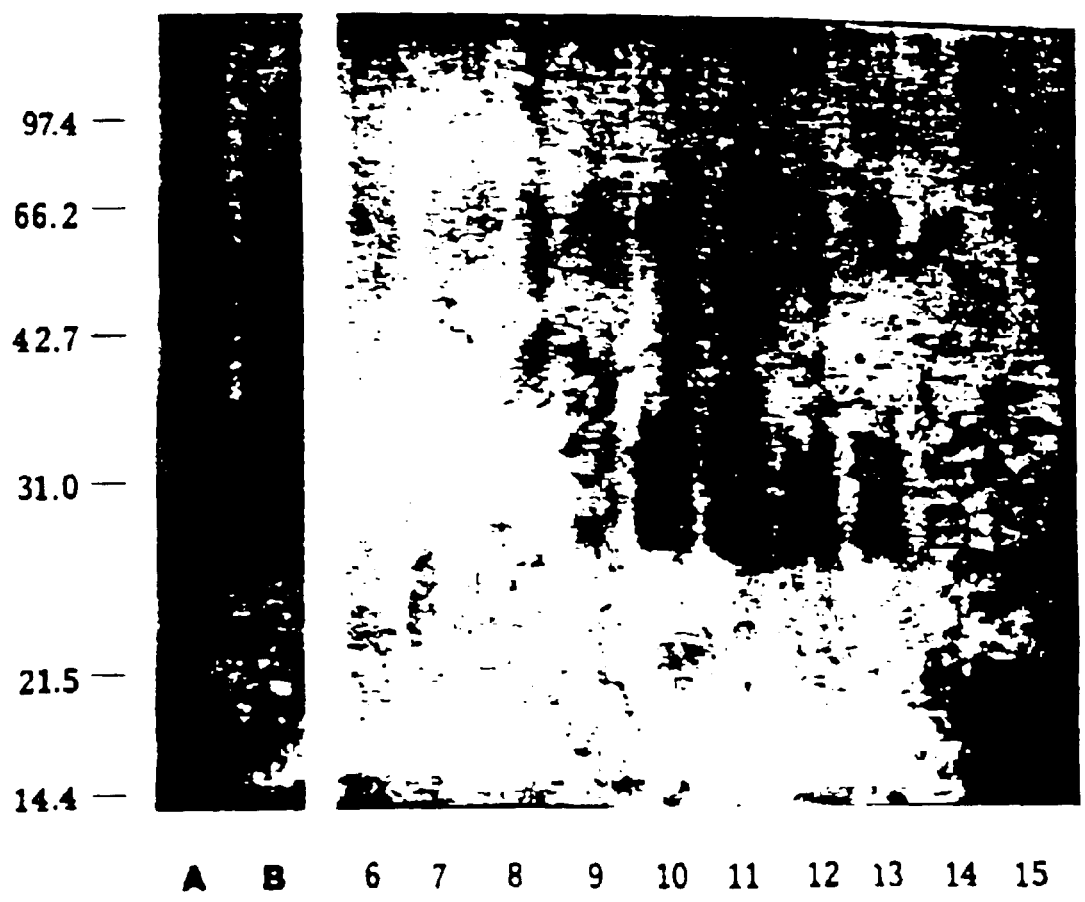
FIG. 8 shows SDS-PAGE of $C_4$ column fractions from FIG. 7.

An analytical $C_4$ column was also performed essentially as stated above and the fractions were assayed in both bioassays. As indicated in FIG. 7 of the fractions from this analytical column, both the MC/9 and HPP-CFC bioactivities co-elute. SDS-PAGE analysis (FIG. 8) reveals the presence of the $M_r$ ~31,000 protein in the column fractions which contain biological activity in both assays.

Active material in the second (relatively minor) activity peak seen in S-Sepharose chromatography (e.g. FIG. 4, fractions 62-72, early fractions in the salt gradient) has also been purified by $C_4$ chromatography. It exhibited the same behavior on SDS-PAGE and had the same N-terminal amino acid sequence (see Example 2D) as the material obtained by $C_4$ chromatography of the S-Sepharose runthrough fractions.

6. Purification Summary

A summary of the purification steps described in 1–5 above is given in Table 2.

TABLE 2

Summary of Purification of Mammalian SCF

| Step | Volume (ml) | Total Protein (mg)[5] |
| --- | --- | --- |
| Conditioned medium | 335,700 | 13,475 |
| DEAE cellulose[1] | 2,900 | 2,164 |
| ACA-54 | 550 | 1,513 |
| Wheat germ agglutinin-agarose[2] | 375 | 431 |
| S-Sepharose | 540[4] | 10 |
| $C_4$ resin[3] | 57.3 | 0.25–0.40[6] |

[1]Values given represent sums of the values for the different batches described in the text.
[2]As described above in this Example, precipitated material which appeared during dialysis of this sample in preparation for S-Sepharose chromatography was removed by centrifugation. The sample after centrifugation (480 ml) contained 264 mg of total protein.
[3]Combination of the active gradient fractions from the two $C_4$ columns run in sequence as described.
[4]Only 450 ml of this material was used for the following step (this Example, above).
[5]Determined by the method of Bradford (supra, 1976) except where indicated otherwise.
[6]Estimate, based on intensity of silver-staining after SDS-PAGE, and on amino acid composition analysis as described in section K of Example 2.

D. SDS-PAGE and Glycosidase Treatments

Figure 9:
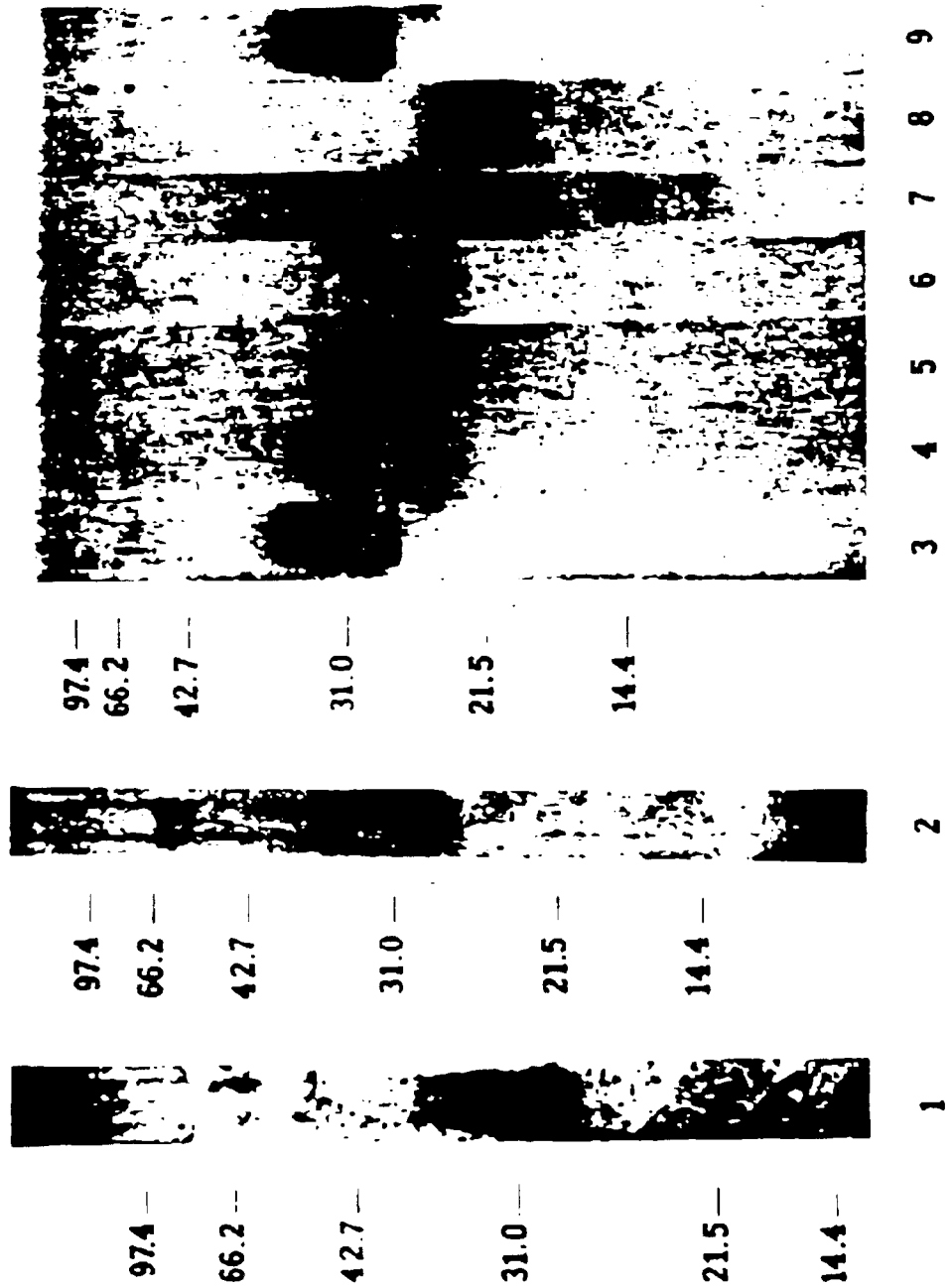
FIG. 9 shows SDS-PAGE of purified mammalian SCF and deglycosylated mammalian SCF.

SDS-PAGE of pooled gradient fractions from the two large scale $C_4$ column runs are shown in FIG. 9. Sixty µl of the pool for the first $C_4$ column was loaded (lane 1), and 40 µl of the pool for the second $C_4$ column (lane 2). These gel lanes were silver-stained. Molecular weight markers were as described for FIG. 6. As mentioned, the diffusely-migrating material above and below the $M_r$ 31,000 marker position represents the biologically active material; the apparent heterogeneity is largely due to heterogeneity in glycosylation.

To characterize the glycosylation, purified material was iodinated with $^{125}$I, treated with a variety of glycosidases, and analyzed by SDS-PAGE (reducing conditions) with autoradiography. Results are shown in FIG. 9. Lanes 3 and 9, $^{125}$I-labeled material without any glycosidase treatment. Lanes 4-8 represent $^{125}$I-labeled material treated with glycosidases, as follows. Lane 4, neuraminidase. Lane 5, neuraminidase and O-glycanase. Lane 6, N-glycanase. Lane 7, neuraminidase and N-glycanase. Lane 8, neuraminidase, O-glycanase, and N-glycanase. Conditions were 5 mM 3-[(3-cholamidopropyl)dimethylammonio]-1-propanesulfonate (CHAPS), 33 mM 2-mercaptoethanol, 10 mM Tris-HCl, pH 7–7.2, for 3 h at 37° C. Neuraminidase (from Arthrobacter ureafaciens; Calbiochem) was used at 0.23 units/ml final concentration. O-Glycanase (Genzyme; endo-alpha-N-acetyl-galactosaminidase) was used at 45 milliunits/ml. N-Glycanase (Genzyme; peptide:N-glycosidase F; peptide-N$^4$[N-acetyl-beta-glucosaminyl] asparagine amidase) was used at 10 units/ml.

Similar results to those of FIG. 9 were obtained upon treatment of unlabeled purified SCF with glycosidases, and visualization of products by silver-staining after SDS-PAGE.

Where appropriate, various control incubations were carried out. These included: incubation in appropriate buffer, but without glycosidases, to verify that results were due to the glycosidase preparations added; incubation with glycosylated proteins (e.g. glycosylated recombinant human erythropoietin) known to be substrates for the glycosidases, to verify that the glycosidase enzymes used were active; and incubation with glycosidases but no substrate, to verify that the glycosidases were not themselves contributing to or obscuring the visualized gel bands.

Glycosidase treatments were also carried out with endo-beta-N-acetylglucosamidase F (endo F; NEN Dupont) and with endo-beta-N-acetylglucosaminidase H (endo H; NEN Dupont), again with appropriate control incubations. Conditions of treatment with endo F were: boiling 3 min in the presence of 1% (w/v) SDS, 100 mM 2-mercaptoethanol, 100 mM EDTA, 320 mM sodium phosphate, pH 6, followed by 3-fold dilution with the inclusion of Nonidet P-40 (1.17%, v/v, final concentration), sodium phosphate (200 mM, final concentration), and endo F (7 units/ml, final concentration). Conditions of endo H treatment were similar except that SDS concentration was 0.5% (w/v) and endo H was used at a concentration of 1 μg/ml. The results with endo F were the same as those with N-glycanase, whereas endo H had no effect on the purified SCF material.

A number of conclusions can be drawn from the glyosidase experiments described above. The various treatments with N-glycanase [which removes both complex and high-mannose N-linked carbohydrate (Tarentino et al., *Biochemistry* 24, 4665–4671) (1985)], endo F [which acts similarly to N-glycanase (Elder and Alexander, *Proc. Natl. Acad. Sci. USA* 79, 4540–4544 (1982)], endo H [which removes high-mannose and certain hybrid type N-linked carbohydrate (Tarentino et al., *Methods Enzymol.* 50C, 574-580 (1978)], neuraminidase (which removes sialic acid residues), and O-glycanase [which removes certain 0-linked carbohydrates (Lambin et al., Biochem. Soc. Trans. 12, 599–600 (1984)], suggest that: both N-linked and O-linked carbohydrates are present; most of the N-linked carbohydrate is of the complex type; and sialic acid is present, with at least some of it being part of the O-linked moieties. Some information about possible sites of N-linkage can be obtained from amino acid sequence data (Example 2). The fact that treatment with N-glycanase, endo F, and N-glycanase/neuraminidase can convert the heterogeneous material apparent by SDS-PAGE to faster-migrating forms which are much more homogeneous is consistent with the conclusion that all of the material represents the same polypeptide, with the heterogeneity being caused by heterogeneity in glycosylation. It is also noteworthy that the smallest forms obtained by the combined treatments with the various glycosidases are in the range of $M_r$ 18,000-20,000, relative to the molecular weight markers used in the SDS-PAGE.

Confirmation that the diffusely-migrating material around the $M_r$ 31,000 position on SDS-PAGE represents biologically active material all having the same basic polypeptide chain is given by the fact that amino acid sequence data derived from material migrating in this region (e.g., after electrophoretic transfer and cyanogen bromide treatment; Example 2) matches that demonstrated for the isolated gene whose expression by recombinant DNA means leads to biologically-active material (Example 4).

EXAMPLE 2

Amino Acid Sequence Analysis of Mammalian SCF

Figure 10:
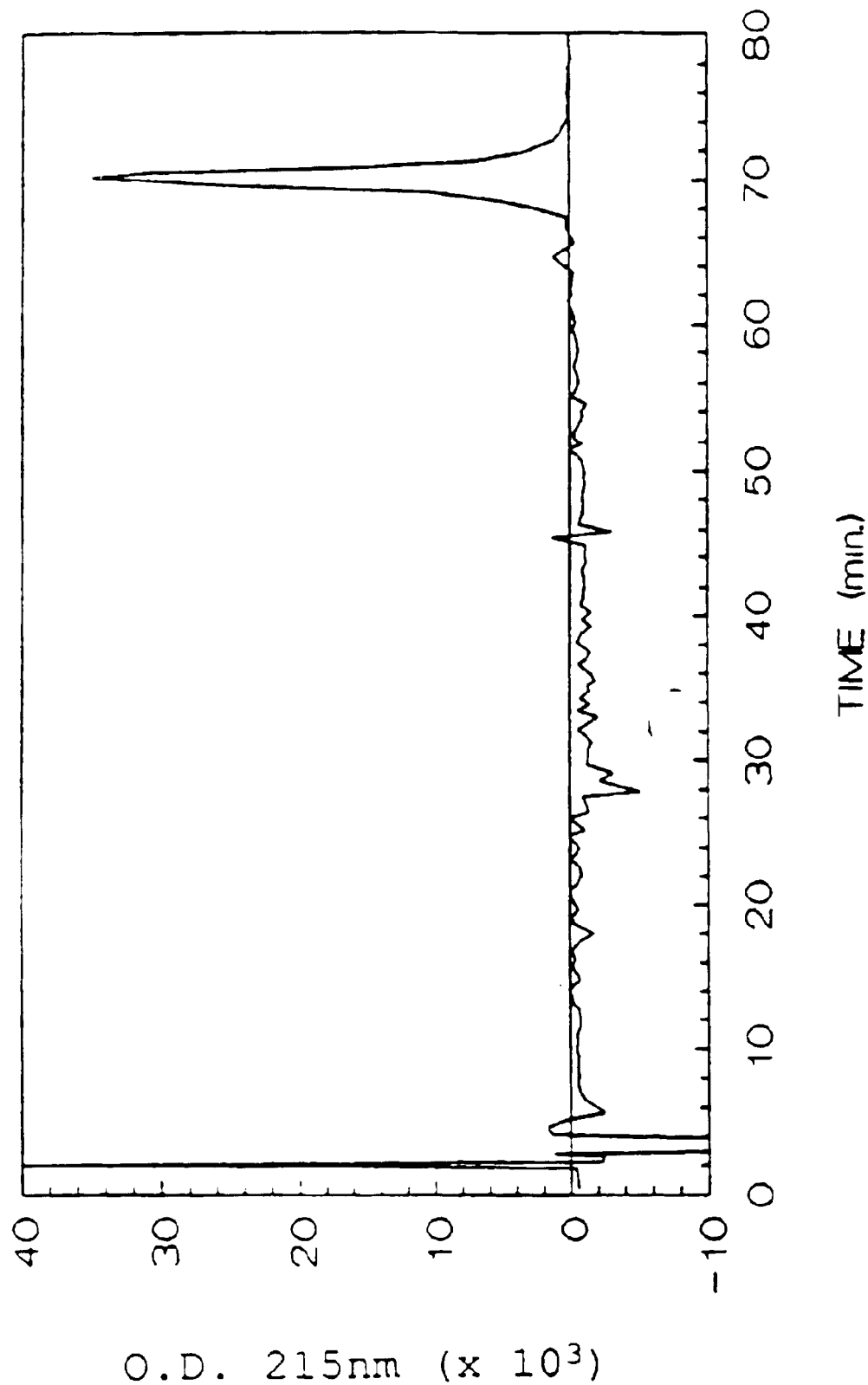
FIG. 10 is an analytical $C_4$ chromatogram of purified mammalian SCF.

A. Reverse-phase High Performance Liquid Chromatography (HPLC) of Purified Protein Approximately 5 μg of SCF purified as in Example 1 (concentration=0.117 mg/ml) was subjected to reverse-phase HPLC using a $C_4$ narrowbore column (Vydac, 300 Å widebore, 2 mm×15 cm). The protein was eluted with a linear gradient from 97% mobile phase A (0.1% trifluoroacetic acid)/3% mobile phase B (90% acetonitrile in 0.1% trifluoroacetic acid) to 30% mobile phase A/70% mobile phase B in 70 min followed by isocratic elution for another 10 min at a flow rate of 0.2 ml per min. After subtraction of a buffer blank chromatogram, the SCF was apparent as a single symmetrical peak at a retention time of 70.05 min as shown in FIG. 10. No major contaminating protein peaks could be detected under these conditions.

B. Sequencing of Electrophoretically-Transferred Protein Bands

SCF purified as in Example 1 (p.5–1.0 nmol) was treated as follows with N-glycanase, an enzyme which specifically cleaves the Asn-linked carbohydrate moieties covalently attached to proteins (see Example 1D). Six ml of the pooled material from fractions 4-6 of the $C_4$ column of FIG. 5 was dried under vacuum. Then 150 μl of 14.25 mM CHAPS, 100 mM 2-mercaptoethanol, 335 mM sodium phosphate, pH 8.6 was added and incubation carried out for 95 min at 37° C. Next 300 μl of 74 mM sodium phosphate, 15 units/ml N-glycanase, pH 8.6 was added and incubation continued for 19 h. The sample was then run on a 9–18% SDS-polyacrylamide gradient gel (0.7 mm thickness, 20×20 cm). Protein bands in the gel were electrophoretically transferred onto polyvinyldifluoride (PVDF, Millipore Corp.) using 10 mM Caps buffer (pH 10.5) at a constant current of 0.5 Amp for 1 h [Matsudaira, *J. Biol. Chem.*, 261, 10035–10038 (1987)]. The transferred protein bands were visualized by Coomassie Blue staining. Bands were present at $M_r$ ~29,000-33,000 and $M_r$ ~26,000, i.e., the deglycosylation was only partial (refer to Example 1D, FIG. 9); the former band represents undigested material and the latter represents material from which N-linked carbohydrate is removed. The bands were cut out and directly loaded (40% for $M_r$ 29,000-33,000 protein and 80% for $M_r$ 26,000 protein) onto a protein sequencer (Applied Biosystems Inc., model 477). Protein sequence analysis was performed using programs supplied by the manufacturer [Hewick et al., *J. Biol. Chem.*, 256 7990–7997 (1981)] and the released phenylthiohydantoinyl amino acids were analyzed on-line using microbore $C_{18}$ reverse-phase HPLC. Both bands gave no signals for 20-28 sequencing cycles, suggesting that both were unsequenceable by methodology using Edman chemistry. The background level on each sequencing run was between 1–7 pmol which was far below the protein amount present in the bands. These data suggested that protein in the bands was N-terminally blocked.

C. In-situ CNBr Cleavage of Electrophoretically-Transferred Protein and Sequencing To confirm that the protein was in fact blocked, the membranes were removed from the sequencer (part B) and in situ cyanogen bromide (CNBr) cleavage of the blotted bands was carried out [CNBr (5%, w/v) in 70% formic acid for 1 h at 45° C] followed by drying and sequence analysis. Strong sequence signals were detected, representing internal peptides obtained from methionyl peptide bond cleavage by CNBr.

Both bands yielded identical mixed sequence signals listed below for the first five cycles.

| | Amino Acids Identified |
|---|---|
| Cycle 1: | Asp; Glu; Val; Ile; Leu |
| Cycle 2: | Asp; Thr; Glu; Ala; Pro; Val |
| Cycle 3: | Asn; Ser; His; Pro; Leu |
| Cycle 4: | Asp; Asn; Ala; Pro; Leu |
| Cycle 5: | Ser; Tyr; Pro; |

Both bands also yielded similar signals up to 20 cycles. The initial yields were 40–115 pmol for the $M_r$ 26,000 band and 40–150 pmol for the $M_r$ 29,000–33,000 band. These values are comparable to the original molar amounts of protein loaded onto the sequencer. The results confirmed that protein bands corresponding to SCF contained a blocked N-terminus. Procedures used to obtain useful sequence information for N-terminally blocked proteins include: (a) deblocking the N-terminus (see section D); and (b) generating peptides by internal cleavages by CNBr (see Section E), by trypsin (see Section F), and by *Staphylococcus aureus* (strain V-8) protease (Glu-C) (see Section G). Sequence analysis can proceed after the blocked N-terminal amino acid is removed or the peptide fragments are isolated. Examples are described in detail below.

D. Sequence Analysis of BRL Stem Cell Factor Treated with Pyroglutamic Acid Aminopeptidase The chemical nature of the blockage moiety present at the amino terminus of SCF was difficult to predict. Blockage can be post-translational in vivo [F. Wold, *Ann. Rev. Biochem.*, 50, 783–814 (1981)] or may occur in vitro during purification. Two post-translational modifications are most commonly observed. Acetylation of certain N-terminal amino acids such as Ala, Ser, etc. can occur, catalyzed by N-α-acetyl transferase. This can be confirmed by isolation and mass spectrometric analysis of an N-terminally blocked peptide. If the amino terminus of a protein is glutamine, deamidation of its gamma-amide can occur. Cyclization involving the gamma-carboxylate and the free N-terminus can then occur to yield pyroglutamate. To detect pyroglutamate, the enzyme pyroglutamate aminopeptidase can be used. This enzyme removes the pyroglutamate residue, leaving a free amino terminus starting at the second amino acid. Edman chemistry can then be used for sequencing.

SCF (purified as in Example 1: 400 pmol) in 50 mM sodium phosphate buffer (pH 7.6 containing dithiothreitol and EDTA) was incubated with 1.5 units of calf liver pyroglutamic acid aminopeptidase (pE-AP) for 16 h at 37° C. After reaction the mixture was directly loaded onto the protein sequencer. A major sequence could be identified through 46 cycles. The initial yield was about 40% and repetitive yield was 94.2%. The N-terminal sequence of SCF including the N-terminal pyroglutamic acid is SEQ ID NO.:64:

```
pE-AP cleavage site
       ↓                                            10
pyroGlu-Glu-Ile-Cys-Arg-Asn-Pro-Val-Thr-Asp-Asn-Val-Lys-Asp-Ile-Thr-Lys- 20                                  30
Leu-Val-Ala-Asn-Leu-Pro-Asn-Asp-Tyr-Met-Ile-Thr-Leu-Asn-Tyr-Val- 40
Ala-Gly-Met-Asp-Val-Leu-Pro-Ser-His-xxx-Trp-Leu-Arg-Asp-. . .
xxx, not assigned at position 43
```

These results indicated that SCF contains pyroglutamic acid as its N-terminus.

E. Isolation and Sequence Analysis of CNBr Peptides

SCF purified as in Example 1 (20–28 µg; 1.0–1.5 nmol) was treated with N-glycanase as described in Example 1. Conversion to the $M_r$ 26,000 material was complete in this case. The sample was dried and digested with CNBr in 70% formic acid (5%) for 18 h at room temperature. The digest was diluted with water, dried, and redissolved in 0.1% trifluoroacetic acid. CNBr peptides were separated by reverse-phase HPLC using a $C_4$ narrowbore column and elution conditions identical to those described in Section A of this Example. Several major peptide fractions were isolated and sequenced, and the results are summarized in the following:

| Peptide | Retention Time (min) | | Sequence[4] |
|---|---|---|---|
| CB-4 | 15.5 | | L-P-P--- |
| CB-6[1] | 22.1 | a. | I-T-L-N-Y-V-A-G-(M) (SEQ ID NO.:65) |
| | | b. | V-A-S-D-T-S-D-C-V-L-S- - -L-G-P-E-K-D-S-R-V-S-V-(_)-K---- (SEQ ID NO.:66) |

-continued

| Peptide | Retention Time (min) | Sequence[4] |
|---|---|---|
| CB-8 | 28.0 | D-V-L-P-S-H-C-W-L-R-D-(M) (SEQ ID NO.:67) |
| CB-10 | 30.1 | (containing sequence of CB-8) |
| CB-15[2] | 43.0 | E-E-N-A-P-K-N-V-K-E-S-L-K-K-P-T-R-(N)-F---T-P-E-E-F-F-S-I-F-D[3]-R-S-I-D-A----- (SEQ ID NO.:68) |
| CB-14 and CB-16 | 37.3 | Both peptides contain identical sequence to CB-15 |

[1] Amino acids were not detected at positions 12, 13 and 25. Peptide b was not sequenced to the end.
[2] (N) in CB-15 was not detected; it was inferred based on the potential N-linked glycosylation site. The peptide was not sequenced to the end.
[3] Designates site where Asn may have been converted into Asp upon N-glycanase removal of N-linked sugar.
[4] Single letter code was used: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

F. Isolation and Sequencing of BRL Stem Cell Factor Tryptic Fragments

SCF purified as in Example 1 (20 $\mu$g in 150 $\mu$l 0.1 M ammonium bicarbonate) was digested with 1 $\mu$g of trypsin at 37° C. for 3.5 h. The digest was immediately run on reverse-phase narrow bore $C_4$ HPLC using elution conditions identical to those described in Section A of this Example. All eluted peptide peaks had retention times different from that of undigested SCF (Section A). The sequence analyses of the isolated peptides are shown below:

G. Isolation and Sequencing of BRL Stem Cell Factor Peptides after S. aureus Glu-C Protease Cleavage SCF purified as in Example 1 (20 $\mu$g in 150 $\mu$l 0.1 M ammonium bicarbonate) was subjected to Glu-C protease cleavage at a protease-to-substrate ratio of 1:20. The digestion was accomplished at 37° C. for 18 h. The digest was immediately separated by reverse-phase narrowbore $C_4$ HPLC. Five major peptide fractions were collected and sequenced as described below:

| Peptide | Retention Time (min) | | Sequence |
|---|---|---|---|
| T-1 | 7.1 | | E-S-L-K-K-P-E-T-R (SEQ ID NO.:69) |
| T-2[1] | 28.1 | | V-S-V-(_)-K (SEQ ID NO.:70) |
| T-3 | 32.4 | | I-V-D-D-L-V-A-A-M-E-E-N-A-P-K (SEQ ID NO.:71) |
| T-4[2] | 40.0 | | N-F-T-P-E-E-F-F-S-I-F-(_)-R (SEQ ID NO.:72) |
| T-5[3] | 46.4 | a. | L-V-A-N-L-P-N-D-Y-M-I-T-L-N-Y-V-A-G M-D-V-L-P-S-H-C-W-L-R (SEQ ID NO.:73) |
| | | b. | S-I-D-A-F-K-D-F-M-V-A-S-D-T-S-D-C-V-L-S-(_)-(_)-L-G---- (SEQ ID NO.:74) |
| T-7[4] | 72.8 | | E-S-L-K-K-P-E-T-R-(N)-F-T-P-E-E-F-F-S-I-F-(_)-R (SEQ ID NO.:75) |
| T-8 | 73.6 | | E-S-L-K-K-P-E-T-R-N-F-T-P-E-E-F-F-S-I-F-D-R (SEQ ID NO.:76) |

[1] Amino acid at position 4 was not assigned.
[2] Amino acid at position 12 was not assigned.
[3] Amino acids at positions 20 and 21 in 6 of peptide T-5 were not identified; they were tentatively assigned as O-linked sugar attachment sites.
[4] Amino acid at position 10 was not detected; it was inferred as Asn based on the potential N-linked glycosylation site. Amino acid at position 21 was not detected.

| Peptides | Retention Time (min) | Sequence |
|---|---|---|
| S-1 | 5.1 | N-A-P-K-N-V-K-E (SEQ ID NO.:77) |
| S-2[1] | 27.7 | S-R-V-S-V-(_)-K-P-F-M-L-P-P-V-A-(A) (SEQ ID NO.:78) |
| S-3[2] | 46.3 | No sequence detected |
| S-5[3] | 71.0 | S-L-K-K-P-E-T-R-N-F-T-P-E-E-F-F-S-I-F-(N)-R-SI-D-A-F-K-D-F-M-V-A-S-D (SEQ ID NO.:79) |

| Peptides | Retention Time (min) | Sequence |
|---|---|---|
| S-6[3] | 72.6 | S-L-K-K-P-E-T-R-N-F-T-P-E-E-F-F-S-I-F-(N)-R-S-I-D-A-F-K-D-F-M-V-A-S-D-T-S-D (SEQ ID NO.:80) |

[1]Amino acid at position 6 of S-2 peptide was not assigned; this could be an O-linked sugar attachment site. The Ala at position 16 of S-2 peptide was detected in low yield.
[2]Peptide S-3 could be the N-terminally blocked peptide derived from the N-terminus of SCF.
[3]N in parentheses was assigned as a potential N-linked sugar attachment site.

H. Sequence Analysis of BRL Stem Cell Factor after BNPS-skatole Cleavage

SCF(2 μg) in 10 mM ammonium bicarbonate was dried to completeness by vacuum centrifugation and then redissolved in 100 μl of glacial acetic acid. A 10–20 fold molar excess of BNPS-skatole was added to the solution and the mixture was incubated at 50°C. for 60 min. The reaction mixture was then dried by vacuum centrifugation. The dried residue was extracted with 100 μl of water and again with 50 μl of water. The combined extracts were then subjected to sequence analysis as described above. The following sequence (SEQ ID NO:81) was detected:

```
1                                        10
Leu-Arg-Asp-Met-Val-Thr-His-Leu-Ser-Val-Ser-Leu-Thr-Thr-Leu-Leu-
          20                                         30
Asp-Lys-Phe-Ser-Asn-Ile-Ser-Glu-Gly-Leu-Ser-(Asn)-Tyr-Ser-Ile-Ile
                        40
Asp-Lys-Leu-Gly-Lys-Ile-Val-Asp    (SEQ ID NO.:81)
```

Position 28 was not positively assigned; it was assigned as Asn based on the potential N-linked glycosylation site.

I. C-Terminal Amino Acid Determination of BRL Stem Cell Factor

An aliquot of SCF protein (500 pmol) was buffer-exchanged into 10 mM sodium acetate, pH 4.0 (final volume of 90 μl) and Brij-35 was added to 0.05% (w/v). A 5 μl aliquot was taken for quantitation of protein. Forty μl of the sample was diluted to 100 μl with the buffer described above. Carboxypeptidase P (from *Penicillium janthinellum*) was added at an enzyme-to-substrate ratio of 1:200. The digestion proceeded at 25° C. and 20 μl aliquots were taken at 0, 15, 30, 60 and 120 min. The digestion was terminated at each time point by adding trifluoroacetic acid to a final concentration of 5%. The samples were dried and the released amino acids were derivatized by reaction with Dabsyl chloride (dimethylaminoazobenzenesulfonyl chloride) in 0.2 M NaHCO$_3$ (pH 9.0) at 70° C. for 12 min [Chang et al., *Methods Enzymol.*, 90, 41–48 (1983)]. The derivatized amino acids (one-sixth of each sample) were analyzed by narrowbore reverse-phase HPLC with a modification of the procedure of Chang et al. [*Techniques in Protein Chemistry*, T. Hugli ed., Acad. Press, NY (1989), pp. 305–311]. Quantitative composition results at each time point were obtained by comparison to derivatized amino acid standards (1 pmol). At 0 time, contaminating glycine was detected. Alanine was the only amino acid that increased with incubation time. After 2 h incubation, Ala was detected at a total amount of 25 pmol, equivalent to 0.66 mole of Ala released per mole of protein. This result indicated that the natural mammalian SCF molecule contains Ala as its carboxyl terminus, consistent with the sequence analysis of a C-terminal peptide, S-2, which contains C-terminal Ala. This conclusion is also consistent with the known specificity of carboxypeptidase P [Lu et al., *J. Chromatog.* 447, 351–364 (1988)].

For example, cleavage ceases if the sequence Pro-Val is encountered. Peptide S-2 has the sequence S-R-V-S-V-(T)-K-P-F-M-L-P-P-V-A-(A) (SEQ ID NO.: 82) and was deduced to be the C-terminal peptide of SCF (see Section J in this Example). The C-terminal sequence of -P-V-A-(A) (SEQ ID NO.: 83) restricts the protease cleavage to alanine only. The be two Ala residues at the C-terminus of this peptide (see table in Section G). Thus the BRL SCF terminates at Ala 164 or Ala 165.

J. Sequence of SCF

By combining the results obtained from sequence analysis of (1) intact stem cell factor after removing its N-terminal pyroglutamic acid, (2) the CNBr peptides, (3) the trypsin peptides, and (4) the Glu-C peptidase fragments, an N-terminal sequence and a C-terminal sequence were deduced (FIG. 11). The N-terminal sequence starts at pyroglutamic acid and ends at Met-48. The C-terminal sequence contains 84/85 amino acids (position 82 to 164/165). The sequence from position 49 to 81 was not detected in any of the peptides isolated. However, a sequence was detected for a large peptide after BNPS-skatole cleavage of BRL SCF as described in Section H of this Example. From these additional data, as well as DNA sequence obtained from rat SCF (Example 3) the N- and C-terminal sequences can be aligned and the overall sequence delineated as shown in FIG. 11. The N-terminus of the molecule is pyroglutamic acid and the C-terminus is alanine as confirmed by pyroglutamate aminopeptidase digestion and carboxypeptidase P digestion, respectively.

From the sequence data, it is concluded that Asn-72 is glycosylated; Asn-109 and Asn-120 are probably glycosylated in some molecules but not in others. Asn-65 could be detected during sequence analysis and therefore may only be partially glycosylated, if at all. Ser-142, Thr-143 and Thr-155, predicted from DNA sequence, could not be detected during amino acid sequence analysis and therefore could be sites of O-linked carbohydrate attachment. These potential carbohydrate attachment sites are indicated in FIG. 11; N-linked carbohydrate is indicated by solid bold lettering; O-linked carbohydrate is indicated by open bold lettering.

K. Amino Acid Compositional Analysis of BRL Stem Cell Factor

Material from the $C_4$ column of FIG. 7 was prepared for amino acid composition analysis by concentration and buffer exchange into 50 mM ammonium bicarbonate.

Two 70 µl samples were separately hydrolyzed in 6 N HCl containing 0.1% phenol and 0.05% 2-mercaptoethanol at 110° C. in vacuo for 24 h. The hydrolysates were dried, reconstituted into sodium citrate buffer, and analyzed using ion exchange chromatography (Beckman Model 6300 amino acid analyzer). The results are shown in Table 3. Using 164 amino acids (from the protein sequencing data) to calculate amino acid composition gives a better match to predicted values than using 193 amino acids (as deduced from PCR-derived DNA sequencing data, FIG. 14C).

TABLE 3

Quantitative Amino Acid Composition of Mammalian Derived SCF

| Amino Acid | Amino Acid Composition Moles per mole of protein[1] | | Predicted Residues per molecule[2] | |
|---|---|---|---|---|
| | Run #1 | Run #2 | (A) | (B) |
| Asx | 24.46 | 24.26 | 25 | 28 |
| Thr | 10.37 | 10.43 | 11 | 12 |
| Ser | 14.52 | 14.30 | 16 | 24 |
| Glx | 11.44 | 11.37 | 10 | 10 |
| Pro | 10.90 | 10.85 | 9 | 10 |
| Gly | 5.81 | 6.20 | 4 | 5 |
| Ala | 8.62 | 8.35 | 7/8 | 8 |
| Cys | nd | nd | 4 | 5 |
| Val | 14.03 | 13.96 | 15 | 15 |
| Met | 4.05 | 3.99 | 6 | 7 |
| Ile | 8.31 | 8.33 | 9 | 10 |
| Leu | 17.02 | 16.97 | 16 | 19 |
| Tyr | 2.86 | 2.84 | 3 | 7 |
| Phe | 7.96 | 7.92 | 8 | 8 |
| His | 2.11 | 2.11 | 2 | 3 |
| Lys | 10.35 | 11.28 | 12 | 14 |
| Trp | nd | nd | 1 | 1 |
| Arg | 4.93 | 4.99 | 5 | 6 |
| Total | 158 | 158 | 164/165 | 193 |
| Calculated molecular weight | | | 18,424[3] | |

[1]Based on 158 residues from protein sequence analysis (excluding Cys and Trp).
[2]Theoretical values calculated from protein sequence data (A) or from DNA sequence data (B).
[3]Based on 1–164 sequence.

Inclusion of a known amount of an internal standard in the amino acid composition analyses also allowed quantitation of protein in the sample; a value of 0.117 mg/ml was obtained for the sample analyzed.

EXAMPLE 3

Cloning of the Genes for Rat and Human SCF
A. Amplification and Sequencing of Rat SCF cDNA Fragments Determination of the amino acid sequence of fragments of the rat SCF protein made it possible to design mixed sequence oligonucleotides specific for rat SCF. The oligonucleotides were used as hybridization probes to screen rat cDNA and genomic libraries and as primers in attempts to amplify portions of the cDNA using polymerase chain reaction (PCR) strategies ([Mullis et al., *Methods in Enzymol.* 155, 335–350 (1987)]. The oligodeoxynucleotides were synthesized by the phosphoramidite method [Beaucage, et al., *Tetrahedron Lett.*, 22, 1859–1862 (1981); McBride, et al., *Tetrahedron Lett.*, 24, 245–248 (1983)]; their sequences are depicted in FIG. 12A. The letters represent A, adenine; T, thymine, C, cytosine; G, guanine; I, inosine. The in FIG. 12A represents oligonucleotides which contain restriction endonuclease recognition sequences. The sequences are written 5'-3'.

A rat genomic library, a rat liver cDNA library, and two BRL cDNA libraries were screened using $^{32}$P-labelled mixed oligonucleotide probes, 219-21 and 219-22 (FIG. 12A), whose sequences were based on amino acid sequence obtained as in Example 2. No SCF clones were isolated in these experiments using standard methods of cDNA cloning [Maniatis, et al., *Molecular Cloning*, Cold Spring Harbor 212-246 (1982)].

An alternate approach which did result in the isolation of SCF nucleic acid sequences involved the use of PCR techniques. In this methodology, the region of DNA encompassed by two DNA primers is amplified selectively in vitro by multiple cycles of replication catalysed by a suitable DNA polymerase (such as TaqI DNA polymerase) in the presence of deoxynucleoside triphosphates in a thermo cycler. The specificity of PCR amplification is based on two oligonucleotide primers which flank the DNA segment to be amplified and hybridize to opposite strands. PCR with double-sided specificity for a particular DNA region in a complex mixture is accomplished by use of two primers with sequences sufficiently specific to that region. PCR with single-sided specificity utilizes one region-specific primer and a second primer which can prime at target sites present on many or all of the DNA molecules in a particular mixture [Loh et al., *Science*, 243, 217–220 (1989)].

The DNA products of successful PCR amplification reactions are sources of DNA sequence information [Gyllensten, *Biotechniques*, 7, 700–708 (1989)] and can be used to make labeled hybridization probes possessing greater length and higher specificity than oligonucleotide probes. PCR products can also be designed, with appropriate primer sequences, to be cloned into plasmid vectors which allow the expression of the encoded peptide product.

Figure 13A:
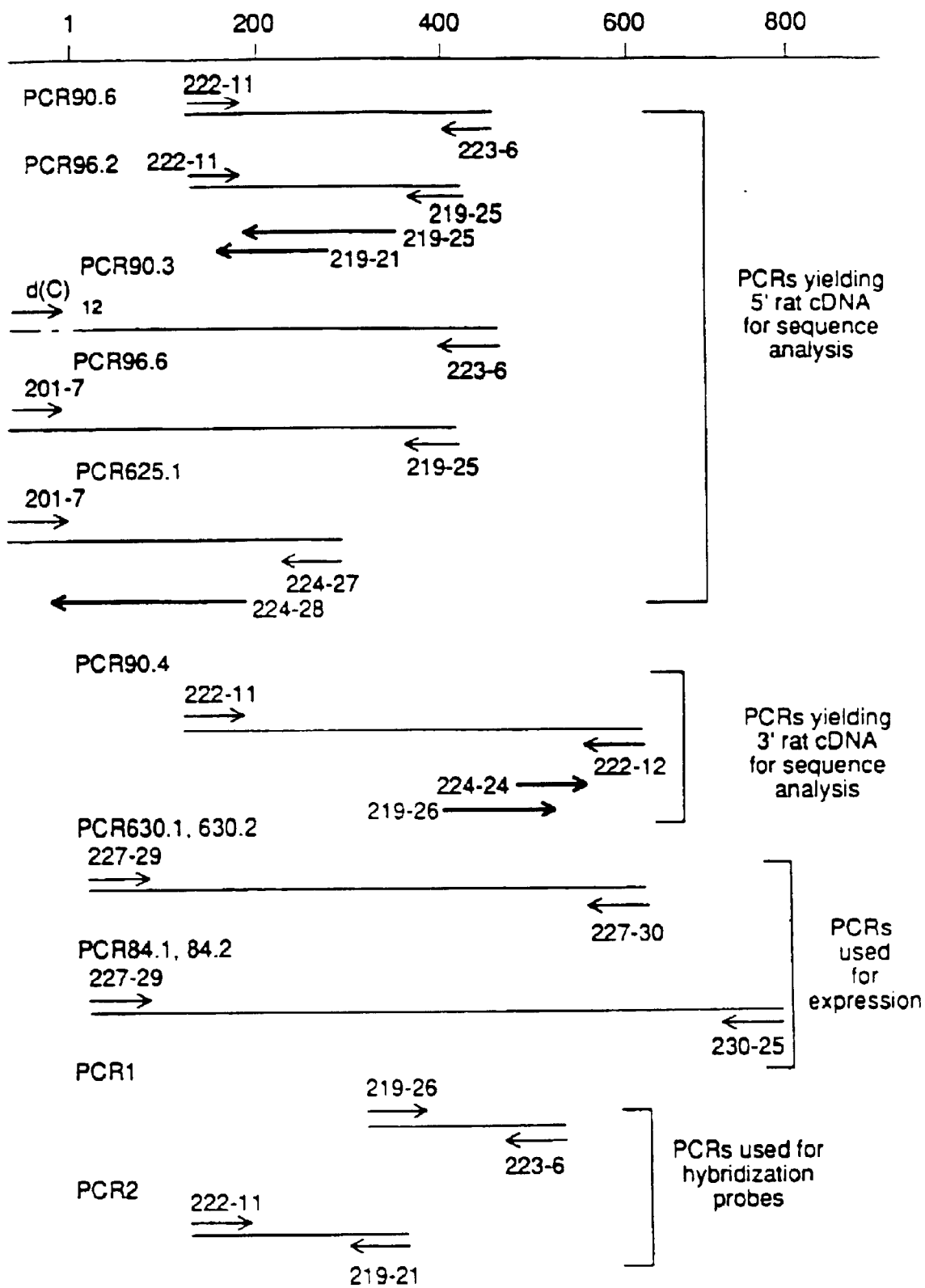

The basic strategy for obtaining the DNA sequence of the rat SCF cDNA is outlined in FIG. 13A. The small arrows indicate PCR amplifications and the thick arrows indicate DNA sequencing reactions. PCRs 90.6 and 96.2, in conjunction with DNA sequencing, were used to obtain partial nucleic acid sequence for the rat SCF cDNA. The primers used in these PCRs were mixed oligonucleotides based on amino acid sequence depicted in FIG. 11. Using the sequence information obtained from PCRs 90.6 and 96.2, unique sequence primers (224-27 and 224-28, FIG. 12A) were made and used in subsequent amplifications and sequencing reactions. DNA containing the 5' end of the cDNA was obtained in PCRs 90.3, 96.6, and 625.1 using single-sided specificity PCR. Additional DNA sequence near the C-terminus of SCF protein was obtained in PCR 90.4. DNA sequence for the remainder of the coding region of rat SCF cDNA was obtained from PCR products 630.1, 630.2, 84.1 and 84.2 as described below in section C of this Example. The techniques used in obtaining the rat SCF cDNA are described below.

RNA was prepared from BRL cells as described by Okayama et al. [*Methods Enzymol.*, 154, 3–28 (1987)]. PolyA+RNA was isolated using an oligo(dT) cellulose column as described by Jacobson in [*Methods in Enzymology*, volume 152, 254–261 (1987)].

First-strand cDNA was synthesized using 1 µg of BRL polyA+ RNA as template and $(dT)_{12-18}$ as primer according to the protocol supplied with the enzyme, Mo-MLV reverse transcriptase (Bethesda Research Laboratories). RNA strand degradation was performed using 0.14 M NaOH at 84° C. for 10 min or incubation in a boiling water bath for 5 min. Excess ammonium acetate was added to neutralize the solution, and the cDNA was first extracted with phenol/chloroform, then extracted with chloroform/iso-amyl alcohol, and precipitated with ethanol. To make possible the use of oligo(dC)-related primers in PCRs with single-sided specificity, a poly(dG) tail was added to the 3' terminus of an aliquot of the first-strand cDNA with terminal transferase from calf thymus (Boeringer Mannheim) as previously described [Deng et al., Methods Enzymol., 100, 96–103 (1983)].

Unless otherwise noted in the descriptions which follow, the denaturation step in each PCR cycle was set at 94° C., 1 min; and elongation was at 72° C. for 3 or 4. min. The temperature and duration of annealing was variable from PCR to PCR, often representing a compromise based on the estimated requirements of several different PCRs being carried out simultaneously. When primer concentrations were reduced to lessen the accumulation of primer artifacts [Watson, Amplifications, 2, 56 (1989)], longer annealing times were indicated; when PCR product concentration was high, shorter annealing times and higher primer concentrations were used to increase yield. A major factor in determining the annealing temperature was the estimated Td of primer-target association [Suggs et al., in Developmental Biology Using Purified Genes eds. Brown, D. D. and Fox, C. F. (Academic, New York) pp. 683–693 (1981)]. The enzymes used in the amplifications were obtained from either of three manufacturers: Stratagene, Promega, or Perkin-Elmer Cetus. The reaction compounds were used as suggested by the manufacturer. The amplifications were performed in either a Coy Tempcycle or a Perkin-Elmer Cetus DNA thermocycler.

Amplification of SCF cDNA fragments was usually assayed by agarose gel electrophoresis in the presence of ethidium bromide and visualization by fluorescence of DNA bands stimulated by ultraviolet irradiation. In some cases where small fragments were anticipated, PCR products were analyzed by polyacrylamide gel electrophoresis. Confirmation that the observed bands represented SCF cDNA fragments was obtained by observation of appropriate DNA bands upon subsequent amplification with one or more internally-nested primers. Final confirmation was by dideoxy sequencing [Sanger et al., Proc. Natl. Acad. Sci. USA, 74, 5463–5467 (1977)] of the PCR product and comparison of the predicted translation products with SCF peptide sequence information.

In the initial PCR experiments, mixed oligonucleotides based on SCF protein sequence were used [Gould, Proc. Natl. Acad. Sci. USA, 86, 1934–1938 (1989)]. Below are descriptions of the PCR amplifications that were used to obtain DNA sequence information for the rat cDNA encoding amino acids -25 to 162.

In PCR 90.6, BRL cDNA was amplified with 4 pmol each of 222-11 and 223-6 in a reaction volume of 20 $\mu$l. An aliquot of the product of PCR 90.6 was electrophoresed on an agarose gel and a band of about the expected size was observed. One $\mu$l of the PCR 90.6 product was amplified further with 20 pmol each of primers 222-11 and 223-6 in 50 $\mu$l for 15 cycles, annealing at 45° C. A portion of this product was then subjected to 25 cycles of amplification in the presence of primers 222-11 and 219-25 (PCR 96.2), yielding a single major product band upon agarose gel electrophoresis. Asymmetric amplification of the product of PCR 96.2 with the same two primers produced a template which was successfully sequenced. Further selective amplification of SCF sequences in the product of 96.2 was performed by PCR amplification of the product in the presence of 222-11 and nested primer 219-21. The product of this PCR was used as a template for asymmetric amplification and radiolabelled probe production (PCR2).

To isolate the 5' end of the rat SCF cDNA, primers containing (dC)n sequences, complimentary to the poly(dG) tails of the cDNA, were utilized as non-specific primers. PCR 90.3 contained (dC)$_{12}$ (10 pmol) and 223-6 (4 pmol) as primers and BRL cDNA as template. The reaction product acted like a very high molecular weight aggregate, remaining close to the loading well in agarose gel electrophoresis. One $\mu$l of the product solution was further amplified in the presence of 25 pmol of (dC)$_{12}$ and 10 pmol 223-6 in a volume of 25 $\mu$l for 15 cycles, annealing at 45° C. One-half $\mu$l of this product was then amplified for 25 cycles with internally nested primer 219-25 and 201-7 (PCR 96.6). The sequence of 201-7 is shown in FIG. 12C. No bands were observed by agarose gel electrophoresis. Another 25 cycles of PCR, annealing at 40° C., were performed, after which one prominent band was observed. Southern blotting was carried out and a single prominent hybridizing band was observed. An additional 20 cycles of PCR (625.1), annealing at 45° C., were performed using 201-7 and nested primer 224-27. Sequencing was performed after asymmetric amplification by PCR, yielding sequence which extended past the putative amino terminus of the presumed signal peptide coding sequence of pre-SCF. This sequence was used to design oligonucleotide primer 227-29 containing the 5' end of the coding region of the rat SCF cDNA. Similarly, the 3' DNA sequence ending at amino acid 162 was obtained by sequencing PCR 90.4 (see FIG. 13.A).

The sequence of the rat SCF coding region downstream of codon 162 was obtained by direct sequencing of the products of PCRs in which rat SCF (+)-strand primers were combined with (−)- strand primers designed from the human SCF 3'-untranslated region sequence. Rat SCF primers 224-24(SEQ ID NO.: 10) (FIG. 12A) or 227-31 (5'-CCTGAGAAAGATTCCAGAGTC-3') (SEQ ID NO.: 84) were used in combination with either of the two human SCF primers 283-19 (5'-CTGCAGTTTGTATCTGAAG-3') SEQ ID NO.: 85 or 283-20 (5'-CATATAAAGTCATGGGTAG-3') (SEQ ID NO.: 86). The rat SCF cDNA sequence is shown in FIG. 14C.

B. Cloning of the Rat Stem Cell Factor Genomic DNA

Probes made from PCR amplification of cDNA encoding rat SCF as described in section A above were used to screen a library containing rat genomic sequences (obtained from CLONTECH Laboratories, Inc.; catalog number RL1022 j). The library was constructed in the bacteriophage $\lambda$ vector EMBL-3 SP6/T7 using DNA obtained from an adult male Sprague-Dawley rat. The library, as characterized by the supplier, contains 2.3×10$^6$ independent clones with an average insert size of 16 kb.

PCRs were used to generate $^{32}$P-labeled probes used in screening the genomic library. Probe PCR1(FIG. 13A) was prepared in a reaction which contained 16.7 $\mu$M $^{32}$P[alpha]-dATP, 200 $\mu$M dCTP, 200 $\mu$M dGTP, 200 $\mu$M dTTP, reaction buffer supplied by Perkin Elmer Cetus, Taq polymerase (Perkin Elmer Cetus) at 0.05 units/ml, 0.5 $\mu$M 219-26, 0.05 $\mu$M 223-6 and 1 $\mu$l of template 90.1 containing the target sites for the two primers. Probe PCR 2 was made using similar reaction conditions except that the primers and template were changed. Probe PCR 2 was made using 0.5 $\mu$M 222-11, 0.05 $\mu$M 219-21 and 1 $\mu$l of a template derived from PCR 96.2.

Approximately 10$^6$ bacteriophage were plated as described in Maniatis et al. [supra (1982)]. The plaques were transferred to GeneScreen Plus™ filters (22 cm×22 cm; NEN/DuPont) which were denatured, neutralized and dried as described in a protocol from the manufacturer. Two filter transfers were performed for each plate.

The filters were prehybridized in 1M NaCl, 1% SDS, 0.1% bovine serum albumin, 0.1% ficoll, 0.1% polyvinylpyrrolidone (hybridization solution) for approximately 16 h at 65° C. and stored at −20° C. The filters were transfered to fresh hybridization solution containing $^{32}$P-labeled PCR 1 probe at 1.2×10$^5$ cpm/ml and hybridized for 14 h at 65° C. The filters were washed in 0.9 M NaCl, 0.09 M sodium citrate, 0.1% SDS, pH 7.2 (wash solution) for 2 h at room temperature followed by a second wash in fresh wash solution for 30 min at 65° C. Bacteriophage clones from the areas of the plates corresponding to radioactive spots on autoradiograms were removed from the plates and rescreened with probes PCR1 and PCR2.

DNA from positive clones was digested with restriction endonucleases BamHI, SphI or SstI, and the resulting fragments were subcloned into pUC119 and subsequently sequenced. The strategy for sequencing the rat genomic SCF DNA is shown schematically in FIG. 14A. In this figure, the line drawing at the top represents the region of rat genomic DNA encoding SCF. The gaps in the line indicate regions that have not been sequenced. The large boxes represent exons for coding regions of the SCF gene with the corresponding encoded amino acids indicated above each box. The arrows represent the individual regions that were sequenced and used to assemble the consensus sequence for the rat SCF gene. The sequence for rat SCF gene is shown in FIG. 14B.

Using PCR 1 probe to screen the rat genomic library, clones corresponding to exons encoding amino acids 19 to 176 of SCF were isolated. To obtain clones for exons upstream of the coding region for amino acid 19, the library was screened using oligonucleotide probe 228-30. The same set of filters used previously with probe PCR 1 were prehybridized as before and hybridized in hybridization solution containing $^{32}$P-labeled oligonucleotide 228-30 (0.03 picomole/ml) at 50° C. for 16 h. The filters were washed in wash solution at room temperature for 30 min followed by a second wash in fresh wash solution at 45° C. for 15 min. Bacteriophage clones from the areas of the plates corresponding to radioactive spots on autoradiograms were removed from the plates and rescreened with probe 228-30. DNA from positive clones was digested with restriction endonucleases and subcloned as before. Using probe 228-30, clones corresponding to the exon encoding amino acids −20 to 18 were obtained.

Several attempts were made to isolate clones corresponding to the exon(s) containing the 5'-untranslated region and the coding region for amino acids −25 to −21. No clones for this region of the rat SCF gene have been isolated.

C. Cloning Rat cDNA for Expression in Mammalian Cells

Mammalian cell expression systems were devised to ascertain whether an active polypeptide product of rat SCF could be expressed in and secreted by mammalian cells. Expression systems were designed to express truncated versions of rat SCF (SCF$^{1-162}$ and SCF$^{1-164}$) and a protein (SCF$^{1-193}$) predicted from the translation of the gene sequence in FIG. 14C.

The expression vector used in these studies was a shuttle vector containing pUC119, SV40 and HTLVI sequences. The vector was designed to allow autonomous replication in both E. coli and mammalian cells and to express inserted exogenous DNA under the control of viral DNA sequences. This vector, designated V19.8, harbored in E. coli DH5, is deposited with the American Type Culture Collection, 12301 Parklawn Drive, Rockville, Md. (ATCC# 68124). This vector is a derivative of pSVDM19 described in Souza U.S. Pat. No. 4,810,643 hereby incorporated by reference.

The cDNA for rat SCF$^{1-162}$ was inserted into plasmid vector V19.8. The cDNA sequence is shown in FIG. 14C. The cDNA that was used in this construction was synthesized in PCR reactions 630.1 and 630.2, as shown in FIG. 13A. These PCRs represent independent amplifications and utilized synthetic oligonucleotide primers 227-29 and 227-30. The sequence for these primers was obtained from PCR generated cDNA as described in section A of this Example. The reactions, 50 µl in volume, consisted of 1× reaction buffer (from a Perkin Elmer Cetus kit), 250 µM dATP, 250 µM dCTP, 250 µM dGTP, and 250 µM dTTP, 200 ng oligo(dT)-primed cDNA, 1 picomole of 227-29, 1 picomole of 227-30, and 2.5 units of Taq polymerase (Perkin Elmer Cetus). The cDNA was amplified for 10 cycles using a denaturation temperature of 94° C. for 1 min, an annealing temperature of 37° C. for 2 min, and an elongation temperature of 72° C. for 1 min. After these initial rounds of PCR amplification, 10 picomoles of 227-29 and 10 picomoles of 227-30 were added to each reaction. Amplifications were continued for 30 cycles under the same conditions with the exception that the annealing temperature was changed to 55° C. The products of the PCR were digested with restriction endonucleases HindIII and SstII. V19.8 was similarly digested with HindIII and SstII, and in one instance, the digested plasmid vector was treated with calf intestinal alkaline phosphatase; in other instances, the large fragment from the digestion was isolated from an agarose gel. The cDNA was ligated to V19.8 using T4 polynucleotide ligase. The ligation products were transformed into competent E. coli strain DH5 as described [Okayama, et. al., supra (1987)]. DNA prepared from individual bacterial clones was sequenced by the Sanger dideoxy method. FIG. 17 shows a construct of V19.8 SCF. These plasmids were used to transfect mammalian cells as described in Example 4 and Example 5.

The expression vector for rat SCF$^{1-164}$ was constructed using a strategy similar to that used for SCF$^{1-162}$ in which cDNA was synthesized using PCR amplification and subsequently inserted into V19.8. The cDNA used in the constructions was synthesized in PCR amplifications with V19.8 containing SCF$^{1-162}$ cDNA (V19.8:SCF$^{1-162}$) as template, 227-29 as the primer for the 5'-end of the gene and 237-19 as the primer for the 3'-end of the gene. Duplicate reactions (50 ul) contained 1× reaction buffer, 250 u M each of dATP, dCTP, dGTP and dTTP, 2.5 units of Taq polymerase, 20 ng of V19.8:SCF$^{1-162}$, and 20 picomoles of each primer. The cDNA was amplified for 35 cycles using a denaturation temperature of 94° C. for 1 min, an annealing temperature of 55° C. for 2 min and an elongation temperature of 72° C. for 2 min. The products of the amplifications were digested with restriction endonucleases HindIII and SstII and inserted into V19.8. The resulting vector contains the coding region for amino acids −25 to 164 of SCF followed by a termination codon.

The cDNA for a 193 amino acid form of rat SCF, (rat SCF$^{1-193}$ is predicted from the translation of the DNA sequence in FIG. 14C) was also inserted into plasmid vector V19.8 using a protocol similar to that used for the rat SCF$^{1-162}$. The cDNA that was used in this construction was synthesized in PCR reactions 84.1 and 84.2 (FIG. 13A) utilizing oligonucleotides 227-29 and 230-25. The two reactions represent independent amplifications starting from different RNA preparations. The sequence for 227-29 was obtained via PCR reactions as described in section A of this Example and the sequence for primer 230-25 was obtained from rat genomic DNA (FIG. 14B). The reactions, 50 µl in volume, consisted of 1× reaction buffer (from a Perkin Elmer Cetus kit), 250 µM dATP, 250 µM dCTP, 250 µM dGTP, and 250 µM dTTP, 200 ng oligo(dT)-primed cDNA, 10 picomoles of 227-29, 10 picomoles of 230-25, and 2.5 units of Taq polymerase (Perkin Elmer Cetus). The cDNA was amplified for 5 cycles using a denaturation temperature of 94° C. for 1½ minutes, an annealing temperature of 50° C. for 2 min, and an elongation temperature of 72° C. for 2 min. After these initial rounds, the amplifications were continued for 35 cycles under the same conditions with the exception that the annealing temperature was changed to 60° C. The products of the PCR amplification were digested with restriction endonucleases HindIII and SstII. V19.8 DNA was digested with HindIII and SstII and the large fragment from the digestion was isolated from an agarose gel. The cDNA was ligated to V19.8 using T4 polynucleotide ligase. The ligation products were transformed into competent *E. coli* strain DH5 and DNA prepared from individual bacterial clones was sequenced. These plasmids were used to transfect mammalian cells in Example 4.

D. Amplification and Sequencing of Human SCF cDNA PCR Products

Figure 13B:
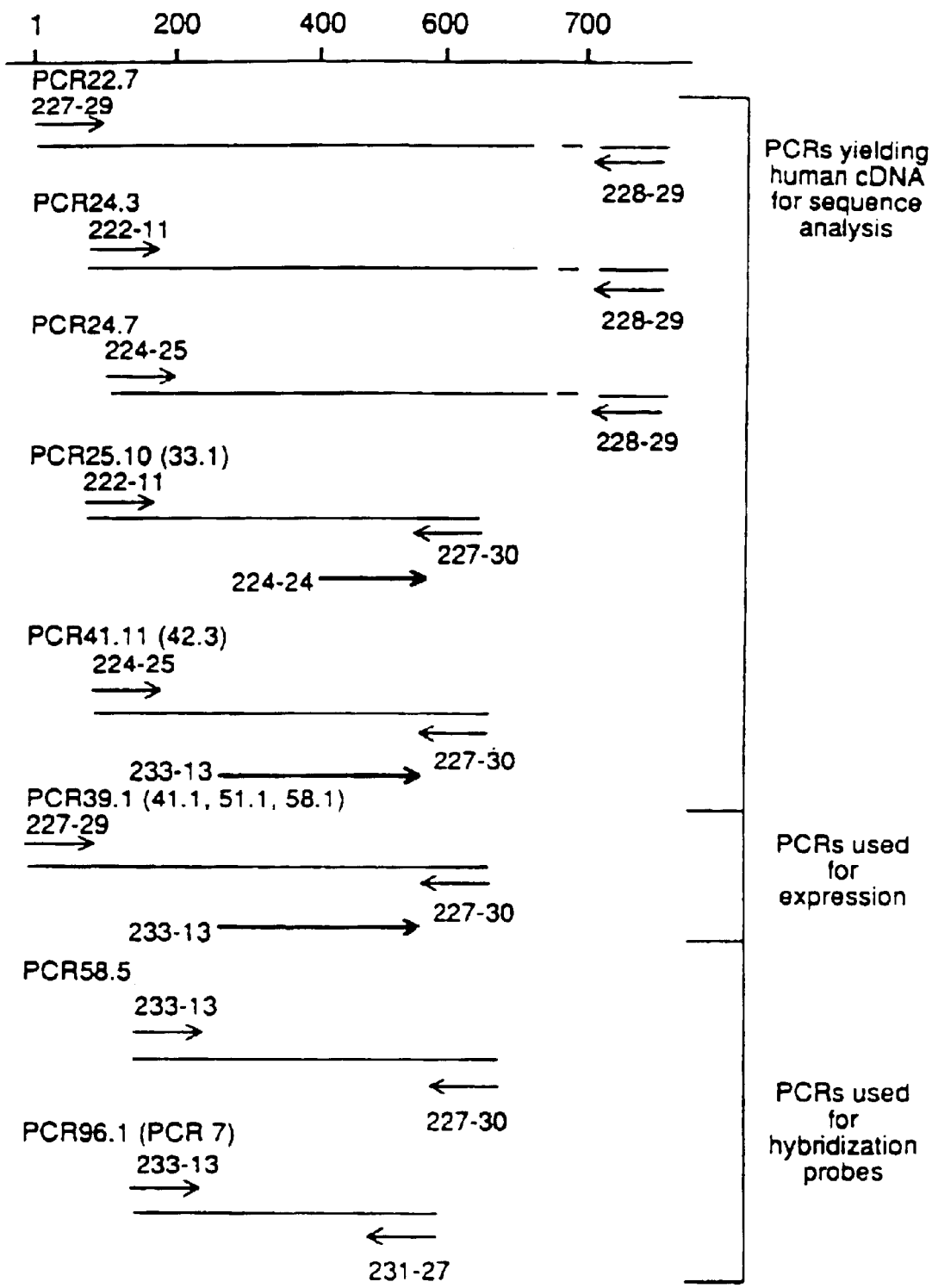

The human SCF cDNA was obtained from a hepatoma cell line HepG2 (ATCC HB 8065) using PCR amplification as outlined in FIG. 13B. The basic strategy was to amplify human cDNA by PCR with primers whose sequence was obtained from the rat SCF cDNA.

RNA was prepared as described by Maniatis et al. [supra (1982)]. PolyA+RNA was prepared using oligo dT cellulose following manufacturers directions. (Collaborative Research Inc.).

First strand cDNA was prepared as described above for BRL cDNA, except that synthesis was primed with 2 µM oligonucleotide 228-28, shown in FIG. 12C, which contains a short random sequence at the 3' end attached to a longer unique sequence. The unique-sequence portion of 228-28 provides a target site for amplification by PCR with primer 228-29 as non-specific primer. Human cDNA sequences related to at least part of the rat SCF sequence were amplified from the HepG2 cDNA by PCR using primers 227-29 and 228-29 (PCR 22.7, see FIG. 13B; 15 cycles annealing at 60° C. followed by 15 cycles annealing at 55° C.). Agarose gel electrophoresis revealed no distinct bands, only a smear of apparently heterogeneously sized DNA. Further preferential amplification of sequences closely related to rat SCF cDNA was attempted by carrying out PCR with 1 µl of the PCR 22.7 product using internally nested rat SCF primer 222-11 and primer 228-29 (PCR 24.3; 20 cycles annealing at 55° C.). Again only a heterogeneous smear of DNA product was observed on agarose gels. Double-sided specific amplification of the PCR 24.3 products with primers 222-11 and 227-30 (PCR 25.10; 20 cycles) gave rise to a single major product band of the same size as the corresponding rat SCF cDNA PCR product. Sequencing of an asymmetric PCR product (PCR 33.1) DNA using 224-24 as sequencing primer yielded about 70 bases of human SCF sequences.

Similarly, amplification of 1 µl of the PCR 22.7 product, first with primers 224-25 and 228-29 (PCR 24.7, 20 cycles), then with primers 224-25 and 227-30 (PCR 41.11) generated one major band of the same size as the corresponding rat SCF product, and after asymmetric amplification (PCR 42.3) yielded a sequence which was highly homologous to the rat SCF sequence when 224-24 was used as sequencing primer. Unique sequence oligodeoxynucleotides targeted at the human SCF cDNA were synthesized and their sequences-are given in FIG. 12B.

To obtain the human counterpart of the rat SCF PCR-generated coding sequence which was used in expression and activity studies, a PCR with primers 227-29 and 227-30 was performed on 1 µl of PCR 22.7 product in a reaction volume of 50 µl (PCR 39.1). Amplification was performed in a Coy Tempcycler. Because the degree of mismatching between the human SCF cDNA and the rat SCF unique primer 227-30 was unknown, a low stringency of annealing (37° C.) was used for the first three cycles; afterward annealing was at 55° C. A prominent band of the same size (about 590 bp) as the rat homologue appeared, and was further amplified by dilution of a small portion of PCR 39.1 product and PCR with the same primers (PCR 41.1). Because more than one band was observed in the products of PCR 41.1, further PCR with nested internal primers was performed in order to determine at least a portion of its sequence before cloning. After 23 cycles of PCR with primers 231-27 and 227-29 (PCR 51.2), a single, intense band was apparent. Asymmetric PCRs with primers 227-29 and 231-27 and sequencing confirmed the presence of the human SCF cDNA sequences. Cloning of the PCR 41.1 SCF DNA into the expression vector V19.8 was performed as already described for the rat SCF 1-162 PCR fragments in Section C above. DNA from individual bacterial clones was sequenced by the Sanger dideoxy method.

E. Cloning of the Human Stem Cell Factor Genomic DNA

A PCR7 probe made from PCR amplification of cDNA, see FIG. 13B, was used to screen a library containing human genomic sequences. A riboprobe complementary to a portion of human SCF cDNA, see below, was used to re-screen positive plaques. PCR 7 probe was prepared starting with the product of PCR 41.1 (see FIG. 13B). The product of PCR 41.1 was further amplified with primers 227-29 and 227-30. The resulting 590 bp fragment was eluted from an agarose gel and reamplified with the same primers (PCR 58.1). The product of PCR 58.1 was diluted 1000-fold in a 50 µl reaction containing 10 pmoles 233-13 and amplified for 10 cycles. After the addition of 10 pmoles of 227-30 to the reaction, the PCR was continued for 20 cycles. An additional 80 pmoles of 233-13 was added and the reaction volume increased to 90 µl and the PCR was continued for 15 cycles. The reaction products were diluted 200-fold in a 50 µl reaction, 20 pmoles of 231-27 and 20 pmoles of 233-13 were added, and PCR was performed for 35 cycles using an annealing temperature of 480 in reaction 96.1. To produce $^{32}$P-labeled PCR7, reaction conditions similar to those used to make PCR1 were used with the following exceptions: in a reaction volume of 50 µl, PCR 96.1 was diluted 100-fold; 5 pmoles of 231-27 was used as the sole primer; and 45 cycles of PCR were performed with denaturation at 94° for 1 minute, annealing at 48° for 2 minutes and elongation at 72° for 2 minutes.

The riboprobe, riboprobe 1, was a $^{32}$P-labelled single-stranded RNA complementary to nucleotides 2-436 of the hSCF DNA sequence shown in FIG. 15B. To construct the vector for the production of this probe, PCR 41.1 (FIG. 13B) product DNA was digested with HindIII and EcoRI and cloned into the polylinker of the plasmid vector pGEM3 (Promega, Madison, Wisconsin). The recombinant pGEM3: hSCF plasmid DNA was then linearized by digestion with HindIII. $^{32}$P-labeled riboprobe 1 was prepared from the linearized plasmid DNA by runoff transcription with T7 RNA polymerase according to the instructions provided by Promega. The reaction (3 µl) contained 250 ng of linearized plasmid DNA and 20 µM $^{32}$P-rCTP (catalog #NEG-008H, New England Nuclear (NEN) with no additional unlabeled CTP.

The human genomic library was obtained from Stratagene (La Jolla, Calif.; catalog #:946203). The library was constructed in the bacteriophage Lambda Fix II vector using DNA prepared from a Caucasian male placenta. The library, as characterized by the supplier, contained 2×10⁶ primary plaques with an average insert size greater than 15 kb. Approximately 10⁶ bacteriophage were plated as described in Maniatis, et al. [supra (1982)]. The plaques were transferred to Gene Screen Plus™ filters (22 cm²; NEN/DuPont) according to the protocol from the manufacturer. Two filter transfers were performed for each plate.

The filters were prehybridized in 6×SSC (0.9 M NaCl, 0.09 M sodium citrate pH 7.5), 1% SDS at 60° C. The filters were hybridized in fresh 6×SSC, 1% SDS solution containing ³²P-labeled PCR 7 probe at 2×10⁵ cpm/ml and hybridized for 20 h at 62° C. The filters were washed in 6×SSC, 1% SDS for 16 h at 62° C. A bacteriophage plug was removed from an area of a plate which corresponded to radioactive spots on autoradiograms and rescreened with probe PCR 7 and riboprobe 1. The rescreen with PCR 7 probe was performed using conditions similar to those used in the initial screen. The rescreen with riboprobe 1 was performed as follows: the filters were prehybridized in 6×SSC, 1% SDS and hybridized at 62° C. for 18 h in 0.25 M NaPO₄₁, (pH 7.5), 0.25 M NaCl, 0.001 M EDTA, 15% formamide , 7% SDS and riboprobe at 1×10⁶ cpm/ml. The filters were washed in 6×SSC, 1% SDS for 30 min at 62° C. followed by 1×SSC, 1% SDS for 30 min at 62° C. DNA from positive clones was digested with restriction endonucleases Bam HI, SphI or SstI and the resulting fragments were subcloned into pUC119 and subsequently sequenced.

Using probe PCR 7, a clone was obtained that included exons encoding amino acids 40 to 176 and this clone is deposited at the ATCC (deposit #40681). To obtain clones for additional SCF exons, the human genomic library was screened with riboprobe 2 and oligonucleotide probe 235-29. The library was screened in a manner similar to that done previously with the following exceptions: the hybridization with probe 235-29 was done at 37° C. and the washes for this hybridization were for 1 h at 37° C. and 1 h at 44° C. Positive clones were rescreened with riboprobe 2, riboprobe 3 and oligonucleotide probes 235-29 and 236-31. Riboprobes 2 and 3 were made using a protocol similar to that used to produce riboprobe 1, with the following exceptions: (a) the recombinant pGEM3: hSCF plasmid DNA was linearized with restriction endonuclease PvuII (riboprobe 2) or PstI (riboprobe 3) and (b) the SP6 RNA polymerase (Promega) was used to synthesize riboprobe 3.

Figure 15A:
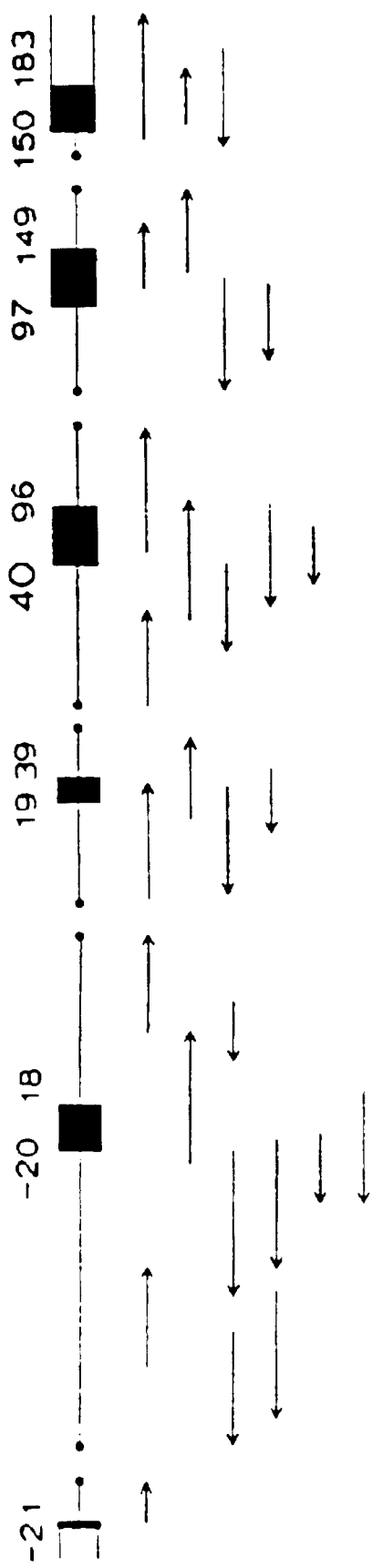

FIG. 15A shows the strategy used to sequence human genomic DNA. In this figure, the line drawing at the top represents the region of human genomic DNA encoding SCF. The gaps in the line indicate regions that have not been sequenced. The large boxes represent exons for coding regions of the SCF gene with the corresponding encoded amino acids indicated above each box. The sequence of the human SCF gene is shown in FIG. 15B. The sequence of human SCF cDNA obtained PCR techniques is shown in FIG. 15C.

The sequence of exons 7, 8 and 9, which include the coding region for amino acids 177 to 248, were obtained from a bacteriophage lambda clone isolated as described above using PCR7 as probe.

To isolate a clone of exon 1 of the human SCF gene, a second genomic library was screened. The library, purchased from Clontech (Palo Alto, Calif.: catalog #HL 1067 J), was constructed in bacteriophage lambda vector EMBL3 SP6/T7 and contained 2.5×10⁶ independent clones with an average insert size of 15 kb. Approximately 10⁶ clones were plated and screened as described above using oligonucleotide probe 249-31 (5'-ACTTGTGCTTCTTCATAAGGAAAGGC-3) (SEQ ID NO.: 87). SacI restriction fragment of the lambda clone was cloned into plasmid vector pGEM4 for subsequent sequence analysis. The sequence of the human SCF gene including exons 1, 7, 8 and 9 is shown in FIG. 15D.

F. Sequence of the Human SCF cDNA 5' Region

Sequencing of products from PCRS primed by two gene-specific primers reveals the sequence of the region bounded by the 3' ends of the two primers. One-sided PCRS, as indicated in Example 3A, can yield the sequence of flanking regions. One-sided PCR was used to extend the sequence of the 5'-untranslated region of human SCF cDNA.

First strand cDNA was prepared from poly A+RNA from the human bladder carcinoma cell line 5637 (ATCC HTB 9) using oligonucleotide 228-28 (FIG. 12C) as primer, as described in Example 3D. Tailing of this cDNA with dG residues, followed by one-sided PCR amplification using primers containing (dC)n sequences in combination with SCF-specific primers, failed to yield cDNA fragments extending upstream (5') of the known sequence.

A small amount of sequence information was obtained from PCR amplification of products of second strand synthesis primed by oligonucleotioe 228-28. The untailed 5637 first strand cDNA described above (about 50 ng) and 2 pmol of 228-28 were incubated with Klenow polymerase and 0.5 mM each of dATP, dCTP, dGTP and dTTP at 10–12° C. for 30 minutes in 10 uL of 1×Nick-translation buffer [Maniatis et al., *Molecular Cloning, a Laboratory Manual*, Cold Spring Harbor Laboratory (1982)]. Amplification of the resulting cDNA by sequential one-sided PCRs with primer 228-29 in combination with nested SCF primers (in order of use: 235–30, 233-14, 236–31 and finally 235-29) yielded complex product mixtures which appeared as smears on agarose gels. Significant enrichment of SCF-related cDNA fragments was indicated by the increasing intensity of the specific product band observed when comparable volumes of the successive one-sided PCR products were amplified with two SCF primers (227-29 and 235-29, for example, yielding a product of about 150 bp). Attempts to select for a particular size range of products by punching out portions of the agarose gel smears and reamplifying by PCR in most cases failed to yield a well-defined band which contained SCF-related sequences.

One reaction, PCR 16.17, which contained only the 235-29 primer, gave rise to a band which apparently arose from priming by 235-29 at an unknown site 5' of the coding region in addition to the expected site, as shown by mapping with the restriction enzymes PvuII and PstI and PCR analysis with nested primers. This product was gel-purified and reamplified with primer 235-29, and sequencing was attempted by the Sanger dideoxy method using ³²P-labelled primer 228-30. The resulting sequence was the basis for the design of oligonucleotide 254-9 (FIG. 12B). When this 3' directed primer was used in subsequent PCRs in combination with 5' directed SCF primers, bands of the expected size were obtained. Direct Sanger sequencing of such PCR products yielded nucleotides 180 through 204 of a human SCP cDNA sequence, FIG. 15C.

In order to obtain more sequence at the 5' end of the hSCF cDNA, first strand cDNA was prepared from 5637 poly A⁺ RNA (about 300 ng) using an SCF-specific primer (2 pmol of 233-14) in a 16 uL reaction containing 0.2 U MMLV reverse transcriptase (purchased from BRL) and 500 uM each dNTP. After standard phenol-chloroform and chloroform extractions and ethanol precipitation (from 1 M ammonium acetate) steps, the nucleic acids were resuspended in 20 uL of water, placed in a boiling water bath for 5 minutes, then cooled and tailed with terminal transferase in the presence of 8 uM dATP in a CoCl$_2$-containing buffer [Deng and Wu, *Methods in Enzymology*, 100, pp. 96–103]. The product, (dA)n-tailed first-strand cDNA was purified by phenol-chloroform extraction and ethanol precipitation and resuspended in 20 uL of 10 mM tris, pH 8.0, and 1 mM EDTA.

Enrichment and amplification of human SCF-related cDNA 5' end fragments from about 20 ng of the (dA)$_n$-tailed 5637 cDNA was performed as follows: an initial 26 cycles of one-sided PCR were performed in the presence of SCF-specific primer 236-31 and a primer or primer mixture containing (dT)$_n$ sequences at or near the 3' end, for instance primer 221-12 or a mixture of primers 220-3, 220–7, and 220-11 (FIG. 12C). The products (1 μl) of these PCRs were then amplified in a second set of PCRs containing primers 221-12 and 235-29. A major product band of approximately 370 bp was observed in each case upon agarose gel analysis. A gel plug containing part of this band was punched out of the gel with the tip of a Pasteur pipette and transferred to a small microfuge tube. 10 uL of water was added and the plug was melted in an 84° C. heating block. A PCR containing primers 221-12 and 235-29 (8 pmol each) in 40 uL was inoculated with 2 uL of the melted, diluted gel plug. After 15 cycles, a slightly diffuse band of approximately 370 bp was visible upon agarose gel analysis. Asymmetric PCRs were performed to generate top and bottom strand sequencing templates: for each reaction, 4 μL of PCR reaction product and 40 pmol of either primer 221-12 or primer 235-29 in a total reaction volume of 100 uL were subjected to 25 cycles of PCR (1 minute, 95° C.; 30 seconds, 55° C.; 40 seconds, 72° C.). Direct sequencing of the 221-12 primed PCR product mixtures (after the standard extractions and ethanol precipitation) with $^{32}$P-labelled primer 262-13 (FIG. 12B) yielded the 5' sequence from nucleotide 1 to 179 (FIG. 15C).

G. Amplification and Sequencing of Human Genomic DNA at the Site of the First Coding Exon of the Stem Cell Factor Screening of a human genomic library with SCF oligonucleotide probes failed to reveal any clones containing the known portion of the first coding exon. An attempt was then initiated to use a one-sided PCR technique to amplify and clone genomic sequences surrounding this exon.

Primer extension of heat-denatured human placental DNA (purchased from Sigma) was performed with DNA polymerase I (Klenow enzyme, large fragment; Boehringer-Mannheim) using a non-SCF primer such as 228-28 or 221-11 under non-stringent (low temperature) conditions, such as 12° C., to favor priming at a very large number of different sites. Each reaction was then diluted five-fold into TaqI DNA polymerase buffer containing TaqI polymerase and 100 uM of each dNTP, and elongation of DNA strands was allowed to proceed at 72° C. for 10 minutes. The product was then enriched for stem cell factor first exon sequences by PCR in the presence of an SCF first exon oligonucleotide (such as 254-9) and the appropriate non-SCF primer (228-29 or 221-11). Agarose gel electrophoresis revealed that most of the products were short (less than 300 bp). To enrich for longer species, the portion of each agarose gel lane corresponding to length greater than 300 bp was cut out and electrophoretically eluted. After ethanol precipitation and resuspension in water, the gel purified PCR products were cloned into a derivative of pGEM4 containing an SfiI site as a HindIII to SfiI fragment.

Colonies were screened with a $^{32}$P-labelled SCF first exon oligonucleotide. Several positive colonies were identified and the sequences of the inserts were obtained by the Sanger method. The resulting sequence, which extends downstream from the first exon through a consensus exon-intron boundary into the neighboring intron, is shown in FIG. 15B.

H. Amplification and Sequencing of SCF cDNA Coding Regions from Mouse, Monkey, Dog, Cat, Cow and Chicken First strand cDNA was prepared from total RNA or poly A$^+$ RNA from monkey liver (purchased from Clontech) and from the cell lines NIH-3T3 (mouse, ATCC CRL 1658), D17 (dog, ATCC CCL 183), bovine endothelial cell line (provided by Yves DeClerck, Childrens Hospital Los Angeles, Los Angeles, Calif.), feline embryonic fibroblast cell line (Jarrett et al., *J. Gen. Virology*, 20:169–175 (1973)) and chicken brain RNA. The primer used in first strand cDNA synthesis was either the nonspecific primer 228-28 or an SCF primer (227-30, 237–19, 237-20, 230–25 or 241-6).

PCR amplification with primer 227–29 and one of the primers 227–30,237–19 or 237–20 in each case except chicken yielded a fragment of the expected size which was sequenced either directly or after cloning into V19.8 or a PGEM vector. Additional sequences near the 5' end of the SCF cDNAs were obtained from PCR amplilications utilizing an SCF-specific primer in combination with either 254–9 or one of the non-specific primers 228–29 and 221–11. Additional sequences at the 3 end of the SCF coding regions were obtained after PCR amplification of 228–28 primed cDNA with combinations of SCF coding region (+)-strand primers with (−)-primers based on the human SCF 3' untranslated region as described in example 3A. The primers 283–19 (SEQ ID NO.: 85) and 2839–20 (SEQ ID NO.:87) (Example 3A) and primer 287–9 (5'-TGTACGAAAGTAACAGTGTTG-3') (SEQ ID NO.: 88) were used. In the case of chicken, amplification was accomplished with primers to 227–29 (SEQ ID NO.: 14) or 247–1 (5'-ACTGCTCCTATTTAATCCTCTC-3') (SEQ ID NO.: 89) in combination with 247–2 (5'-CACTGACTCTGGAATCTTTCTCA-3 SEQ ID NO.: 90) or 287–9. The aligned amino acid sequences of human (FIG. 42), monkey, dog, mouse, rat, cat, cow and chicken. SCF mature proteins are shown in FIG. 16.

The known SCF amino acid sequences are highly homologous throughout much of their length. Identical consensus signal peptide sequences are present in the coding regions of all seven species. The amino acid expected to be at the amino terminus of the mature protein by analogy with the rat SCF is designated by the numeral 1 in this figure. The dog and cow cDNA sequence contains an ambiguity which results in a valine/leucine ambiguity in the amino acid sequence at codon 129. The human, monkey, rat and mouse amino acid sequences co-align without any insertions or deletions. The dog sequence has a single extra residue at position 130 as compared to the other species. Human and monkey differ at only one position, a conservative replacement of valine (human) by alanine (monkey) at position 130. The predicted SCF sequence immediately before and after the putative processing site near residue 164, is highly conserved between species.

EXAMPLE 4

Expression of Recombinant Rat SCF in COS-1 Cells

For transient expression in COS-1 cells (ATCC CRL 1650), vector V19.8 (Example 3C) containing the rat SCF$^{1-}$$_{162}$ and SCF$^{1-193}$ genes was transfected into duplicate 60 mm plates [Wigler et al., *Cell*, 14, 725–731 (1978)]. The plasmid V19.8 SCF is shown in FIG. 17. As a control, the vector without insert was also transfected. Tissue culture supernatants were harvested at various time points post-transfection and assayed for biological activity. Table 4 summarizes the HPP-CFC bioassay results and Table 5 summarizes the MC/9³H-thymidine uptake data from typical transfection experiments. Bioassay results of supernatants from COS-1 cells transfected with the following plasmids are shown in Tables 4 and 5: a C-terminally-truncated form of rat SCF with the C-terminus at amino acid position 162 (V19.8 rat SCF$^{1-162}$), SCF$^{1-162}$ containing a glutamic acid at position 81 [V19.8 rat SCF$^{1-162}$ (Glu81)], and SCF$^{1-162}$ containing an alanine at position 19 [V19.8 rat SCF$^{1-162}$ (Ala19)]. The amino acid substitutions were the product of PCR reactions performed in the amplification of rat SCF$^{1-162}$ as indicated in Example 3. Individual clones of V19.8 rat SCF$^{1-162}$ were sequenced and two clones were found to have amino acid substitutions. As can be seen in Tables 4 and 5, the recombinant rat SCF (also referred to throughout this application as rrat SCF or rrSCF), is active in the bioassays used to purify natural mammalian SCF in Example 1.

TABLE 4

HPP-CFC Assay of COS-1 Supernatants from Cells Transfected with Rat SCF DNA

| Sample | Volume of CM Assayed (µl) | Colony #/200,000 cells |
|---|---|---|
| V19.8 (no Insert) | 100 | 0 |
|  | 50 | 0 |
|  | 25 | 0 |
|  | 12 | 0 |
| V19.8 rat SCF$^{1-162}$ | 100 | >50 |
|  | 50 | >50 |
|  | 25 | >50 |
|  | 12 | >50 |
|  | 6 | 30 |
|  | 3 | 8 |
| V19.8 rat SCF$^{1-162}$ (Glu81) | 100 | 26 |
|  | 50 | 10 |
|  | 25 | 2 |
|  | 12 | 0 |
| V19.8 rat SCF$^{1-162}$ (Ala19) | 100 | 41 |
|  | 50 | 18 |
|  | 25 | 5 |
|  | 12 | 0 |
|  | 6 | 0 |
|  | 3 | 0 |

TABLE 5

MC/9³H-Thymidine Uptake Assay of COS-1 Supernatants from Cells Transfected with Rat SCF DNA

| Sample | Volume of CM Assayed (µl) | cpm |
|---|---|---|
| v19.8(no insert) | 25 | 1,936 |
|  | 12 | 2,252 |
|  | 6 | 2,182 |
|  | 3 | 1,682 |
| v19.8 SCF$^{1-162}$ | 25 | 11,648 |
|  | 12 | 11,322 |
|  | 6 | 11,482 |
|  | 3 | 9,638 |
| v19.8 SCF$^{1-162}$ (Glu81) | 25 | 6,220 |
|  | 12 | 5,384 |
|  | 6 | 3,692 |
|  | 3 | 1,980 |
| v19.8 SCF$^{1-162}$ (Ala19) | 25 | 8,396 |
|  | 12 | 6,646 |
|  | 6 | 4,566 |
|  | 3 | 3,182 |

Recombinant rat SCF, and other factors, were tested individually in a human CFU-GM [Broxmeyer et al., supra (1977)] assay which measures the proliferation of normal bone marrow cells and the data are shown in Table 6. Results for COS-1 supernatants from cultures 4 days after transfection with V19.8 SCF$^{1-162}$ in combination with other factors are also shown in Table 6. Colony numbers are the average of triplicate cultures.

The recombinant rat SCF has primarily a synergistic activity on normal human bone marrow in the CFU-GM assay. In the experiment in Table 6, SCF synergized with human GM-CSF, human IL-3, and human CSF-1. In other assays, synergy was observed with G-CSF also. There was some proliferation of human bone marrow after 14 days with rat SCF; however, the clusters were composed of <40 cells. Similar results were obtained with natural mammalian-derived SCF.

TABLE 6

Human CFU-GM Assay of COS-1 Supernatants from Cells Transfected with Rat SCF DNA

| Sample | Colony #/100,000 cells (±SEM) |
|---|---|
| Saline | 0 |
| GM-CSF | 7 ± 1 |
| G-CSF | 24 ± 1 |
| IL-3 | 5 ± 1 |
| CSF-1 | 0 |
| SCF$^{1-162}$ | 0 |
| GM-CSF + SCF$^{1-162}$ | 29 ± 6 |
| G-CSF + SCF$^{1-162}$ | 20 ± 1 |
| IL-3 + SCF$^{1-162}$ | 11 ± 1 |
| CSF-1 + SCF$^{1-162}$ | 4 ± 0 |

EXAMPLE 5

Expression of Recombinant SCF in Chinese Hamster Ovary Cells

This example relates to a stable mammalian expression system for secretion of SCF from CHO cells (ATCC CCL 61 selected for DHFR-).

A. Recombinant Rat SCF

The expression vector used for SCF production was V19.8 (FIG. 17). The selectable marker used to establish stable transformants was the gene for dihydrofolate reductase in the plasmid pDSVE.1. Plasmid pDSVE.1 (FIG. 18) is a derivative of pDSVE constructed by digestion of PDSVE by the restriction enzyme SalI and ligation to an oligonucleotide fragment consisting of the two oligonucleotides

```
5'TCGAC CCGGA TCCCC 3'

3'G GGCCT AGGGG AGCT 5'.
```

Vector pDSVE is described in commonly owned U.S. Ser. Nos. 025,344, now U.S. Pat. No. 5,175,255 issued Dec. 12, 1992, and 152,045, now abandoned, hereby incorporated by reference. The vector portion of V19.8 and pDSVE1 Coll:1 origin of replication and ampicillin resistance gene and the SV40 origin of replication. This overlap may contribute to homologous recombination during the translormation proCesS, thereby facilitating co-transformation.

Calcium phosphate co-precipitates of V19.8 SCF constructs and pDSVE.1 were made in the presence or absence of 10 µg of carrier mouse DNA using 1.0 or 0.1 µg of pDSVE.1 which had been linearized with the restriction endonuclease PvuI and 10 µg of V19.8 SCF as described [Wigler et al., supra (1978)]. Colonies were selected based upon expression of the DHFR gene from pDSVE.1. Colonies capable of growth in the absence of added hypoxanthine and thymidine were picked using cloning cylinders and expanded as independent cell lines. Cell supernatants from individual cell lines were tested in an MC/9 $^3$H-thymidine uptake assay. Results from a typical experiment are presented in Table 7.

TABLE 7

MC/9 $^3$H-Thymidine Uptake Assay of Stable CHO Cell Supernatants From Cells Transfected With Rat SCF DNA

| Transfected DNA | Volume of Conditioned Medium Assayed | cpm |
|---|---|---|
| V19.8 SCF$^{1-162}$ | 25 | 33,926 |
| | 12 | 34,973 |
| | 6 | 30,657 |
| | 3 | 14,714 |
| | 1.5 | 7,160 |
| None | 25 | 694 |
| | 12 | 1,082 |
| | 6 | 880 |
| | 3 | 672 |
| | 1 | 1,354 |

B. Recombinant Human SCF

Expression of SCF in CHO cells was also achieved using the expression vector pDSVRα2 which is described in commonly owned Ser. No. 501,904 filed Mar. 29, 1990, hereby incorporated by reference. This vector includes a gene for the selection and amplification of clones based on expression of the DHFR gene. The clone pDSRα2 SCF was generated by a two step process. The V19.8 SCF was digested with the restriction enzyme BamHI and the SCF insert was ligated into the BamHI site of pGEM3. DNA from pGEM3 SCF was digested with HindIII and SalI and ligated into pDSRα2 digested with HindIII and SalI. The same process was repeated for human genes encoding a COOH-terminus at the amino acid positions 162, 164 and 183 of the sequence shown in FIG. 15C.

Genes encoding proteins with the COOH-terminus at position 248 of the sequences shown in FIG. 42 and amino acids 1–220 of the sequence in FIG. 44 were generated as follows: DNA encoding the 1-164 amino acid SCF insert in pGEM3 was isolated by digestion with HindIII and ligated into the HindIII site of M13 mp18. The sequence preceding the ATG initiation codon was changed by site directed mutagenesis using the oligonucleotide

5'-TCTTCTTCAVGGCGGCGGCAAGCTT-3' (SEQ ID NO.: 93).

and a kit from Amersham (Arlington Heights, Ill.). The resulting clone was digested with HindIII and the SCF sequences were ligated to pDSRα2 digested with HindIII. This clone was designated pDSRα2-Δ12. The 3' end of this gene was exchanged with the 3' end of the 248 or 220 sequences by digesting pDSRα2-Δ12 with XbaI, filling in the resulting ends with DNA polymerase I (Klenow fragment) and dATP, dCTP, dGTP and TTP to generate a blunt end and subsequent digestion with SpeI. The 220 and 248 sequences were digested with DraI, which leaves a blunt end and SpeI. The vector and inserts were then ligated together to generate pDSRα2-Δ23 (248 amino acid sequence) or pDSRα2-Δ220 (220 amino acid sequence). These plasmids were used to generate cell lines by calcium phosphate precipitation as described in Example SA except that pDSVE.1 was not used for selection.

Established cell lines were challenged with methotrexate [Shimke, in *Methods in Enzymology*, 151 85–104 (1987)] at 10 nM to increase expression levels of the DHFR gene and the adjacent SCF gene. Expression levels of recombinant human SCF were assayed by radioimmune assay, as in Example 7, and/or induction of colony formation in vitro using human peripheral blood leucocytes. This assay is performed as described in Example 9 (Table 12) except that peripheral blood is used instead of bone marrow and the incubation is performed at 20% $O_2$, 5% $CO_2$, and 75% $N_2$ in the presence of human EPO (10 U/ml). Results from typical experiments are shown in Table 8. The SCF$^{220}$ and SCF$^{248}$ also showed similar expression in these assays and as determined by Western blot analysis. The CHO clone expressing human SCF$^{1-164}$ has been deposited on Sep. 25, 1990 with ATCC (CRL 10557) and designated Hul64SCF17.

TABLE 8 hPBL Colony Assay of Conditioned Media From Stable CHO Cell Lines Transfected With Human SCF DNA

| Transfected DNA | Media assayed(µl) | Number of Colonies/10$^5$ |
|---|---|---|
| pDSRα2 hSCF$^{1-164}$ | 50 | 53 |
| | 25 | 45 |
| | 12.5 | 27 |
| | 6.25 | 13 |
| pDSRα2 hSCF$^{1-162}$ | 10 | 43 |
| | 5 | 44 |
| | 2.5 | 31 |
| | 1.25 | 17 |
| | 0.625 | 21 |
| None (CHO control) | 50 | 4 |

C. Secreted Product of CHO Cells Transfected with pDSRα2-Δ23.

CHO cells transfected with pDSRα2-Δ23 (248 amino acid sequence; see Example 5B) were cultured as described in Example 11A. As previously described, the sequences shown in FIG. 42 include a putative hydrophobic transmembrane region represented by amino acids numbered 190-212, which could anchor a synthesized protein in the cell membrane. This is also the case for the encoded rat sequences of FIG. 14, yet soluble rat SCF representing amino acids 1–164/165 was recovered from conditioned medium of BRL-3A cells as described in Examples 1 and 2. This is indicative of proteolytic processing leading to release of soluble SCF. To study such processing for a case involving the human protein, the CHO cells transfected with pDSRα2-Δ23 were cultured as described in Example 5B. Conditioned medium contained soluble human SCF, which was purified essentially by the methods outlined in Example 11B. By SDS-PAGE, combined with the use of glycosidases as outlined in Examples 10 and 11C, it was found that the behavior of the purified material was much like that described for BRL-3A derived rat SCF (Example 11D) and for human SCF purified from conditioned medium of CHO cells transfected with pDSRα2 human SCF$^{1-162}$ (see Example 11C). The mobility on SDS-PAGE of the major band remaining after treatment with neuraminidase, O-glycanase, and N-glycanase was slightly less that the mobility seen for the major band after such treatment of the CHO cell-derived human SCF 1-162 described in Example 11C. This mobility difference corresponded to less than 1000 in molecular weight difference and indicated that the less mobile product was larger by a few amino acids.

The purified material from the CHO cells transfected with pDSRα2-Δ23 was subjected to detailed structural analysis, by methods including those given in Example 2. The N-terminal amino acid sequence is Glu-Gly-Ile . . . , indicating that it is the product of processing/cleavage between residues indicated as numbers (−1) Thr and (+1) (Glu) in FIG. 42.

To determine the precise C-terminal processing site(s), the purified material was subjected to AspN peptidase digestion (20–50 μg SCF in 100–200 μl 0.1 M sodium phosphate, pH 7.2, for 18 h at 37°C. with AspN:SCF ratio of 1:200 by weight) followed by HPLC to isolate resulting peptides. The elution profile shown in FIG. 16C was obtained. Collected peptide fractions were sequenced to identify the C-terminal peptide. A peptide eluting at 36.8 mm represents the C-terminal peptide. The sequence Asp-Ser-Arg-Val-Ser-Val-(X)-Lys-Pro-Phe-Phe-Met-Leu-Pro-Pro-Val-Ala-(Ala) (SEQ ID NO.: 94) was assigned, where (X) denotes an unassigned residue, and (Ala) denotes tentative assignment due to low recovery. The indicated amino acids corresponds to position 148–165 of the sequence shown in FIG. 42.

After treatment of the C-terminal peptide with neuraminidase and ( )-glycanase to remove carbohydrate, fast atom bombardment—mass spectroscopy (FAB-MS) analysis indicated a molecular weight of 1815.19 for the protonated monoisotopic ion (NII$^-$), consistent with the sequence Asp-Ser-Arg-Val-Ser-Val-Thr-Lys-Pro-Phe-Phe-Met-Len-Pro-Pro-Val-Ala-Ala (SEQ ID NO.: 95) (calculated molecular weight of MH=1815.98). A less abundant ion species of mass 1744.37, corresponding to the above-mentioned peptide truncated by one Ala at the C-terminus (calculated MII-1744.17)was also detected.

Further analyses were performed using electrospray mass spectroscopy (ES-MS). The deglycosylated C-terminal peptide fraction of the CHO cell-derived SCF and the C-terminal peptide fraction from $E.$ $coli$-derived SCF$^{1-165}$ (obtained as described in Example 2) were analyzed. A major signal with mass 1815 and a second signal with mass 1743 were detected for the peptide of CHO cell-derived SCF. Only an 1814 signal was detected for the peptide of $E.$ $coli$-derived SCF.

These data indicate that soluble SCF is released from CHO cells transfected with pDSRα2-Δ23 by proteolytic cleavage after amino acid 164 or 165. This processing matches that found for BRL-3A cell derived rat SCF (Example 2).

EXAMPLE 6

Expression of Recombinant SCF in $E.$ $coli$

A. Recombinant Rat SCF

This example relates to expression in $E.$ $coli$ of SCF polypeptides by means Of a DNA sequence encoding [Mer$^{-1}$] rat SCF$^{1193}$(FIG. 14C). Although any suitable vector may be employed for protein expression using this DNA, the plasmid chosen was pCFM1156 (FIG. 19). This plasmid can be readily constructed from PCFM 836 (see U.S. Pat. No. 4,710,473 hereby incorporated by reference) by destroying the two endogenous NdeI restriction sites by end-filling with T4 polymerase enzyme followed by blunt end ligation and substituting the small DNA sequence between the unique (ClaI and KpnI restriction sites with the small oligonucleotide shown below. The 5' to 3' sequence below is SEQ ID NO:96 and the 3' to 5' sequence below is SEQ ID NO:97.

5' CGATTTGATTCTAGAAGGAGGAATM-CATATGGTTAACGCGTTGGAATTCGGTAC 3'

3' TAAACTMGATCTTCCTCCTTATTG-TATACCAATTGCGCAACCTTAAGC 5'

Control of protein expression in the pCFM1156 plasmid is by means of a synthetic lambda PL promoter which is itself under the control of a temperature sensitive lambda CI857 repressor gene [such as is provided in $E.$ $coli$ strains FM5 (ATCC deposit #53911) or K12ΔHtrp]. The pCFM1156 vector is constructed so as to have a DNA sequence containing an optimized ribosome binding site and initiation codon immediately 3' of the synthetic PL promoter. A unique NdeI restriction site, which contains the ATG initiation codon, precedes a multi-restriction site cloning cluster followed by a lambda t-oop transcription stop sequence.

Plasmid V19.8 SCF$^{1-193}$ containaing the rat SCF$^{1-193}$ gene cloned from PCR amplified cDNA (FIG. 14C) as described in Example 3 was digested with BglII and SstII and a 603 bp DNA fragment isolated. In order to provide a Met initiation codon and restore the codons for the first three amino acid residues (Gln, Glu, and Ile) of the rat SCF polypeptide, a synthetic oligonucleotide linker (sequences below 5' to 3' direction: SEQ ID NO:98 and 3' to 5' direction: SEQ ID NO:99).

5' TATGCAGGA 3'

3' ACGTCCTCTAG 5' with NdeI and BglII sticky ends was made. The small oligonucleotide and rat SCF$^{1-193}$ gene fragment were inserted by ligation into pCFM1156 at the unique NdeI and SstII sites in the plasmid shown in FIG. 19. The product of this reaction is an expression plasmid, pCFM1156 rat SCF$^{1-193}$.

The pCFM1156 rat SCF$^{1-193}$ plasmid was transformed into competent FM5 $E.$ $coli$ host cells. Selection for plasmid-containing cells was on the basis of the antibiotic (kanamycin) resistance marker gene carried on the pCFM1156 vector. Plasmid DNA was isolated from cultured cells and the DNA sequence of the synthetic oligonucleotide and its junction to the rat SCF gene confirmed by DNA sequencing.

To construct the plasmid pCFM1156 rat SCF$^{1-162}$ encoding the (Met$^{-1}$ rat SCF$^{1-162}$ polypeptide, an EcoRI to SstII restriction fragment was isolated from V19.8 rat SCF$^{1-162}$ and inserted by ligation into the plasmid pCFM rat SCF$^{1-193}$ at the unique EcoRI and SstII (restriction sites thereby replacing the coding region for the carboxyl terminus of the rat SCF gene.

To construct the plasmids pCFM1156 rat SCF$^{1-164}$ and pCFM1156 rat SCF$^{1-165}$ encoding the [Met$^{-1}$]rat SCF$^{1-164}$ and [Met$^{-1}$] rat SCF$^{1-165}$ polypeptides, respectively, EcoRI to SstII restriction fragments were isolated from PCR amplified DNA encoding the 3' end of the SCF gene and designed to introduce site directed changes in the DNA in the region encoding the carboxyl terminus of the SCF gene. The DNA amplifications were performed using the oligonucleotide primers 227-29 and 237-19 in the construction of pCFM1156 rat SCF$^{1-164}$ and 227-29 and 237-20 in the construction of pCFM1156 rat SCF$^{1-165}$.

B. Recombinant Human SCF

This example relates to the expression in $E.$ $coli$ of human SCF polypeptide by means of a DNA sequence encoding [Met$^{-1}$] human SCF$^{1-163}$ and [Met$^{-1}$] human SCF$^{1-183}$ (FIG. 15C): and [MET$^{-1}$] human SCF$^{1-165}$ (FIG. 15C). Plasmid V19.8 human SCF$^{1-162}$ containing the human SCF$^{1-162}$ gene was used as template for PCR amplification of the human SCE gene. Oligonucleotide primers 227-29 and 237-19 were used to generate the PCR DNA which was then digested with PstI and SstII restriction endonucleases. In order to provide a Met initiation codon and restore the codons for the first four amino acid residues (Glu, Gly, Ile, Cys) of the human SCF polypeptide, a synthetic oligonucleotide linker (sequences below 5' to 3' direction: SEQ ID NO:100 and 3' to 5' direction: SEQ ID NO: 101).

5' TATGGAAGGTATCTGCA 3'

3' ACCTTCCATAG 5' with NdeI and PstI sticky ends was made. The small oligo linker and the PCR derived human SCF gene fragment were inserted by ligation into the expression plasmid pCFM1156 (as described previously) at the unique NdeI and SstII sites in the plasmid shown in FIG. 19.

The pCFM1156 human $SCF^{1-164}$ plasmid was transformed into competent FM5 E. coli host cells. Selection for plasmid containing cells was on the basis of the antibiotic (kanamycin) resistance marker gene carried on the pCFM1156 vector. Plasmid DNA was isolated from cultured cells and the DNA sequence of the human SCF gene confirmed by DNA sequencing.

To construct the plasmid pCFM1156 human $SCF^{1-183}$ encoding the $[Met^{-1}]$ human $SCF^{1-183}$ (FIG. 15C) polypeptide, a EcoRI to HindIII restriction fragment encoding the carboxyl terminus of the human SCF gene was isolated from pGEM human $SCF^{114-183}$ (described below), a SstI to EcoRI restriction fragment encoding the amino terminus of the human SCF gene was isolated from pCFM1156 human $SCF^{1-164}$, and the larger HindIII to SstI restriction fragment from pCFM1156 was isolated. The three DNA fragments were ligated together to form the pCFM1156 human $SCF^{1-183}$ plasmid which was then transformed into FM5 E. coli host cells. After colony selection using kanamycin drug resistance, the plasmid DNA was isolated and the correct DNA sequence confirmed by DNA sequencing. The pGEM human $SCF^{114-183}$ plasmid is a derivative of pGEM3 that contains an EcoRI-SphI fragment that includes nucleotides-609 to,820 of the human SCF cDNA sequence shown in FIG. 15C. The EcoRI-SphI insert in this plasmid was isolated from a PCR that used oligonucleotide primers 235-31 and 241-6 (FIG. 12B) and PCR 22.7 (FIG. 13B) as template. The sequence of primer 241-6 was based on the human genomic sequence to the 3' side of the exon containing the codon for amino acid 176.

A plasmid encoding human $[Met^{-1}]$ $SCF^{1-165}$ was constructed as follows. Sixteen oligonucleotides were "stitched together" to create a 221 base pair fragment with EcoRl and BamHl sticky ends (FIG. 16D). This nucleotide sequence codes for the C-terminal 68 amino acids of human $SCF^{1-183}$ (amino acid numbering and designation as in FIG. 15C). The codons in this nucleotide sequence reflected those most commonly used by E. coli (i.e., optimized for expression in E. coli). In addition, a unique BstEII site is present in the fragment. The EcoRl to BamHl fragment of the human $SCF^{1-183}$ DNA (FIG. 15C) was removed and replaced by the fragment containing the optimized codons. This construct was digested with BstEII and BamHl and the 39 base pair fragment shown in FIG. 16E was introduced. The resulting plasmid codes for human $[Met^{-1}]$ $SCF^{1-165}$ with the codons for the C-terminal 50 amino acis optimized for expression in E. coli.

Another plasmid encoding human $[Met^{-1}]$ $SCF^{1-165}$, with the codons of FIG. 15C, was also constructed, by PCR utilizing pCFM1156 human $SCF^{1-164}$. A 5' oligonucleotide was made 5' of the EcoRl site and a 3' oligonucleotide was made which included the final codons of the 1-164 sequence plus an extra codon for the position 165 and nucleotides through the SstII site. After the PCR reaction, the fragment was cut with EcoRI and SstII, gel purified, and cloned into pCFM1156 human $SCF^{1-164}$ cut with EcoRl and SstII.

The generation of other expression plasmids including those encoding human $[Met^{-1}]$ $SCF^{1-248}$ (sequence of FIG. 42) and encoding human $[Met^{-1}]SCF^{1-220}$ (sequence of FIG. 44) is described in Example 28.

C. Fermentation of E. coli producing Human $SCF^{1-164}$ and E. coli producing Human $SCF^{1-165}$ Fermentations for the production of $SCF^{1-164}$ were carried out in 16 liter fermentors using an FM5 E. coli K12 host containing the plasmid pCFM 1156 human $SCF^{1-164}$. Seed stocks of the producing culture were maintained at −80° C. in 17% glycerol in Luria broth. For inoculum production, 100 µl of the thawed seed stock was transferred to 500 ml of Luria broth in a 2 L erlenmeyer flask and grown overnight at 30° C. on a rotary shaker (250 RPM).

For the production of E. coli cell paste used as starting material for the purification of human $SCF^{1-164}$ outlined in Example 10, the following fermentation conditions were used.

The inoculum culture was aseptically transferred to a 16 L fermentor containing 8 L of batch medium (see Table 9). The culture was grown in batch mode until the OD-600 of the culture was approximately 3-5. At this time, a sterile feed (Feed 1, Table 10) was introduced into the fermentor using a peristaltic pump to control the feed rate. The feed rate was increased exponentially with time to give a growth rate of 0.15 $hr^{-1}$. The temperature was controlled at 30° C. during the growth phase. The dissolved oxygen concentration in the fermentor was automatically controlled at 50% saturation using air flow rate, agitation rate, vessel back pressure and oxygen supplementation for control. The pH of the fermentor was automatically controlled at 7.0 using phosphoric acid and ammonium hydroxide. At an OD-600 of approximately 30, the production phase of the fermentation was induced by increasing the fermentor temperature to 42° C. At the same time the addition of Feed 1 was stopped and the addition of Feed 2 (Table 11) was started at a rate of 200 ml/hr. Approximately six hours after the temperature of the fermentor was increased, the fermentor contents were chilled to 15° C. The yield of $SCF^{1-164}$ was approximately 30 mg/OD-L. The cell pellet was then harvested by centrifugation in a Beckman J6-B rotor at 3000×g for one hour. The harvested cell paste was stored frozen at −70° C.

An advantageous method for production of $SCF^{1-164}$ is similar to the method described above except for the following modifications.

1) The addition of Feed 1 is not initiated until the OD-600 of the culture reaches 5-6.

2) The rate of addition of Feed 1 is increased more slowly, resulting in a slower growth rate (approximately 0.08).

3) The culture is induced at OD-600 of 20.

4) Feed 2 is introduced into the fermentor at a rate of 300 mL/hr.

All other operations are similar to the method described above, including the media.

Using this process, yields of $SCF^{1-164}$ approximately 35–40 mg/OD-L at OD=25 have been obtained.

TABLE 9

| Composition of Batch Medium | |
|---|---|
| Yeast extract | $10^a$ g/L |
| Glucose | 5 |
| $K_2HPO_4$ | 3.5 |
| $KH_2PO_4$ | 4 |
| $M_GSO_4.7H_2O$ | 1 |
| NaCl | 0.625 |
| Dow P-2000 antifoam | 5 mL/8 L |

TABLE 9-continued

Composition of Batch Medium

| | |
|---|---|
| Vitamin solution[b] | 2 mL/L |
| Trace metals solution[c] | 2 mL/L |

[a]Unless otherwise noted, all ingredients are listed as g/L.
[b]Trace Metals solution: $FeCl_3.6H_2O$, 27 g/L; $ZnCl_2.4 H_2O$, 2 g/L; $CaCl_2.6H_2O$, 2 g/L; $Na_2MoO_4.2 H_2O$, 2 g/L, $CuSO_4.5 H_2O$, 1.9 g/L; concentrated HCl, 100 ml/L.
[c]Vitamin solution: riboflavin, 0.42 g/l; pantothenic acid, 5.4 g/L; niacin, 6 g/L; pyridoxine, 1.4 g/L; biotin, 0.06 g/L; folic acid, 0.04 g/L.

TABLE 10

Composition of Feed Medium

| | |
|---|---|
| Yeast extract | 50[a] |
| Glucose | 450 |
| $MgSO_4.7H_2O$ | 8.6 |
| Trace metals solution[b] | 10 mL/L |
| Vitamin solution[c] | 10 mL/L |

[a]unless otherwise noted, all ingredients are listed as g/L.
[b]Trace Metals solution: $FeCl_3.6H_2O$, 27 g/L; $ZnCl_2.4 H_2O$, 2 g/L; $CaCl_2.6H_2O$, 2 g/L; $Na_2MoO_4.2 H_2O$, 2 g/L, $CuSO_4.5 H_2O$, 1.9 g/L; concentrated HCl, 100 ml/L.
[c]Vitamin solution: riboflavin, 0.42 g/l; pantothenic acid, 5.4 g/L; niacin, 6 g/L; pyridoxine, 1.4 g/L; biotin, 0.06 g/L; folic acid, 0.04 g/L.

TABLE 11

Composition of Feed Medium 2

| | |
|---|---|
| Tryptone | 172[a] |
| Yeast extract | 86 |
| Glucose | 258 |

[a]All ingredients are listed as g/L.

For the production of *E. coli* cell paste used as starting material for the purification of human $SCF^{1-165}$ (Example 10), fermentation conditions differed in the following ways from those described for the $SCF^{1-164}$ cases. Feed 1 was introduced when the OD-600 of the culture was approximately 5-6. Feed 1 contained 13 g/L $K_2HPO_4$ in addition to the components listed in Table 10. The feed rate was increased exponentially with time to give a growth rate of 0.2 hr$^{-1}$. Production phase was induced by temperature increase at OD-600 of about 40, and the rate of addition of Feed 2 was 600 ml/hr. Feed 2 contained 258 g/L tryptone, 129 g/L yeast extract, 50 g/L glucose, and 6.4 g/L $K_2HPO_4$. Chilling of the fermentor and harvesting of cells was done about eight hours after the temperature increase.

EXAMPLE 7

Immunoassays for Detection of SCF

Radioimmunoassay (RIA) procedures applied for quantitative detection of SCF in samples were conducted according to the following procedures.

An SCF preparation from BRL 3A cells purified as in Example 1 was incubated together with antiserum for two hours at 37° C. After the two hour incubation, the sample tubes were then cooled on ice, $^{125}I$-SCF was added, and the tubes were incubated at 4° C. for at least 20 h. Each assay tube contained 500 μl of incubation mixture consisting of 50 μl of diluted antisera, ~60,000 5 μl trasylol and 0–400 μl of SCF standard, with buffer (phosphate buffered saline, 0.1% bovine serum albumin, 0.05% Triton X-100, 0.025% azide) making up the remaining volume. The antiserum was the second test bleed of a rabbit immunized with a 50% pure preparation of natural SCF from BRL 3A conditioned medium. The final antiserum dilution in the assay was 1:2000.

Figure 20A:
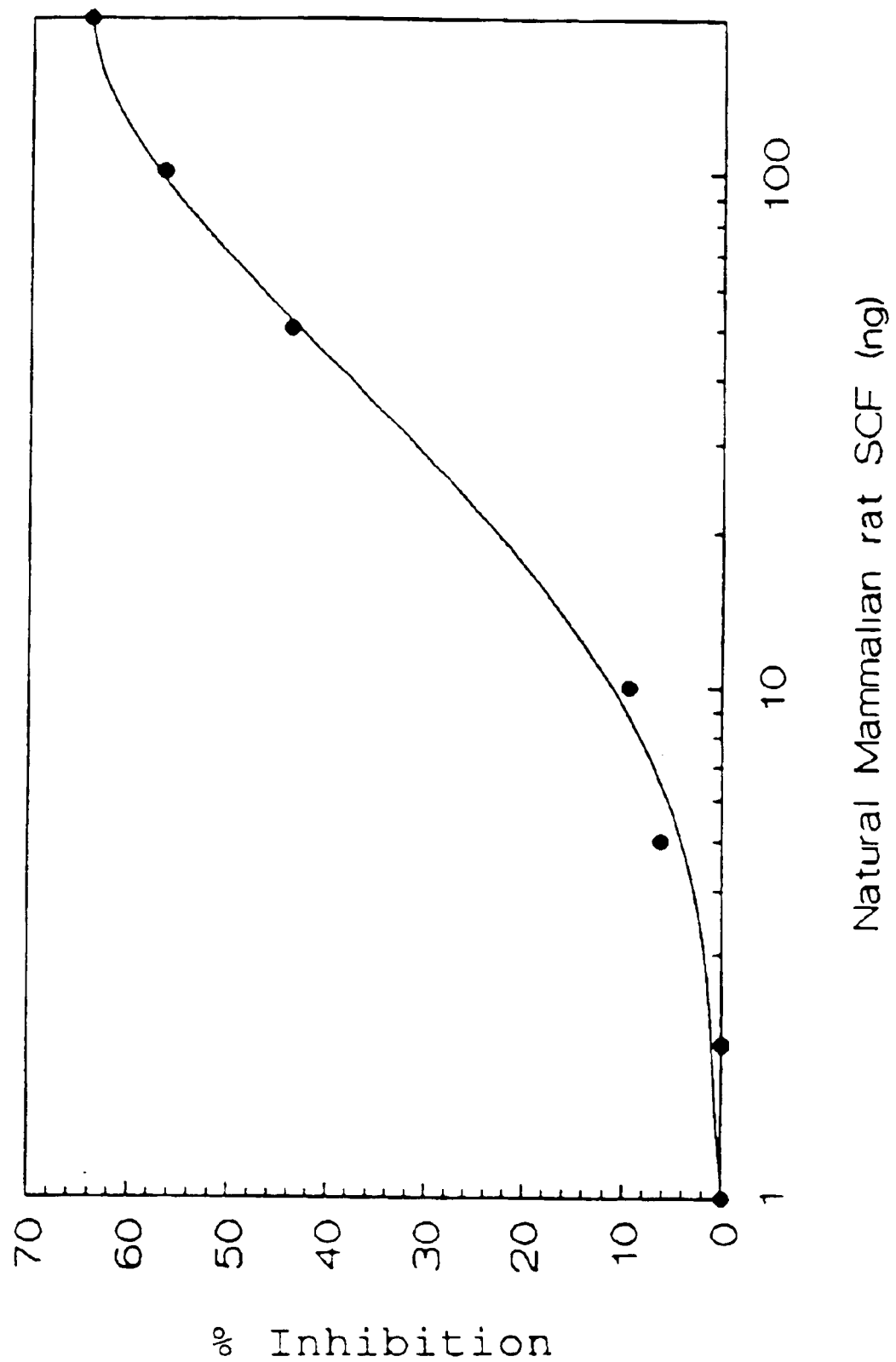
Figure 20B:
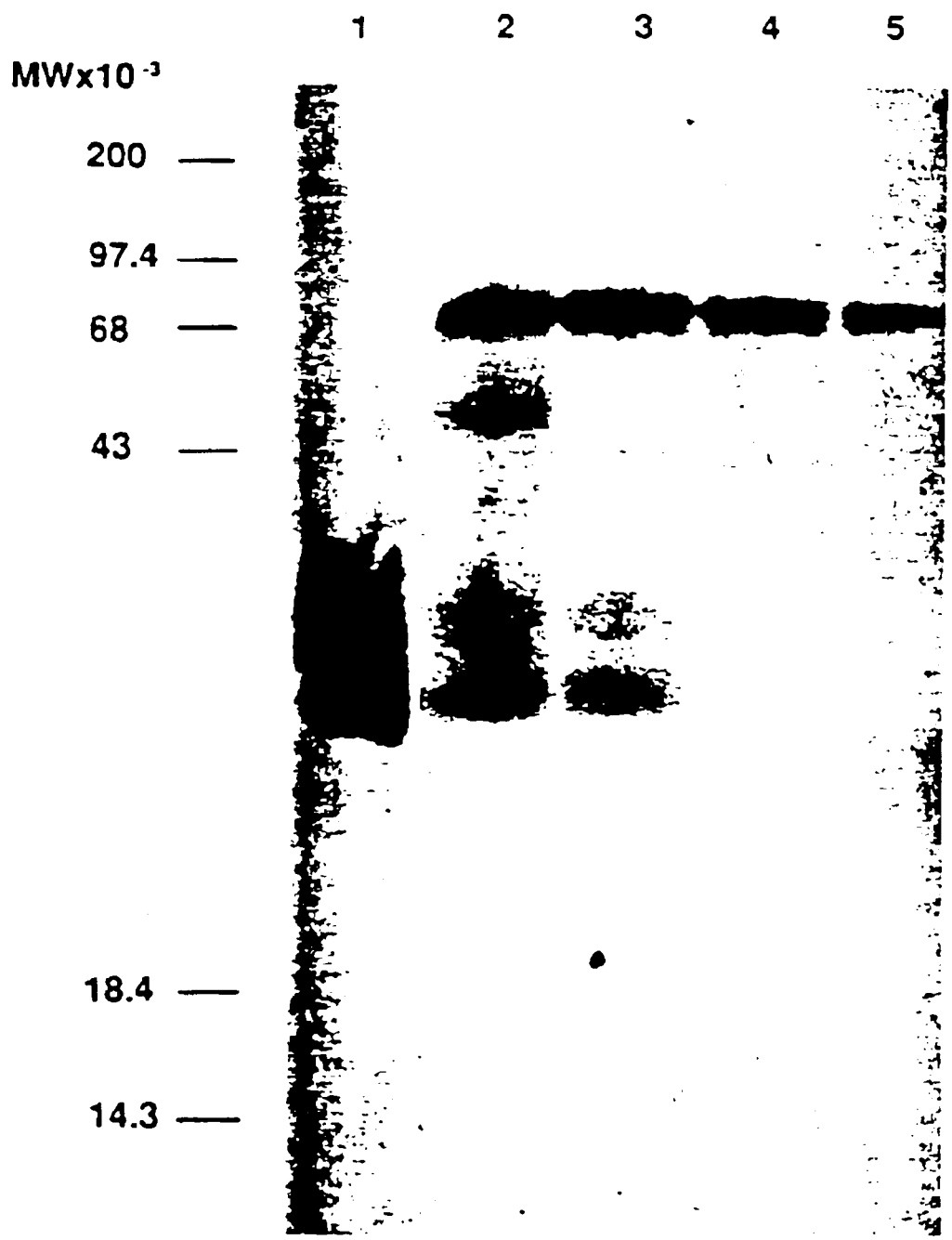

The antibody-bound $^{125}I$-SCF was precipitated by the addition of 150 μl Staph A (Calbiochem). After a 1 h incubation at room temperature, the samples were centrifuged and the pellets were washed twice with 0.75 ml 10 mM Tris-HCL pH 8.2, containing Q.15M NaCl, 2 mM EDTA, and 0.05% Triton X-100. The washed pellets were counted in a gamma counter to-determine the percent of $^{125}I$-SCF bound. Counts bound by tubes lacking serum were subtracted from all final values to correct for nonspecific precipitation. A typical RIA is shown in FIG. 20. The percent inhibition of $^{125}I$-SCF binding produced by the unlabeled standard is dose dependent (FIG. 20A), and, as indicated in FIG. 20B, when the immune precipitated pellets are examined by SDS-PAGE and autoradiography, the $^{125}I$-SCF protein band is competed. In FIG. 20B, lane 1 is $^{125}I$-SCF, and lanes 2, 3, 4 and 5 are immune-precipicated $^{125}I$-SCF competed with 0, 2, 100, and 200 ng of SCF standard, respectively. As determined by both the decrease in antibody-precipitable cpm observed in the RIA tubes and decrease in the immune-precipitated $^{125}I$-SCF protein band (migrating at approximately $M_r$ 31,000) the polyclonal antisera recognizes the SCF standard which was purified as in Example 1.

Western procedures were also applied to detect recombinant SCF expressed in *E. coli*, COS-1, and CHO cells. Partially purified *E. coli* expressed rat $SCF^{1-193}$ (Example 10), COS-1 cell expressed rat $SCF^{1-162}$ and $SCF^{1-193}$ as well as human $SCF^{1-162}$ (Examples 4 and 9), and CHO cell expressed rat $SCF^{1-162}$ (Example 5), were subjected to SDS-PAGE. Following electrophoresis, the protein bands were transferred to 0.2 μm nitrocellulose using a Bio-Rad Transblot apparatus at 60V for 5 h. The nitrocellulose filters were blocked for 4 h in PBS, pH 7.6, containing 10% goat serum followed by a 14 h room temperature incubation with a 1:200 dilution of either rabbit preimmune or immune serum (immunization described above). The antibody-antiserum complexes were visualized using horseradish peroxidase-conjugated goat anti-rabbit IgG reagents (Vector laboratories) and 4-chloro-l-napthol color development reagent.

Examples of two Western analyses are presented in FIGS. 21 and 22. In FIG. 21, lanes 3 and 5 are 200 μl of COS-1 cell produced human $SCF^{1-162}$; lanes 1 and 7 are 200 μl of COS-1 cell produced human EPO (COS-1 cells transfected with V19.8 EPO); and lane 8 is prestained molecular weight markers. Lanes 1-4 were incubated with pre-immune serum and lanes 5-8 were incubated with immune serum. The immune serum specifically recognizes a diffuse band with an apparent $M_r$ of 30,000 daltons from COS-1 cells producing human $SCF^{1-162}$ but not from COS-1 cells producing human EPO.

In the Western shown in FIG. 22, lanes 1 and 7 are 1 μg of a partially purified preparation of rat $SCF^{1-193}$ produced in *E. coli* ; lanes 2 and 8 are wheat germ agglutinin-agarose purified COS-1 cell produced rat $SCF^{1-193}$; lanes 4 and 9 are wheat germ agglutinin-agarose purified COS-1 cell produced rat $SCF^{1-162}$; lanes 5 and 10 are wheat germ agglutinin-agarose purified CHO cell produced rat $SCF^{1-162}$; and lane 6 is prestained molecular weight markers. Lanes 1-5 and lanes 6-10 were incubated with rabbit preimmune and immune serum, respectively. The *E. coli* produced rat $SCF^{1-193}$ (lanes 1 and 7) migrates with an apparent $M_r$ of 24,000 daltons while the COS-1 cell produced rat $SCF^{1-193}$ (lanes 2 and 8) migrates with an apparent $M_r$ of 24-36,000 daltons. This difference in molecular weights is expected since mammalian cells, but not bacteria, are capable of glycosylation. Transfection of the sequence encoding rat $SCF^{1-162}$ into COS-1 (lanes 4 and 9), or CHO cells (lanes 5 and 10), results in expression of SCF with a lower average molecular weight than that produced by transfection with $SCF^{1-193}$ (lanes 2 and 8).

The expression products of rat $SCF^{1-162}$ from COS-1 and CHO cells are a series of bands ranging in apparent $M_r$ between 24-36,000 daltons. The heterogeneity of the expressed SCF is likely due to carbohydrate variants, where the SCF polypeptide is glycosylated to different extents.

In summary, Western analyses indicate that immune serum from rabbits immunized with natural mammalian SCF recognize recombinant SCF produced in *E. coli*, COS-1 and CHO cells but fail to recognize any bands in a control sample consisting of COS-1 cell produced EPO. In further support of the specificity of the SCF antiserum, preimmune serum from the same rabbit failed to react with any of the rat or human SCF expression products.

Radioimmunoassay (RIA) procedures were also developed to quantify SCF in human serum samples. Purified CHO-derived human SCF (expression of the 1-248 transcript) was used as the standard in this assay over the range of 0.01–10.0 ng/tube. Pooled normal human serum samples, obtained from Irvine Scientific (Lots 500080713 and 500081015), were each assayed at 25, 50, 100 and 200 $\mu$l per tube. Each tube was adjusted to contain 5 $\mu$l of trasylol, and 900 $\mu$l total volume by the addition of the appropriate amount of assay diluent (phosphate-buffered saline containing 0.1% bovine serum albumin and 0.025% sodium azide). Rabbit anti-human SCF antiserum (100 $\mu$l of a 1:50,000 dilution) was added, the tubes were mixed and incubated at 4° C. for approximately 24 hours. The antiserum was the bleed-out of a rabbit hyperimmunized with a purified preparation of CHO-derived human $SCF^{1-162}$.

Following the 24 hours incubation, approximately 60,000 cpm of $^{125}$I-CHO-derived human SCF (expression of the 1-248 transcript, 57.9 mCi/mg) was added to all tubes; the tubes were vortexed and incubated at 4° C. for an additional 19 hours. The antibody-bound $^{125}$I-human SCF was precipitated by the addition of 100 $\mu$l of a 1:50 dilution of normal rabbit serum (Research Products International) and 100 $\mu$l of a 1:20 dilution of goat anti-rabbit IgG (Research Products International) to all tubes. After a two hour incubation at room temperature, the tubes were centrifuged and the pellets were washed once with 0.75 ml of 10 mM Tris-HCl, pH 8.2, containing 0.15 M NaCl, 2 mM EDTA, and 0.05% Triton X-100. The washed pellets were counted in a gamma counter to determine the percent of $^{125}$I-human SCF bound. Counts bound by tubes lacking antiserum were subtracted from all final values to correct for nonspecific precipitation. A typical RIA is shown in FIG. 22A. The percent inhibition of $^{125}$I-human SCF binding by the unlabeled standard and normal human serum was dose-dependent. Increasing aliquots of the normal human serum, over the range of 25–200 $\mu$l produced a dose response line which was parallel to that of the standard. Both of the normal human serum samples were assayed twice in this assay. Values plotted in FIG. 22A are the average percent inhibitions obtained for the respective aliquots for each serum sample. Values of 2.16 ng/ml and 2.93 ng/ml were obtained for SCF levels in Lot 500080713 and Lot 500081015 normal human serum, respectively.

EXAMPLE 8

In Vivo Activity of Recombinant SCF

A. Rat SCF in Bone Marrow Transplanation

COS-1 cells were transfected with V19.8 $SCF^{1-162}$ in a large scale experiment (T175 cm$^2$ flasks instead of 60 mm dishes) as described in Example 4. Approximately 270 ml of supernatant was harvested. This supernatant was chromatographed on wheat germ agglutinin-agarose and S-Sepharose essentially as described in Example 1. The recombinant SCF was evaluated in a bone marrow transplantation model based on murine W/W$^v$ genetics. The W/W$^v$. mouse has a stem cell defect which among other features results in a macrocytic anemia (large red cells) and allows for the transplantation of bone marrow from normal animals without the need for irradiation of the recipient animals [Russel, et al., *Science*, 144, 844–846 (1964)]. The normal donor stem cells outgrow the defective recipient cells after transplantation.

In the following example, each group contained six age matched mice. Bone marrow was harvested from normal donor mice and transplanted into W/W$^v$ mice. The blood profile of the recipient animals is followed at different times post transplantation and engraftment of the donor marrow is determined by the shift of the peripheral blood cells from recipient to donor phenotype. The conversion from recipient to donor phenotype is detected by monitoring the forward scatter profile (FASCAN, Becton Dickenson) of the red blood cells. The profile for each transplanted animal was compared to that for both donor and recipient un-transplanted control animals at each time point. The comparison was made utilizing a computer program based on Kolmogorov-Smirnov statistics for the analysis of histograms from flow systems [Young, *J. Histochem. and Cytochem.*, 25, 935–941 (1977)]. An independent qualitative indicator of engraftment is the hemoglobin type detected by hemoglobin electrophoresis of the recipient blood [Wong, et al., *Mol. and Cell. Biol.*, 9, 798–808 (1989)] and agrees well with the goodness of fit determination from Kolmogorov-Smirnov statistics.

Approximately 3×10$^5$ cells were transplanted without SCF treatment (control group in FIG. 23) from C56BL/6J donors into W/W$^v$ recipients. A second group received 3×10$^5$ donor cells which had been treated with SCF (600 U/ml) at 37° C. for 20 min and injected together (pre-treated group in FIG. 23). (One unit of SCF is defined as the amount which results in half-maximal stimulation in the MC/9 bioassay). In a third group, the recipient mice were injected sub-cutaneously (sub-Q) with approximately 400 U SCF/day for 3 days after transplantation of 3×10$^5$ donor cells (Sub-Q inject group in FIG. 23). As indicated in FIG. 23, in both SCF-treated groups the donor marrow is engrafted faster than in the untreated control group. By 29 days post-transplantation, the SCF pre-treated group had converted to donor phenotype. This Example illustrates the usefulness of SCF therapy in bone marrow transplantation.

B. In vivo activity of Rat SCF in Steel Mice

Mutations at the S1 locus cause deficiencies in hematopoietic cells, pigment cells, and germ cells. The hematopoietic defect is manifest as reduced numbers of red blood cells [Russell, In:Al Gordon, *Regulation of Hematopoiesis*, Vol. I, 649-675 Appleton-Century-Crafts, New York (1970)], neutrophils [Ruscetti, *Proc. Soc. Exp. Biol. Med.*, 152, 398 (1976)], monocytes [Shibata, *J. Immunol.* 135, 3905 (1985)], megakaryocytes [Ebbe, *Exp. Hematol.*, 6, 201 (1978)], natural killer cells [(Clark, *Immunogenetics*, 12, 601 (1981)], and mast cells [Hayashi, *Dev. Biol.*, 109, 234 (1985)]. Steel mice are poor recipients of a bone marrow transplant due to a reduced ability to support stem cells [Bannerman, *Prog. Hematol.*, 8, 131 (1973)]. The gene encoding SCF is deleted in Steel (S1/S1) mice.

Steel mice provide a sensitive in vivo model for SCF activity. Different recombinant SCF proteins were tested in Steel-Dickie (S1/S1$^d$) mice for varying lengths of time. Six to ten week old Steel mice (WCB6F1-S1/S1$^d$) were purchased from Jackson Labs, Bar Harbor, ME. Peripheral blood was monitored by a SYSMEX F-800 microcell counter (Baxter, Irvine, Calif.) for red cells, hemoglobin, and platelets. For enumeration of peripheral white blood cell (WBC) numbers, a Coulter Channelyzer 256 (Coulter Electronics, Marietta, Ga.) was used.

In the experiment in FIG. 24, Steel-Dickie mice were treated with *E. coli* derived SCF$^{1-164}$, purified as in Example 10, at a dose of 100 μg/kg/day for 30 days, then at a dose of 30 μg/kg/day for an additional 20 days. The protein was formulated in injectable saline (Abbott Labs, North Chicago, Ill.) +0.1% fetal bovine serum. The injections were performed daily, subcutaneously. The peripheral blood was monitored via tail bleeds of −50 μl at the indicated times in FIG. 24. The blood was collected into 3% EDTA coated syringes and dispensed into powdered EDTA microfuge tubes (Brinkmann, Westbury, N.Y.). There is a significant correction of the macrocytic anemia in the treated animals relative to the control animals. Upon cessation of treatment, the treated animals return to the initial state of macrocytic anemia.

In the experiment shown in FIG. 25 and 26, Steel-Dickie mice were treated with different recombinant forms of SCF as described above, but at a dose of 100 μg/kg/day for 20 days. Two forms of *E. coli* derived rat SCF, SCF$^{1-164}$ and SCF$^{1-193}$, were produced as described in Example 10. In addition, *E. coli* SCF$^{1-164}$, modified by the addition of polyethylene glycol (SCF$^{1-164}$ PEG25) as in Example 12, was also tested. CHO derived SCF$^{1-162}$ produced as in Example 5 and purified as in Example 11, was also tested. The animals were bled by cardiac puncture with 3% EDTA coated syringes and dispensed into EDTA powdered tubes. The peripheral blood profiles after 20 days of treatment are shown in FIG. 25 for white blood cells (WBC) and FIG. 26 for platelets. The WBC differentials for the SCF$^{1-164}$ PEG25 group are shown in FIG. 27. There are absolute increases in neutrophils, monocytes, lymphocytes, and platelets. The most dramatic effect is seen with SCF1-164 PEG 25.

An independent measurement of lymphocyte subsets was also performed and the data is shown in FIG. 28. The murine equivalent of human CD4, or marker of T helper cells, is L3T4 (Dialynas, *J. Immunol.*, 131, 2445 (1983)]. LyT-2 is a murine antigen on cytotoxic T cells [Ledbetter, *J. Exp. Med.*, 153, 1503 (1981)]. Monoclonal antibodies against these antigens were used to evaluate T cell subsets in the treated animals.

Whole blood was stained for T lymphocyte subsets as follows. Two hundred microliters of whole blood was drawn from individual animals into EDTA treated tubes. Each sample of blood was lysed with sterile deionized water for 60 seconds and then made isotonic with 10× Dulbecco's Phosphate Buffered Saline (PBS) (Gibco, Grand Island, N.Y.). This lysed blood was washed 2 times with 1×PBS (Gibco, Grand Island, N.Y.) supplemented with 0.1% Fetal Bovine Serum (Flow Laboratory, McLean, Va.) and 0.1% sodium azide. Each sample of blood was deposited into round bottom 96 well cluster dishes and centrifuged. The cell pellet (containing 2–10×10$^5$ cells) was resuspended with 20 microliters of Rat anti-Mouse L3T4 conjugated with phycoerythrin (PE) (Becton Dickinson, Mountain View, Calif.) and 20 microliters of Rat anti-Mouse Lyt-2 conjugated with Fluorescein Isothiocyanate incubated on ice (4° C.) for 30 minutes (Becton Dickinson). Following incubation the cells were washed 2 times in 1×PBS supplemented as indicated aboved. Each sample of blood was then analyzed on a FACScan cell analysis system (Becton Dickinson, Mountain View, Calif.). This system was standardized using standard autocompensation procedures and Calibrite Beads (Becton Dickinson, Mountain View, Calif.). These data indicated an absolute increase in both helper T cell populations as well as cytotoxic T cell numbers.

C. In Vivo Activity of SCF in Primates

Human SCF$^{1-164}$ expressed in *E. coli* (Example 6B) and purified to homogeneity as in Example 10, was tested for in vivo biological activity in normal primates. Adult male baboons (Papio sp.) were studied in three groups: untreated, n=3; SCF 100 μg/kg/day, n=6; and SCF 30 ug/kg/day, n=6. The treated animals received single daily subcutaneous injections of SCF. Blood specimens were obtained from the animals under ketamine restraint. Specimens for complete blood count, reticulocyte count, and platelet count were obtained on days 1, 6, 11, 15, 20 and 25 of treatment.

All animals survived the protocol and had no adverse reactions to SCF therapy. The white blood cell count increased in the 100 ug/kg treated animals as depicted in FIG. 29. The differential count, obtained manually from Wright Giemsa stained peripheral blood smears, is also indicated in FIG. 29. There was an absolute increase in neutrophils, lymphocytes, and monocytes. As indicated in FIG. 30 there was also an increase at the 100 ug/kg dose in the hemtocrits as well as platelets.

Human SCF (hSCF$^{1-164}$ modified by the addition of polyethylene glycol as in Example 12) was also tested in normal baboons, at a dose of 200 μg/kg-day, administered by continuous intravenous infusion and compared to the unmodified protein. The animals started SCF at day 0 and were treated for 28 days. The results for the peripheral WBC are given in the following table. The PEG modified SCF elicited an earlier rise in peripheral WBC than the unmodified SCF. The same results are obtained with human SCF$^{1-165}$ modified by the addition of polyethylene glycol.

Treatment with 200 μg/kg-day hSCF$^{1-164}$:

| Animal # M88320 | | Animal # M88129 | |
| --- | --- | --- | --- |
| DAY | WBC | DAY | WBC |
| 0 | 5800 | 0 | 6800 |
| +7 | 10700 | +7 | 7400 |
| +14 | 12600 | +14 | 20900 |
| +16 | 22000 | +21 | 18400 |
| +22 | 31100 | +23 | 24900 |
| +24 | 28100 | +29 | 13000 |
| +29 | 9600 | +30 | 23000 |
| +36 | 6600 | +37 | 12100 |
| +43 | 5600 | +44 | 10700 |
| | | +51 | 7800 |

Treatment with 200 μg/kg-day PEG-hSCF$^{1-164}$:

| Animal # M88350 | | Animal # M89116 | |
| --- | --- | --- | --- |
| DAY | WBC | DAY | WBC |
| −7 | 12400 | −5 | 7900 |
| −2 | 11600 | 0 | 7400 |

-continued

| Animal # M88350 | | Animal # M89116 | |
| --- | --- | --- | --- |
| DAY | WBC | DAY | WBC |
| +4 | 24700 | +6 | 16400 |
| +7 | 20400 | +9 | 17100 |
| +11 | 24700 | +13 | 18700 |
| +14 | 32600 | +16 | 19400 |
| +18 | 33600 | +20 | 27800 |
| +21 | 26400 | +23 | 20700 |
| +25 | 16600 | +27 | 20200 |
| +28 | 26900 | +29 | 18600 |
| +32 | 9200 | +33 | 7600 |

Human $SCF^{1-165}$ expressed in E. coli (Example 6) and purified to homogeneity as in Example 10B, demonstrates the same in vivo biological activity in primates as E. coli derived recombinant human $SCF^{1-164}$

EXAMPLE 9

In vitro Activity of Recombinant Human SCF
A. Human bone marrow assay, murine HPP-CFC assay, and murine MC/9 assay.

The cDNA of human SCF corresponding to amino acids 1–162 obtained by PCR reactions outlined in Example 3D, was expressed in COS-1 cells as described for the rat SCF in Example 4. COS-1 supernatants were assayed on human bone marrow as well as in the murine HPP-CFC and MC/9 assays. The human protein was not active at the concentrations tested in either murine assay; however, it was active on human bone marrow. The culture conditions of the assay were as follows: human bone marrow from healthy volunteers was centrifuged over Ficoll-Hypaque gradients (Pharmacia) and cultured in 2.1% methyl cellulose, 30% fetal calf serum, $6 \times 10^{-5}$ M 2-mercaptoethanol, 2 mM glutamine, ISCOVE'S medium (GIBCO), 20 U/ml EPO, and $1 \times 10^5$ cells/ml for 14 days in a humidified atmosphere containing 7% $O_2$, 10% $CO_2$, and 83% $N_2$. The colony numbers generated with recombinant human and rat SCF COS-1 supernatants are indicated in Table 12. Only those colonies of 0.2 mm in size or larger are indicated.

TABLE 12

Growth of Human Bone Marrow Colonies in Response to SCF

| Plasmid Transfected | Volume of CM Assayed (µl) | Colony #/100,000 cells ± SD |
| --- | --- | --- |
| V19.8 (no insert) | 100 | 0 |
| | 50 | 0 |
| V19.8 human $SCF^{1-162}$ | 100 | 33 ± 7 |
| | 50 | 22 ± 3 |
| V19.8 rat $SCF^{1-162}$ | 100 | 13 ± 1 |
| | 50 | 10 |

The colonies which grew over the 14 day period are shown in FIG. 31A (magnification 12×). The arrow indicates a typical colony. The colonies resembled the murine HPP-CFC colonies in their large size (average 0.5 mm). Due to the presence of EPO, some of the colonies were hemoglobinized. When the colonies were isolated and centrifuged onto glass slides using a Cytospin (Shandon) followed by staining with Wright-Giemsa, the predominant cell type was an undifferentiated cell with a large nucleus:cytoplasm ratio as shown in FIG. 31B (magnification 400×). The arrows in FIG. 31B point to the following structures: arrow 1, cyto- plasm; arrow 2, nucleus; arrow 3, vacuoles. Immature cells as a class are large and the cells become progressively smaller as they mature [Diggs et al., The Morphology of Human Blood Cells, Abbott Labs, 3 (1978)]. The nuclei of early cells of the hemotopoietic maturation sequence are relatively large in relation to the cytoplasm. In addition, the cytoplasm of immature cells stains darker with Wright-Giemsa than does the nucleus. As cells mature, the nucleus stains darker than the cytoplasm. The morphology of the human bone marrow cells resulting from culture with recombinant human SCF is consistent with the conclusion that the target and immediate product of SCF action is a relatively immature hematopoietic progenitor.

Recombinant human SCF was tested in agar colony assays on human bone marrow in combination with other growth factors as described above. The results are shown in Table 13. SCF synergizes with G-CSF, GM-CSF, IL-3, and EPO to increase the proliferation of bone marrow targets for the individual CSFs.

TABLE 13

Recombinant human SCF Synergy with Other Human Colony Stimulating Factors

| | Colony #/$10^5$ cells (14 Days) |
| --- | --- |
| mock | 0 |
| hG-CSF | 32 ± 3 |
| hG-CSF + hSCF | 74 ± 1 |
| hGM-CSF | 14 ± 2 |
| hGM-CSF | 108 ± 5 |
| hIL-3 | 23 ± 1 |
| hIL-3 + hSCF | 108 ± 3 |
| hEPO | 10 ± 5 |
| hEPO + IL-3 | 17 ± 1 |
| hEPO + hSCF | 86 ± 10 |
| hSCF | 0 |

Another activity of recombinant human SCF is the ability to cause proliferation in soft agar of the human acute myelogenous leukemia (AML) cell line, KG-1 (ATCC CCL 246). COS-1 supernatants from transfected cells were tested in a KG-1 agar cloning assay [Koeffler et al., Science, 200, 1153–1154 (1978)] essentially as described except cells were plated at 3000/ml. The data from triplicate cultures are given in Table 14.

TABLE 14

KG-1 Soft Agar Cloning Assay

| Plasmid Transfected | Volume Assayed (µl) | Colony #/3000 Cells ± SD |
| --- | --- | --- |
| V19.8 (no insert) | 25 | 2 ± 1 |
| V19.8 human $SCF^{1-162}$ | 25 | 14 ± 0 |
| | 12 | 8 ± 0 |
| | 6 | 9 ± 5 |
| | 3 | 6 ± 4 |
| | 1.5 | 6 ± 6 |
| V19.8 rat $SCF^{1-162}$ | 25 | 6 ± 1 |
| human GM-CSF | 50 (5 ng/ml) | 14 ± 5 |

B. UT-7 $^3$H-Thymidine Uptake Assay

UT-7 cells are a human megakaryocyte, huGM-CSF responsive cell line obtained from John Adamson, New York Blood Center, New York, New York. UT-7 cells were cultured in Iscove's Modified Dulbecco's Medium, 10% FBS, 1×glutamine, 5 \g/ml huGM-CSF. Cells are passaged twice a week at $1 \times 10^5$ cells/ml.

Cells were washed twice in phosphate buffered saline (PBS) and resuspended in RPMI medium with 4% FBS and glutamine penicillin streptomycin (GPS) (Irvine Scientific Cat No. 9316 used at 1% volume per volume) at $4\times10^4$ cells/ml before use. Human SCF along with specific samples were added to 4000 cells/well in 96 well plates and were cultured for 72 hrs. 0.5 uCi/well of $^3$H-Thymidine was then added to each plate, plates were harvested and counted 4 hours later. A typical assay is shown in FIG. 31C.

Activity of human [Met$^{-1}$]SCF$^{1-164}$ and human [Met$^{-1}$]SCF$^{1-165}$, prepared from *E. coli* as described in Example 10, are also equally active in stimulating the proliferation of the UT-7 cell line, as shown in FIG. 31C.

C. SCF Radio-Receptor Assay Protocol

OCIM1 cells, [Papayannopoulou et al., Blood 72:1029–1038 (1988)] are a human erythroleukemic cell line expressing many human SCF receptors per cell. These cells are grown in Iscove's Modified Dulbecco's Medium, 10% FBS, and 1× glutamine and passaged 3 times a week to $1\times10^5$ cells/ml.

Preparation of the OCIM1 plasma membrane is as follows with all steps performed on ice.

First, 40 T175 flasks of cells were grown-up in OCIM1 culture medium, for a total of $1.9\times10^9$ cells/ml. The conditioned medium and 1 mM Phenyl Methyl Sulfonyl Fluoride (PMSF) protease inhibitor, was spun down in 8×250 ml tubes at 1000 rpm for 10 minutes at 4° C. Cells were washed with PBS and repelleted in 4×50 ml centrifuge tubes at 1000 rpm for 10 minutes at 4° C. Cells were resuspended in 20 ml ice cold PBS with glucose sodium pyruvate (Gibco Cat #310$^{-4287}$). The 20 ml cell solution was put into a pre-pressurized, pre-chilled (4° C.) "cell bomb" designed to lyse the cells. Cells were pressurized at 400-650 PSI for 10 minutes to establish equilibrium. When the pressure is released cell lysis occurs.

At this point the cells were checked for the percentage of cell lysis. 90% lysis was common. The cell suspension was resuspended in 80 mls sucrose buffer (0.25M sucrose, 10 mM Tris, 1 mM EDTA in double distilled (dd) $H_2O$, filtered through a 0.45u filter, pH 7.0) and divided between two 40 ml screwcap tubes. Tubes were spun at 5900 RPM for 10 minutes in a Beckman J2-21 centrifuge, JA-20 rotor at 4° C. The supernatants were saved and spun one more time as above to further remove any unwanted material. Supernatants were saved and distributed equally into 2 nalgene 40 ml centrifuge tubes. These supernatants were centrifuged at 16,000 RPM 4° C. for 30 min. in J2-21 centrifuge, JA-20 rotor. These supernatants were discarded being careful to save pellets. Each pellet was resuspended in sucrose buffer so there were 20 mls per tube in 4×36 ml plastic ultracentrifuge tubes. Using a 20 ml syringe and a large trochar, the solution was carefully underlayered in each tube with ice cold 36% sucrose solution (36.1 g sucrose/100 mls dd$H_2O$), bringing the level of the liquid to within 2 mm of the top of the tube. Without disturbing the interface, each tube was carefully placed into each of 6 titanium ultracentrifuge tubes. Tubes were centrifuged at 27,000 RPM, 4° C. for 75 minutes in an ultracentrifuge. These tubes were carefully removed from the rotor and from titanium buckets, placed in a rack with the 36% sucrose interface visible. The membraneous material at the interface was collected with a pasteur pipet and transfered into 2 clean nalgene 40 ml centrifuge tubes. Volume was brought up to 40 mls with ice cold sucrose buffer. Tubes were balanced and centrifuged as before at 5900 RPM in J2-21 centrifuge. The supernatant was discarded and each pellet was resuspended in 4 mls ice cold Tris buffer (10 mM Tris, 1 mM EDTA, pH 7.0 in dd$H_2$) with a 1 ml micropipet repeatedly, to ensure homogeneity of the solutions. Storage was in 50ul aliquots at −70° C. in freezing vials.

The SCF radioreceptor assay was conducted as follows with all steps being performed on ice. Human SCF samples were diluted in RRA buffer (50 mM Tris, 0.25% BSA pH 7.5) and added to 1.5 ml eppendorf tubes up to 150 ul total volume. 50,000 counts in 50 ul buffer of $^{125}$I-huSCF (provided by ICN radiochemicals) were added to each tube. A dilution of isolated OCIM1 plasma membrane in 50 ul buffer known to give 20% specific binding was then added to each tube. Tubes were vortexed and allowed to incubate for 24 hrs at 4° C. 400 ul of buffer was then added to each tube and the tubes were centrifuged for 8 minutes at 18,000 RPM in J2-21 centrifuge, JA-18.1 fixed angle (45%) rotor, 4° C. All tubes were oriented with lid opening tabs straight up. Supernatants were carefully aspirated by a sliding a 21 gauge needle down the side opposite the pellet (hinge side of tube) to bottom of each tube. Tubes were counted in gamma counter for 1 min. each.

In the radioreceptor assay, human [Met$^{-1}$]SCF$^{1-164}$ and human [Met$^{-1}$]SCF$^{1-165}$, prepared from *E. coli* as described in Example 10, compete equally well with the binding of human [$^{125}$I][Met $^{-1}$]SCF$^{1-164}$, indicating that they bind equally well to the SCF receptor.

EXAMPLE 10

Purification of Recombinant SCF Products Expressed in *E. coli*

A. SCF$^{1-164}$

Fermentation of *E. coli* human SCF$^{1-164}$ was performed according to Example 6C. The harvested cells (912 g wet weight) were suspended in water to a volume of 4.6 L and broken by three passes through a laboratory homogenizer (Gaulin Model 15MR-8TBA) at 8000 psi. A broken cell pellet fraction was obtained by centrifugation (17700×g, 30 min, 4° C.), washed once with water (resuspension and recentrifugation), and finally suspended in water to a volume of 400 ml.

The pellet fraction containing insoluble SCF (estimate of 10-12 g SCF) was added to 3950 ml of an appropriate mixture such that the final concentrations of components in the mixture were 8 M urea (ultrapure grade), 0.1 mM EDTA, 50 mM sodium acetate, pH 6–7; SCF concentration was estimated as 1.5 mg/ml. Incubation was carried out at room temperature for 4 h to solubilize the SCF. Remaining insoluble material was removed by centrifugation (17700×g, 30 min, room temperature). For refolding/reoxidation of the solubilized SCF, the supernatant fraction was added slowly, with stirring, to 39.15 L of an appropriate mixture such that the final concentrations of components in the mixture were 2.5 M urea (ultrapure grade), 0.01 mM EDTA, 5 mM sodium acetate, 50 mM Tris-HCl pH 8.5, 1 mM glutathione, 0.02% (wt/vol) sodium azide. SCF concentration was estimated as 150 μg/ml. After 60 h at room temperature [shorter times (e.g. ~20 h) are suitable also], with stirring, the mixture was concentrated two-fold using a Millipore Pellicon ultrafiltration apparatus with three 10,000 molecular weight cutoff polysulfone membrane cassettes (15 ft$^2$ total area) and then diafiltered against 7 volumes of 20 mM Tris-HCl, pH B. The temperature during the concentration/ultrafiltration was 4° C., pumping rate was 5 L/min, and filtration rate was 600 ml/min. The final volume of recovered retentate was 26.5 L. By the use of SDS-PAGE carried out both with and without reduction of samples, it is evident that most (>80%) of the pellet fraction SCF is solubilized by the incubation with 8 M urea, and that after the folding/oxidation multiple species (forms) of SCF are present, as visualized by the SDS-PAGE of unreduced samples. The major form, which represents correctly oxidized SCF (see below), migrates with apparent $M_r$ of about 17,000 (unreduced) relative to the molecular weight markers (reduced) described for FIG. 9. Other forms include material migrating with apparent $M_r$ of about 18-20,000 (unreduced), thought to represent SCF with incorrect intrachain disulfide bonds; and bands migrating with apparent $M_r$s in the range of 37,000 (unreduced), or greater, thought to represent various SCF forms having interchain disulfide bonds resulting in SCF polypeptide chains that are covalently linked to form dimers or larger oligomers, respectively. The following fractionation steps result in removal of remaining E. coli contaminants and of the unwanted SCF forms, such that SCF purified to apparent homogeneity, in biologically active conformation, is obtained.

The pH of the ultrafiltration retentate was adjusted to 4.5 by addition of 375 ml of 10% (vol/vol) acetic acid, leading to the presence of visible precipitated material. After 60 min, at which point much of the precipitated material had settled to the bottom of the vessel, the upper 24 L were decanted and filtered through a Cuno™ 30SP depth filter at 500 ml/min to complete the clarification. The filtrate was then diluted 1.5-fold with water and applied at 4° C. to an S-Sepharose Fast Flow (Pharmacia) column (9×18.5 cm) equilibrated in 25 mM sodium acetate, pH 4.5. The column was run at a flow rate of 5 L/h, at 4° C. After sample application, the column was washed with five column volumes (~6 L) of column buffer and SCF material, which was bound to the column, was eluted with a gradient of 0 to 0.35 M NaCl in column buffer. Total gradient volume was 20 L and fractions of 200 ml were collected. The elution profile is depicted in FIG. 33. Aliquots (10 µl) from fractions collected from the S-Sepharose column were analyzed by SDS-PAGE carried out both with (FIG. 32 A) and without (FIG. 32 B) reduction of the samples. From such analyses it is apparent that virtually all of the absorbance at 280 nm (FIGS. 32 and 33) is due to SCF material.

The correctly oxidized form predominates in the major absorbance peak (fractions 22-38, FIG. 33). Minor species (forms) which can be visualized in fractions include the incorrectly oxidized material with apparent $M_r$ of 18-20,000 on SDS-PAGE (unreduced), present in the leading shoulder of the main absorbance peak (fractions 10-21, FIG. 32B); and disulfide-linked dimer material present throughout the absorbance region (fractions 10-38, FIG. 32B). Fractions 22-38 from the S-Sepharose column were pooled, and the pool was adjusted to pH 2.2 by addition of about 11 ml 6 N HCl and applied to a Vydac $C_4$ column (height 8.4 cm, diameter 9 cm) equilibrated with 50% (vol/vol) ethanol, 12.5 mM HCl (solution A) and operated at 4° C. The column resin was prepared by suspending the dry resin in 80% (vol/vol) ethanol, 12.5 mM HCl (solution B) and then equilibrating it with solution A. Prior to sample application, a blank gradient from solution A to solution B (6 L total volume) was applied and the column was then re-equilibrated with solution A. After sample application, the column was washed with 2.5 L of solution A and SCF material, bound to the column, was eluted with a gradient from solution A to solution B (18 L total volume) at a flow rate of 2670 ml/h. 286 fractions of 50 ml each were collected, and aliquots were analyzed by absorbance at 280 nm (FIG. 35), and by SDS-PAGE (25 µl per fraction) as described above (FIG. 34 A, reducing conditions; FIG. 34 B, nonreducing conditions). Fractions 62-161, containing correctly oxidized SCF in a highly purified state, were pooled [the relatively small amounts of incorrectly oxidized monomer with $M_r$ of about 18–20,000 (unreduced) eluted later in the gradient (about fractions 166-211) and disulfide-linked dimer material also eluted later (about fractions 199-235) (FIG. 35)].

To remove ethanol from the pool of fractions 62-161, and to concentrate the SCF, the following procedure utilizing Q-Sepharose Fast Flow (Pharamcia) ion exchange resin was employed. The pool (5 L) was diluted with water to a volume of 15.625 L, bringing the ethanol concentration to about 20% (vol/vol). Then 1 M Tris base (135 ml) was added to bring the pH to 8, followed by 1 M Tris-HCl, pH 8, (23.6 ml) to bring the total Tris concentration to 10 mM. Next 10 mM Tris-HCl, pH 8 (~15.5 L) was added to bring the total volume to 31.25 L and the ethanol concentration to about 10% (vol/vol). The material was then applied at 4° C. to a column of Q-Sepharose Fast Flow (height 615 cm, diameter 7 cm) equilibrated with 10 mM Tris-HCl, pH 8, and this was followed by washing of the column with 2.5 L of column buffer. Flow rate during sample application and wash was about 5.5 L/h. To elute the bound SCF, 200 mM NaCl, 10 mM Tris-HCl, pH 8 was pumped in reverse direction through the column at about 200 ml/h. Fractions of about 12 ml were collected and analyzed by absorbance at 280 nm, and SDS-PAGE as above. Fractions 16-28 were pooled (157 ml).

The pool containing SCF was then applied in two separate chromatographic runs (78.5 ml applied for each) to a Sephacryl S-200 HR (Pharmacia) gel filtration column (5×138 cm) equilibrated with phosphate-buffered saline at 4° C. Fractions of about 15 ml were collected at a flow rate of about 75 ml/h. In each case a major peak of material with absorbance at 280 nm eluted in fractions corresponding roughly to the elution volume range of 1370 to 1635 ml. The fractions representing the absorbance peaks from the two column runs were combined into a single pool of 525 ml, containing about 2.3 g of SCF. This material was sterilized by filtration using a Millipore Millipak 20 membrane cartridge.

Alternatively, material from the $C_4$ column can be concentrated by ultrafiltration and the buffer exchanged by diafiltration, prior to sterile filtration.

The isolated recombinant human $SCF^{1-164}$ material is highly pure (>98% by SDS-PAGE with silver-staining) and is considered to be of pharmaceutical grade. Using the methods outlined in Example 2, it is found that the material has amino acid composition and amino acid sequence matching those expected from analysis of the SCF gene. The N-terminal amino acid sequence is Met-Glu Gly-Ile., i.e., the initiating Met residue is retained.

By procedures comparable to those outlined for human $SCF^{1-164}$ expressed in E. coli, rat $SCF^{1-164}$ (also present in insoluble form inside the cell after fermentation) can be recovered in a purified state with high biological specific activity. Similarly, human $SCF^{1-183}$ and rat $SCF^{1-193}$ can be recovered. The rat $SCF^{1-193}$, during folding/oxidation, tends to form more variously oxidized species, and the unwanted species are more difficult to remove chromatographically.

The rat $SCF^{1-193}$ and human $SCF^{1-183}$ are prone to proteolytic degradation during the early stages of recovery, i.e., solubilization and folding/oxidation. A primary site of proteolysis is located between residues 160 and 170. The proteolysis can be minimized by appropriate manipulation of conditions (e.g., SCF concentration; varying pH; inclusion of EDTA at 2–5 mM, or other protease inhibitors), and degraded forms to the extent that they are present can be removed by appropriate fractionation steps.

While the use of urea for solubilization, and during folding/oxidation, as outlined, is a preferred embodiment, other solubilizing agents such as guanidine-HCl (e.g. 6 M during solubilization and 1.25 M during folding/oxidation) and sodium N-lauroyl sarcosine can be utilized effectively.

Upon removal of the agents after folding/oxidation, purified SCFs, as determined by SDS-PAGE, can be recovered with the use of appropriate fractionation steps.

In addition, while the use of glutathione at 1 mM during folding/oxidation is a preferred embodiment, other conditions can be utilized with equal or nearly equal effectiveness. These include, for example, the use in place of 1 mM glutathione of 2 mM glutathione plus 0.2 mM oxidized glutathione, or 4 mM glutathione plus 0.4 mM oxidized glutathione, or 1 mM 2-mercaptoethanol, or other thiol reagents also.

In addition to the chromatographic procedures described, other procedures which are useful in the recovery of SCFs in a purified active form include hydrophobic interaction chromatography [e.g., the use of phenyl-Sepharose (Pharmacia), applying the sample at neutral pH in the presence of 1.7 M ammonium sulfate and eluting with a gradient of decreasing ammonium sulfate]; immobilized metal affinity chromatography [e.g., the use of chelating-Sepharose (Pharmacia) charged with $Cu^{2+}$ ion, applying the sample at near neutral pH in the presence of 1 mM imidazole and eluting with a gradient of increasing imidazole]; hydroxylapatite chromatography, [applying the sample at neutral pH in the presence of 1 mM phosphate and eluting with a gradient of increasing phosphate]; and other procedures apparent to those skilled in the art.

Other forms of human SCF, corresponding to all or part of the open reading frame encoding by amino acids 1–248 in FIG. 42, or corresponding to the open reading frame encoded by alternatively spliced mRNAs that may exist (such as that represented by the cDNA sequence in FIG. 44), can also be expressed in *E. coli* and recovered in purified form by procedures similar to those described in this Example, and by other procedures apparent to those skilled in the art.

The purification and formulation of forms including the so-called transmembrane region referred to in Example 16 may involve the utilization of detergents, including non-ionic detergents, and lipids, including phospholipid-containing liposome structures. B. $SCF^{1-165}$ For the purification of human $SCF^{1-165}$ expressed in *E. coli*, the following information is relevant. After harvesting of cells expressing the human $SCF^{1-165}$ pharmaceutical grade human $SCF^{1-165}$ was recovered by procedures the same as those described for human $SCF^{1-164}$ (above), but with the following modifications. After cell lysis, the homogenate was diluted to a volume representing twice the volume of the original cell suspension, with the inclusion of EDTA to 10 mM final concentration. Centrifugation was then done using a Sharples AS-16 centrifuge at 15,000 rpm and flow rate of 0.5 L/min, to obtain a pellet fraction. This pellet fraction, without washing, was then subjected to the solubilization with urea, essentially as described for human $SCF^{1-164}$ except that sodium acetate was omitted, the mixture was titratated to pH 3 using HCl, the estimated SCF concentration was 3.2 mg/ml, and incubation was for 1-2 h at room temperature. All subsequent steps were at room temperature also. For refolding/reoxidation, the mixture was then diluted directly, by a factor of 3.2, such that the final conditions included the SCF at about 1 mg/ml, 2.5 M urea, 60 mM NaCl, 1 mM glutathione, 50 mM Tris-HCl$_1$, with pH at 8.5. After stirring for 20-24 h, clarification was accomplished by filtration through a Cuno Zeta Plus 30SP depth filtration device. A 19 ft$^2$ filter was used per 100 L of mixture to be filtered. Flow rate during filtration was about 2.9 L/min. For a 19 ft$^2$ filter, washing of the filter with 50 L of 20 mM Tris-HCl, pH 8.5 was done. The following description applies to the handling of fractions derived from 100 L of refolding/reoxidation mixture. The 150 L of filtrate plus wash was concentrated to 50 L by ultrafiltration, and diafiltration against 300 L of 20 mM Tris-HCl, pH 8.5 was then done. The diafiltered material was then diluted to 150 L by addition of the Tris buffer. pH was then adjusted to 4.55 using 10% acetic acid, whereupon the mixture became turbid. 2-24 h later, clarification was accomplished by depth filtration using a 19 ft$^2$ Cuno Zeta Plus 10SP filter, pre-washed with 0.1 M sodium chloride, 50 mM sodium acetate, pH 4.5. After the filtration, the filter was washed with 50 L of the same sodium chloride/sodium acetate buffer. The resulting filtrate plus wash (about 200 L) was applied to an S-Sepharose Fast Flow (Pharmacia) column (10 L bed volume; 30 cm diameter) equilibrated with 50 mM sodium acetate, 100 mM sodium chloride, pH 4.5. Flow rate was 1.4 L/min. After sample application, the column was washed with 100 L of the column buffer, at a flow rate of 1.2 L/min. Elution was carried out with a linear gradient from the starting column buffer to 50 mM sodium acetate, 300 mM NaCl, pH 4.5 (200 L total gradient volume), at flow rate of 0.65 L/min. The various forms described for the S-Sepharose Fast Flow fractions obtained in preparation of *E. coli*-derived human $SCF^{1-164}$ above were present in essentially the same fashion, and pooling of fractions was based on the same criteria as described above. The pooled material (about 25 g SCF in about 20–25 L) was adjusted to pH 2.2 using 6 N HCl, and loaded onto a C4 column (1.2 L bed volume; 14 cm diameter; Vydac Proteins $C_4$, Cat. No. 214TPB2030), at 100 ml/min. The column was next washed with 10 L of 25% ethanol, 12.5 mM HCl, and theneluted with a linear gradient from this buffer to 75% ethanol, 12.5 mM HCl (25 L total gradient volume). Again, the various species present in the eluted fractions, and the pooling of fractions, were essentially as described for the $SCF^{1-164}$. The pool, containing about 16 g $SCF^{1-165}$ correctly-oxidized monomer in a volume of about 9 ml, was diluted 6.25-fold, made 10 mM in sodium phosphate by addition of 0.5 M sodium phosphate, pH 6.5, and titrated to pH 6.5 using 1 N sodium hydroxide. The material was then applied at a flow rate of 400 ml/min to a Q-Sepharose Fast Flow (Pharmacia) column (2 L bed volume; 14 cm diamter) equilibrated with 10 mM sodium phosphate, pH 6.5. After washing the column with 20 L of 10 mM sodium phosphate, 25 mM sodium chloride, pH 6.5, elution was carried out with a linear gradient from the wash buffer to 10 mM sodium phosphate, 100 mM NaCl, pH 6.5. Fractions corresponding to the main absorbance (at 280 nm) peak represent the correctly-oxidized $SCF^{1-165}$. These fractions were pooled; typically the pool contained about 12–15 g $SCF^{1-165}$, in a volume of about 17-18 L. The SCF material was then concentrated by ultrafiltration and other buffers optionally introduced by diafiltration, a preferred buffer being 10 mM sodium acetate, 140 mM sodium chloride, pH 5.

C. $SCF^{1-248}$

The full length recombinant human stem cell factor ($SCF^{1-248}$) is formed in *E. coli* as inclusion bodies. After isolation of the inclusion bodies, treatment with 8M urea, 50 mM sodium acetate, 0.1 mM EDTA, pH 5.0 does not solubilize any $SCF^{1-248}$. This is in contrast to shorter SCFs which solubilize well in this buffer. To solubilize $SCF^{1-248}$, the urea-washed inclusion bodies are suspended in 50 mM Tris-HCl, 1 mM EDTA, 2% sodium deoxycholate (NaDOC), pH 8.5 at an approximate $SCF^{1-248}$ concentration of 0.2 to 1.0 mg/mL. To this is added powdered dithiothreitol (DTT) to a concentration of 20 mM. The mixture is stirred for 2.5 hours at room temperature. Unsolubilized debris is removed by centrifuging at 20,000×g for 20 min. The supernatant contains all of the SCF$^{1-248}$ which runs as a fuzzy 33,000 dalton band on a reducing SDS polyacrylamide gel. Both NaDOC, an anionic detergent, and DTT, a reducing agent are required for solubilization.

Soluble oxidized SCF$^{1-248}$ can be prepared by diluting the solubilization mixture supernatant with nine volumes of 50 mM Tris, 1 mM EDTA, 2% NaDOC (no pH adjustment). The pH of the diluted mixture is approximately 9.5. This mixture is stirred vigorously at room temperature for approximately 40 hours. This mixture can be clarified by filtration through a 0.45µ cellulose acetate membrane. The filtrate contains SCF$^{1-248}$ which runs as a 28,000 dalton band on a non-reducing SDS polyacrylamide gel. Under reducing conditions, the fuzzy 33,000 dalton band is visible. The filtrate also contains smaller but variable amounts of incompletely oxidized SCF$^{1-248}$ and an apparent disulfide-linked dimer at approximately 80,000 daltons on the gels. Upon removal of NaDOC by diafiltration using a 10,000 dalton molecular. weight cut-off membrane, the oxidized SCF$^{1-248}$ remains in solution.

SCF$^{1-248}$ was subsequently purified to 80–90% purity by a combination of anion exchange, gel filtration, and cation exchange chromatography. The protein requires the presence of the non-ionic detergent, Triton X-100, to remain unaggregated. Material following anion exchange chromatography was active in the UT-7 assay (Example 9B). The final material after cation exchange chromatography showed no activity in the UT-7 assay. It may be that earlier samples contained some active proteolyzed SCF. The SCF$^{1-248}$ diluted in detergent-free buffer for assay may be incapable of interaction with the SCF receptor because of aggregation.

EXAMPLE 11

Recombinant SCF from Mammalian Cells

A. Fermentation of CHO Cells Producing SCF Recombinant Chinese hamster ovary (CHO) cells (strain CHO pDSRα2 hSCF$^{1-162}$) were grown on microcarriers in a 20 liter perfusion culture system for the production of human SCF$^{1-162}$. The fermentor system is similar to that used for the culture of BRL 3A cells, Example 1B, except for the following: The growth medium used for the culture of CHO cells was a mixture of Dulbecco's Modified Eagle Medium (DMEM) and Ham's F-12 nutrient mixture in a 1:1 proportion (GIBCO), supplemented with 2 mM glutamine, nonessential amino acids (to double the existing concentration by using 1:100 dilution of Gibco #320-1140) and 5% fetal bovine serum. The harvest medium was identical except for the omission of serum. The reactor was inoculated with 5.6×10$^9$ CHO cells grown in two 3-liter spinner flasks. The cells were allowed to grow to a concentration of 4×10$^5$ cells/ml. At this point 100 grams of presterilized cytodex-2 microcarriers (Pharmacia) were added to the reactor as a 3-liter suspension in phosphate buffered saline. The cells were allowed to attach and grow on the microcarriers for four days. Growth medium was perfused through the reactor as needed based on glucose consumption. The glucose concentration was maintained at approximately 2.0 g/L. After four days, the reactor was perfused with six volumes of serum-free medium to remove most of the serum (protein concentration <50 µg/ml). The reactor was then operated batch-wise until the glucose concentration fell below 2 g/L. From this point onward, the reactor was operated at a continuous perfusion rate of approximately 20 L/day. The pH of the culture was maintained at 6.9±0.3 by adjusting the $CO_2$ flow rate. The dissolved oxygen was maintained higher than 20% of air saturation by supplementing with pure oxygen as necessary. The temperature was maintained at 37±0.5° C.

Approximately 450 liters of serum-free conditioned medium was generated from the above system and was used as starting material for the purification of recombinant human SCF$^{1-162}$.

Approximately 589 liters of serum-free conditioned medium was also generated in similar fashion but using strain CHO pDSRα2 rSCF$^{1-162}$ and used as starting material for purification of rat SCF$^{1-162}$.

B. Purification of Recombinant Mammalian Expressed Rat SCF$^{1-162}$ and Other Recombinant Mammalian SCFs All purification work was carried out at 4° C. unless indicated otherwise.

1. Concentration and Diafiltration

Conditioned medium generated by serum-free growth of cell strain CHO pDSRα2 rat SCF$^{1-162}$ as performed in Section A above, was clarified by filtration thru 0.45µ Sartocapsules (Sartorius). Several different batches (36 L, 101 L, 102 L, 200 L and 150 L) were separately subjected to concentration and diafiltration/buffer exchange. To illustrate, the handling of the 36 L batch was as follows. The filtered condition medium was concentrated to ~500 ml using a Millipore Pellicon tangential flow ultrafiltration apparatus with three 10,000 molecular weight cutoff cellulose acetate membrane cassettes (15 ft$^2$ total membrane area; pump rate ~2,200 ml/min and filtration rate ~750 ml/min). Diafiltration/buffer exchange in preparation for anion exchange chromatography was then accomplished by adding 1000 ml of 10 mM Tris-HCl, pH 6.7–6.8 to the concentrate, reconcentrating to 500 ml using the tangential flow ultrafiltration apparatus, and repeating this 5 additional times. The concentrated/diafiltered preparation was finally recovered in a volume of 1000 ml. The behavior of all conditioned medium batches subjected to the concentration and diafiltration/buffer exchange was similar. Protein concentrations for the batches, determined by the method of Bradford [Anal. Bioch. 72, 248–254 (1976)] with bovine serum albumin as standard, were in the range 70–90 µg/ml. The total volume of conditioned medium utilized for this preparation was about 589 L.

2. Q-Sepharose Fast Flow Anion Exchange Chromatography

The concentrated/diafiltered preparations from each of the five conditioned medium batches referred to above were combined (total volume 5,000 ml). pH was adjusted to 6.75 by adding 1 M HCl. 2000 ml of 10 mM Tris-HCl, pH 6.7 was used to bring conductivity to about 0.700 mmho. The preparation was applied to a Q-Sepharose Fast Flow anion exchange column (36×14 cm; Pharmacia Q-Sepharose Fast Flow resin) which had been equilibrated with the 10 mM Tris-HCl, pH 6.7 buffer. After sample application, the column was washed with 28,700 ml of the Tris buffer. Following this washing the column was washed with 23,000 ml of 5 mM acetic acid/1 mM glycine/6 M urea/20 µM $CuSO_4$ at about pH 4.5. The column was then washed with 10 mM Tris-HCl, 20 µm $CuSO_4$, pH 6.7 buffer to return to neutral pH and remove urea, and a salt gradient (0–700 mM NaCl in the 10 mM Tris-HCl, 20 µM $CuSO_4$, pH 6.7 buffer; 40 L total volume) was applied. Fractions of about 490 ml were collected at a flow rate of about 3,250 ml/h. The chromatogram is shown in FIG. 36. "MC/9 cpm" refers to biological activity in the MC/9 assay; 5 µl from the indicated fractions was assayed. Eluates collected during the sample application and washes are not shown in the Figure; no biological activity was detected in these fractions.

3. Chromatography Using Silica-Bound Hydrocarbon Resin

Fractions 44-66 from the run shown in FIG. 36 were combined (11,200 ml) and EDTA was added to a final concentration of 1 mM. This material was applied at a flow rate of about 2000 ml/h to a $C_4$ column (Vydac Proteins $C_4$; 7×6 cm) equilibrated with buffer A (10 mM Tris pH 6.7/20% ethanol). After sample application the column was washed with 1000 ml of buffer A. A linear gradient from buffer A to buffer B (10 mM Tris pH 6.7/94% ethanol) (total volume 6000 ml) was then applied, and fractions of 30–50 ml were collected. Portions of the $C_4$ column starting sample, runthrough pool and wash pool in addition to 0.5 ml aliquots of the gradient fractions were dialyzed against phosphate-buffered saline in preparation for biological assay. These various fractions were assayed by the MC/9 assay (5 µl aliquots of the prepared gradient fractions; cpm in FIG. 37). SDS-PAGE [Laemmli, Nature 227, 680–685 (1970); stacking gels contained 4% (w/v) acrylamide and separating gels contained 12.5% (w/v) acrylamide] of aliquots of various fractions is shown in FIG. 38. For the gels shown, sample aliquots (100 µl) were dried under vacuum and then redissolved using 20 µl sample treatment buffer (reducing, i.e., with 2-mercaptoethanol) and boiled for 5 min prior to loading onto the gel. The numbered marks at the left of the Figure represent migration positions of molecular weight markers (reduced) as in FIG. 6. The numbered lanes represent the corresponding fractions collected during application of the last part of the gradient. The gels were silver-stained [Morrissey, Anal. Bioch. 117, 307–310 (1981)].

4. Q-Sepharose Fast Flow Anion Exchange Chromatography
Fractions 98-124 from the $C_4$ column shown in FIG. 37 were pooled (1050 ml). The pool was diluted 1:1 with 10 mM Tris, pH 6.7 buffer to reduce ethanol concentration. The diluted pool was then applied to a Q-Sepharose Fast Flow anion exchange column (3.2×3 cm, Pharmacia Q-Sepharose Fast Flow resin) which had been equilibrated with the 10 mM Tris-HCl, pH 6,7 buffer. Flow rate was 463 ml/h. After sample application the column was washed with 135 ml of column buffer and elution of bound material was carried out by washing with 10 mM Tris-HCl, 350 mM NaCl, pH 6.7. The flow direction of the column was reversed in order to minimize volume of eluted material, and 7.8 ml fractions were collected during elution.

5. Sephacryl S-200 HR Gel Filtration Chromatography
Fractions containing eluted protein from the salt wash of the Q-Sepharose Fast Flow anion exchange column were pooled (31 ml). 30 ml was applied to a Sephacryl S-200 HR (Pharmacia) gel filtration column, (5×55.5 cm) equilibrated in phosphate-buffered saline. Fractions of 6.8 ml were collected at a flow rate of 68 ml/hr. Fractions corresponding to the peak of absorbance at 280 nm were pooled and represent the final purified material.

Table 15 shows a summary of the purification.

TABLE 15

Summary of Purification of Mammalian Expressed Rat $SCF^{1-162}$

| Step | Volume (ml) | Total Protein (mg)* |
| --- | --- | --- |
| Conditioned medium (concentrated) | 7,000 | 28,420 |
| Q-Sepharose Fast Flow | 11,200 | 974 |
| $C_4$ resin | 1,050 | 19 |
| Q-Sepharose Fast Flow | 31 | 20 |
| Sephacryl S-200 HR | 82 | 19** |

*Determined by the method of Bradford (supra, 1976).
**Determined as 47.3 mg by quantitative amino acid analysis using methodology similar to that outlined in Example 2.

The N-terminal amino acid sequence of purified rat $SCF^{1-162}$ is approximately half Gln-Glu-Ile . . . and half PyroGlu-Glu-Ile . . . , as determined by the methods outlined in Example 2. This result indicates that rat $SCF^{1-162}$ is the product of proteolytic processing/cleavage between the residues indicated as numbers (−1) (Thr) and (+1) (Gln) in FIG. 14C. Similarly, purified human $SCF^{1-162}$ from transfected CHO cell conditioned medium (below) has N-terminal amino acid sequence Glu-Gly-Ile, indicating that it is the product of processing/cleavage between residues indicated as numbers (−1) (Thr) and (+1) (Glu) in FIG. 15C.

Using the above-described protocol will yield purified human SCF protein, either recombinant forms expressed in CHO cells or naturally derived.

Additional purification methods that are of utility in the purification of mammalian cell derived recombinant SCFs include those outlined in Examples 1 and 10, and other methods apparent to those skilled in the art.

Other forms of human SCF, corresponding to all or part of the open reading frame encoded by amino acids 1–248 shown in FIG. 42, or corresponding to the open reading frame encoded by alternatively spliced mRNAs that may exist (such as that represented by the cDNA sequence in FIG. 44), can also be expressed in mammalian cells and recovered in purified form by procedures similar to those decribed in this Example, and by other procedures apparent to those skilled in the art.

C. SDS-PAGE and Glycosidase Treatments

SDS-PAGE of pooled fractions from the Sephacryl S-200 HR gel filtration column is shown in FIG. 39; 2.5 µl of the pool was loaded (lane 1). The lane was silver-stained. Molecular weight markers (lane 6) were as described for FIG. 6. The different migrating material above and slightly below the $M_r$ 31,000 marker position represents the biologically active material; the apparent heterogeneity is largely due to the heterogeneity in glycosylation.

To characterize the glycosylation purified material was treated with a variety of glycosidases, analyzed by SDS-PAGE (reducing conditions) and visualized by silver-staining. Results are shown in FIG. 39. Lane 2, neuraminidase. Lane 3, neuraminidase and O-glycanase. Lane 4, neuraminidase, O-glycanase and N-glycanase. Lane 5, neuraminidase and N-glycanase. Lane 7, N-glycanase. Lane 8, N-glycanase without substrate. Lane 9, O-glycanase without substrate. Conditions were 10 mM 3-[(3-cholamidopropyl) dimethyl ammonio]-1-propane sulfonate (CHAPS), 66.6 mM 2-mercaptoethanol, 0.04% (wt/vol) sodium azide, phosphate buffered saline, for 30 min at 37° C., followed by incubation at half of described concentrations in presence of glycosidases for 18 h at 37° C. Neuraminidase (from *Arthrobacter ureafaciens*; supplied by Calbiochem) was used at 0.5 units/ml final concentration. O-Glycanase (Genzyme; endo-alpha-N-acetyl galactosaminidase) was used at 7.5 milliunits/ml. N-Glycanase (Genzyme; peptide: N-glycosidase F; peptide-$N^4$[N-acetyl-beta-glucosaminyl] asparagine amidase) was used at 10 units/ml.

Where appropriate, various control incubations were carried out. These included: incubation without glycosidases, to verify that results were due to the glycosidase preparations added; incubation with glycosylated proteins (e.g. glycosylated recombinant human erythropoietin) known to be substrates for the glycosidases, to verify that the glycosidase enzymes used were active; and incubation with glycosidases but no substrate, to judge where the glycosidase preparations were contributing to or obscuring the visualized gel bands (FIG. 39, lanes 8 and 9).

A number of conclusions can be drawn from the experiments described above. The various treatments with N-glycanase [which removes both complex and high-mannose N-linked carbohydrate (Tarentino et al., Biochemistry 24, 4665–4671 (1988)1, neuraminidase (which removes sialic acid residues), and O-glycanase [which removes certain O-linked carbohydrates (Lambin et al., Biochem. Soc. Trans. 12, 599–600 (1984)1, suggest that: both N-linked and O-linked carbohydrates are present; and sialic acid is present, with at least some of it being part of the O-linked moieties. The fact that treatment with N-glycanase can convert the heterogeneous material apparent by SDS-PAGE to a faster-migrating form which is much more homogeneous indicates that all of the material represents the same polypeptide, with the heterogeneity being caused mainly by heterogeneity in glycosylation.

While the results of this section apply to purified CHO cell-derived rat $SCF^{1-162}$, equivalent results of SDS-PAGE and glycosidase treatments are obtained for CHO cell-derived human $SCF^{1-162}$.

EXAMPLE 12

Preparation of Recombinant SCF PEG

A. Preparation of Recombinant $SCF^{1-164}$ PEG Rat $SCF^{1-164}$, purified from a recombinant *E. coli* expression system according to Examples 6A and 10, was used as starting material for polyethylene glycol modification described below.

Figure 40A:
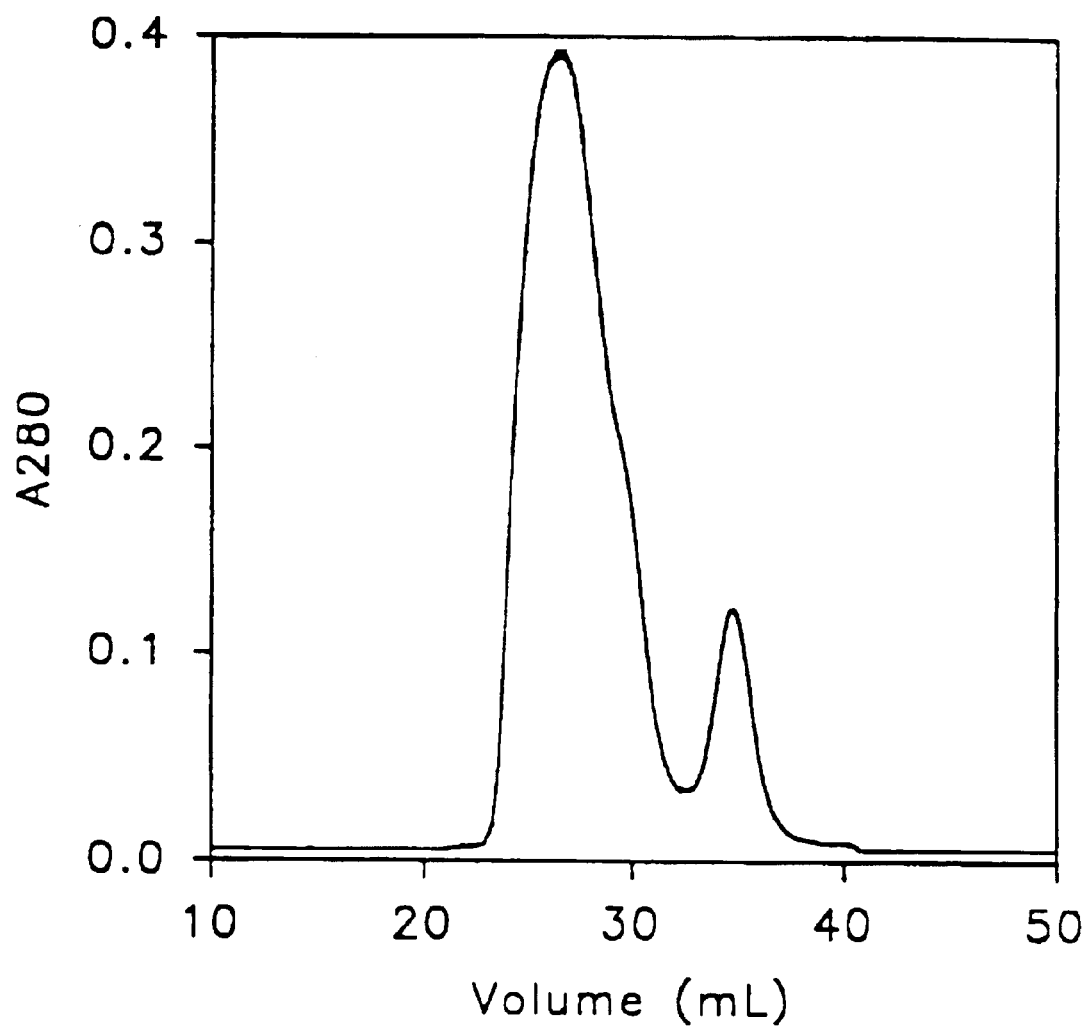
Figure 40B:
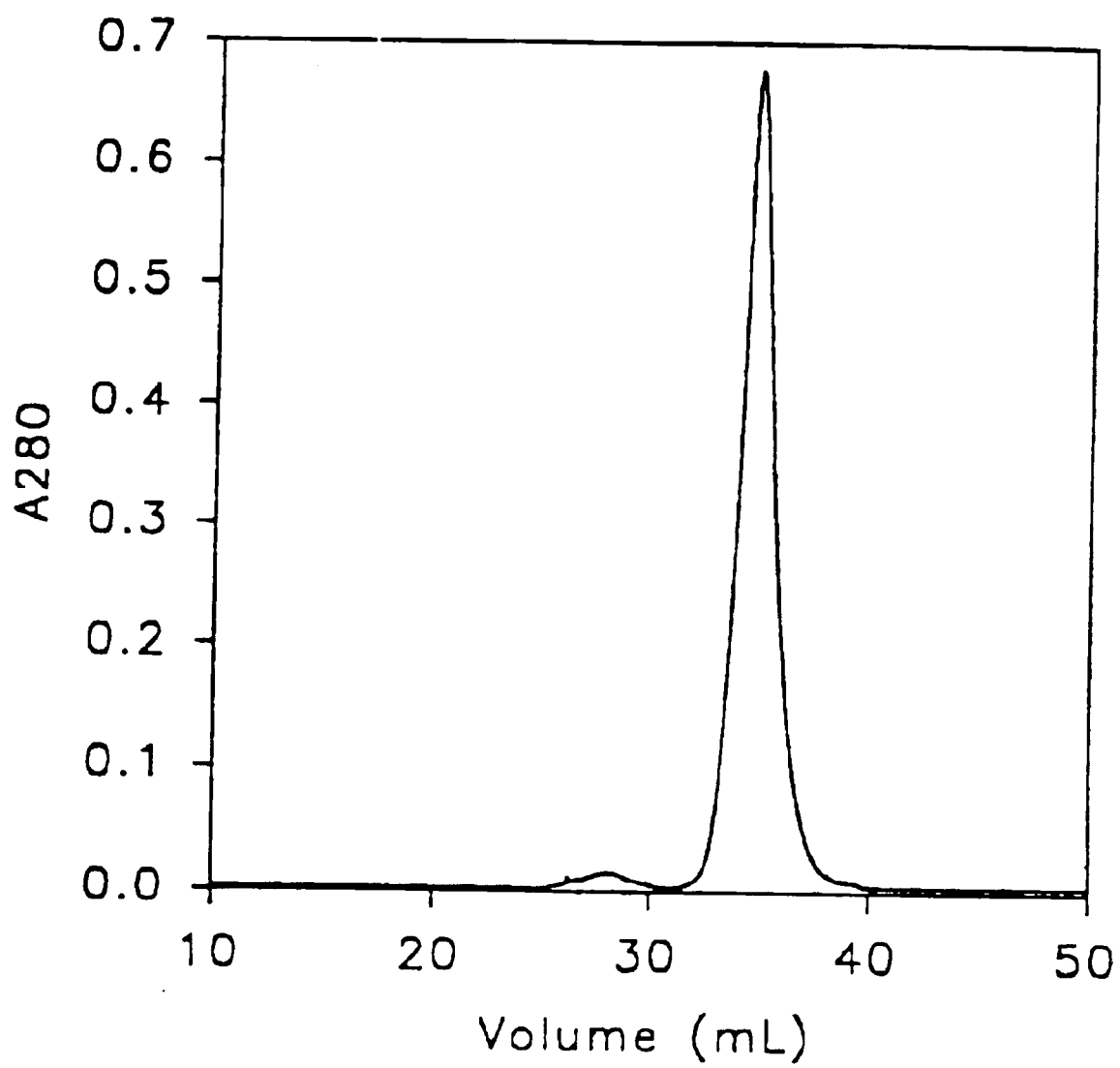

Methoxypolyethylene glycol-succinimidyl succinate (18.1 mg=3.63 umol; SS-MPEG=Sigma Chemical Co. no. M3152, approximate molecular weight=5,000) in 0.327 mL deionized water was added to 13.3 mg (0.727 umol) recombinant rat $SCF^{1-164}$ in 1.0 mL 138 mM sodium phosphate, 62 mM NaCl, 0.62 mM sodium acetate, pH 8.0. The resulting solution was shaken gently (100 rpm) at room temperature for 30 minutes. A 1.0 mL aliquot of the final reaction mixture (10 mg protein) was then applied to a Pharmacia Superdex 75 gel filtration column (1.6×50 cm) and eluted with 100 mM sodium phosphate, pH 6.9, at a rate of 0.25 mL/min at room temperature. The first 10 mL of column effluent were discarded, and 1.0 mL fractions were collected thereafter. The UV absorbance (280 nm) of the column effluent was monitored continuously and is shown in FIG. 40A. Fractions number 25 through 27 were combined and sterilized by ultrafiltration through a 0.2 $\mu$polysulfone membrane (Gelman Sciences no. 4454), and the resulting pool was designated PEG-25. Likewise, fractions number 28 through 32 were combined, sterilized by ultrafiltration, and designated PEG-32. Pooled fraction PEG-25 contained 3.06 mg protein and pooled fraction PEG-32 contained 3.55 mg protein, as calculated from A280 measurements using for calibration an absorbance of 0.66 for a 1.0 mg/mL solution of unmodified rat $SCF^{1-164}$. Unreacted rat $SCF^{1-164}$, representing 11.8% of the total protein in the reaction mixture, was eluted in fractions number 34 to 37. Under similar chromatographic conditions, unmodified rat $SCF^{1-164}$ was eluted as a major peak with a retention volume of 45.6 mL, FIG. 40B. Fractions number 77 to 80 in FIG. 40A contained N-hydroxysuccinimide, a by-product of the reaction of rat $SCF^{1-164}$ with SS-MPEG.

Potentially reactive amino groups in rat $SCF^{1-164}$ include 12 lysine residues and the alpha amino group of the N-terminal glutamine residue. Pooled fraction PEG-25 contained 9.3 mol of reactive amino groups per mol of protein, as determined spectroscopic titration with trinitrobenzene sulfonic acid (TNBS) using the method described by Habeeb, Anal. Biochem. 14:328–336 (1966). Likewise, pooled fraction PEG-32 contained 10.4 mol and unmodified rat $SCF^{1-164}$ contained 13.7 mol of reactive amino groups per mol of protein, respectively. Thus, an average of 3.3 (13.7 minus 10.4) amino groups of rat $SCF^{1-164}$ in pooled fraction PEG-32 were modified by reaction with SS-MPEG. Similarly, an average of 4.4 amino groups of rat $SCF^{1-164}$ in pooled fraction PEG-25 were modified. Human SCF ($hSCF^{1-164}$) produced as in Example 10 was also modified using the procedures noted above. Specifically, 714 mg (38.5 umol) $hSCF^{1-164}$ were reacted with 962.5 mg (192.5 umol) SS-MPEG in 75 mL of 0.1 M sodium phosphate buffer, pH 8.0 for 30 minutes at room temperature. The reaction mixture was applied to a Sephacryl S-200HR column (5×134 cm) and eluted with PBS (Gibco Dulbecco's phosphate-buffered saline without CaCl$_2$ and MgCl$_2$) at a rate of 102 mL/hr, and 14.3-mL fractions were collected. Fractions no. 39-53, analogous to the PEG-25 pool described above and in FIG. 40A, were pooled and found to contain a total of 354 mg of protein. In vivo activity of this modified SCF in primates is presented in Example 8C.

B. Preparation of Recombinant $SCF^{1-165}$PEG

Recombinant human $SCF^{1-165}$ produced as in Example 10 was coupled to methoxypolyethylene glycol (MW =6,000) by reacting 334 mg (18.0 $\mu$mol) of $rhuSCF^{165}$ with 433 mg (72.2 $\mu$mol) of the N-hydroxysuccinimidyl ester of carboxymethyl-MPEG [prepared by procedures described by Veronese, F. M., et al., *J. Controlled Release*, 10:145–154 (1989) in 33.4 ml of 0.1 M bicine buffer, pH 8.0 for 1 hour at room temperature. The reaction mixture was diluted with 134 ml of water for injection (WFI), titrated to pH 4.0 with 0.5 N HCl, filtered through a 0.20$\mu$ cellulose acetate filter (Nalgene no. 156-4020), and applied at a rate of 5.0 ml/min to a 2.6×19.5 cm column of S-Sepharose FF (Pharmacia) which had been previously equilibrated with 20 mM sodium acetate, pH 4.0 at room temperature. Effluent from the column was collected in 8.0-ml fractions (no. 1-18) during sample loading, and the ultraviolet absorbance ($A_{280}$) of the effluent was monitored continuously. The column was then sequentially washed with 200 ml of the equilibration buffer at 5.0 ml/min (fractions no. 19-44), with 200 ml of 20 mM sodium acetate, 0.5 M NaCl, pH 4.0 at 8.0 ml/min (fractions no. 45-69), and finally with 200 ml of 20 mM sodium acetate, 1.0 M NaCl, pH 4.0 at 8.0 ml/min (fractions no. 70-94). Fractions (no. 28-31 and 55-62) containing MPEG-rhu-$SCF^{1-165}$ were combined and dialyzed by ultrafiltration (Amicon YM-10 membrane) against 10 mM sodium acetate, 140 mM NaCl, pH 5.0 to yield 284 mg of final product in a volume of 105 ml. The resulting MPEG-rhu-$SCF^{165}$ was shown to be free of unbound MPEG and other reaction by-products by analytical size-exclusion HPLC [Toso-Haas TSK G3000 SWXL and G4000 SWXL columns (each 0.68×30 cm; 5 u) connected in tandem; 0.1 M sodium phosphate, pH 6.9 at 1.0 ml/min at room temperature; UV absorbance (280 nm) and refractive index detectors in series].

EXAMPLE 13

SCF Receptor Expression on Leukemic Blasts

Leukemic blasts were harvested from the peripheral blood of a patient with a mixed lineage leukemia. The cells were purified by density gradient centrifugation and adherence depletion. Human $SCF^{1-164}$ was iodinated according to the protocol ip Example 7. The cells were incubated with different concentrations of iodinated SCF as described [Broudy, *Blood*, 75 1622–1626 (1990)]. The results of the receptor binding experiment are shown in FIG. 41. The receptor density estimated is approximately 70,000 receptors/cell.

EXAMPLE 14

Rat SCF Activity on Early Lymphoid Precursors

The ability of recombinant rat $SCF^{1-164}$ ($rrSCF^{1-164}$), to act synergistically with IL-7 to enhance lymphoid cell proliferation was studied in agar cultures of mouse bone marrow. In this assay, the colonies formed with rrSCF$^{1-164}$ alone contained monocytes, neutrophils, and blast-cells, while the colonies stimulated by IL-7 alone or in combination with rrSCF$^{1-164}$ contained primarily pre-B cells. Pre-B cells, characterized as B220$^+$, sIg$^-$, cμ$^+$, were identified by FACS analysis of pooled cells using fluorescence-labeled antibodies to the B220 antigen [Coffman, *Immunol. Rev.*, 69, 5 (1982)] and to surface Ig (FITC-goat anti-K, Southern Biotechnology Assoc., Birmingham, Ala.); and by analysis of cytospin slides for cytoplasmic μ expression using fluorescence-labeled antibodies (TRITC-goat anti-μ, Southern Biotechnology Assoc., ). Recombinant human IL-7 (rhIL-7) was obtained from Biosource International (Westlake Village, Calif.). When rrSCF$^{1-164}$ was added in combination with the pre-B cell growth factor IL-7, a synergistic increase in colony formation was observed (Table 16), indicating a stimulatory role of rrSCF$^{1-164}$ on early B cell progenitors.

TABLE 16

Stimulation of Pre-B Cell Colony Formation by rrSCF$^{1-164}$ in Combination with hIL-7

| Growth Factors | | | Colony Number[1] |
|---|---|---|---|
| Saline | | | 0 |
| rrSCF$^{1-164}$ | 200 ng | | 13 ± 2 |
| | 100 ng | | 7 ± 4 |
| | 50 ng | | 4 ± 2 |
| rhIL-7 | 200 ng | | 21 ± 6 |
| | 100 ng | | 18 ± 6 |
| | 50 ng | | 13 ± 6 |
| | 25 ng | | 4 ± 2 |
| rhIL-7 | 200 ng + rrSCF$^{1-164}$ | 200 ng | 60 ± 0 |
| | 100 ng + | 200 ng | 48 ± 8 |
| | 50 ng + | 200 ng | 24 ± 10 |
| | 25 ng + | 200 ng | 21 ± 2 |

[1] Number of colonies per 5 × 10$^4$ mouse bone marrow cells plated.

Each value is the mean of triplicate dishes±SD.

EXAMPLE 15

Identification of the Receptor for SCF

A. c-kit is the Receptor for SCF$^{1-164}$

To test whether SCF$^{1-164}$ is the ligand for c-kit, the cDNA for the entire murine c-kit [Qiu et al., *EMBO J.*, 7, 1003–1011 (1988)] was amplified using PCR from the SCF$^{1-164}$ responsive mast cell line MC/9 [Nabel et al., *Nature*, 291, 332–334 (1981)] with primers designed from the published sequence. The ligand binding and transmembrane domains of human c-kit, encoded by amino acids 1–549 [Yarden et al., *EMBO J.*, 6, 3341–3351 (1987)], were cloned using similar techniques from the human erythroleukemia cell line, HEL [Martin and Papayannopoulou, *Science*, 216, 1233–1235 (1982)]. The c-kit cDNAs were inserted into the mammalian expression vector V19.8 transfected into COS-1 cells, and membrane fractions prepared for binding assays using either rat or human $^{125}$I-SCF$^{1-164}$ according to the methods described in Sections B and C below. Table 17 shows the data from a typical binding assay. There was no detectable specific binding of $^{125}$I human SCF$^{1-164}$ to COS-1 cells transfected with V19.8 alone. However, COS-1 cells expressing human recombinant c-kit ligand binding plus transmembrane domains (hckit-LT1) did bind $^{125}$I-hSCF$^{1-164}$ (Table 17). The addition of a 200 fold molar excess of unlabelled human SCF$^{1-164}$ reduced binding to background levels. Similarly, COS-1 cells transfected with the full length murine c-kit (mckit-L1) bound rat $^{125}$I-SCF$^{1-164}$. A small amount of rat $^{125}$I-SCF$^{1-164}$ binding was detected in COS-1 cells transfectants with V19.8 alone, and has also been observed in untransfected cells (not shown), indicating that COS-1 cells express endogenous c-kit. This finding is in accord with the broad cellular distribution of c-kit expression. Rat $^{125}$I-SCF$^{1-164}$ binds similarly to both human and murine c-kit, while human $^{125}$I-SCF$^{1-164}$ bind with lower activity to murine c-kit (Table 17). This data is consistent with the pattern of SCF$^{1-164}$ cross-reactivity between species. Rat SCF$^{1-164}$ induces proliferation of human bone marrow with a specific activity similar to that of human SCF$^{1-164}$, while human SCF$^{1-164}$ induced proliferation of murine mast cells occurs with a specific activity 800 fold less than the rat protein.

In summary, these findings confirm that the phenotypic abnormalities expressed by W or S1 mutant mice are the consequences of primary defects in c-kit receptor/ligand interactions which are critical for the development of diverse cell types.

TABLE 17

SCF$^{1-164}$ Binding to Recombinant c-kit Expressed in COS-1 Cells

| Plasmid | CPM Bound[a] | | | |
|---|---|---|---|---|
| Trans- | Human SCF$^{1-164}$ | | Rat SCF$^{1-164}$ | |
| fected | $^{125}$I-SCF[b] | $^{125}$I-SCF + cold[c] | $^{125}$I-SCF[d] | $^{125}$I-SCF + cold[e] |
| V19.8 | 2,160 | 2,150 | 1,100 | 550 |
| V19.8: hckit-LT1 | 59,350 | 2,380 | 70,000 | 1,100 |
| V19.8: mckit-L1 | 9,500 | 1,100 | 52,700 | 600 |

[a] The average of duplicate measurements is shown; the experiment has been independently performed with similar results three times.
[b] 1.6 nM human $^{125}$I-SCF$^{1-164}$
[c] 1.6 nM human $^{125}$I-SCF$^{1-164}$ + 320 nM unlabelled human SCF$^{1-164}$
[d] 1.6 nM rat $^{125}$I-SCF$^{1-164}$
[e] 1.6 nM rat $^{125}$I-SCF$^{1-164}$ + 320 nM unlabelled rat SCF$^{1-164}$ B. Recombinant c-kit Expression in COS-1 Cells Human and murine c-kit cDNA clones were derived using PCR techniques [Saiki et al., *Science*, 239, 487–491 (1988)] from total RNA isolated by an acid phenol/chloroform extraction procedure [Chomczynsky and Sacchi, *Anal. Biochem.*, 162, 156–159, (1987)] from the human erythroleukemia cell line HEL and MC/9 cells, respectively. Unique sequence oligonucleotides were designed from the published human and murine c-kit sequences. First strand cDNA was synthesized from the total RNA according to the protocol provided with the enzyme, Mo-MLV reverse transcription (Bethesda Research Laboratories, Bethesda, Md), using c-kit antisense oligonucleotides as primers. Amplification of overlapping regions of the c-kit ligand binding and tyrosine kinase domains was accomplished using appropriate pairs of c-kit primers. These regions were cloned into the mammalian expression vector V19.8 (FIG. 17) for expression in COS-1 cells. DNA sequencing of several clones revealed independent mutations, presumably arising during PCR amplification, in every clone. A clone free of these mutations was constructed by reassembly of mutation-free restriction fragments from separate clones. Some differences from the published sequence appeared in all or in about half of the clones; these were concluded to be the actual sequences present in the cell lines used, and may represent allelic differences from the published sequences. The following plasmids were constructed in V19.8: V19.8:mckit-LT1, the entire murine c-kit; and V19.8: hckit-L1, containing the ligand binding plus transmembrane region (amino acids 1–549) of human c-kit.

The plasmids were transfected into COS-1 cells essentially as described in Example 4.

C. $^{125}$I-SCF$^{1-164}$ Binding to COS-1 Cells Expressing Recombinant c-kit

Two days after transfection, the COS-1 cells were scraped from the dish, washed in PBS, and frozen until use. After thawing, the cells were resuspended in 10 mM Tris-HCl, 1 mM MgCl$_2$ containing 1 mM PMSF, 100 µg/ml aprotinin, 25 µg/ml leupeptin, 2 µg/ml pepstatin, and 200 µg/ml TLCK-HCl. The suspension was dispersed by pipetting up and down 5 times, incubated on ice for 15 minutes, and the cells were homogenized with 15–20 strokes of a Dounce homogenizer. Sucrose (250 mM) was added to the homogenate, and the nuclear fraction and residual undisrupted cells were pelleted by centrifugation at 500×g for 5 min. The supernatant was centrifuged at 25,000 g for 30 min. at 4° C. to pellet the remaining cellular debris. Human and rat SCF$^{1-164}$ were radioiodinated using chloramine-T [Hunter and Greenwood, *Nature*, 194, 495–496 (1962)]. COS-1 membrane fractions were incubated with either human or rat $^{125}$I-SCF$^{1-164}$ (1.6 nM) with or without a 200 fold molar excess of unlabelled SCF$^{1-164}$ in binding buffer consisting of RPMI supplemented with 1% bovine serum albumin and 50 mM HEPES (pH 7.4) for 1 h at 22° C. At the conclusion of the binding incubation, the membrane preparations were gently layered onto 150 µl of phthalate oil and centrifuged for 20 minutes in a Beckman Microfuge 11 to separate membrane bound $^{125}$I-SCF$^{1-164}$ from free $^{125}$I-SCF$^{1-164}$. The pellets were clipped off and membrane associated $^{125}$I-SCF$^{1-164}$ was quantitated.

EXAMPLE 16

Isolation of a Human SCF cDNA

A. Construction of the HT-1080 cDNA Library

Total RNA was isolated from human fibrosarcoma cell line HT-1080 (ATCC CCL 121) by the acid guanidinium thiocyanate-phenol-chloroform extraction method [Chomczynski et al., *Anal. Biochem.* 162, 156 (1987)], and poly(A) RNA was recovered by using oligo(dT) spin column purchased from Clontech. Double-stranded cDNA was prepared from 2 µg poly(A) RNA with a BRL (Bethesda Research Laboratory) cDNA synthesis kit under the conditions recommended by the supplier. Approximately 10 ng of column fractionated double-stranded cDNA with an average size of 2 kb was ligated to 300 ng SalI/NotI digested vector pSPORT 1 [D'Alessio et al., *Focus*, 12, 47–50 (1990)] and transformed into DH5α (BRL, Bethesda, Md.) cells by electroporation [Dower et al., *Nucl. Acids Res.*, 16, 6127–6145 (1988)].

B. Screening of the cDNA Library

Approximately 2.2×10$^5$ primary transformants were divided into 44 pools with each containing ~5000 individual clones. Plasmid DNA was prepared from each pool by the CTAB-DNA precipitation method as described [Del Sal et al., *Biotechniques*, 7, 514–519 (1989)]. Two micrograms of each plasmid DNA pool was digested with restriction enzyme NotI and separated by gel electrophoresis. Linearized DNA was transferred onto GeneScreen Plus membrane (DuPont) and hybridized with $^{32}$P-labeled PCR generated human SCF cDNA (Example 3) under conditions previously described (Lin et al., *Proc. Natl. Acad. Sci. USA*, 82, 7580–7584 (1985)]. Three pools containing positive signal were identified from the hybridization. These pools of colonies were rescreened by the colony-hybridization procedure [Lin et al., *Gene* 44, 201–209 (1986)] until a single colony was obtained from each pool. The cDNA sizes of these three isolated clones are between 5.0 to 5.4 kb. Restriction enzyme digestions and nucleotide sequence determination at the 5' end indicate that two out of the three clones are identical (10-1a and 21-7a). They both contain the coding region and approximately 200 bp of 5' untranslated region (5' UTR). The third clone (26-1a) is roughly 400 bp shorter at the 5' end than the other two clones. The sequence of this human SCF cDNA is shown in FIG. 42. Of particular note is the hydrophobic transmembrane domain sequence starting in the region of amino acids 186–190 and ending at amino acid 212.

C. Construction of pDSRα2 hSCF$^{1-248}$

PDSRα2 hSCF$^{1-248}$ was generated using plasmids 10-1a (as described in Example 16B) and pGEM3 hSCF$^{1-163}$ as follows: The HindIII insert from pGEM3 hSCF$^{1-163}$ was transferred to M13mp18. The nucleotides immediately upstream of the ATG initiation codon were changed by site directed mutagenesis from tttccttATG (SEQ ID NO:102) to gccgccgccATG (SEQ ID NO:103) using the antisense oligonucleotide

5'-TCT TCT TCA TGG CGG CGG CAA GCT T 3' (SEQ ID NO:104).

and the oligonucleotide-directed in vitro mutagenesis system kit and protocols from Amersham Corp. to generate M13 mpl8 hSCF$^{K1-164}$. This DNA was digested with HindIII and inserted into pDSRα2 which had been digested with RindIII. This clone is designated pDSRα2 hSCF$^{K1-164}$. DNA from pDSRα2 hSCF$^{K1-164}$ was digested with XbaI and the DNA made blunt ended by the addition of Klenow enzyme and four dNTPs. Following termination of this reaction the DNA was further digested with the enzyme SpeI. Clone 10-1a was digested with DraI to generate a blunt end 3' to the open reading frame in the insert and with SpeI which cuts at the same site within the gene in both pDSRα2 hSCF$^{K1-164}$ and 10-1a. These DNAs were ligated together to generate pDSRα2 hSCF$^{K1-248}$.

D. Transfection and immunoprecipitation of COS cells with pDSRα2 hSCF$^{1-248}$ DNA.

COS-7 (ATCC CRL 1651) cells were transfected with DNA constructed as described above. 4×10$^6$ cells in 0.8 ml DMEM±5% FBS were electroporated at 1600 V with either 10 µg pDSRα2 hSCF$^{K1-248}$ DNA or 10 µg pDSRα2 vector DNA (vector control). Following electroporation, cells were replated into two 60-mm dishes. After 24 hrs, the medium was replaced with fresh complete medium.

72 hrs after transfection, each dish was labelled with $^{35}$S-medium according to a modification of the protocol of Yarden et al. (*PNAS* 87, 2569–2573, 1990). Cells were washed once with PBS and then incubated with methionine-free, cysteine-free DMEM (met$^-$cys$^-$DMEM) for 30 min. The medium was removed and 1 ml met$^-$cys$^-$DMEM containing 100 µCi/ml Tran$^{35}$S-Label (ICN) was added to each dish. Cells were incubated at 37° C. for 8 hr. The medium was harvested, clarified by centrifugation to remove cell debris and frozen at −20° C.

Aliquots of labelled conditioned medium of COS/pDSRα2 hSCF$^{K1-248}$ and COS/pDSRα2 vector control were immunoprecipitated along with medium samples of $^{35}$S-labelled CHO/pDSRα2 hSCF$^{1-164}$ clone 17 cells (see Example 5) according to a modification of the protocol of Yarden et al. (*EMBO, J.*, 6, 3341–3351, 1987). One ml of each sample of conditioned medium was treated with 10 µl of pre-immune rabbit serum (#1379 P.I.). Samples were incubated for 5 h. at 4° C. One hundred microliters of a 10% suspension of *Staphylococcus aureus* (Pansorbin, Calbiochem.) in 0.15 M NaCl, 20 mM Tris pH 7.5, 0.2% Triton X-100 was added to each tube. Samples were incubated for an additional one hour at 4° C. Immune complexes were pelleted by centrifugation at 13,000×g for 5 min. Supernatants were transferred to new tubes and incubated with 5 µl rabbit polyclonal antiserum (#1381 TB4), purified as in Example 11, against CHO derived hSCF$^{1-162}$ overnight at 4° C. 100 µl Pansorbin was added for 1 h. and immune complexes were pelleted as before. Pellets were washed 1×with lysis buffer (0.5% Na-deoxycholate, 0.5% NP-40, 50 mM NaCl, 25 mM Tris pH 8), 3× with wash buffer (0.5 M NaCl, 20 mM Tris pH 7.5, 0.2% Triton X-100), and 1× with 20 mm Tris pH 7.5. Pellets were resuspended in 50 µl 10 mM Tris pH 7.5, 0.1% SDS, 0.1 M α-mercaptoethanol. SCF protein was eluted by boiling for 5 min. Samples were centrifuged at 13,000×g for 5 min. and supernatants were recovered.

Treatment with glycosidases was accomplished as follows: three microliters of 75 mM CHAPS containing 1.6 mU O-glycanase, 0.5 U N-glycanase, and 0.02 U neuraminidase was added to 25 µl of immune complex samples and incubated for 3 hr. at 37° C. An equal volume of 2×PAGE sample buffer was added and samples were boiled for 3 min. Digested and undigested samples were electrophoresed on a 15% SDS-polyacrylamide reducing gel overnight at 8 mA. The gel was fixed in methanol-acetic acid, treated with Enlightening enhancer (NEN) for 30 min., dried, and exposed to Kodak XAR-5 film at −70°.

FIG. 43 shows the autoradiograph of the results. Lanes 1 and 2 are samples from control COS/pDSRα2 cultures, lanes 3 and 4 from COS/pSRα2hSCF$^{1-248}$, lanes 5 and 6 from CHO/pDSRα2 hSCF$^{1-164}$. Lanes 1, 3, and 5 are undigested immune precipitates; lanes 2, 4, and 6 have been digested with glycanases as described above. The positions of the molecular weight markers are shown on the left. Processing of the SCF in COS transfected with pDSRα2 hSCF$^{1-248}$ closely resembles that of hSCF$^{1-164}$ secreted from CHO transfected with pDSRα2 hSCF$^{1-164}$, (Example 11). This strongly suggests that the natural proteolytic processing site releasing SCF from the cell is in the vicinity of amino acid 164.

EXAMPLE 17

Quaternary Structure Analysis of Human SCF.

Upon calibration of the gel filtration column (ACA 54) described in Example 1 for purification of SCF from BRL cell medium with molecular weight standards, and upon elution of purified SCF from other calibrated gel filtration columns, it is evident that SCF purified from BRL cell medium behaves with an apparent molecular weight of approximately 70,000-90,000 relative to the molecular weight standards. In contrast, the apparent molecular weight by SDS-PAGE is approximately 28,000-35,000. While it is recognized that glycosylated proteins may behave anomalously in such analyses, the results suggest that the BRL-derived,rat SCF may exist as non-covalently associated dimer under non-denaturing conditions. Similar results apply for recombinant SCF forms (e.g. rat and human SCF$^{1-164}$ derived from *E. coli*, rat and human SCF$^{1-162}$ derived from CHO cells) in that the molecular size estimated by gel filtration under non-denaturing conditions is roughly twice that estimated by gel filtration under denaturing conditions (i.e., presence of SDS), or by SDS-PAGE, in each particular case. Furthermore sedimentation velocity analysis, which provides an accurate determination of molecular weight in solution, gives a value of about 36,000 for molecular weight of *E. coli*-derived recombinant human SCF$^{1-164}$. This value is again approximately twice that seen by SDS-PAGE (~18,000-19,000). Therefore, while it is recognized that there may be multiple oligomeric states (including the monomeric state), it appears that the dimeric state predominates under some circumstances in solution. CHO cell-derived human SCF$^{1-162}$ has a molecular weight of about 53,000 by sedimentation equilibrium analysis; this indicates that it is dimeric also, and that it is about 30% carbohydrate by weight.

EXAMPLE 18

Isolation of Human SCF cDNA Clones from the 5637 Cell Line

A. Construction of the 5637 cDNA Libraryk

Total RNA was isolated from human bladder carcinoma cell line 5637 (ATCC HTB-9) by the acid guanidinium thiocyanate-phenol-chloroform extraction method [Chomczynski et al., *Anal. Biochem*, 162, 156 (1987)], and poly(A) RNA was recovered by using an oligo(dT) spin column purchased from Clontech. Double-stranded cDNA was prepared from 2 µg poly(A) RNA with a BRL cDNA synthesis kit under the conditions recommended by the supplier. Approximately 80 ng of column fractionated double-stranded cDNA with an average size of 2 kb was ligated to 300 ng SalI/NotI digested vector pSPORT 1 (D'Alessio et al., *Focus*, 12, 47–50 (1990)] and transformed into DH5α cells by electroporation [Dower et al., *Nucl. Acids Res.*, 16, 6127–6145 (1988)].

B. Screening of the cDNA Library

Approximately 1.5×10$^5$ primary tranformants were divided into 30 pools with each containing approximately 5000 individual clones. Plasmid DNA was prepared from each pool by the CTAB-DNA precipitation method as described [Del Sal et al., *Biotechniques*, 7, 514–519 (1989)]. Two micrograms of each plasmid DNA pool was digested with restriction enzyme NotI and separated by gel electrophoresis. Linearized DNA was transferred to GeneScreen Plus membrane (DuPont) and hybridized with $^{32}$P-labeled full length human SCF cDNA isolated from HT1080 cell line (Example 16) under the conditions previously described [Lin et al., *Proc. Natl. Acad. Sci. USA*, 82, 7580–7584 (1985)]. Seven pools containing positive signal were identified from the hybridization. The pools of colonies were rescreened with $^{32}$P-labeled PCR generated human SCF cDNA (Example 3) by the colony hybridization procedure [Lin et al., *Gene*, 44, 201–209 (1986)] until a single colony was obtained from four of the pools. The insert sizes of four isolated clones are approximately 5.3 kb. Restriction enzyme digestions and nucleotide sequence analysis of the 5'-ends of the clones indicate that the four clones are identical. The sequence of this human cDNA is shown in FIG. 44. The cDNA of FIG. 44 codes for a polypeptide in which amino acids 149–177 of the sequences in FIG. 42 are replaced by a single Gly residue.

EXAMPLE 19

SCF Enhancement of Survival After Lethal Irradiation ps A. SCF in vivo activity on Survival After Lethal Irradiation.

The effect of SCF on survival of mice after lethal irradiation was tested. Mice used were 10 to 12 week-old female Balb/c. Groups of 5 mice were used in all experiments and the mice were matched for body weight within each experiment. Mice were irradiated at 850 rad or 950 rad in a single dose. Mice were injected with factors alone or factors plus normal Balb/c bone marrow cells. In the first case, mice were injected intravenously 24 hrs. after irradiation with rat PEG-SCF$^{1-164}$ (20 μg/kg), purified from E. coli and modified by the addition of polyethylene glycol as in Example 12, or with saline for control animals. For the transplant model, mice were injected i.v. with various cell doses of normal Balb/c bone marrow 4 hours after irradiation. Treatment with rat PEG-SCF was performed by adding 200 μg/kg of rat PEG-SCF$^{1-164}$ to the cell suspension 1 hour prior to injection and given as a single i.v. injection of factor plus cells.

After irradiation at 850 rads, mice were injected with rat PEG-SCF$^{1-164}$ or saline. The results are shown in FIG. 45. Injection of rat PEG-SCF$^{1-164}$ significantly enhanced the survival time of mice compared to control animals (P<0.0001). Mice injected with saline survived an average of 7.7 days, while rat PEG-SCF$^{1-164}$ treated mice survived an average of 9.4 days (FIG. 45). The results presented in FIG. 45 represent the compilation of 4 separate experiments with 30 mice in each treatment group.

The increased survival of mice treated with rat PEG-SCF$^{1-164}$ suggests an effect of SCF on the bone marrow cells of the irradiated animals. Preliminary studies of the hematological parameters of these animals show slight increases in platelet levels compared to control animals at 5 days post irradiation, however at 7 days post irradiation the platelet levels are not significantly different to control animals. No differences in RBC or WBC levels or bone marrow cellularity have been detected.

B. Survival of Transplanted Mice Treated with SCF

Doses of 10% femur of normal Balb/c bone marrow cells transplanted into mice irradiated at 850 rad can rescue 90% or greater of animals (data not presented). Therefore a dose of irradiation of 850 rad was used with a transplant dose of 5% femur to study the effects of rat PEG-SCF$^{1-164}$ on survival. At this cell dose it was expected that a large percentage of mice not receiving SCF would not survive; if rat PEG-SCF$^{1-164}$ could stimulate the transplanted cells there might be an increase in survival. As shown in FIG. 46, approximately 30% of control mice survived past 8 days post irradiation. Treatment with rat PEG-SCF$^{1-164}$ resulted in a dramatic increase of survival with greater than 95% of these mice surviving out to at least 30 days (FIG. 46). The results presented in FIG. 46 represent the compilation of results from 4 separate experiments representing 20 mice in both the control and rat PEG-SCF$^{1-164}$ treated mice. At higher doses of irradiation, treatment of mice with rat PEG-SCF$^{1-164}$ in conjunction with marrow transplant also resulted in increased survival (FIG. 47). Control mice irradiated at 950 rads and transplanted with 10% of a femur were dead by day 8, while approximately 40% of mice treated with rat PEG-SCF$^{1-164}$ survived 20 days or longer. 20% of control mice transplanted with 20% of a femur survived past 20 days while 80% of rSCF treated animals survived (FIG. 47).

C. Radioprotective Effects of SCF on Lethally Irradiated Mice Without a Bone Marrow Transplant.

The effects of SCF administration prior to irradiation were compared to the effects of SCF administration post-irradiation.

Female BDF1 mice (Charles River Laboratories, were used. All mice were between 7 and 8 weeks old and averaged 20–24 g each. Irradiation consisted of a lethal split dose of 575 RADS each (total 1150 RADS) delivered 4 hours apart from a Gamma Cell to 40 duel cobalt source, (Atomic Energy Of Canada Limited).

In the experiment shown in FIG. 19-1, the ability of SCF, administered prior to irradiation, to save mice from an otherwise lethal exposure was tested. Rat SCF, purified from E. coli as in Example 10 and modified by the addition of polyethylene glycol as in Example 12, was administered to two groups of mice (n=30), either intra-peritoneally or intravenously at a dose of 100 μg/kg. Control animals received excipient only which consisted of phosphate-buffered saline, 0.1% fetal bovine serum. The times of administration were t=−20 hours and t=−2 hours to the irradiation event (t=0). The survival of the animals was monitored daily. The results are shown in FIG. 48. Both routes of administration of rat SCF-PEG enhanced survival of the irradiated mice. At 30 days post irradiation, 100% of the animals treated with SCF were alive, whereas only 35% of the animals in the control group were alive. Since similar experiments, outlined in Example 19 A where SCF was administered post-irradiation only, yielded different results, the two modes of administration were compared directly in a single experiment. The experiment was performed as described above for FIG. 49 except the groups were as follows (irradiation was at t=0): group 1, control; group 2, rat SCF-PEG administered at t=−20 hours and t=−2 hours; group 3, rat SCF-PEG administered at t=−20 hours, t=−2 hours, and t=+4 hours; and group 4, rat SCF-PEG administered at t=+4 hours only. Both groups receiving rat SCF-PEG prior to irradiation survived at 95–100% at day 14 (groups 2 and 3). In accordance with the experiment described in Example 19 A, the animals receiving rat SCF-PEG post irradiation only did not survive the irradiation event, although they survived longer than controls.

These experiments demonstrate the utility of SCF administration to protect against the lethal effects of irradiation. These protective effects are most effective when SCF is administered prior to the irradiation event as well as after. This aspect of in vivo activity of SCF can be utilized in dose intensification regimes in anti-neoplastic radiotherapy.

EXAMPLE 20

Production of Monoclonal Antibodies Against SCF 8-week old female BALB/c mice (Charles River, Wilmington, Mass.) were injected subcutaneously with 20 μg of human SCF$^{1-164}$ expressed from E. coli in complete Freund's adjuvant (H37-Ra; Difco Laboratories, Detroit, Mich.). Booster immunizations of 50 μg of the same antigen in Incomplete Freund's adjuvant were subsequently administered on days 14, 38 and 57. Three days after the last injection, 2 mice were sacrificed and their spleen cells fused with the sp 2/0 myeloma line according to the procedures described by Nowinski et al., [*Virology* 93, 111–116 (1979)].

The media used for cell culture of sp 2/0 and hybridoma was Dulbecco's Modified Eagle's Medium (DMEM), (Gibco, Chagrin Falls, Ohio) supplemented with 20% heat inactivated fetal bovine serum (Phibro Chem., Fort Lee, N.J.), 110 mg/ml sodium pyruvate, 100 U/ml penicillin and 100 mcg/ml streptomycin (Gibco). After cell fusion (hybrids were selected in HAT medium, the above medium containing $10^{-4}$M hypoxanthine, $4 \times 10^{-7}$M aminopterin and $1.6 \times 10^{-5}$M thymidine, for two weeks, then cultured in media containing hypoxanthine and thymidine for two weeks.

Hybridomas were screened as follows: Polystyrene wells (Costar, Cambridge, Mass.) were sensitized with 0.25 μg of human SCF$^{1-164}$ (E. coli) in 50 μl of 50 mM bicarbonate buffer pH 9.2 for two hours at room temperature, then overnight at 4° C. Plates were then blocked with 5% BSA in PBS for 30 minutes at room temperature, then incubated with hybridoma culture supernatant for one hour at 37° C. The solution was decanted and the bound antibodies incubated with a 1:500 dilution of Goat-anti-mouse IgG conjugated with Horse Radish Peroxidase (Boehringer Mannheim Biochemicals, Indianapolis, Ind.) for one hour at 37° C. The plates were washed with wash solution (KPL, Gaithersburg, MD) then developed with mixture of $H_2O_2$ and ABTS (KPL). Colorimetry was conducted at 405 nm.

Hybridoma cell cultures secreting antibody specific for human $SCF^{1-164}$ (*E. coli*) were tested by ELISA, same as hybridoma screening procedures, for crossreactivities to human $SCF^{1-162}$ (CHO). Hybridomas were subcloned by limiting dilution method. 55 wells of hybridoma supernatant tested strongly positive to human $SCF^{1-164}$ (*E. coli*); 9 of them crossreacted to human $SCF^{1-162}$ (CHO)

Several hybridoma cells have been cloned as follows:

| Monoclone | IgG Isotype | Reactivity to human $SCF^{1-162}$ (CHO) |
| --- | --- | --- |
| 4G12-13 | IgG1 | No |
| 6C9A | IgG1 | No |
| 8H7A | IgG1 | Yes |

Hybridomas 4G12-13 and 8H7A were deposited with the ATCC on Sep. 26, 1990.

EXAMPLE 21

Synergistic Effect of SCF and Other Growth Factors.

A. Synergistic Effect of SCF and G-CSF in Rodents

Lewis rats, male, weighing approximately 225 gms, were injected intravenously via the dorsal vein of the penis with either polyethylenesporeglycol-modified ratSCF-PEG (Examples 10 and 12), recombinant human G-CSF, a combination of both growth factors, or with carrier consisting of 1% normal rat serum in sterile saline. Quantitative peripheral blood and bone marrow differentials were performed at various timepoints as previously described [Hulse, *Acta Haematol*. 31:50 (1964); Chervenick et al., *Am. J. Physiol*. 215: 353 (1968)]. Histologic examination of the spleen was performed with Bouin's-fixed paraffin-embedded sections stained with hematoxylin-and-eosin as well as by the Giemsa method. The numbers of normoblasts, megakaryocytes, and mast cells per 400× or 1000× high power field (HPF) in the spleen was quantitated by counting the number of each cell type in randomly selected fields of the red pulp. Increases in circulating numbers of neutrophils over extended time periods were when so stated calculated by planimetry as previously described. [Ulich et al., *Blood* 75:48 (1990)]. Data is expressed as the mean plus-or-minus one standard deviation and statistical analysis is by the unpaired t-test.

A single coinjection of ratSCF-PEG (25 ug/rat) plus G-CSF (25 ug/rat) causes an increase in circulating neutrophils that is approximately additive (FIG. 50 CSF) as compared to ratSCF-PEG alone (25 ug/rat) or G-CSF alone (25 ug/rat) as measured by planimetry over a 35 hour time period. The kinetics of ratSCF-PEG plus G-CSF-induced peripheral neutrophilia reflect the combined effect of the differing kinetics of ratSCF-induced neutrophilia peaking at 6 hours and G-CSF-induced neutrophilia peaking at 12 hours (FIG. 50). The bone marrow at 6 hours after a single coinjection of ratSCF-PEG plus G-CSF (Table 18) shows a greater than additive decrease in mature marrow neutrophils (9.94i0.3×10 PMN/humerus in carrier control rats vs. $2.11\pm0.3\times10^6$ PMN/humerus in ratSCF-PEG plus G-CSF-treated rats, 79% decrease) as compared to ratSCF-PEG alone-treated rats ($7.55\times0.2\times10^6$ PMN/humerus, 24% decrease) or G-CSF alone-treated rats ($5.55\pm0.5\times10^6$ PMN/humerus, 44% decrease). A significant increase in myeloblasts and promyelocytes was seen in ratSCF-PEG, G-CSF-, and ratSCF-PEG plus G-CSF-treated rats at 6 hours as compared to carrier controls (Table 18), but no significant increase in any form of immature myeloid cells is noted in ratSCF-PEG plus G-CSF-treated rats as compared to ratSCF-PEG alone-or G-CSF alone-treated rats. A significant increase in myeloblasts is noted at 24 hours, however, in the ratSCF-PEG plus G-CSF group as compared to either ratSCF-PEG, G-CSF, or carrier alone (p<0.01, Table 19).

Daily coinjection of ratSCF-PEG (25 ug/rat) plus G-CSF (25 ug/rat) for one week causes a highly synergistic increase in circulating neutrophils (FIG. 51) as compared to ratSCF-PEG alone (25 ug/rat) or G-CSF alone (25 ug/rat). A marked linear increase rise in the number of circulating neutrophils occurs between day 4 and 6 after the coinjection of ratSCF-PEG plus G-CSF to $41.4\pm1.2\times10^3$ $PMN/mm^3$ at 24 hours after the last injection of the week as compared to $10.6\pm3.6\times10^3$ $PMN/mm^3$ in G-CSF treated rats and $2.4\pm1.3\times10^3$ $PMN/mm^3$ in ratSCF-PEG alone treated rats (FIG. 51). A more detailed kinetic study of ratSCF-PEG plus G-CSF-induced neutrophilia after the last injection of the week showed that the peak of circulating neutrophils occurs at 12 hours and reaches a level of $69.2\pm2.5\times10^3$ $PMN/mm^3$ as compared to $25.3\pm0.3\times10^3$ $PMN/mm^3$ in G-CSF-treated rats and $5.6\pm3.4\times10^3$ in ratSCF-PEG-treated rats (FIG. 52). The neutrophils of ratSCF-PEG plus G-CSF-treated rats were extremely hypersegmented (FIG. 52). In addition to the overwhelming increase in mature neutrophils in the circulation, an increase in immature myeloid forms was noted as well as the appearance of immature monocytoid forms, rare macrophage-like cells that contained vacuoles and. ingested erythroid or lymphoid cells, rare basophils, rare mononuclear promegakaryocytic forms and occasional late normoblasts in peripheral blood smears. As many as 3% of the nucleated circulating blood cells were normoblasts in some of the peripheral blood smears of ratSCF-PEG plus G-CSF-treated rats after daily treatment for one week.

Two of the four rats in the ratSCF-PEG plus G-CSF-treated group died (one on the fifth day and one on the sixth day of the experiment), one of the surviving rats appeared ill on the day of sacrifice (the seventh day), and both of the surviving rats were thrombocytopenic. None of the rats in the ratSCF-PEG alone, G-CSF alone, or carrier control groups showed any evidence of morbidity or were thrombocytopenic.

The bone marrow at 24 hours after the daily coinjection of ratSCF-PEG plus G-CSF for one week demonstrated a synergistic increase in mature neutrophils form $10.6\pm0.6\times10^6$ PMN/humerus in carrier controls, $14.5\pm1.0\times10^6$ PMN/humerus in ratSCF-PEG alone-treated rats, and $28.5\pm2.1\times10^6$ PMN/humerus in G-CSF alone-treated rats (Table 20). The neutrophils in the marrow are generally hypersegmented and are often hypergranulated due to an increase in primary azurophilic granules.

The spleens of ratSCF-PEG plus G-CSF-treated rats were much larger and histologic examination showed increased myelopoiesis, erythropoiesis, and megakaryocytopoiesis as compared to the spleens of control or single factor-treated rats. The spleens of ratSCF-PEG plus G-CSF-treated rats showed atrophy of the white pulp concomitant with a tremendous expansion of the red pulp which was replaced by nearly confluent extramedullary hematopoiesis. The number of granulocytic precursors (myeloblasts to metamyelocytes) was readily seen by scanning histologic sections of the spleen to be markedly increased in the ratSCF-PEG plus G-CSF group as compared to all other groups. Interestingly, the number of normoblasts in the spleen was also increased in the ratSCF-PEG plus G-CSF group (4.1±5.8 in the ratSCF-PEG alone group, 0±0 in the G-CSF alone group, and 36.4±26.1 in the ratSCF-PEG plus G-CSF group; 18 1,000×HPF/spleen/rat; p<0.0001 comparing ratSCF-PEG plus G-CSF vs. ratSCF-PEG alone). The number of megakaryocytes in the spleen was also significantly increased in the ratSCF-PEG plus G-CSF group (1.8±1.5 in the ratSCF-PEG alone group, 2.0±1.1 in the G-CSF alone group, and 5.2±3.1 in the ratSCF-PEG plus G-CSF group; 12 400×HPF/spleen/rat; p<0.0001 comparing ratSCF-PEG plus G-CSF to either ratSCF-PEG or G-CSF alone).

These results demonstrate that the in vivo combination of ratSCF-PEG and G-CSF causes a synergistic myeloid hyperplasia in the bone marrow and spleen and a synergistic increase in circulating neutrophils. The synergism between a single dose of ratSCF-PEG and G-CSF becomes most dramatically apparent as a rapidly increasing number of circulating neutrophils between 4 and 6 hours after commencement of administration of growth factors. Daily coinjection plus G-CSF for one week causes a highly synergistic increase in circulating neutrophils as compared to ratSCF-PEG alone or G-CSF alone.

B. Synergistic Effect of SCF and Other Growth Factors in Canines

Though single factors such as G-CSF have been shown to have important effects on hematopoietic recovery, the combination of SCF with G-CSF has a dramatic hematologic response. In the first set of experiments, 3 normal dogs were treated with recombinant canine SCF alone at 200 μg/kg/day subcutaneously or by continuous intravenous infusion. These animals responded with an increase in the white blood cell count to 30-50,000/mm$^3$, from a baseline of 10–15,000 mm$^3$ by day 8-12. When another group of normal dogs were treated for 28 days with recombinant canine SCF (200 μg/kg/day SCF and G-CSF (10 μg/kg/day SC), the white blood cell count increased from a normal range of 10-11,000/ mm$^3$ to 200–240,000 cells /mm$^3$ by day 17-21. This demonstrates that the effects of SCF are dramatically enhanced in combination with other hematopoietic growth factors. Similarly, in vitro data show that SCF in combination with EPO dramatically enhances BFU-E growth (number and size, see Example 9), again demonstrating that combinations of hematopoietic growth factors are more effective in eliciting a hematopoietic response and/or may allow for lower doses of other factors to elicit the same response.

EXAMPLE 22

The Use of SCF in Hematopoietic Transplantation
A. The Effects of SCF on Amplification of Bone Marrow and Peripheral Blood Hematopoietic Progenitors The effects of SCF administration on circulating hematopoietic progenitors in normal baboons was studied. The experimental design was identical to that described in Example 8C. Briefly, normal baboons were administered 200 μg/kg/day human SCF$^{1-164}$, produced in E. coli as in Example 10 and modified by the addition of polyethylene glycol as in Example 12, as a continuous intravenous infusion. At various times bone marrow and peripheral blood was harvested and cultured at a density of 2×10$^5$ per ml in Iscoves' Modified Dulbecco's Medium (Gibco, Grand Island, N.Y.) in 0.3% (W/v) agar (FMC, Rockland, Me.), supplemented with 25% fetal bovine serum (Hyclone, Logan, Utah), and 10$^{-4}$ 2-mercaptoethanol in 35 mm culture dishes (Nunc, Naperville, Ill.). Cells were cultured in the presence of human IL-3, IL-6, G-CSF, GM-CSF, SCF at 100 ng/ml and EPO at 10 U/ml. Cultures were incubated at 37° C. in 5% CO$_2$ in a humidified incubator. At day 14 of culture, colonies were enumerated using an inverted microscope. Macroscopic BFU-E were defined as those greater than 0.5 mm in diameter.

Marrow CFU-GM and BFU-E were assayed from four baboons before and at the end of the SCF infusion. The number of colonies per 10$^5$ cells, i.e., CFU-GM (41+/−12 pre-SCF, 36+/−post-SCF) and BFU-E (78+/−28 pre-SCF, 52+/−26 post-SCF), were not statistically different. Given the dramatic increases in marrow cellularity, the absolute numbers of CFU-GM and BFU-E were estimated to be increased.

A fifth baboon given SCF was studied weekly for changes in peripheral blood and marrow colony-forming cells. In marrow, the incidence of CFU-GM increased 1.1 to 1.3 fold and BFU-E increased 2.5 to 6.5 fold. In peripheral blood, however, the incidence of colony-forming cells was markedly increased (25 to 100 fold), and absolute numbers of colony-forming cells were increased up to 96 fold for CFU-GH, 934 fold for BFU-E, and greater than 1000 fold for the most primitive colony-forming cells, CFU-MIX. This expansion of colony-forming cells was apparent after as little as seven days of SCF administration and was maintained throughout the period that SCF was given.

B. Use of SCF in Bone Marrow Transplantation

As noted above, there are several ways that SCF is useful to improve hematopoietic transplantation. One method, as illustrated above is to use SCF to augment the harvest of bone marrow and/or peripheral blood progenitors and stem cells by pretreating the donor with SCF. Another use is to treat the recipient of the transplanted cells with SCF after the patient has been infused. The recipient is treated with SCF alone or in combination with other early and late acting recombinant hematopoietic growth factors, including EPO, G-CSF, GM-CSF, M-CSF, IL-1, IL-3, IL-6, etc.

SCF alone enhances hematopoietic recovery following bone marrow transplantation. A variety of experimental variables have been tested in a canine model of bone marrow transplantation, Schuening et al., 76 636-640. In one set of experiments for the present invention, dogs received either G-CSF or SCF after 920 cGy of total body irradiation and 4×10$^8$ mononuclear marrow cells per kilogram from a DLA-identical littermate. The hematologic recovery, as measured by day of neutrophil recovery to 500 or 1000/ mm$^3$, is accelerated when either SCF or G-CSF is administered compared to control animals that received no growth factor (Table 21). Recovery was 2–6 days earlier in animals that received SCF than it was in those that received no growth factor. As noted above, combinations of appropriate growth factors with SCF will accelerate and enhance the response to those growth factors following hematopoietic transplantation.

TABLE 21

Effects of rcG-CSF and SCF on Recovery From
DLA-indentical Littermate Marrow Transplantation[1]

| Treatment | Recovery of ANC > 500 mm$^3$ | Recovery of ANC > 1000/mm$^3$ |
|---|---|---|
| Control | Day 10 | Day 14 |
| rcG-CSF[2] | Day 7 | Day 8 |
| rcSCF[3] #1 | Day 7 | Day 8 |
| rcSCF[3] #2 | Day 8 | Day 9 |

[1]920 cGY TBI followed by infusion of 4 × 10$^8$ mononuclear cells per kg DLA-identical lettermate bone marrow
[2]rCG-CSF administered 10 μg/kg/day$_{SC}$ for 10 days following transplant
[3]rcSCF administered 200 μg/kg/day$_{sc}$ for 10 days following transplant This aspect of in vivo biological activity can be utilized to enhance the recovery from marrow ablative therapy if the peripheral blood or bone marrow is harvested after SCF administration and then re-infused after the ablative regimen (i.e., in bone marrow transplantation or peripheral blood autologous transplantation).

EXAMPLE 23

Effect of SCF on Platelet Formation

Balb/c mice (female, 6–12 weeks of age, Charles River) were treated with rratSCF-PEG (100 μg/kg/day) or excipient control, subcutaneously, 1 time daily for 7 days (n=7). Blood was sampled through a small incision in the lateral tail vein on the indicated days after cessation of SCF treatment. Twenty microliters blood were collected directly into 20 μl microcapillary tubes and immediately dispensed into the manufacturers diluent for the Sysmex Cell Analyzer. Data points are the mean of the data, error bars are standard error of the mean. Blood platelet counts were determined at the time points indicated in FIG. 53. Platelet counts rose to approximately 160% of control values by Day 4 post-SCF, fell to normal by Day 10, and rose again to 160% of normal by Day 15. Platelet counts stabilized at control values by Day 20.

A dose response curve of the SCF effect on platelet counts was generated when Balb/c mice were treated as above with 10, 50, or 100 ug/kg/day rratSCF-PEG (n=7). Blood was collected and analyzed on the fourth day following cessation of SCF treatment. These data are shown in FIG. 54 and demonstrate that concentrations of rratSCF-PEG between 50-100 ug/kg/day are optimal in inducing a rise in platelet counts. Recombinant rat SCF-PEG administration to normal mice also resulted in an increase in platelet size and in the number of megakaryocytes found in the spleen and bone marrow (Table 22). Rodent megakaryocytes were identified by expression of the enzyme acetylcholinesterase (ACH+) which was detected by cytochemical assays, [Long, Blood 58:1032 (1981)].

Certain similarities were noted between mice given SCF and mice during rebound thrombocytosis after experimental induction of thrombocytopenia. FIG. 55 demonstrates one model of experimental thrombocytopenia, namely that of treatment of 5-fluorouracil (5-FU). Balb/c mice were either untreated or treated intravenously with 5-fluorouracil (150 mg/kg) on Day 0 (n=5). Blood analyses were performed on the indicated days as in legend to FIG. 53. Error bars are present, but not discernable, in some of the control points. As has been demonstrated in the past [Radley et al., Blood 55:164 (1980)], animals become thrombocytopenic by Day 5 post-5-FU. However, by Day 12 animals were in a state of rebound thrombocytosis where platelet counts far exceed normal (the "overshoot" effect). After Day 12, platelet counts appeared to cycle from normal to high levels throughout the 40 day testing period. As shown in FIG. 56, megakaryocyte numbers also rise dramatically after 5-FU appearing first in the bone marrow (Panel A) and then in the spleen (Panel B). The megakaryocyte numbers were determined in parallel with that shown in FIG. 55. Two Balb/c mice per group were sacrificed at the indicated days. Cells from bone marrow (Panel A) or spleen (Panel B) were aliquoted at 100,000/well of a microtiter plate and stained for acetylcholinesterase according to published procedures, Long et al., Immature megakaryocytes in the mouse: Morphology and quantitation by acetlycholinesterase staining. Blood 58: 1032, 1981. Data points are the percentage of ACH+ cells per well for individual animals.

Platelet volumes also increase after 5-FU (FIG. 57). The data in this figure were generated from the same blood samples collected in FIG. 55. Mean Platelet Volume (MPV) is one of the parameters analyzed by the Sysmex Cell Analyzer.

The possibility of a relationship between SCF and the physiological regulator of platelet production induced in the 5-FU thrombocytopenic model was explored. 5-FU was given to normal mice and SCF mRNA expression levels quantitated in bone marrow cells collected on the days indicated in FIG. 58. In FIG. 58, one million cells were lysed in SDS buffer and the lysate was analyzed for the presence of mRNA specific for murine SCF. Probes for mouse SCF or human actin mRNA (which detects the corresponding murine MRNA) were generated by runoff transcription of cloned gene regions in vectors containing SP6 or T7 promoters using $^{35}$S-UTP according to standard protocols (Promega Biotech), or from synthetic oligonucleotide partial duplexes, Mulligan et al., Nuc. Acids Res. 15:8783 (1987). RNA sense strand standards for quantitation of the hybridization assays were produced by runoff transcription of the same region in the direction opposite to the direction of probe synthesis using tracer quantities of $^{35}$S-UTP and 0.2 mM unlabeled UTP.

SCF or actin MRNA levels were quantitated as follows. Bone marrow cells were explanted from animals at the given time post-5FU, enriched for light density cells by centrifugation on 65% Percoll (Pharmacia; Pistcataway, N.J.) and lysed at 3×10$^6$ nucleated cells/ml in 0.2% SDS, 10 mM Tris pH 8, 1 mM EDTA, 20 mM dithiothreitol and 100 ug/ml proteinase K (Boerhinger Mannheim; Indianapolis, Ind.). Samples (30 ul) were added to 70 ul of hybridization mix consisting of 30 ug/ml yeast tRNA, 30 ug/ml carrier DNA, 145,000 CμM/ml $^{35}$S-labeled probe in 3.0-3.7 M sodium phosphate, pH 7.2 (depending on length of probe). Samples were incubated at 84° C. for 2–3 hours then cooled to room temperature before addition of RNase A to 0.03 mg/ml and RNase T1 to 5000 U/ml. Samples were incubated at 37° C. for 20 minutes before addition of 120 ul of 0.0025% bromophenol blue in formamide. Entire sample was then loaded onto 3.8 ml Sephacryl S200 Superfine gel filtration column (0.7 cm×10 cm) and eluted with 2.0 mls of 10 mM Tris pH 8, 1 mM EDTA, 50 mM NaCl. Effluents containing hybridized RNA duplexes were collected directly into scintillation vials. After addition of 5 mls Liquiscint (New England Nuclear; Boston, Mass.) samples were counted 20 minutes or to 3% error. CPM were converted to molecules mRNA by comparison to the linear portion of the standard curve (correlation coefficient =0.97). The data point for each sample is the mean of replicate tests; bone marrow samples from 3 individual animals were taken for each time point so that the data shown is the mean of those determinations. Error bars are standard error of the mean. Statistical significance is assigned as described above.

SCF mRNA levels rose dramatically at Days 5 and 7, coinciding exactly with the nadir of platelet counts immediately preceding thrombocytosis (FIG. 58).

The data in this section show that SCF is active as a thrombopoietic agent in vivo and furthermore that SCF may be involved in the physiological regulation of platelet production after 5-FU-induced thrombocytopenia.

TABLE 22

Megakaryocyte and platelet parameters measured on fourth day following SCF administration in vivo.

| Factor | Platelet Count | MPV* | % Ach + Cells in Spleen | % Ach + Cells in Marrow |
|---|---|---|---|---|
| none | 1018 ± 29 | 6.07 ± 0.5 | .22 ± .3 | .02 ± .01 |
| SCF** | 1429 ± 56 | 6.24 ± .05 | .85 ± .9 | .59 ± .05 |

*MPV; mean platelet volume
**ratSCF-PEG administered SC 2 × daily for 7 days at 100 ug/kg/day. Data were collected 4 days later after last injection.

EXAMPLE 24

Treatment of Bone Marrow Failure States

A variety of congenital and acquired disorders of hematopoiesis have been reported to cause clinically significant reductions in the number of mature circulating peripheral blood cells of one or more lineages. Therefore, the existing data supports that these disorders are treatable with SCF. For example, aplastic anemia is a clinical syndrome characterized by pancytopenia due to reduced or absent production of blood cells in the bone marrow. It is heterogeneous in severity, etiology and pathogenesis. Most attention has focused on abnormalities of the hematopoietic stem cell, microenvironment or immunologic injury of one of these. The response to immunosuppressive therapy is variable and incomplete. Because aplastic anemia is a defect of the hematopoietic stem cell or proliferative signals from the microenvironment, and is modeled by the Steel mouse [Zsebo et al., Cell 63 213 (1990)], this disorder is successfully treated with SCF.

Another bone marrow failure disorder which is responsive to SCF is Diamond-Blackfan anemia (DBA) or congenital pure red cell aplasia. This congenital abnormality results in a selective defect in the production of red blood cells and often results in chronic transfusion dependency. In vitro data indicate that the defect is overcome by the addition of exogenous SCF. Bone marrow from patients with DBA (or control marrow) was cultured with or without SCF (100 ng/ml) in the presence of erythropoietin (EPO) (1-5 U/ml), EPO plus IL-3 (1-1000 U/ml), EPO plus GM-CSF (>100 U/ml), or EPO plus lymphocyte-conditioned media (2–5%). Culture of bone marrow from patients with DBA demonstrate two patterns of response to SCF. The majority were hyper-responsive to SCF and showed approximately 3 fold increase in the frequency of BFU-E at less than or equal to 10 ng/ml, as well as an increase in the size of BFU-E at concentrations up to 200 ng/ml. Control marrow demonstrated only a 1.5 fold increase in frequency of BFU-E. This pattern of response to SCF could indicate a defect in endogenous SCF and/or its production by the microenvironment in this group of patients with DBA. The other group of patients with DBA demonstrated an increase in the frequency of BFU-E at concentrations of SCF greater than or equal to 50 ng/ml. This pattern of response reflects an intrinsic defect in the receptor for SCF (c-kit) on the progenitor cell. In either case (abnormal production of SCF by the microenvironment or decreased stimulation of the hematopoietic progenitor by SCF) SCF overcomes the block to hematopoiesis which characterizes bone marrow failure syndromes such as DBA.

Other bone marrow failure syndromes that are treatable with SCF include, but are not limited to: Fanconi's anemia, dyskeratosis congenita, amegakaryocytic thrombocytopenia, thrombocytopenia with absent radii, and congenital agranulocytosis (e.g. Kostmann's syndrome, Shwachman-Diamond syndrome) as well as other causes of severe neutropenia such as idiopathic and cyclic neutropenia. Severe chronic neutropenia congenital, cyclic or idiopathic are treatable with recombinant G-CSF.

Cyclic neutropenia, in particular, is a defect in the regulation of stem cell division since other lineages (e.g., platelet, erythrocyte and monocyte) are also effected. In the canine model of cyclic neutropenia, the cycling of neutrophils, as well as other lineages, is sharply reduced or even eliminated by SCF treatment. A typical dog with cyclic neptropenia was treated with rcanineSCF (recombinant canine SCF) at 100 mg/kg/day subcutaneously over several weeks. The typical 21 day cycle for neutrophils was eliminated during the first predicted cycle and the second predicted nadir was significantly atenuated. This is in contrast to treatment with G-CSF which increases the frequency and amplitude of neutrophil cycling, but does not eliminate it. Thus, SCF is useful in treating a variety of bone marrow failure syndromes, either alone or in combination with other hematopoietic growth factors.

EXAMPLE 25

SCF Treatment of Patients With HIV-1 Infection
A. Source and Preparation of Peripheral Blood Mononuclear Cells Leukopaks were obtained from HIV-, CMV-, and EBV-seronegative normal donors from the American Red Cross. Peripheral blood was obtained from 6 patients with HIV-infection after informed consent was obtained. Two patients were asymptomatic, one had AIDS-related complex and three had AIDS. None of the 6 patients had received zidovudine within the last six months. None of the patients were anemic (hemoglobin <135 g/L) at the time of study. All studies were conducted in accordance with UCLA Human Subject Protection Committee regulations.

Peripheral blood mononuclear cells were isolated from leukopaks and peripheral blood using ficoll-hypaque sedimentation followed by extensive washing with Hank's Balance Salt Solution (HBSS). Blood cells were enumerated and viability ascertained by trypan blue dye exclusion.
B. Burst Forming Unit Erythro (BFU-E) Assay Assays for BFU-E were performed in a standard protocol using normal human bone marrow as the control. Heparinized blood was diluted with an equal volume of HBSS (GIBCO, Grand Island, N.Y.), layered over Ficol-Paque (Pharmacia, Piscataway, N.J.) and centrifuged at 400 g for 30 minutes at room temperature. Light density cells (s.g. <1.077) were collected and washed twice in HBSS. Cells were resuspended in Iscove's Medium with 10% Fetal Bovine Serum (GIBCO, Grand Island, N.Y.) at a concentration of $1\times10^7$/ml. Cells ($1\times10^5$) were cultured in Iscove's Media supplemented with $5\times10^{-5}$ M 2-Mercaptoethanol (2ME) (Sigma Chemicals, St. Louis, Mo.), 30% Fetal Bovine Serum (GIBCO, Grand Island, N.Y.), and either 1 or 4 units of human recombinant erythropoietin (Amgen Inc., Thousand Oaks, Calif.) in 0.3% agar. Four concentrations of E. coli derived human stem cell factor (hSCF$^{1-164}$), obtained as described in Examples 6 and 10, were added (0,10,100 and 1000 ng/ml). Zidovudine (AZT) was added to the mixture resulting in final concentrations of 0, 0.0 $\mu$M, 0. $\mu$M, 1.0 $\mu$M. Erythroid burst colonies were scored after 14 days of culture in a humidified atmosphere containing 5% $CO_2$. Each assay was done in duplicate and colonies with >50 cells present on day 14 with hemoglobinization were scored as BFU-E.

The 50% inhibitory concentration for zidovudine was calculated by expressing the mean of four determinations of BFU-E for each level of zidovudine and huSCF as a percentage of control (no added zidovudine). Linear regression was used to calculate the slope of inhibition. The 50% inhibitory concentration was calculated by interpolation and the value used as the exponent for the base of 10. This results in direct calculation of the $ID_{50}$. The $r^2$ for all the slopes were >0.90.

C. Effects of HuSCF on Stimulated Peripheral Blood Mononuclear Cells

Peripheral blood mononuclear cells were isolated from the leukopaks of two additional normal donors as described above. Cells were resuspended in Iscove's Modified Dulbecco's Medium containing 20% fetal bovine serum, penn/strep, 1.0% PHA (Sigma Chemical, St. Louis, Mo.) and 10 units/ml of interleukin-2 (Amgen Inc. Thousand Oaks, Calif.). Four concentrations of human stem cell factor (0, 10, 100, 1,000 ng/ml) were added to the media. Complete lymphocyte subset analysis of cellular antigens were analyzed in duplicate by two color fluorescent cytometry on day 0, 3, 7 and 10. Differences in percentages of cell populations were detected using independent and paired t-tests (2-tailed). Comparisons were made between drug-treated and non-drug-treated values for a single day and between single days values and baseline. Cytometric analysis was done in duplicate.

D. Results

Exposure of peripheral blood mononuclear cells to erythropoietin and human stem cell factor (HUSCF) resulted in a dose-dependent increase in BFU-E formation in the 2 normal patients studied (FIG. 59A). Significant increases (up to 100%) were seen with concentrations of human stem cell factor between 10 and 1,000 ng/ml. Near maximal activity was seen at 10 ng/ml suggesting that lower concentrations may be active. There were significant increases in BFU-E when the dose of erythropoietin was increased from 1 IU to 4 IU/ml (FIG. 59B). The colonies observed were significantly larger in size than the bursts seen in the absence of HuSCF.

In the 6 HIV-infected individuals studied, significant dose-dependent increases in BFU-E were also seen with HuSCF treatment (FIG. 60). Although the number of BFU-E in the absence of HuSCF was markedly reduced compared to normal (range 2-26 BFU-E/$10^5$ peripheral blood mononuclear cells compared to approximately 74 BFU-E/$10^5$ PBMC for normals), the percentage increases in BFU-E were significantly higher in the HIV-infected individuals. Near normal numbers of BFU-E were obtained for 2 individuals at the 1,000 ng/ml concentration of HuSCF. Although the absolute number of BFU-E seen for some of the patients were still well below normal, all 6 individuals responded in vitro to HuSCF.

Because previous studies showed that cytokines could alter the intracellular uptake or intracellular metabolism of deoxynucleosides. [Perno et al., *J. Exp. Med.* 169:933 (1989)] the capacity of hSCF to modulate the inhibition of red cell progenitors by zidovudine was evaluated. Each of the normals and all of the HIV individuals had BFU-E assays performed in the presence and absence of 3 concentrations of zidovudine and 4 concentrations of huSCF. As observed, (FIGS. 59 and size of BFU-E bursts) the addition of HuSCF markedly reduced inhibition of early red cell progenitors by zidovudine. Significant alterations in the 50% inhibitory dose of zidovudine for BFU-E was seen at all three concentrations of human stem cell factor. The $IC_{50}$ (fifty percent inhibitory concentration) ranged from 2.65 to 1376 $\mu$M of zidovudine (FIG. 61). All three of these inhibitory concentrations of zidovudine are well above normal serum levels obtained after 1,000 mg/day of zidovudine [Klecher et al., *Clin. Pharmacol. Ther.*; 41:407–12 (1987)]. Similar results were observed for all 6 individuals infected with HIV. However, because of the few number of red cell progenitors in 2 of the patients, the increases in the 50% inhibitory concentrations of zidovudine for BFU-E did not reach statistical significance. Nonetheless, the trends were clearly present and replicated the effects of human stem cell factor on BFU-E in the presence of zidovudine in the normal individuals.

The effect of SCF on the protection of bone marrow derived cells as well as peripheral blood progenitors (above) was examined. Normal human bone marrow was prepared as described above for peripheral blood progenitors. Bone marrow cells were exposed to different concentrations of AZT (zidouvidine), and the protective effects of SCF for both erythroid as well as myeloid cells was determined in semi-solid cultures. Colonies were scored after 14 day incubation as described above. The results for the protection of bone marrow derived erythroid cells (FIG. 62) and myeloid cells (FIG. 63) are indicated. As is seen for peripheral blood, SCF protects bone marrow cells from AZT as well. Another toxic compound used to fight the opportunistic infections associated with HIV infection is ganciclovir. Once again, SCF protects bone marrow cells against the toxic effects of ganciclovir for both erythroid development (FIG. 64) and myeloid development (FIG. 65).

In summary, this example details the effects of HUSCF on early red blood cell progenitors. Exposure to HuSCF in vitro resulted in a dose and time-dependent increase in red blood cell progenitors and significantly altered the inhibition of red cell progenitors by zidovudine. This was observed in both normal and HIV-infected study populations. HuSCF had no effect on HIV virus replication in primary monocytes or primary human lymphocytes nor did it alter the efficacy of 2',3',-dideoxynucleoside analogues. This is a significant difference from other cytokines which have effects on red cell progenitors such as granulocyte-macrophage colony-stimulating factor (GM-CSF) and interleukin-3 (IL-3). As shown in other studies [Koyanagi et al., *Science* 241:1773 (1981); Folks et al., *Science* 238:800 (1987); Hammer et al., *Proc. Natl. Acad. Sci.* USA 83:8734 (1986)], both GM-CSF and IL-3 significantly increase replication of HIV in partially purified primary peripheral blood monocytes.

These studies demonstrate that human stem cell factor (HuSCF) is an ideal candidate drug for use as adjunctive therapy in the treatment of HIV-related pan-cytopenia. This cytokine appears to directly stimulate human hematopoietic progenitor cells and synergizes with IL-7, G-CSF, GM-CSF, and IL-3 in the production of pre-B lymphocytes, megakaryocytes, monocytes, granulocytes, and mast cells [Martin et al., *Cell* 63:203–211 (1990); Zsebo et al., *Cell*, 63:213–224 (1990)].

EXAMPLE 26

Use of Stem Cell Factor to Facilitate Gene Transfer into Hematopoietic Stem Cells The in vitro survival and proliferation of primitive stem cells is critical to the success of gene Do transfer mediated by retroviral insertion or other known methods of gene transfer. The effect of SCF on the in vitro maintenance and/or proliferation of primitive progenitor cells has been studied in two systems which have been described previously [Bodine et al., Proc. Natl. Acad. Sci. 86 8897-8901, 1989]. The first is a pre-CFU-S assay wherein bone marrow cells are incubated for up to six days in suspension culture in the presence of growth factors. Aliquots are injected into lethally iradiated mice and the mice sacrificed at 12–14 days for quantitation of spleen focus formation. IL-3 and IL-6 synergize in enhancing the proliferation of CFU-S between 2–6 days in culture. The second is a competitive repopulation assay which measures the effects of growth factors on recovery and biological activity of cells capable of sustaining long-term hematopoiesis. Cells from two congenic strains of mice differing for a hemoglobin marker are incubated in suspension independently, cells from one strain as a control and cells from a second under experimental conditions. After incubation, equal numbers of bone marrow cells from both cultures are mixed and injected into W/W$^v$ recipients.

Rat SCF has been evaluated both in the pre-CFU-S and competitive repopulation assays. SCF alone has very little activity in the pre-CFU-S assay, similar to IL-3 alone. For enhancing CFU-S activity, the combination of SCF and IL-3 is equivalent to the previous optimal combination of IL-3 and IL-6 whereas the combination of SCF and IL-6 is 5-fold more active than IL-3 and IL-6 (FIG. 66). A most advantageous combination is SCF, IL-3 and IL-6; it is 6-fold more active than the combination of IL-3 and IL-6.

In the competitive repopulation assay, the repopulating ability of cells cultured in the combination of SCF and IL-6 is superior at 35 days (short-term reconstitution) (FIG. 67). A most advantageous combination for long term reconstitution is SCF, IL-3 and IL-6, approximately 1.5-fold greater than any combination of two factors. Based on these data, a most advantageous combination of soluble growth factors for enhancing retroviral mediated gene transfer into stem cells would be SCF, IL-3 and IL-6.

SCF presentation by stromal cells induces the proliferation of primitive bone marrow progenitors. The ultimate in vitro stimulus for proliferation of stem cells is provided by stromal cell lines transfected with human SCF cDNAs with sequences as shown in FIGS. 42 and 44. When human bone marrow is cultured on artificial feeder layers expressing the membrane bound form of human SCF 220 (FIG. 44), there is a continued proliferation of hematopoietic progenitors over time. An example of this is given in Table 23. Stromal cells derived from S1/S1 embryos prior to their death in utero [Zsebo et al., Cell 63 213 (1990)] were transfected with human SCF cDNAs (either expressing the 220, FIG. 44 or 248, FIG. 42, amino acid forms of SCF] and used as feeder layers for human marrow. Briefly, adherent layers were treated with mitomycin C and plated at confluence in 6 well plates. Normal human bone marrow, 7.5×10$^5$ adherence depleted cells, were plated in 5 ml of Iscove's Modified Dulbeccos Medium (Gibco), 10% fetal calf serum, and 10-6 M hydrocortisone onto the transfected adherent layers. At the indicated time points, cells were withdrawn and plated in semi-solid agar using EPO and IL-3 as a stimulus. For the experiment in Table 24, normal adherence depleted human bone marrow was first enriched for hematopoietic progenitors expressing the CD34 antigen using magnetic particle concentration [Dynal, Inc., Great Neck, NY] prior to plating on the adherent feeder cells. In this case, 3.5×10$^4$ cells were cultured on top of the adherent layers as described above. At the indicated time points, cells were withdrawn from the cultures and plated in semi-solid agar as described above. For both experiments, colony formation was enumerated after 14 days of culture in a humidified atmosphere. The generation of colony forming cells over time was enumerated. As is indicated, the membrane bound form of SCF (220 amino acid, FIG. 44) is more potent at supporting hematopoiesis over time.

The S1/S1 cell line expressing human SCF$^{1-220}$ amino acid form is advantageous for retroviral mediated gene transfer into hematopoietic stem cells. Human bone marrow is infected with retrovirus in the presence of mammalian cells expressing human SCF$^{1-220}$. In addition, the viral producer line optimally is transfected with the human SCF$^{1-220}$ gene and used for the viral infection as a co-culture.

TABLE 23

Generation of colony forming cells from normal human bone marrow by cells expressing different splice variants of human SCF.

| Cells; | Days of Culture | CFU-Macs | CFU-GM | BFU-E | CFU-Mix |
|---|---|---|---|---|---|
| S1/S1-4 | 7 | 1.3 ± 1 | 6 ± 3 | 3 ± 3 | 0 |
|  | 14 | 0 | 0 | 0 | 0 |
|  | 21 | 0 | 0 | 0 | 0 |
| S1/S1-4 SCF 220 | 7 | 31 ± 13 | 51 ± 8 | 3 ± 2 | 0 |
|  | 14 | 57 ± 2 | 69 ± 5 | 0 | 0 |
|  | 21 | 46 ± 16 | 23 ± 13 | 0 | 0 |
| S1/S1-4 SCF 248 | 7 | 57 ± 14 | 89 ± 7 | 11 ± 8 | 1 ± 1 |
|  | 14 | 5 ± 4 | 9 ± 5 | 5 ± 3 | 0 |
|  | 21 | 1 ± 1 | 0 | 0 | 0 |

TABLE 24

Generation of colony forming cells from CD34 + bone marrow cells expressing different splice variants of human SCF.

| | | Total colonies/culture well | | | |
|---|---|---|---|---|---|
| Cells; | Days of Culture | CFU-Macs | CFU-GM | BFU-E | CFU-Mix |
| S1/S1-4 | 7 | 4 ± 2 | 10 ± 6 | 11 ± 3 | 1 ± 1 |
|  | 14 | 0 | 0 | 0 | 0 |
|  | 21 | 0 | 0 | 0 | 0 |
| S1/S1-4 SCF 220 | 7 | 90 ± 7 | 70 ± 2 | 18 ± 10 | 13 ± 4 |
|  | 14 | 14 ± 13 | 60 ± 11 | 2 ± 1 | 0 |
|  | 21 | 36 ± 3 | 23 ± 5 | 0 | 0 |
| S1/S1-4 SCF 248 | 7 | 260 ± 64 | 135 ± 20 | 80 ± 20 | 15 ± 5 |
|  | 14 | 0 | 0 | 0 | 0 |
|  | 21 | 0 | 0 | 0 | 0 |

EXAMPLE 27

Further Characterization of Recombinant Human SCF Obtained from E. coli or CHO Cells As noted in Example 10, human [Met$^{-1}$]SCF$^{1-164}$ from E. coli has amino acid composition and amino sequence expected from analysis of the gene. Using the methods outlined in Example 2, it has been determined that human SCF$^{1-165}$ obtained from E. coli as described in Example 10 also has the amino acid composition and amino acid sequence expected from analysis of the gene, and also retains Met at position (−1).

Purified E. coli-derived human [Met$^{-1}$]SCF$^{1-164}$ and CHO cell-derived human [Met$^{-1}$]SCF$^{1-162}$ have been studied by methods indicative of secondary and tertiary structure. Fluorescence emission spectra, with excitation at 280 nm, have been obtained. These are shown in FIG. 68. The molecules were dissolved in phosphate-buffered saline. The spectra consist of a single peak with a maximum at 325 nm, and a full width at half maximum (FWHM) of between 45 and 50 nm. Both the emission wavelength and the FWHM suggest that the single Trp is present in a hydrophobic environment, and that this environment is the same in both molecules.

Circular dichroism studies have also been carried out. FIG. 69 shows the far ultraviolet (UV) spectra and near UV spectra (B) for the E. coli-derived SCF (solid lines) and CHO cell-derived SCF (dotted lines). The molecules were dissolved in phosphate-buffered saline. The far UV spectra contain minima at 208 nm and 222 nm. Using the Greenfield-Fasman equation [Greenfield and Fasman, *Biochemistry* 8, 4108–4116 (1969)], the spectra suggest 47% α-helix, while the method of Chang et al. [*Anal. Biochem.* 91, 13–31 (1978)] indicates about 38% a-helix, 33% B-sheet, and 29% disordered structure. The near UV spectra have minima at 295 nm and 286 nm attributable to tryptophan, minima at 261 nm and 268 nm attributable to phenylalanine, and minima at 278 probably attributable to tyrosine, with some overlap between chromophores. The results indicate that the aromatic chromophores are located in asymmetric environments. Both the far UV and near UV results are the same for E. coli-derived SCF and CHO cell-derived SCF, indicating similarity of structure.

Second derivative infrared spectra in the amide I region (1700–1620 cm$^{-1}$) of the E. coli-derived SCF (A) and CHO cell-derived SCF (B) are shown in FIG. 70. These spectra are related to polypeptide backbone conformation [Byler and Susi, *Biopolymers* 25, 469–487 (1986); Surewicz and Mantsch, *Biochim. Biophys. Acta* 952, 115–130 (1988)] and are essentially identical for the two proteins. Band assignments [Byler and Susi (1986), supra; Surewicz and Mantsch (1988), supra] allow one to estimate that the two SCFs have predominantly helical structures, ~31% α-helix and 19% $3_{10}$α-helix, with lesser fractions of β-strands (~25%), turns (~15%), and disordered structures (~14%).

Disulfide structure of various molecules referred to in previous examples have been determined. These include BRL 3A cell-derived natural rat SCF, E. coli-derived rat [Met$^{-1}$]SCF$^{1-164}$, CHO cell-derived rat SCF$^{1-162}$, E. coli-derived human [Met$^{-1}$]SCF$^{1-164}$, E. coli-derived human [Met$^{-1}$]SCF$^{1-165}$, and CHO cell-derived human SCF$^{1-162}$. The methods used include those outlined in Example 2 for amino acid sequence and structure determination. The proteins are digested with proteases, and the resulting peptides isolated by reverse-phase HPLC. If this is done with and without prior reduction, it is possible to isolate and identify disulfide-linked peptides. Isolated disulfide-linked peptides can also be identified by plasma desorption mass spectroscopy. By such methods it has been demonstrated that all of the above-mentioned molecules have intrachain disulfide bonds linking Cys-4 and Cys-89, and linking Cys-43 and Cys-138.

EXAMPLE 28

Production and Characteristics of SCF Analogs and Fragments Expressed in E. coli Plasmid constructions for expression of numerous SCF analogs and fragments have been made. Site-directed mutagenesis had been used to prepare plasmids with initiating methionine codon followed by codons for amino acids 1 to 178, 173, 168, 166, 163, 162, 161, 160, 159 158 157 156 148 145 141 137, using the numbering of FIG. 15C. The DNA for human SCF$^{1-183}$ (Example 6B was cloned into MPII from XbaI to BamH1. Phage from this cloning was used to transfect an E. coli dut ung strain. R21032. Single stranded M13 DNA was prepared from this strain and site-directed mutagenesis was performed (reference IL-2 patent). After the site-directed mutagenesis reactions, the DNAs were transformed into an E. coli dut ung strain, JM101. Clones were screened and sequences as described in U.S. application Ser. No. 717,334, filed Mar. 29, 1985, now abandoned. Plasmid DNA preps were made from positive clones and the SCF regions from XbaI to BamHI were cloned into pCFM1656 as described in copending U.S. patent application Ser. No. 501,904, filed Mar. 29, 1990, now abandoned. The oligonucleotides for each cloning were designed to substitute a stop codon for an amino acid codon at the appropriate position for each analog.

Plasmids with initiating methionine codon followed by codons for amino acids 1 to 130, 120, 110, 100, 133, 127, and 123 (using the numbering of FIG. 42) have been made using the polymerase chain reaction. The pCFM1156 human SCF$^{1-164}$ plasmid DNA (Example 6B) was used to prime the reaction using a 5' oligonucleotide 5' to the XbaI site and a 3' oligonucleotide which included a direct match to the desired 3' end of the analog DNA, followed by a stop codon, followed by a BamHl site. After the polymerase chain reaction, the polymerase chain reaction fragments were cleaved with XbaI and BamHl, gel purified, and cloned into pCFM1656 cut with XbaI and BamHl.

Plasmids with initiating methionine codon followed by codons for amino acids 2 to 164, 5 to 164, and 11 to 164 (using the numbering of FIG. 42) were also made using polymerase chain reaction. The pCFM1156 human SCF$^{1-164}$ plasmid DNA (Example 6B) was used with two primers. The 5' oligonucleotide primer included an NdeI site (which includes the ATG codon for the initiating methionine) and a homologous stretch of DNA starting at the codon for the first desired amino acids. The 3' oligonucleotide primer was totally homologous and was 3' to the EcoRI site in the gene. After the polymerase chain reaction, the fragment was cut with NdeI and EcoRI, gel purified, and cloned back into the pCFM1156 human SCF$^{1-164}$ plasmid cut with NdeI and EcoRI.

A plasmid with initiating methionine codon followed by codons for amino acids 1 to 248 (using the numbering of FIG. 42) was made using DNA obtained directly from the cDNA clone (Example 16). The cDNA was cleaved with SpeI and DraI (blunt end) and the fragment with the SCF region was gel purified. This was cloned into the pCFM1156 human SCF$^{1-183}$ plasmid (Example 6B) which had been cut with HindIII, end filled with the Klenow fragment of DNA polymerase 1 (to yield a blunt end), and then cut with SpeI and gel purified. To allow for site-directed mutagenesis as above, the SCF$^{1-248}$ fragment was cloned into MPll from XbaI to BamHI; analog plasmids encoding initiating methionine followed by amino acids 1–189, 1-188, 1–185, or 1-180 (using numbering of FIG. 42) were then made using site-directed mutagenesis.

A plasmid with initiating methionine codon followed by codons for amino acids 1 to 220 (using the numbering of FIG. 44) was made using DNA directly from the cDNA clone (Example 18), using the same methods outlined in the preceding paragraph. Similarly, analog plasmids encoding initiating methionine followed by amino acids 1–161, 1-160, 1–157, or 1-152 (using the numbering of FIG. 44) were made.

A pCFM1156 human SCF$^{2\text{-}165}$ plasmid was made by cloning the XbaI to EcoRI SCF fragment from pCFM1156 human SCF$^{2\text{-}164}$ into the plasmid pCFM1156 human SCF$^{1\text{-}165}$ (having synthetic codons; see Example 6B). Both DNAs were cut with XbaI and EcoRI and the fragments gel purified for cloning. The small fragment from pCFM1156 human SCF$^{2\text{-}164}$ was ligated to the large fragment of pCFM1156 human SCF$^{1\text{-}165}$ (synthetic codons).

In considering the analog plasmids described above, it is noted that amino acids 4, 43, 89, and 138 are Cys in human SCFs, and the codons for Cys-4 or Cys-138 are missing in certain of the plasmids described. Amino acids of the hydrophobic transmembrane region are at positions 190 (about) to 212 in the numbering of FIG. 42, and positions 162 (about) to 184 in the numbering of FIG. 44. Thus most of the plasmids described encode amino acids that would be in the extracellular domain of membrane bound human SCF$^{1\text{-}248}$ (FIG. 42 numbering) or human SCF$^{1\text{-}220}$ (FIG. 44 numbering), and some include virtually all of these extracellular domains.

Plasmids encoding various other human SCF analogs and fragments can also be prepared by the methods described, and by other methods known to those skilled in the art. These include plasmids with codons for Cys residues replaced by codons for other amino acids such as Ser.

E. coli host strain FM5 (Example 6) has been transformed with many of the analog plasmids described. These strains have been grown, with temperature induction, in flasks, and in fermentors as described in Example 6C.

After fermentation and harvesting of cells, many folded, oxidized, purified SCF analogs have been recovered by the methods outlined in Example 10. These include (by the numbering of FIG. 42) SCF$^{1\text{-}189}$, SCF$^{1\text{-}188}$, SCF$^{1\text{-}185}$, SCF$^{1\text{-}180}$, SCF$^{1\text{-}156}$, SCF$^{1\text{-}141}$ SCF$^{1\text{-}137}$, SCF$^{1\text{-}130}$, SCF$^{2\text{-}164}$, SCF$^{5\text{-}164}$, SCF$^{11\text{-}164}$ and (by the numbering of FIG. 44) SCF$^{1\text{-}161}$, SCF$^{1\text{-}160}$, SCF$^{1\text{-}157}$ SCF$^{1\text{-}152}$. Like SCF$^{1\text{-}164}$ and SCF$^{1\text{-}165}$ (Examples 17 and 27), these analogs are all dimeric in solution, as judged using gel filtration. Most of these have biological specific activities in the radioreceptor assay (Example 9) and UT-7 proliferation assay (Example 9) similar to those of SCF$^{1\text{-}164}$ and SCF$^{1\text{-}165}$ (Example 9). Some, such as SCF$^{2\text{-}164}$ and SCF$^{5\text{-}164}$ have lowered specific activities in the radioreceptor assay and/or UT-7 assay (30–80% of the values for SCF$^{1\text{-}164}$ and SCF$^{1\text{-}165}$) while others, such as SCF$^{11\text{-}164}$, have negligible specific activity in both assays. SCF$^{1\text{-}130}$ has lowered specific activity in both the radioreceptor assay (about 50% of the value for SCF$^{1\text{-}164}$) and the UT-7 assay (about 15% of the value for SCF$^{1\text{-}164}$). SCF$^{1\text{-}137}$ has full specific activity in the radioreceptor assay but lowered specific activity in the UT-7 assay (about 25% of the value for SCF$^{1\text{-}164}$ and SCF$^{1\text{-}165}$); this analog therefore may be preferable as an SCF antagonist in situations where it would be advantageous to block the biological activity of SCF.

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. A composition which comprises a therapeutically effective amount of an isolated stem cell factor (SCF) polypeptide, or a biologically active SCF fragment comprising at least 130 contiguous amino acids of any of sequences set forth in SEQ ID NO:46, SEQ ID NO:61 or SEQ ID NO:63 that enhances hematopoiesis and one or more cytokines in a pharmaceutically acceptable carrier.

2. The composition of claim 1, wherein SCF polypeptide is a product of a recombinant prokaryote cell or eukaryote cells.

3. The composition of claim 2, wherein the SCF polypeptide is a human SCF polypeptide.

4. The composition of claim 3, wherein the SCF polypeptide is selected from the group of polypeptides consisting of the amino acid sequence set out as 1–162, 1–164 and 1–165 in SEQ ID NO:46 said polypeptides optionally consisting of an N-terminal methionine.

5. The composition of claim 3, wherein the SCF polypeptide is a polypeptide which comprises a polypeptide sequence selected from the group consisting of the amino acid sequence set out as 1–130, 1–133, 1–137, 1–141, 1–145, 1–148, 1–152, 1–156, 1–157, 1–158, 1–159, 1–160, 1–161, 1–163, 1–166, 1–168, 1–173, 1–178, 2–164, 2–165, 5–164, 11–164, 1–180, 1–183, 1–185, 1–188, 1–189, 1–220 and 1–248 in SEQ ID NO:61 said polypeptide optionally consisting of an N-terminal methionine.

6. The composition of claim 3, wherein the SCF polypeptide is selected from the group consisting of amino acids 1–152, 1–157, 1–160, 1–161 and 1–220 as set out in SEQ ID NO:63 said polypeptide optionally consisting of N-terminal methionine.

7. The method of claim 4, 5, or 6, wherein the stem cell factor is covalently conjugated to a water-soluble polymer.

8. The method of claim 7, wherein the water soluble polymer is polyethylene glycol.

9. The composition of claim 4, 5, or 6 wherein the amount of SCF in the composition is effective to treat hematopoietic disorders.

10. The composition of claim 7, wherein the amount of SCF in the composition is effective to treat hematopoietic disorders.

11. The composition of claim 9, wherein the composition contains at least one cytokine selected from the group consisting of Interleukin-1, Interleukin-2, Interleukin-3, Interleukin-4, Interleukin-5, Interleukin-6, Interleukin-7, Interleukin-8, Interleukin-9, Interleukin-10, Interleukin-11, Interleukin-12, erythropoietin, Granulocyte Colony-stimulating Growth Factor, Granulocyte-Macrophage Colony-Stimulating Factor, Colony Stimulating Factor-1, Insulin-like Growth Factor-1, and Leukemic Inhibitory Factor.

12. The composition of claim 10, wherein the composition contains at least one cytokine selected from the group consisting of Interleukin-1, Interleukin-2, Interleukin-3, Interleukin-4, Interleukin-5, Interleukin-6, Interleukin-7, Interleukin-8, Interleukin-9, Interleukin-10, Interleukin-11, Interleukin-12, erythropoietin, Granulocyte Colony-stimulating Growth Factor, Granulocyte-Macrophage Colony-Stimulating Factor, Colony Stimulating Factor-1, Insulin-like Growth Factor-1, and Leukemic Inhibitory Factor.

13. The composition of claim 4, 5, or 6, wherein the composition contains a pharmaceutically effective carrier for the controlled release of SCF and other cytokines in the composition.

14. The composition of claim 7, wherein the composition contains a pharmaceutically effective carrier for the controlled release of SCF and other cytokines in the composition.

15. The composition of claim 4, 5, or 6, wherein the composition contains a pharmaceutically effective carrier for parenteral delivery of the composition.

16. The composition of claim 7, wherein the composition contains a pharmaceutically effective carrier for parenteral delivery of the composition.

17. The composition of claim 4, 5, or 6, wherein the composition contains a pharmaceutically effective carrier for pulmonary delivery of the composition.

18. The composition of claim 7, wherein the composition contains a pharmaceutically effective carrier for pulmonary delivery of the composition.

19. The composition of claim 4, 5, or 6, wherein the composition contains a pharmaceutically effective carrier for nasal delivery of the composition.

20. The composition of claim 7, wherein the composition contains a pharmaceutically effective carrier for nasal delivery of the composition.

21. The composition of claim 4, 5, or 6, wherein the composition contains a pharmaceutically effective carrier for the oral delivery of the composition.

22. The composition of claim 7, wherein the composition contains a pharmaceutically effective carrier for the oral delivery of the composition.

23. The composition of claim 4, 5, or 6, wherein the composition contains a pharmaceutically effective carrier for the topical delivery of the composition.

24. The composition of claim 7, wherein the composition contains a pharmaceutically effective carrier for the topical delivery of the composition.

* * * * *